(12) United States Patent
Chen et al.

(10) Patent No.: US 11,208,414 B2
(45) Date of Patent: *Dec. 28, 2021

(54) ECTONUCLEOTIDASE INHIBITORS AND METHODS OF USE THEREOF

(71) Applicant: Calithera Biosciences, Inc., South San Francisco, CA (US)

(72) Inventors: Lijing Chen, Cupertino, CA (US); Jim Li, San Francisco, CA (US); Eric B. Sjogren, Mountain View, CA (US); Roland J. Billedeau, Santa Clara, CA (US)

(73) Assignee: CALITHERA BIOSCIENCES, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/585,195

(22) Filed: Sep. 27, 2019

(65) Prior Publication Data

US 2020/0087310 A1    Mar. 19, 2020

Related U.S. Application Data

(63) Continuation of application No. 15/699,109, filed on Sep. 8, 2017, now Pat. No. 10,472,364.

(60) Provisional application No. 62/385,730, filed on Sep. 9, 2016.

(51) Int. Cl.
| | | |
|---|---|---|
| *A61K 31/52* | (2006.01) | |
| *C07D 487/04* | (2006.01) | |
| *C07D 473/16* | (2006.01) | |
| *C07D 473/40* | (2006.01) | |
| *C07D 405/04* | (2006.01) | |
| *C07D 405/14* | (2006.01) | |

(52) U.S. Cl.
CPC ......... *C07D 487/04* (2013.01); *C07D 405/04* (2013.01); *C07D 405/14* (2013.01); *C07D 473/16* (2013.01); *C07D 473/40* (2013.01)

(58) Field of Classification Search
CPC ........ A61K 31/52; C07D 473/40; A61P 35/00
USPC ........................ 514/263.22, 263.23; 544/277
See application file for complete search history.

(56) References Cited

U.S. PATENT DOCUMENTS

| | | | |
|---|---|---|---|
| 5,635,608 A | 6/1997 | Haugland et al. | |
| 6,426,337 B1 | 7/2002 | Cox et al. | |
| 8,962,636 B2 | 2/2015 | Pfrengle et al. | |
| 10,472,364 B2* | 11/2019 | Chen ....................... | A61P 25/16 |
| 10,570,167 B2 | 2/2020 | Billedeau et al. | |
| 2010/0249055 A1 | 9/2010 | Mueller et al. | |
| 2013/0323836 A1 | 12/2013 | Manoharan et al. | |
| 2017/0044203 A1 | 2/2017 | Cacatian et al. | |
| 2018/0186827 A1 | 7/2018 | Billedeau et al. | |

FOREIGN PATENT DOCUMENTS

| | | |
|---|---|---|
| EP | 0572669 A1 | 12/1993 |
| EP | 1860113 A1 | 11/2007 |
| WO | WO-1994/10128 A1 | 5/1994 |
| WO | WO-1998/34943 A1 | 8/1998 |
| WO | WO-2004/096233 A2 | 11/2004 |
| WO | WO-2008/011406 A2 | 1/2008 |
| WO | WO-2009/061781 A1 | 5/2009 |
| WO | WO-2012/006351 A1 | 1/2012 |
| WO | WO-2012/151142 A2 | 11/2012 |
| WO | WO-2014/079903 A1 | 5/2014 |
| WO | WO-2015/164573 A1 | 10/2015 |
| WO | 2017/024310 A1 | 2/2017 |
| WO | WO-2017/066781 A1 | 4/2017 |
| WO | WO-2017/066782 A1 | 4/2017 |
| WO | WO-2017/066791 A1 | 4/2017 |
| WO | WO-2017/079195 A1 | 5/2017 |
| WO | WO-2018/119284 A1 | 6/2018 |

OTHER PUBLICATIONS

Bonaate et al., "Discovery and development of clofarabine: a nucleoside analogue for treating cancer," Nat Rev Drug Discov, 5(10): 855-863 (2006).
CAS Registry No. 1259875-56-3: STN Entry Date: Jan. 19, 2011.
CAS Registry No. 1260067-78-4; STN Entry Date: Jan. 20, 2011.
CAS Registry No. 1260067-82-0; STN Entry Date: Jan. 20, 2011.
Debarge et al., "Design and Synthesis of α-Carboxy Phosphononucleosides," J Org Chem, 76(1): 105-126 (2011).
Hladezuk et al., "Development of O—H Insertion for the Attachment of Phosphonates to Nucleosides; Synthesis of α-Carboxy Phosphononucleosides," Tetrahedron, 68(7):1894-1909 (2012).
International Search Report and Written Opinion for International Application No. PCT/US2017/050659 dated Jan. 10, 2018.
International Search Report and Written Opinion for International Application No. PCT/US2017/067980 dated Mar. 28, 2018.
International Search Report and Written Opinion for International Application No. PCT/US2019/038245 dated Sep. 22, 2019.
Jordheim et al., "Determination of the enzymatic activity of cytosolic 5'-nucleotidase cN-II in cancer cells: development of a simple analytical method and related cell line models," Anal Bioanal Chem, 407(19):5747-5758 (2015).
Périgaud et al., "Nucleoside analogues as chemotherapeutic agents: a review," Nucleos Nucleot, 11(2-4):903-945 (1992).
Allard et al., "Targeting CD73 Enhances the Antitumor Activity of Anti-PD-1 and Anti-CTLA-4 mAbs," Clinical Cancer Research, 19(20): 5626-5635 (2013).
Berkow et al., "The Merck Manual," 16th Edition: 1403-04, 1488-1489, 1493-1494 (1992).
Bhattarai et al., "α,β-Methylene-ADP (AOPCP) Derivatives and Analogs: Development of Potent and Selective ecto-5'-Nucleotidase (CD73) Inhibitors," J Med Chem, 58(15):6248-6263 (2015).

(Continued)

*Primary Examiner* — Jeffrey H Murray
(74) *Attorney, Agent, or Firm* — Scully, Scott, Murphy & Presser, P.C.

(57) ABSTRACT

The invention relates to novel heterocyclic compounds having CD73 inhibitory activity and pharmaceutical preparations thereof. The invention further relates to methods of treating or preventing cancer using the novel heterocyclic compounds of the invention.

61 Claims, No Drawings

(56) References Cited

OTHER PUBLICATIONS

Extended European Search Report for EP Application No. 17849598.2 dated May 4, 2020.
Extended European Search Report for EP Application No. 17883974.2 dated May 12, 2020.
Gura, "Systems for Identifying New Drugs Are Often Faulty," Science, 278(5340): 1041-1042 (1997).
International Search Report and Written Opinion for International Application No. PCT/US2020/038395 dated Nov. 12, 2020.
Mawe, "Colitis-induced neuroplasticity disrupts motility in the inflamed and post-inflamed colon," The Journal of Clinical Investigation, 125(3): 949-955 (2015).
Notice of Reasons for Rejection dated Oct. 8, 2021, issued in Japanese Patent Application No. 2019-513067, 9 pages.

\* cited by examiner

ECTONUCLEOTIDASE INHIBITORS AND METHODS OF USE THEREOF

RELATED APPLICATIONS

This application is a continuation of U.S. application Ser. No. 15/699,109 filed Sep. 8, 2017, which claims the benefit of priority to U.S. Provisional Patent Application No. 62/385,730, filed Sep. 9, 2016, each of which applications are hereby incorporated by reference in their entirety.

BACKGROUND

CD73, also referred to as 5'-nucleotidase (5'-NT) or ecto-5'-nucleotidase (Ecto 5'NTase), is a membrane-bound cell surface enzyme whose primary role is to catalyze the conversion of extracellular nucleotides (e.g., AMP) to their corresponding nucleosides (e.g., adenosine). CD73 is found in most tissues and expressed on lymphocytes, endothelial cells, and epithelial cells. It is also widely expressed in many tumor cell lines and, notably, is upregulated in cancerous tissues (Antonioli et al., *Nat. Rev. Cancer*, 13: 842-857, 2013).

In tandem with CD39 (ecto-ATPase), CD73 generates adenosine from ATP/AMP, which is often released from damaged or inflamed cells into the extracellular environment. Extracellular adenosine produced by CD73 interacts with G-protein coupled receptors on target cells. An important downstream effect of this signaling is increased immunosuppression via a number of pathways. For example, CD73 is a co-signaling molecule on T lymphocytes. Under normal circumstances, extracellular adenosine levels promote a self-limiting immune response that prevents excessive inflammation and tissue damage. For tumors, an advantage of abnormally increased CD73 is that the resulting increased CD73-catalyzed adenosine levels yield inhibition of anti-tumor immune system responses.

Even though CD73 plays a role in cancer immunosuppression, higher expression of CD73 is associated with a variety of stages of tumor progression, including tumor vascularization, invasiveness, and metastasis, and with shorter breast cancer patient survival time. Some of these observations result from CD73's enzyme-independent function as an adhesion molecule required for lymphocyte binding to the endothelium.

Overall, CD73 has become an important target for developing new cancer therapies, either as single agents or in combination with other cancer therapies. Indeed, combining CD73 monoclonal antibodies with antibodies for other chemotherapy targets enhances response and survival in animal cancer models (Allard et al., *Clin. Cancer Res.*, 19:5626-35, 2013).

Many of the current cancer treatments and chemotherapeutic agents fail to successfully treat all patients or all symptoms in treated patients, and many of these therapies are associated with undesirable side effects. As certain cancers develop resistance to various chemotherapeutic agents, alternate cancer therapies are needed. Thus, there is a need for additional compounds and methods for treating cancer and other diseases.

SUMMARY

Disclosed herein are compounds of Formula (I):

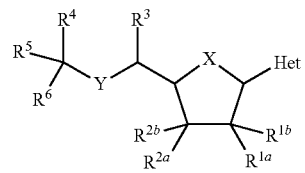

or a pharmaceutically acceptable salt thereof, wherein

X is O, $NR^7$ or $CR^7R^8$;

Y is O or S;

Z is $NR^{19}$, O or S;

Het is heterocyclyl or heteroaryl;

$R^{1a}$ is selected from H, halo, hydroxy, cyano, azido, amino, $C_{1-6}$alkyl, hydroxy$C_{1-6}$alkyl, amino-$C_{1-6}$alkyl, $C_{1-6}$acyloxy, $C_{1-6}$alkoxy, $C_{2-6}$alkenyl, and $C_{2-6}$alkynyl; and $R^{1b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl; or $R^{1a}$ and $R^{1b}$, together with the carbon atom to which they are attached, form a $C=CH_2$ or $C=C(H)C_{1-6}$alkyl;

$R^{2a}$ is selected from H, halo, hydroxy, cyano, azido, amino, $C_{1-6}$alkyl, hydroxy-$C_{1-6}$alkyl, amino-$C_{1-6}$alkyl, $C_{1-6}$acyloxy, $C_{1-6}$alkoxy, $C_{2-6}$alkenyl, and $C_{2-6}$alkynyl;

$R^{2b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl; or $R^{2a}$ and $R^{2b}$, together with the carbon atom to which they are attached, form a $C=CH_2$ or $C=C(H)C_{1-6}$alkyl;

$R^3$ is selected from H, alkyl, cycloalkyl, cycloalkylalkyl, heterocyclyl, heterocyclylalkyl, aryl, aralkyl, heteroaryl, heteroaralkyl, and —$(CH_2)$—C(O)$OR^9$;

$R^4$ is selected from alkyl, —C(O)$OR^9$, —C(O)$NR^{11}R^{12}$, —S(O)$_2R^{10}$, —P(O)($OR^{11}$)($OR^{12}$), and —P(O)($OR^{11}$)($NR^{13}R^{15}$);

$R^5$ is selected from H, cyano, alkyl, cycloalkylalkyl, heterocyclylalkyl, aralkyl, heteroaralkyl, and —C(O)$OR^9$;

$R^6$ is selected from —C(O)$OR^9$ and —P(O)($OR^{11}$)($OR^{12}$);

each $R^7$ and $R^8$ is independently selected from H, alkyl, acyloxyalkyl, alkenyl, alkynyl, cycloalkyl, cycloalkylalkyl, heterocyclyl, heterocyclylalkyl, aryl, aralkyl, heteroaryl, and heteroaralkyl;

$R^9$ is independently selected from H, alkyl, acyloxyalkyl, alkenyl, alkynyl, cycloalkyl, cycloalkylalkyl, heterocyclyl, heterocyclylalkyl, aryl, aralkyl, heteroaryl, and heteroaralkyl, and —$(CHR^{13})_m$—Z—C(O)—$R^{14}$;

each $R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and each $R^{11}$ and $R^{12}$ is independently selected from H, alkyl, alkenyl, alkynyl, —S(O)$_2R^{10}$, cycloalkyl, cycloalkylalkyl, heterocyclyl, heterocyclylalkyl, aryl, aralkyl, heteroaryl, heteroaralkyl and —$(CHR^{13})_m$—Z—C(O)—$R^{14}$; or $R^{11}$ and $R^{12}$, together with the atoms to which they are attached, form a 5- to 7-membered heterocyclyl; and each $R^{13}$ is independently H or alkyl;

each $R^{14}$ is independently selected from alkyl, aminoalkyl, heterocyclyl, and heterocyclylalkyl;

$R^{15}$ is selected from alkyl, aralkyl, —C($R^{16}$)($R^{17}$)—C(O)O—$R^{18}$;

each $R^{16}$ and $R^{17}$ are selected from H, alkyl, amino-alkyl, hydroxy-alkyl, mercapto-alkyl, sulfonyl-alkyl, cycloalkyl, aryl, aralkyl, heterocyclylalkyl, heteroaralkyl, and —($CH_2$)C(O)$OR^9$;

$R^{18}$ is selected from H, alkyl, alkoxyalkyl, aminoalkyl, haloalkyl, amido, cycloalkyl, cycloalkylalkyl, heterocyclyl, heterocyclylalkyl, aryl, aralkyl, heteroaryl, heteroaralkyl;

$R^{19}$ is H or alkyl, preferably H; and m is 1 or 2;

provided that if $R^3$ is H and $R^{1a}$ and $R^{2a}$ are each hydroxy, then at least one of $R^{1b}$ and $R^{2b}$ is $C_{1-6}$alkyl.

In certain embodiments, the present invention provides a pharmaceutical composition suitable for use in a subject in the treatment or prevention of cancer comprising an effective amount of any of the compounds described herein (e.g., a compound of the invention, such as a compound of Formula (I), or a pharmaceutically acceptable salt thereof), and one or more pharmaceutically acceptable excipients. In certain embodiments, the pharmaceutical preparations may be for use in treating or preventing a condition or disease as described herein.

Disclosed herein are methods of treating diseases and conditions that benefit from the inhibition of CD73, comprising administering to a subject in need thereof an effective amount of a compound as disclosed herein (e.g., a compound of Formula (I) or any of the embodiments thereof disclosed herein). In certain embodiments, the human subject is in need of such treatment. These diseases include, but are not limited to cancers, such as lung cancer, kidney cancer, skin cancer, breast cancer, and ovarian cancer. Other diseases and conditions that can be treated using the methods described herein include, but are not limited to, neurological, neurodegenerative and CNS disorders and diseases such as depression and Parkinson's disease, cerebral and cardiac ischemic diseases, sleep disorders, fibrosis, immune and inflammatory disorders.

Provided herein are combination therapies of compounds of Formula (I) with monoclonal antibodies and other chemotherapeutic agents that can enhance the therapeutic benefit beyond the ability of the adjuvant therapy alone.

DETAILED DESCRIPTION

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In some embodiments, chemical structures are disclosed with a corresponding chemical name. In case of conflict, the chemical structure controls the meaning, rather than the name.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

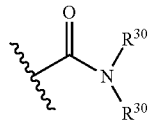

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

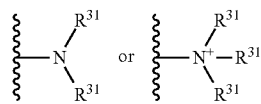

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

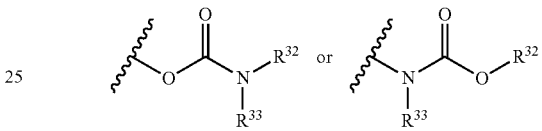

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{34}$, wherein R$^{34}$ represents a hydrocarbyl group.

The term "carboxy", as used herein, refers to a group represented by the formula —CO$_2$H.

The term "ester", as used herein, refers to a group —C(O)OR$^{35}$ wherein R$^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

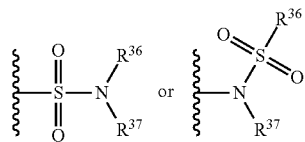

wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group —S(O)—$R^{38}$, wherein $R^{38}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{39}$, wherein $R^{39}$ represents a hydrocarbyl.

The term "thioalkyl", as used herein, refers to an alkyl group substituted with a thiol group.

The term "thioester", as used herein, refers to a group —C(O)SR$^{40}$ or —SC(O)R$^{40}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

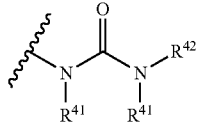

wherein $R^{41}$ and $R^{42}$ independently represent hydrogen or a hydrocarbyl, such as alkyl, or either occurrence of $R^{41}$ taken together with $R^{42}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethyl silyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In the pictorial representation of the compounds given through this application, a thickened tapered line (⬤) indicates a substituent which is above the plane of the ring to which the asymmetric carbon belongs and a dotted line (⋯) indicates a substituent which is below the plane of the ring to which the asymmetric carbon belongs.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of Formula (I) in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

The present invention provides compounds of Formula (I):

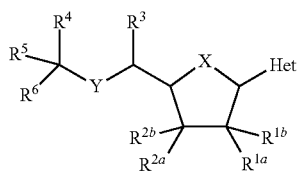

or a pharmaceutically acceptable salt thereof, wherein
X is O, $NR^7$ or $CR^7R^8$;
Y is O or S;
Z is $NR^{19}$, O or S;
Het is heterocyclyl or heteroaryl;

$R^{1a}$ is selected from H, halo, hydroxy, cyano, azido, amino, $C_{1-6}$alkyl, hydroxy$C_{1-6}$alkyl, amino-$C_{1-6}$alkyl, $C_{1-6}$acyloxy, $C_{1-6}$alkoxy, $C_{2-6}$alkenyl, and $C_{2-6}$alkynyl; and $R^{1b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl; or $R^{1a}$ and $R^{1b}$, together with the carbon atom to which they are attached, form a $C{=}CH_2$ or $C{=}C(H)C_{1-6}$alkyl;

$R^{2a}$ is selected from H, halo, hydroxy, cyano, azido, amino, $C_{1-6}$alkyl, hydroxy-$C_{1-6}$alkyl, amino-$C_{1-6}$alkyl, $C_{1-6}$acyloxy, $C_{1-6}$alkoxy, $C_{2-6}$alkenyl, and $C_{2-6}$alkynyl;

$R^{2b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl; or $R^{2a}$ and $R^{2b}$, together with the carbon atom to which they are attached, form a $C{=}CH_2$ or $C{=}C(H)C_{1-6}$alkyl;

$R^3$ is selected from H, alkyl, cycloalkyl, cycloalkylalkyl, heterocyclyl, heterocyclylalkyl, aryl, aralkyl, heteroaryl, heteroaralkyl, and —$(CH_2)$—$C(O)OR_9$;

$R^4$ is selected from alkyl, —$C(O)OR^9$, —$C(O)NR^{11}R^{12}$, —$S(O)_2R^{10}$, —$P(O)(OR^{11})(OR^{12})$, and —$P(O)(OR^{11})(NR^{13}R^{15})$;

$R^5$ is selected from H, cyano, alkyl, cycloalkylalkyl, heterocyclylalkyl, aralkyl, heteroaralkyl, and —$C(O)OR^9$;

$R_6$ is selected from —$C(O)OR^9$ and —$P(O)(OR^{11})(OR^{12})$;

each $R_7$ and $R_8$ is independently selected from H, alkyl, acyloxyalkyl, alkenyl, alkynyl, cycloalkyl, cycloalkylalkyl, heterocyclyl, heterocyclylalkyl, aryl, aralkyl, heteroaryl, and heteroaralkyl;

$R^9$ is independently selected from H, alkyl, acyloxyalkyl, alkenyl, alkynyl, cycloalkyl, cycloalkylalkyl, heterocyclyl, heterocyclylalkyl, aryl, aralkyl, heteroaryl, and heteroaralkyl, and —$(CHR^{13})_m$—Z—$C(O)$—$R^{14}$;

each $R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and each $R^{11}$ and $R^{12}$ is independently selected from H, alkyl, alkenyl, alkynyl, —$S(O)_2R^{10}$, cycloalkyl, cycloalkylalkyl, heterocyclyl, heterocyclylalkyl, aryl, aralkyl, heteroaryl, heteroaralkyl and —$(CHR^{13})_m$—Z—$C(O)$—$R^{14}$; or $R^{11}$ and $R^{12}$, together with the atoms to which they are attached, form a 5- to 7-membered heterocyclyl; and each $R^{13}$ is independently H or alkyl;

each $R^{14}$ is independently selected from alkyl, aminoalkyl, heterocyclyl, and heterocyclylalkyl;

$R^{15}$ is selected from alkyl, aralkyl, —$C(R^{16})(R^{17})$—$C(O)O$—$R^{18}$;

each $R^{16}$ and $R^{17}$ are selected from H, alkyl, amino-alkyl, hydroxy-alkyl, mercapto-alkyl, sulfonyl-alkyl, cycloalkyl, aryl, aralkyl, heterocyclylalkyl, heteroaralkyl, and —$(CH_2)C(O)OR^9$;

$R^{18}$ is selected from H, alkyl, alkoxyalkyl, aminoalkyl, haloalkyl, amido, cycloalkyl, cycloalkylalkyl, heterocyclyl, heterocyclylalkyl, aryl, aralkyl, heteroaryl, heteroaralkyl;

$R^{19}$ is H or alkyl, preferably H; and m is 1 or 2;

provided that if $R^3$ is H and $R^{1a}$ and $R^{2a}$ are each hydroxy, then at least one of $R^{1b}$ and $R^{2b}$ is $C_{1-6}$alkyl.

In certain embodiments, $R^{1a}$ is fluoro, chloro or bromo, preferably fluoro. In certain embodiments, $R^{1a}$ is $C_{1-6}$alkoxy. In certain embodiments, $R^{1a}$ is $C_{1-6}$alkyl. In certain embodiments, $R^{1a}$ is hydroxy. In certain embodiments, $R^{1a}$ is ethynyl or vinyl. In certain embodiments, $R^{1a}$ is cyano. In certain embodiments, $R^{1a}$ is azido. In certain embodiments, $R^{1a}$ is amino. In certain embodiments, $R^{1a}$ is hydrogen.

In other embodiments, $R^{2a}$ is fluoro, chloro, or bromo, preferably fluoro. In certain embodiments, $R^{2a}$ is $C_{1-6}$alkoxy. In certain embodiments, $R^{2a}$ is $C_{1-6}$alkyl. In certain embodiments, $R^{2a}$ is hydroxy. In certain embodiments, $R^{2a}$ is cyano. In certain embodiments, Rea is azido. In certain embodiments, $R^{2a}$ is amino. In certain embodiments, $R^{2a}$ is $C_{1-6}$acyloxy.

In certain embodiments, $R^{1b}$ is H. In other embodiments, $R^{1b}$ is fluoro. In other embodiments, $R^{1b}$ is $C_{1-6}$alkyl. In certain embodiments, $R^{2b}$ is H. In other embodiments, $R^{2b}$ is fluoro. In other embodiments, $R^{2b}$ is $C_{1-6}$alkyl.

In certain embodiments, $R^{1a}$ is fluoro and $R^{1b}$ is H. In other embodiments, $R^{2a}$ is fluoro and $R^{2b}$ is H. In certain embodiments, $R^{1a}$ and $R^{1b}$ are each fluoro. In other embodiments, $R^{2a}$ and $R^{2b}$ are each fluoro. In some embodiments, $R^{1a}$ is fluoro and $R^{2a}$ is $C_{1-6}$alkoxy. In some embodiments, $R^{1a}$ is fluoro and $R^{2a}$ is $C_{1-6}$alkyl, such as methyl or ethyl. In certain embodiments, $R^{2a}$ is hydroxy and $R^{2b}$ is methyl.

In certain embodiments, the compound of Formula (I) has the following structure:

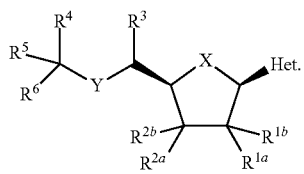

In certain embodiments, $R^{1a}$ is in the α-configuration. In some such embodiments, the compound of Formula (I) has the structure (IA):

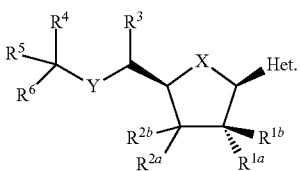

(IA)

In other embodiments, $R^{1a}$ is in the β-configuration. In some such embodiments, the compound of Formula (I) has the structure (IB):

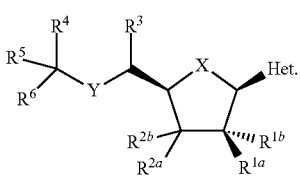

(IB)

In certain embodiments, $R^{2a}$ is in the α-configuration. In some such embodiments, the compound of Formula (I) has the structure (IC):

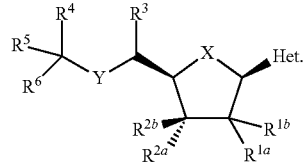

(IC)

In other embodiments, $R^{2a}$ is in the β-configuration. In some embodiments, the compound of Formula (I) has the structure (ID):

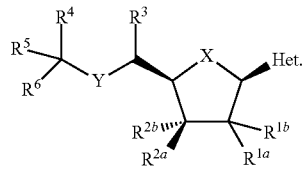

(ID)

In certain embodiments, the compound of Formula (I) has the structure (IE):

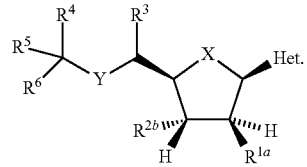

(IE)

In certain embodiments, $R^3$ is alkyl, and the alkyl is unsubstituted or substituted, e.g., with one or more substituents selected from halo, CN, $NO_2$, azido, hydroxy, alkoxy, alkylthio, thioalkoxy, carbonyl, thiocarbonyl, amidino, imino, amino, amido, alkoxycarbonyl, carbamate, urea, sulfinamido, sulfonamido, sulfinyl, sulfinamido, sulfonyl, phosphoryl, phosphate, phosphonate, and phosphinate. In certain embodiments, the substituents are selected from halo, CN, azido, alkoxy, carbonyl, amino, amido, and alkoxycarbonyl. In certain preferred embodiments, $R_3$ is H. In other preferred embodiments, $R^3$ is unsubstituted $C_{1-6}$alkyl.

In certain embodiments, $R^4$ is selected from —C(O)OR$^9$, —C(O)NR$^{11}$R$^{12}$, —S(O)$_2$R$^{10}$, and —P(O)(OR$^{11}$)(OR$^{12}$). In some preferred embodiments, $R^4$ is —C(O)OR$^9$. In certain embodiments, $R^9$ is H or $C_{1-6}$alkyl. In some embodiments, $R_4$ is —C(O)NR$^{11}$R$^{12}$. In certain such embodiments, $R^{11}$ and $R^{12}$ are each alkyl, such as methyl. In alternative such embodiments, $R^{11}$ is alkyl and $R^{12}$ is hydrogen. In other embodiments, $R^4$ is alkyl substituted with carboxyl or ester (e.g., alkoxycarbonyl).

In certain embodiments, $R^5$ is selected from H, alkyl, cycloalkylalkyl, heterocyclylalkyl, aralkyl, and heteroaralkyl. In certain embodiments, $R^5$ is selected from alkyl, cycloalkylalkyl, heterocyclylalkyl, aralkyl and heteroaralkyl, and each is unsubstituted or substituted with one or more substituents, e.g., selected from halo, CN, $NO_2$, azido, hydroxy, alkoxy, alkylthio, thioalkoxy, carbonyl, thiocarbonyl, amidino, imino, amino, amido, alkoxycarbonyl, carbamate, urea, sulfinamido, sulfonamido, sulfinyl, sulfinamido, sulfonyl, phosphoryl, phosphate, phosphonate, phosphinate, cycloalkyl, heterocyclyl, arylalkyl and heteroarylalkyl. In certain embodiments, the substituents are selected from halo, CN, azido, alkoxy, carbonyl, amino, amido, and alkoxycarbonyl. In some preferred embodiments, $R^5$ is H or aralkyl.

In some embodiments, $R^5$ is aralkyl, e.g., wherein the aryl ring is substituted or unsubstituted phenyl or naphthyl. In other embodiments, $R^5$ is heteroaralkyl, e.g., wherein the heteroaryl ring is selected from substituted or unsubstituted benzofuranyl, benzothienyl, benzothiazolyl, pyridyl, thienyl, furanyl, pyrazolyl, thiazolyl, oxazolyl, and oxadiazolyl.

In some embodiments, $R^5$ is aralkyl or heteroaralkyl, wherein the aryl or heteroaryl ring, respectively, is unsubstituted or substituted with one or more substituents, e.g., selected from halo, CN, OH, alkyl, alkenyl, haloalkyl, hydroxyalkyl, alkoxy, haloalkoxy, aryloxy, aralkyloxy, alkylsulfonyl, sulfonamido, amido, amino, carboxyl, ester (e.g., lower alkyl ester), heteroaryl, aryl, aralkyl, and heteroaralkyl. In certain such embodiments, the substituents on the aryl or heteroaryl ring of the aralkyl or heteroaralkyl, respectively, are selected from halo, CN, haloalkyl, haloalkoxy, carboxy, ester (e.g., lower alkyl ester), and aryl. In other such embodiments, the substituents on the aryl or heteroaryl ring of the aralkyl or heteroaralkyl, respectively, are selected from tetrazolyl, substituted or unsubstituted phenyl, or substituted or unsubstituted benzyl.

In certain embodiments, $R^6$ is —C(O)OR$^9$. In some embodiments, $R^9$ is H or $C_{1-6}$alkyl. In other embodiments, $R^6$ is —P(O)(OR$^{11}$)(OR$^{12}$), and $R^{11}$ and $R^{12}$ are each H. In certain embodiments, $R^7$ is H or $C_{1-6}$alkyl. In certain embodiments, $R^8$ is H. In certain embodiments, $R^9$ is H or $C_{1-6}$alkyl, such as methyl or ethyl. In certain embodiments, $R^{11}$ and $R^{12}$ are each H.

In certain embodiments, each $R^7$, $R^8$, $R^9$, $R^{10}$, $R^{11}$ and $R^{12}$ is independently selected from alkyl, alkenyl, alkynyl, cycloalkyl, cycloalkylalkyl, heterocyclyl, heterocyclylalkyl, aryl, aralkyl, heteroaryl, and heteroaralkyl, and each is unsubstituted or substituted, e.g., with one or more selected from halo, CN, $NO_2$, azido, hydroxy, alkoxy, alkylthio, thioalkoxy, carbonyl, thiocarbonyl, amidino, imino, amino, amido, alkoxycarbonyl, carbamate, urea, sulfinamido, sulfonamido, sulfinyl, sulfinamido, sulfonyl, phosphoryl, phosphate, phosphonate, and phosphinate. In some embodiments, the substituents are selected from halo, CN, azido, alkoxy, carbonyl, amino, amido, and alkoxycarbonyl.

In certain embodiments, X is O. In certain embodiments, Y is O. In certain embodiments, the Y-bearing substituent is in the R-configuration. In other embodiments, the Y-bearing substituent is in the S-configuration. In certain embodiments, Z is O. In other embodiments, Z is NH.

In certain embodiments, Het is a nitrogen-containing heterocyclyl or heteroaryl. In certain embodiments, Het is attached via a nitrogen atom. In some embodiments, Het is a 5- to 8-membered monocyclic or 5- to 10-membered bicyclic heteroaryl and is unsubstituted or substituted, e.g., with one or more substituents selected from halo, CN, $NO_2$, azido, hydroxy, alkoxy, alkylthio, thioalkoxy, carbonyl, thiocarbonyl, amidino, imino, amino, amido, alkoxycarbonyl, carbamate, urea, sulfinamido, sulfonamido, sulfinyl, sulfinamido, sulfonyl, phosphoryl, phosphate, phosphonate, and phosphinate. In certain embodiments, the substituents are selected from halo, CN, azido, alkoxy, carbonyl, amino, amido, and alkoxycarbonyl. In certain preferred embodiments, Het is selected from purinyl, imidazopyrimidinyl, and pyrrolopyrimidinyl. In some embodiments, Het is substituted with one halo and one amino substituent. In other embodiments, Het is substituted with one or two substituents independently selected from halo, aralkyl, amino, azido and hydroxy. In certain preferred embodiments, Het is

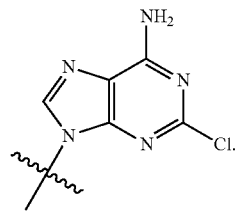 [SMILES: *n1cnc2c(N)nc(Cl)nc21]

In certain embodiments. Het is selected from

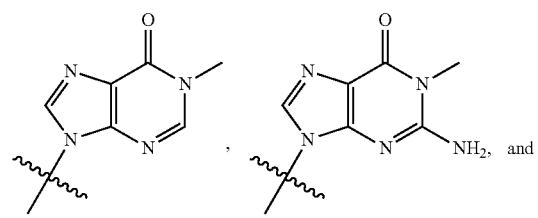

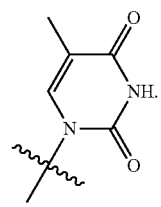

In certain embodiments, Het is selected from

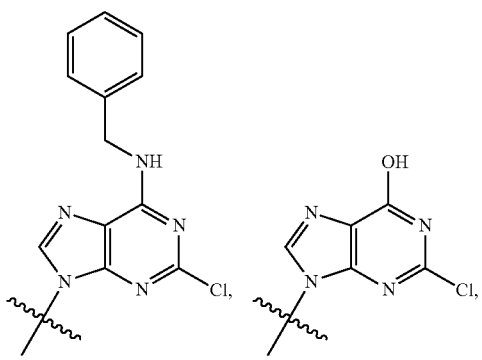

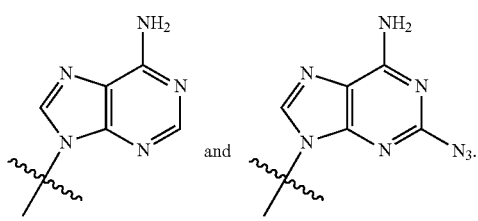

In certain embodiments, Het is a group of formula (i) through (xiv) below:
(i)
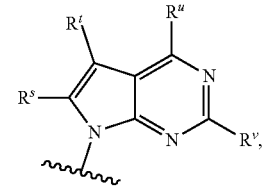
(ii)
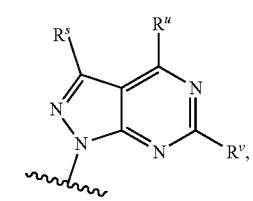
(iii)
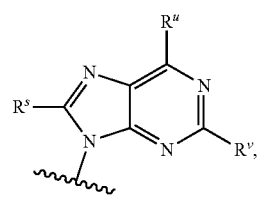
(iv)
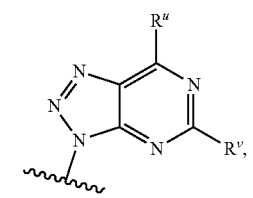
(v)
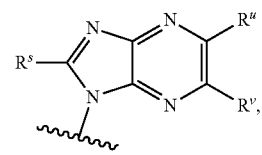
(vi)
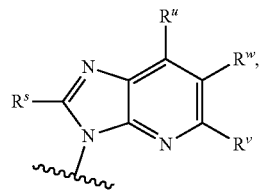
(vii)
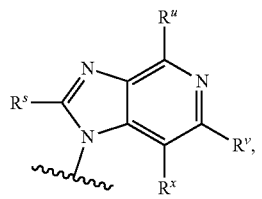
(viii)
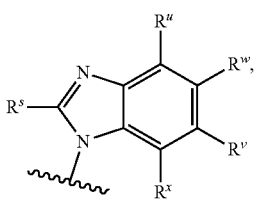
(ix)
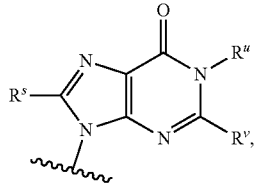
(x)
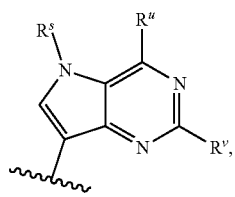
(xi)
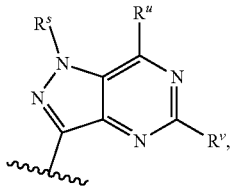
(xii)
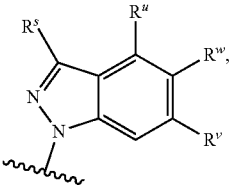
(xiii)
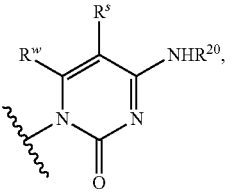
(xiv)
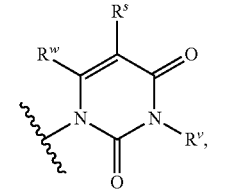
(xv)
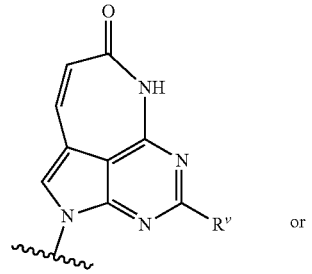
or -continued

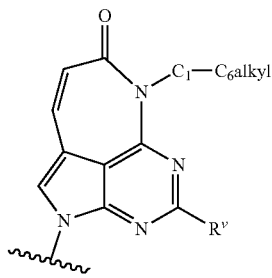

(xvi)

wherein:

$R^u$ is hydrogen, halo, cyano, —NH$_2$, —NHR$^{20}$, —NH-COR$^{20}$, —NR$^{20}$R$^{21}$, —R$^{20}$, —SR$^{20}$, —OH, and —OR$^{20}$;

$R^w$ is hydrogen, halo, —NHR$^{22}$, —NR$^{22}$R$^{23}$, —R$^{22}$, —OH, and —OR$^{22}$;

$R^v$ and $R^x$ are independently hydrogen, halo, haloC$_{1-6}$alkyl, —NH$_2$, —NHR$^{24}$, —NR$^{24}$R$^{25}$, —R$^{24}$, —SR$^{24}$, cyano, —OH, —OR$^{24}$, —SO$_2$R$^{24}$, —C$_{1-6}$alkyleneNH$_2$, —C$_{1-6}$alkyleneNHR$^{24}$, —C$_{1-6}$alkyleneNR$^{24}$R$^{25}$, —R$^{24}$, —C$_{1-6}$alkyleneSR$^{24}$, —C$_{1-6}$alkyleneOH, —C$_{1-6}$alkyleneOR$^{24}$, C$_{1-6}$alkyleneSO$_2$R$^{24}$, $R^s$ and $R^t$ are independently hydrogen, halo, or C$_{1-6}$alkyl; and wherein:

$R^{20}$, $R^{21}$, $R^{22}$, $R^{23}$, $R^{24}$ and $R^{25}$ are independently optionally substituted C$_{1-6}$alkyl, —C$_2$-C$_6$alkenyl, —C$_2$-C$_6$alkynyl, optionally substituted cycloalkyl, optionally substituted cycloalkylC$_{1-6}$ alkyl, optionally substituted heterocyclyl, optionally substituted heterocyclylC$_{1-6}$ alkyl, optionally substituted aryl, optionally substituted arylC$_{1-6}$alkyl, optionally substituted heteroaryl, or optionally substituted heteroarylC$_{1-6}$ alkyl; or $R^{20}$ and $R^{21}$, $R^{22}$ and $R^{23}$, and $R^{24}$ and $R^{25}$ together with the nitrogen to which they are attached form an optionally substituted nitrogen-containing heterocyclyl.

In certain embodiments,

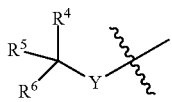

represents

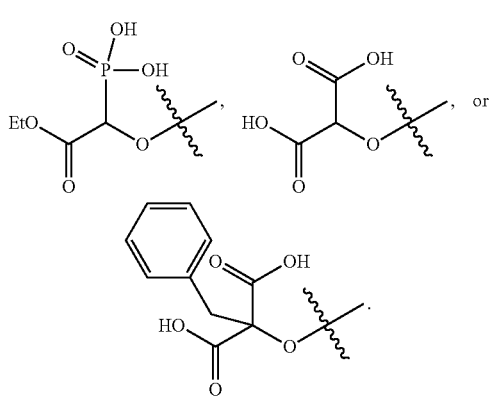

In certain embodiments,

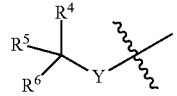

represents

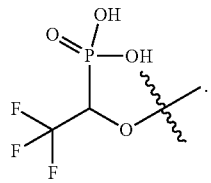 [SMILES: *OC(C(F)(F)F)P(=O)(O)O]

In certain embodiments,

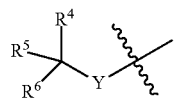

represents

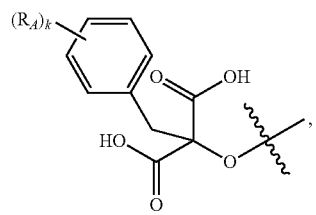

wherein
each $R_A$ is independently selected from halo, CN, OH, alkyl, haloalkyl, hydroxyalkyl, alkoxy, haloalkoxy, aryloxy, aralkyloxy (e.g., substituted or unsubstituted benzyloxy), alkylsulfonyl, sulfonamido, amido, amino, hydroxycarbonyl, alkoxycarbonyl, heteroaryl, aryl, aralkyl, and heteroaralkyl; and
k is 1, 2, or 3.

Further Embodiments

In the following numbered embodiments, unless otherwise specified:

C$_{1-6}$alkyl is unsubstituted;

C$_{1-6}$alkyl of C$_{1-6}$alkyloxy is unsubstituted;

haloC$_{1-6}$alkyl is C$_{1-6}$alkyl substituted with one to five halo atoms;

haloC$_{1-6}$alkyloxy is C$_{1-6}$alkyloxy substituted with one to five halo atoms;

C$_{2-6}$alkenyl is unsubstituted;

C$_{2-6}$alkynyl is unsubstituted;

C$_{1-6}$alkylene group is unsubstituted;

C$_{2-6}$alkenylene group is unsubstituted;

optionally substituted C$_{1-6}$alkyl is optionally substituted with one or two substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), —N(C$_{1-6}$alkyl)$_2$, optionally substituted carbocyclyl, optionally substituted aryl, optionally substituted heteroaryl, and optionally substituted heterocyclyl;

carbocyclyl is an unsubstituted saturated or partially unsaturated mono or bicyclic ring containing 3 to 10 carbon atoms;

optionally substituted carbocyclyl is optionally substituted with one, two, or three substituents independently selected from $C_{1-6}$alkyl, halo, hydroxy, or $C_{1-6}$alkoxy;

aryl is phenyl or naphthyl;

optionally substituted aryl is optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$, optionally substituted carbocyclyl, aryl [optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), and —N($C_{1-6}$alkyl)$_2$], heteroaryl [optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$], and heterocyclyl [optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N(unsubstituted $C_{1-6}$alkyl)$_2$];

heteroaryl is an unsubstituted five to ten membered or five to six membered aromatic ring containing one to four or one to three heteroatoms independently selected from N, O, and S, the remaining ring atoms being carbon;

optionally substituted heteroaryl is a five to ten membered aromatic ring containing one to four heteroatoms independently selected from N, O, and S, the remaining ring atoms being carbon, that is optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$, optionally substituted carbocyclyl, aryl [optionally substituted with one, two, or three substituents independently selected from hydroxy, $C_{1-6}$alkyloxy, halo, halo$C_{1-6}$ alkyl, halo$C_{1-6}$alkyloxy, cyano, —$NH_2$, —NH($C_{1-6}$alkyl), and —N($C_{1-6}$alkyl)$_2$], heteroaryl [optionally substituted with one, two, or three substituents independently selected from hydroxy, unsubstituted $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$], and heterocyclyl [optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$];

heterocyclyl is an unsubstituted monocyclic, saturated or partially unsaturated 4 to 8 membered ring containing one to three heteroatoms independently selected from N, O, S, SO, and $SO_2$ and optionally contains one or two CO, the remaining atoms in the ring being carbon that is optionally fused to phenyl or 5 to 6 membered carbocyclyl or 5 or 6 heteroaryl ring;

nitrogen-containing heterocyclyl is a heterocyclyl ring that has at least a nitrogen atom;

optionally substituted heterocyclyl is heterocyclyl that is optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$, optionally substituted carbocyclyl, aryl [optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), and —N($C_{1-6}$alkyl)$_2$], heteroaryl [optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$], and heterocyclyl optionally substituted with one, two, or three substituents independently selected from hydroxy, $C_{1-6}$alkyloxy, halo, halo$C_{1-6}$alkyl, halo$C_{1-6}$alkyloxy, cyano, —$NH_2$, —NH($C_{1-6}$alkyl), —N($C_{1-6}$alkyl)$_2$];

optionally substituted carbocyclyl $C_{1-6}$alkyl is optionally substituted carbocyclyl attached via $C_{1-6}$alkyl;

optionally substituted heterocyclyl$C_{1-6}$alkyl is optionally substituted heterocyclyl attached via $C_{1-6}$alkyl;

optionally substituted aryl$C_{1-6}$ alkyl is optionally substituted aryl attached via $C_{1-6}$ alkyl; and optionally substituted heteroaryl$C_{1-6}$ alkyl is optionally substituted heteroaryl attached via $C_{1-6}$alkyl.

Embodiment 1

In embodiment 1, the compound of Formula (I) is as defined in the Summary.

In a subembodiment of embodiment 1, the compounds of Formula (I) are those wherein when $R^5$ is hydrogen, $R^{1a}$ and $R^{1b}$ are independently hydrogen, hydroxy, halo, $C_1$-$C_3$alkyl, $C_1$-$C_3$alkoxy, $C_2$-$C_3$alkenyl, or $C_2$-$C_3$alkynyl, $R^{2a}$, $R^{2b}$ and $R^3$ are hydrogen, then Het is not 2,4-dioxo-3,4-dihydropyrimidinyl, 2,4-dioxo-3,4,5,6-tetrahydropyrimidinyl, 6-oxopurinyl, 6-amino-9H-purin-9-yl, or oxopyrimidinyl wherein each ring of the aforementioned ring is optionally substituted with $C_{1-6}$alkyl.

Embodiment 2

In embodiment 2, the compounds of embodiment 1 and subembodiments contained therein are those wherein $R^5$ is phenyl$C_{1-6}$alkyl or naphthyl$C_{1-6}$alkyl, preferably benzyl, wherein phenyl and naphthyl are optionally substituted with one, two, or three substituents independently selected from —$C_{1-6}$alkyl, —$C_{1-6}$alkyl substituted with one to five fluoro, —$OC_{1-6}$alkyl (substituted with one to five fluoro), —$C_{1-6}$alkylene-$CO_2H$, —$C_{1-6}$alkylene-$CO_2C_{1-6}$alkyl, —$C_{2-6}$alkenylene-$CO_2H$, —$OC_{1-6}$alkylene-$CO_2H$, —$OC_{1-6}$alkylene-$CO_2C_{1-6}$alkyl, —$C_{1-6}$alkyl substituted with one or two hydroxy, —$OC_{1-6}$alkyl substituted with one or two hydroxy, —$C_{1-6}$alkyl substituted with one or two —$OC_{1-6}$alkyl, —$OC_{1-6}$alkyl (substituted with one or two —$OC_{1-6}$alkyl), —$CO_2H$, —$COOC_{1-6}$alkyl, hydroxy, halo, nitro, —$PO_3H_2$, cyano, —$NH_2$, —NH($C_{1-6}$alkyl), —N($C_{1-6}$alkyl)$_2$, —CON$R^eR^f$ (where $R^e$ and $R^f$ are independently hydrogen, —$C_{1-6}$alkyl, —$C_{1-6}$alkylene-$CO_2H$, —$C_{1-6}$alkylene-$CO_2C_{1-6}$alkyl, or —$C_{1-6}$alkylene-substituted with one or two substituents independently selected from hydroxy, $NH_2$, —NH$C_{1-6}$alkyl or —N($C_{1-6}$alkyl)$_2$), —$SO_2$($C_{1-6}$alkyl), —$SO_2NR^gR^h$ (where $R^g$ and $R^h$ are independently hydrogen, —$C_{1-6}$alkyl, —$C_{1-6}$alkylene-$CO_2H$, or —$C_{1-6}$alkylene-$CO_2C_{1-6}$alkyl), —$SOC_{1-6}$alkyl, —$SO_2NHCOR^j$ (where is —$C_{1-6}$alkyl, —NH$C_{1-6}$alkyl, or —N($C_{1-6}$alkyl)$_2$), phenyl, —$C_{1-6}$alkylenephenyl, phenoxy, —$OC_{1-6}$alkylenephenyl, 5- or 6-membered monocyclic heteroaryl containing one to four heteroatoms independently selected from O, N, and S [wherein the heteroaryl ring is optionally substituted with one, two, or three substituents independently selected from hydroxyl, halo, CN, —$CO_2H$, —$COOC_{1-6}$alkyl, —$C_{1-6}$alkyl, —$OC_{1-6}$alkyl, —$C_{1-6}$alkyl (substituted with one to five fluoro), —$OC_{1-6}$alkyl (substituted with one to five fluoro), —$C_{1-6}$alkylene-$CO_2H$, —$C_{1-6}$alkylene-$CO_2C_{1-6}$alkyl, tetrazolyl, —$SO_2C_{1-6}$alkyl, —$SO_2NH_2$, —$SO_2NHC_{1-6}$alkyl, —$SO_2N$($C_{1-6}$alkyl)$_2$, —$CONH_2$, —$CONHC_{1-6}$alkyl, and —CON($C_{1-6}$alkyl)$_2$], —OR$^i$, —$C_{1-6}$alkylene-R$^1$, —O$C_{1-6}$alkylene-R$^i$, —SR$^i$, —S$C_{1-6}$alkylene-R$^i$, heterocyclyl, —$C_{1-6}$ alkyleneheterocyclyl, —O$C_{1-6}$alkyleneheterocyclyl, —S$C_{1-6}$alkyleneheterocyclyl, —CONR$^m$$C_{1-6}$alkyleneheterocyclyl, —NR$^m$CO$C_{1-6}$ alkyleneNR$^o$R$^p$, —NR$^m$COheterocyclyl, —NR$^m$CO$C_{1-6}$alkyleneheterocyclyl, —COheterocyclyl, —CONR$^m$R$^i$, —CONR$^m$$C_{1-6}$alkylene-R$^i$, —OCONR$^m$R$^m$, —NR$^m$—COR$^y$, —NR$^m$—CO—NR$^m$R$^y$, —NR$^m$—SO$_2$—R$^y$, —NR$^m$—SO$_2$—NR$^m$R$^y$, and —CONHSO$_2$R$^z$; wherein:

each R$^m$ is hydrogen or —$C_{1-6}$alkyl;

R$^o$, R$^p$, and R$^y$ are independently hydrogen or —$C_{1-6}$alkyl;

R$^z$ is —$C_{1-6}$alkyl, —NH$C_{1-6}$alkyl, or —N($C_{1-6}$alkyl)$_2$;

phenyl by itself or as part of —$C_{1-6}$alkylenephenyl, phenoxy, or —O$C_{1-6}$alkylenephenyl is optionally substituted with one, two, or three substituents independently selected from hydroxyl, halo, CN, —CO$_2$H, —COO$C_{1-6}$alkyl, —$C_{1-6}$alkyl, —O$C_{1-6}$alkyl, —$C_{1-6}$alkyl substituted with one to five fluoro, —O$C_{1-6}$alkyl (substituted with one to five fluoro), —$C_{1-6}$alkylene-CO$_2$H, —$C_{1-6}$alkylene-CO$_2$$C_{1-6}$alkyl, tetrazolyl, —SO$_2$$C_{1-6}$alkyl, —SO$_2$NH$_2$, —SO$_2$NH$C_{1-6}$alkyl, —SO$_2$N($C_{1-6}$alkyl)$_2$, —CONH$_2$, —CONH$C_{1-6}$alkyl, and —CON($C_{1-6}$alkyl)$_2$;

each R$^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, halo, CN, —CO$_2$H, —COO$C_{1-6}$alkyl, —$C_{1-6}$alkyl, —O$C_{1-6}$alkyl, —$C_{1-6}$alkyl substituted with one to five fluoro, —O$C_{1-6}$alkyl (substituted with one to five fluoro), —$C_{1-6}$alkylene-CO$_2$H, and —$C_{1-6}$alkylene-CO$_2$$C_{1-6}$alkyl, tetrazolyl, —CO$_2$$C_{1-6}$alkyl, —SO$_2$NH$_2$, —SO$_2$NH$C_{1-6}$alkyl, —SO$_2$N($C_{1-6}$alkyl)$_2$, —CONH$_2$, —CONH$C_{1-6}$alkyl, and —CON($C_{1-6}$alkyl)$_2$;

heterocyclyl by itself or as part of —$C_{1-6}$alkyleneheterocyclyl, —O$C_{1-6}$alkyleneheterocyclyl, —S$C_{1-6}$alkyleneheterocyclyl, —CONR$^m$$C_{1-6}$alkyleneheterocyclyl, —NR$^m$CO$C_{1-6}$alkyleneheterocyclyl, —COheterocyclyl, or —NR$^m$COheterocyclyl is optionally substituted with one, two, or three substituents independently selected from hydroxy, halo, —COO$C_{1-6}$alkyl, —$C_{1-6}$alkyl, —O$C_{1-6}$alkyl, or —$C_{1-6}$alkyl (substituted with hydroxy or —O$C_{1-6}$alkyl).

Embodiment 3

In embodiment 3, the compounds of embodiment 1 or 2 and subembodiments contained therein are those wherein R$^5$ is phenyl$C_{1-6}$alkyl or naphthyl$C_{1-6}$alkyl, preferably benzyl, wherein phenyl and naphthyl (also referred to below as R$^5$ phenyl and naphthyl rings respectively) are optionally substituted, preferably substituted, with one or two substituents independently selected from —$C_{1-6}$alkyl, —O$C_{1-6}$alkyl, —$C_{1-6}$alkyl substituted with one to five fluoro, —O$C_{1-6}$alkyl substituted with one to five fluoro, —$C_{1-6}$alkylene-CO$_2$H, —$C_{1-6}$alkylene-CO$_2$$C_{1-6}$alkyl, —O$C_{1-6}$alkylene-CO$_2$H, —O$C_{1-6}$alkylene-CO$_2$$C_{1-6}$alkyl, —$C_{1-6}$alkyl substituted with one or two hydroxy, —O$C_{1-6}$alkyl substituted with one or two hydroxy, —$C_{1-6}$alkyl substituted with one or two substituents independently selected from —O$C_{1-6}$alkyl, —O$C_{1-6}$alkyl (substituted with one or two —O$C_{1-6}$alkyl), —CO$_2$H, —COO$C_{1-6}$alkyl, halo, hydroxy, nitro, —PO$_3$H$_2$, cyano, —NH$_2$, —NH($C_{1-6}$alkyl), —N($C_{1-6}$alkyl)$_2$, —CONR$^e$R$^f$ (where R$^e$ and R$^f$ are independently hydrogen, —$C_{1-6}$alkyl, —$C_{1-6}$alkylene-CO$_2$H, —$C_{1-6}$alkylene-CO$_2$$C_{1-6}$alkyl, or —$C_{1-6}$alkyl substituted with one or two substituents independently selected from hydroxyl, NH$_2$, —NH$C_{1-6}$alkyl or —N($C_{1-6}$alkyl)$_2$), —SO$_2$($C_{1-6}$alkyl), —SO$_2$NR$^g$R$^h$ (where R$^g$ and R$^h$ are independently hydrogen, —$C_{1-6}$alkyl, —$C_{1-6}$alkylene-CO$_2$H, or —$C_{1-6}$alkylene-CO$_2$$C_{1-6}$alkyl), —S$C_{1-6}$alkyl, —SO$C_{1-6}$alkyl, —SO$_2$NHCOR$^j$ (where R$^j$ is —$C_{1-6}$alkyl, —NH$C_{1-6}$alkyl, or —N($C_{1-6}$alkyl)$_2$), phenyl, phenoxy, benzyl, —O$C_{1-6}$alkylenephenyl, 5- or 6-membered monocyclic heteroaryl containing one to four heteroatoms independently selected from O, N, and S [wherein the heteroaryl ring is optionally substituted with one, two, or three substituents independently selected from hydroxyl, halo, CN, —CO$_2$H, —COO$C_{1-6}$alkyl, —$C_{1-6}$alkyl, —O$C_{1-6}$alkyl, —$C_{1-6}$alkyl substituted with one to five fluoro, —O$C_{1-6}$alkyl (wherein alkyl is substituted with one to five fluoro), —$C_{1-6}$alkylene-CO$_2$H, —$C_{1-6}$alkylene-CO$_2$$C_{1-6}$alkyl, tetrazolyl, —SO$_2$$C_{1-6}$alkyl, —SO$_2$NH$_2$, —SO$_2$NH$C_{1-6}$alkyl, —SO$_2$N($C_{1-6}$alkyl)$_2$, —CONH$_2$, —CONH$C_{1-6}$alkyl, and —CON($C_{1-6}$alkyl)$_2$], —OR$^i$, —$C_{1-6}$alkylene-R$^i$, —O$C_{1-6}$alkylene-R$^i$, —SR$^i$, —S$C_{1-6}$alkylene-R$^i$, heterocyclyl, —$C_{1-6}$alkyleneheterocyclyl, —O$C_{1-6}$alkyleneheterocyclyl, —S$C_{1-6}$alkyleneheterocyclyl, —CONR$^m$$C_{1-6}$alkyleneheterocyclyl, —NR$^m$CO$C_{1-6}$alkyleneNR$^o$R$^p$, —NR$^m$COheterocyclyl, —NR$^m$CO$C_{1-6}$ alkyleneheterocyclyl, —COheterocyclyl, —CONR$^m$R$^i$, —CONR$^m$alkylene-R$^i$, and —CONHSO$_2$R$^z$; and additionally the R$^5$ phenyl and naphthyl rings are optionally substituted with a third substituent selected from —$C_{1-6}$alkyl, —$C_{1-6}$alkyl (wherein alkyl is substituted with one to five fluoro), —O—$C_{1-6}$alkyl, —O$C_{1-6}$alkyl (wherein alkyl is substituted with one to five fluoro), halo, CN, —NH$_2$, and hydroxy; wherein:

each R$^m$ is hydrogen or —$C_{1-6}$alkyl;

R$^o$ and R$^p$ are independently hydrogen or —$C_{1-6}$alkyl;

R$^z$ is —$C_{1-6}$alkyl, —NH$C_{1-6}$alkyl, or —N($C_{1-6}$alkyl)$_2$;

phenyl by itself or as part of phenoxy, benzyl, or —O$C_{1-6}$alkylenephenyl is optionally substituted with one, two, or three substituents independently selected from hydroxyl, halo, CN, —CO$_2$H, —COO$C_{1-6}$alkyl, —$C_{1-6}$alkyl, —O$C_{1-6}$alkyl, —$C_{1-6}$alkyl substituted with one to five fluoro, —O$C_{1-6}$alkyl (substituted with one to five fluoro), —$C_{1-6}$alkylene-CO$_2$H, —$C_{1-6}$alkylene-CO$_2$$C_{1-6}$alkyl, tetrazolyl, —SO$_2$$C_{1-6}$alkyl, —SO$_2$NH$_2$, —SO$_2$NH$C_{1-6}$alkyl, —SO$_2$N($C_{1-6}$alkyl)$_2$, —CONH$_2$, —CONH$C_{1-6}$alkyl, and —CON($C_{1-6}$alkyl)$_2$;

each R$^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, halo, CN, —CO$_2$H, —COO$C_{1-6}$alkyl, —$C_{1-6}$alkyl, —O$C_{1-6}$alkyl, —$C_{1-6}$alkyl substituted with one to five fluoro, —O$C_{1-6}$alkyl (substituted with one to five fluoro), and —$C_{1-6}$alkylene-CO$_2$H, and —$C_{1-6}$alkylene-CO$_2$$C_{1-6}$alkyl, tetrazolyl, —SO$_2$$C_{1-6}$alkyl, —SO$_2$NH$_2$, —SO$_2$NH$C_{1-6}$alkyl, —SO$_2$N($C_{1-6}$alkyl)$_2$, —CONH$_2$, —CONH$C_{1-6}$alkyl, and —CON($C_{1-6}$alkyl)$_2$;

heterocyclyl by itself or as part of —$C_{1-6}$alkyleneheterocyclyl, —O$C_{1-6}$alkyleneheterocyclyl, —S$C_{1-6}$alkyleneheterocyclyl, —CONR$^m$$C_{1-6}$alkylene-heterocyclyl, —NR$^m$COheterocyclyl, —COheterocyclyl, or —NR$^m$CO$C_{1-6}$alkyleneheterocyclyl is optionally substituted with one, two, or three substituents independently selected from hydroxy, halo, —COO$C_{1-6}$alkyl, —$C_{1-6}$alkyl, —O$C_{1-6}$alkyl, or —$C_{1-6}$ alkyl (substituted with hydroxy or —O$C_{1-6}$alkyl).

Embodiment 4

In embodiment 4, the compounds of embodiment 1 or 2 and subembodiments contained therein are those wherein R$^5$ is phenylC$_{1-6}$alkyl, preferably benzyl, wherein phenyl is substituted with one substituent at the meta or para position, preferably para, to the carbon atom of the phenyl ring that is attached to —C$_{1-6}$alkyl in —C$_{1-6}$alkylphenyl or —CH$_2$— in benzyl respectively, which one substituent is selected from —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, —C$_{1-6}$alkylene-CO$_2$C$_{1-6}$alkyl, —OC$_{1-6}$alkylene-CO$_2$H, —OC$_{1-6}$alkylene-CO$_2$C$_{1-6}$alkyl, —CO$_2$H, —COOC$_{1-6}$alkyl, halo, hydroxy, cyano, nitro, —PO$_3$H$_2$, —CONR$^e$R$^f$ (where R$^e$ and R$^f$ are independently hydrogen, —C$_{1-6}$alkyl, —C$_{1-6}$alkylene-CO$_2$H, —C$_{1-6}$alkylene-CO$_2$C$_{1-6}$alkyl, or —C$_{1-6}$alkyl substituted with one or two substituents independently selected from hydroxy, NH$_2$, —NHC$_{1-6}$alkyl or —N(C$_{1-6}$alkyl)$_2$), —SO$_2$(C$_{1-6}$alkyl), —SO$_2$NR$^g$R$^h$ (where R$^g$ and R$^h$ are independently hydrogen, —C$_{1-6}$alkyl, —C$_{1-6}$alkylene-CO$_2$H, or —C$_{1-6}$alkylene-CO$_2$C$_{1-6}$alkyl), phenyl, phenoxy, benzyl, benzyloxy, 5- or 6-membered monocyclic heteroaryl containing one to four heteroatoms independently selected from O, N, and S [wherein the heteroaryl ring is optionally substituted with one, two, or three substituents independently selected from hydroxy, halo, CN, —CO$_2$H, —COOC$_{1-6}$alkyl, —C$_{1-6}$alkyl, —OC$_{1-6}$alkyl, —C$_{1-6}$alkyl (wherein alkyl is substituted with one to five fluoro), —OC$_{1-6}$ alkyl (wherein alkyl is substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$], —OR$^i$, —C$_{1-6}$alkylene-R$^i$, —OC$_{1-6}$alkylene-R$^i$, —SR$^i$, —SC$_{1-6}$alkylene-R$^i$, heterocyclyl, —C$_{1-6}$ alkyleneheterocyclyl, —OC$_{1-6}$alkyleneheterocyclyl, —SC$_{1-6}$alkyleneheterocyclyl, —CONR$^m$C$_{1-6}$alkyleneheterocyclyl, —NR$^m$COC$_{1-6}$ alkyleneNR$^o$R$^p$, —NR$^m$COheterocyclyl, —NR$^m$COC$_{1-6}$alkyleneheterocyclyl, —COheterocyclyl, —CONR$^m$R$^i$, and —CONR$^m$alkylene-R$^i$; and the R$^5$ phenyl ring is additionally optionally substituted with one or two substituents independently selected from —C$_{1-6}$alkyl, —C$_{1-6}$alkyl (wherein alkyl is substituted with one to five fluoro), —O—C$_{1-6}$alkyl, —OC$_{1-6}$alkyl (wherein alkyl is substituted with one to five fluoro), halo, CN, —NH$_2$, and hydroxy; wherein each R$^m$ is hydrogen or —C$_{1-6}$alkyl;

R$^o$ and R$^p$ are independently hydrogen or —C$_{1-6}$alkyl;

phenyl by itself or as part of benzyl, phenoxy, or benzyloxy is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$;

each R$^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, and —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$;

heterocyclyl by itself or as part of —C$_{1-6}$alkyleneheterocyclyl, —OC$_{1-6}$alkyleneheterocyclyl, —SC$_{1-6}$alkyleneheterocyclyl, —CONR$^m$C$_{1-6}$alkyleneheterocyclyl, —NR$^m$CO-heterocyclyl, —COheterocyclyl, or —NR$^m$COC$_{1-6}$alkyleneheterocyclyl is optionally substituted with one, two, or three substituents independently selected from hydroxy, halo, —COOC$_{1-6}$alkyl, —C$_{1-6}$alkyl, —OC$_{1-6}$alkyl, or —C$_{1-6}$alkyl (substituted with hydroxy or —OC$_{1-6}$alkyl).

Embodiment 5

In embodiment 5, the compounds of embodiment 1 or 2 and subembodiments contained therein are those wherein R$^5$ is —CH$_2$phenyl or —(CH$_2$)$_2$phenyl, preferably —CH$_2$phenyl (benzyl) wherein phenyl is optionally substituted, preferably substituted, with one substituent at the meta or para position, preferably para, to the carbon atom of the phenyl ring that is attached to —C$_{1-6}$alkyl in —C$_{1-6}$alkylphenyl and —CH$_2$— in —CH$_2$phenyl (benzyl) respectively, which one substituent is selected from —OC$_{1-6}$alkyl, —C$_{1-6}$alkyl substituted with one to five fluoro, —OC$_{1-6}$alkyl (substituted with one to five fluoro), —C$_{1-6}$alkyl substituted with hydroxy, —C$_{1-6}$alkylene-CO$_2$H, —C$_{1-6}$alkylene-CO$_2$C$_{1-6}$alkyl, —OC$_{1-6}$alkylene-CO$_2$H, —OC$_{1-6}$alkylene-CO$_2$C$_{1-6}$alkyl, —CO$_2$H, nitro, —COOC$_{1-6}$alkyl, halo, hydroxy, cyano, —CONR$^e$R$^f$ (where R$^e$ is hydrogen or —C$_{1-6}$alkyl and R$^f$ is —C$_{1-6}$alkyl, —C$_{1-6}$alkylene-CO$_2$H, —C$_{1-6}$alkylene-CO$_2$C$_{1-6}$alkyl, or —C$_{1-6}$alkyl substituted with one or two hydroxyl, —NH$_2$, —NHC$_{1-6}$alkyl or —N(C$_{1-6}$alkyl)$_2$), —SO$_2$(C$_{1-6}$alkyl), —SO$_2$NR$^g$R$^h$ (where R$^g$ is hydrogen or —C$_{1-6}$alkyl and R$^h$ is hydrogen, —C$_{1-6}$alkyl, —C$_{1-6}$alkylene-CO$_2$H, or —C$_{1-6}$alkylene-CO$_2$C$_{1-6}$alkyl), oxadiazolyl, tetrazolyl, pyridinyl, pyrimidinyl, pyrazinyl, pyridazinyl, pyrazolyl, imidazolyl, oxazolyl, thiazolyl, oxadiazolyl, thiadiazolyl, furanyl, thienyl, pyrrolyl or isoxazolyl (wherein each of the aforementioned heteroaryl rings is optionally substituted with one or two substituents independently selected from C$_{1-6}$alkyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$), and the R$^5$ phenyl ring is additionally optionally substituted with one or two substituents independently selected from —C$_{1-6}$alkyl, —C$_{1-6}$alkyl (wherein alkyl is substituted with one to five fluoro), —O—C$_{1-6}$alkyl, —OC$_{1-6}$alkyl (wherein alkyl is substituted with one to five fluoro), halo, CN, —NH$_2$, and hydroxy.

Embodiment 6

In embodiment 6, the compounds of embodiment 1 or 2 and subembodiments contained therein are those wherein R$^5$ is phenylC$_{1-6}$alkyl, preferably benzyl, wherein phenyl ring in phenylC$_{1-6}$alkyl and benzyl is substituted at the meta or para position, preferably para, to the carbon atom of the phenyl ring that is attached to —C$_{1-6}$alkyl in —C$_{1-6}$alkylphenyl and —CH$_2$— in benzyl respectively, with phenyl, benzyl, benzyloxy, or phenoxy [wherein the phenyl ring either by itself or as part of benzyl, benzyloxy, and phenoxy is optionally substituted with one, two, or three substituents independently selected from hydroxy, halo, CN, —CO$_2$H, —COOC$_{1-6}$alkyl, —C$_{1-6}$alkyl, —OC$_{1-6}$alkyl, —C$_{1-6}$alkyl (substituted with one to five fluoro), —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —$SO_2NH_2$, —$SO_2NHC_{1-6}$alkyl, —$SO_2N(C_{1-6}$alkyl$)_2$, —$CONH_2$, —$CONHC_{1-6}$alkyl, and —$CON(C_{1-6}$alkyl$)_2$]; and $R^5$ phenyl is further optionally substituted with one or two substituents independently selected from —$C_{1-6}$alkyl, —$C_{1-6}$ alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 7

In embodiment 7, the compounds of embodiment 1 or 2 and subembodiments contained therein are those wherein $R^5$ is —$CH_2$-phenyl, —$CH_2$-naphthyl, —$(CH_2)_2$-phenyl, or —$(CH_2)_2$-naphthyl, preferably —$CH_2$-phenyl, wherein the phenyl and naphthyl rings are optionally substituted with one, two, or three substituents independently selected from methyl, ethyl, methoxy, ethoxy, difluoromethyl, trifluoromethyl, difluoromethoxy, trifluoromethoxy, —$CH_2CO_2H$, —$CH_2CH_2CO_2H$, —$OCH_2CO_2H$, —$OCH_2CH_2CO_2H$, —$CH_2CO_2CH_3$, —$CH_2CH_2CO_2CH_3$, —$CH_2CO_2$ethyl, —$CH_2CH_2CO_2$ethyl, —$CH_2OH$, —$CH_2CH_2OH$, —$OCH_2OCH_3$, —$OCH_2CH_2OCH_3$, —$CO_2H$, —COOmethyl, —$CO_2$ethyl, hydroxy, nitro, $PO_3H_2$, methylthio, ethylthio, methylsulfoxide, ethylsulfoxide, methylcarbonylaminosulfonyl, ethylcarbonylaminosulfonyl, fluoro, chloro, cyano, —$NH_2$, —$NHCH_3$, —NHethyl, —N(methyl)$_2$, —N(ethyl)$_2$, —$CONR^eR^f$ (where $R^e$ is hydrogen, methyl, ethyl, or propyl and $R^f$ is hydrogen, methyl, ethyl, propyl, —$(CH_2)_2$—$CO_2H$, —$(CH_2)_3$—$CO_2H$, —$(CH_2)_2$—$CO_2Me$, —$(CH_2)_3$—$CO_2Me$, —$(CH_2)_2$—$CO_2$ethyl, —$(CH_2)_3$—$CO_2$ethyl, —$(CH_2)_2$—$NH_2$, —$(CH_2)_3$—$NH_2$, —$(CH_2)_2$—NHMe, —$(CH_2)_3$—NHMe, —$(CH_2)_2$—N(CH$_3$)$_2$, or —$(CH_2)_3$—N(CH$_3$)$_2$), —$SO_2Me$, —$SO_2NR^gR^h$ (where $R^g$ is hydrogen, methyl, ethyl, or propyl and $R^h$ is hydrogen, methyl, ethyl, propyl, —$(CH_2)_2$—$CO_2H$, —$(CH_2)_3$—$CO_2H$, —$(CH_2)_2$—$CO_2Me$, —$(CH_2)_3$—$CO_2Me$, —$(CH_2)_2$—$CO_2$ethyl, or —$(CH_2)_3$—$CO_2$ethyl), phenyl, phenoxy, —$CH_2$-phenyl, —$CH_2$—$CH_2$-phenyl, —$OCH_2$-phenyl or —$OCH_2$—$CH_2$-phenyl [wherein the phenyl ring, by itself or as part of phenoxy, —$CH_2$-phenyl, —$CH_2$—$CH_2$-phenyl, —$OCH_2$-phenyl, and —$OCH_2$—$CH_2$-phenyl, is optionally substituted with one, two, or three substituents independently selected from hydroxyl, chloro, fluoro, —$CO_2H$, CN, —$CO_2Me$, —$CO_2$ethyl, methyl, ethyl, methoxy, ethoxy, difluoromethoxy, trifluoromethoxy, difluoromethyl, trifluoromethyl, —$CH_2$—$CO_2H$, —$CH_2$—$CO_2$methyl, —$CH_2$—$CO_2$ethyl, tetrazolyl, —$SO_2CH_3$, —$SO_2NH_2$, —$SO_2NHCH_3$, —$SO_2N(CH_3)_2$, —$CONH_2$, —$CONHCH_3$, and —$CON(CH_3)_2$], 5- or 6-membered monocyclic heteroaryl containing one to four heteroatoms independently selected from O, N, and S [wherein the heteroaryl ring is optionally substituted with one, two, or three substituents independently selected from hydroxyl, chloro, fluoro, CN, —$CO_2H$, —$CO_2Me$, —$CO_2$ethyl, methyl, ethyl, methoxy, ethoxy, difluoromethoxy, trifluoromethoxy, difluoromethyl, trifluoromethyl, —$CH_2$—$CO_2H$, —$CH_2$—$CO_2$methyl, and —$CH_2$—$CO_2$ethyl], —$OR^i$, —$SR^i$, —$OCH_2R^i$, —$O(CH_2)_2$—$R^i$, —$CH_2R^i$ and —$(CH_2)_2$—$R^i$ [where each $R^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, chloro, fluoro, CN, —$CO_2H$, —$CO_2Me$, —$CO_2$ethyl, methyl, ethyl, methoxy, ethoxy, difluoromethoxy, trifluoromethoxy, difluoromethyl, trifluoromethyl, —$CH_2$—$CO_2H$, —$CH_2$—$CO_2$methyl, —$CH_2$—$CO_2$ethyl, tetrazolyl, —$SO_2CH_3$, —$SO_2NH_2$, —$SO_2NHCH_3$, —$SO_2N(CH_3)_2$, —$CONH_2$, —$CONHCH_3$, and —$CON(CH_3)_2$].

Embodiment 8

In embodiment 8, the compounds of embodiment 1 or 2 and subembodiments contained therein are those wherein $R^5$ is —$CH_2$-phenyl, —$CH_2$-naphthyl, —$(CH_2)_2$-phenyl, or —$(CH_2)_2$-naphthyl, preferably —$CH_2$-phenyl, wherein phenyl and naphthyl rings are substituted with one or two substituents independently selected from difluoromethyl, trifluoromethyl, difluoromethoxy, trifluoromethoxy, —$CH_2CO_2H$, —$CH_2CH_2CO_2H$, —$OCH_2CO_2H$, —$OCH_2CH_2CO_2H$, —$CH_2CO_2CH_3$, —$CH_2CH_2CO_2CH_3$, —$CH_2CO_2$ethyl, —$CH_2CH_2CO_2$ethyl, —$CH_2OH$, —$CH_2CH_2OH$, —$OCH_2OCH_3$, —$OCH_2CH_2OCH_3$, —$CO_2H$, —COOmethyl, —$CO_2$ethyl, hydroxy, nitro, $PO_3H_2$, methylthio, ethylthio, methylsulfoxide, ethylsulfoxide, methylcarbonylaminosulfonyl, ethylcarbonylaminosulfonyl, fluoro, chloro, cyano, —$NH_2$, —$NHCH_3$, —NHethyl, —N(methyl)$_2$, —N(ethyl)$_2$, —$CONR^eR^f$ (where $R^e$ is hydrogen, methyl, ethyl, or propyl and $R^f$ is hydrogen, methyl, ethyl, propyl, —$(CH_2)_2$—$CO_2H$, —$(CH_2)_3$—$CO_2H$, —$(CH_2)_2$—$CO_2Me$, —$(CH_2)_3$—$CO_2Me$, —$(CH_2)_2$—$CO_2$ethyl, —$(CH_2)_3$—$CO_2$ethyl, —$(CH_2)_2$—$NH_2$, —$(CH_2)_3$—$NH_2$, —$(CH_2)_2$—NHMe, —$(CH_2)_3$—NHMe, —$(CH_2)_2$—N(CH$_3$)$_2$, or —$(CH_2)_3$—N(CH$_3$)$_2$), —$SO_2Me$, —$SO_2NR^gR^h$ (where $R^g$ is hydrogen, methyl, ethyl, or propyl and $R^h$ is hydrogen, methyl, ethyl, propyl, —$(CH_2)_2$—$CO_2H$, —$(CH_2)_3$—$CO_2H$, —$(CH_2)_2$—$CO_2Me$, —$(CH_2)_3$—$CO_2Me$, —$(CH_2)_2$—$CO_2$ethyl, or —$(CH_2)_3$—$CO_2$ethyl), phenyl, phenoxy, —$CH_2$-phenyl, —$CH_2$—$CH_2$-phenyl, —$OCH_2$-phenyl or —$OCH_2$—$CH_2$-phenyl [wherein the phenyl ring by itself or as part of phenoxy, —$CH_2$-phenyl, —$CH_2$—$CH_2$-phenyl, —$OCH_2$-phenyl, and —$OCH_2$—$CH_2$-phenyl is optionally substituted with one, two, or three substituents independently selected from hydroxyl, chloro, fluoro, —$CO_2H$, CN, —$CO_2Me$, —$CO_2$ethyl, methyl, ethyl, methoxy, ethoxy, difluoromethoxy, trifluoromethoxy, difluoromethyl, trifluoromethyl, —$CH_2$—$CO_2H$, —$CH_2$—$CO_2$methyl, —$CH_2$—$CO_2$ethyl, tetrazolyl, —$SO_2CH_3$, —$SO_2NH_2$, —$SO_2NHCH_3$, —$SO_2N(CH_3)_2$, —$CONH_2$, —$CONHCH_3$, and —$CON(CH_3)_2$], 5- or 6-membered monocyclic heteroaryl containing one to four heteroatoms independently selected from O, N, and S [wherein the heteroaryl ring is optionally substituted with one, two, or three substituents independently selected from hydroxyl, chloro, fluoro, CN, —$CO_2H$, —$CO_2Me$, —$CO_2$ethyl, methyl, ethyl, methoxy, ethoxy, difluoromethoxy, trifluoromethoxy, difluoromethyl, trifluoromethyl, —$CH_2$—$CO_2H$, —$CH_2$—$CO_2$methyl, —$CH_2$—$CO_2$ethyl, tetrazolyl, —$SO_2CH_3$, —$SO_2NH_2$, —$SO_2NHCH_3$, —$SO_2N(CH_3)_2$, —$CONH_2$, —$CONHCH_3$, and —$CON(CH_3)_2$], —$OR^i$, —$SR^i$, —$OCH_2R^i$, —$O(CH_2)_2$—$R^i$, —$CH_2R^i$ and —$(CH_2)_2$—$R^i$ [where each $R^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, chloro, fluoro, CN, —$CO_2H$, —$CO_2Me$, —$CO_2$ethyl, methyl, ethyl, methoxy, ethoxy, difluoromethoxy, trifluoromethoxy, difluoromethyl, trifluoromethyl, —$CH_2$—$CO_2H$, —$CH_2$—$CO_2$methyl, and —$CH_2$—$CO_2$ethyl]; and the R⁵ phenyl and naphthyl rings are additionally optionally substituted with a third substituent independently selected from methyl, ethyl, fluoro, chloro, methoxy, ethoxy, hydroxy, —NH₂, and cyano.

Embodiment 9

In embodiment 9, the compounds of embodiment 1 or 2 and subembodiments contained therein are those wherein R⁵ is —CH₂-phenyl or —(CH₂)₂-phenyl, preferably —CH₂-phenyl, wherein phenyl is substituted with one substituent at a meta or para position, preferably para, to the carbon atom of the phenyl ring that is attached to —CH₂— or —(CH₂)₂— in —CH₂-phenyl or —(CH₂)₂-phenyl respectively, and is selected from trifluoromethyl, difluoromethoxy, trifluoromethoxy, —CH₂CO₂H, —CH₂CH₂CO₂H, —OCH₂CO₂H, —OCH₂CH₂CO₂H, —CH₂CO₂CH₃, —CH₂CH₂CO₂CH₃, —CH₂CO₂ethyl, —CH₂CH₂CO₂ethyl, —CH₂OH, —CH₂CH₂OH, —OCH₂CH₂OH, —OCH₂OCH₃, —OCH₂CH₂OCH₃, —CO₂H, —COOmethyl, —COOethyl, hydroxy, fluoro, chloro, cyano, —CONR$^e$R$^f$ (where R$^e$ is hydrogen, methyl, ethyl, or propyl and R$^f$ is hydrogen, methyl, ethyl, propyl, —(CH₂)₂—CO₂H, —(CH₂)₃—CO₂H, —(CH₂)₂—CO₂Me, —(CH₂)₃—CO₂Me, —(CH₂)₂—CO₂ethyl, —(CH₂)₃—CO₂ethyl, —(CH₂)₂—NH₂, —(CH₂)₃—NH₂, —(CH₂)₂—NHMe, —(CH₂)₃—NHMe, —(CH₂)₂—NHCH₃, —(CH₂)₃—N(CH₃)₂), —SO₂Me, or —SO₂NR$^g$R$^h$ (where R$^g$ is hydrogen, methyl, ethyl, or propyl and R$^h$ is hydrogen, methyl, ethyl, propyl, —(CH₂)₂—CO₂H, —(CH₂)₃—CO₂H, —(CH₂)₂—CO₂Me, —(CH₂)₃—CO₂Me, —(CH₂)₂—CO₂ethyl, or —(CH₂)₃—CO₂ethyl), tetrazolyl, pyridinyl, pyrimidinyl, pyrazinyl, pyridazinyl, pyrazolyl, imidazolyl, oxazolyl, thiazolyl, oxadiazolyl, thiadiazolyl, furanyl, thienyl, pyrrolyl or isoxazolyl, wherein each of the aforementioned heteroaryl rings is optionally substituted with one or two substituents independently selected from $C_{1-6}$alkyl, halo, CN, —CO₂H, —COOC$_{1-6}$alkyl, —C$_{1-6}$alkyl, —OC$_{1-6}$alkyl, —C$_{1-6}$alkyl substituted with one to five fluoro, or —OC$_{1-6}$alkyl (substituted with one to five fluoro); and the R⁵ phenyl ring is additionally optionally substituted with one or two substituents independently selected from methyl, ethyl, fluoro, chloro, methoxy, ethoxy, hydroxy, —NH₂, difluoromethyl, trifluoromethyl, difluoromethoxy, trifluoromethoxy, and cyano.

Embodiment 10

In embodiment 10, the compounds of embodiment 1 or 2 and subembodiments contained therein are those wherein R⁵ is —CH₂-phenyl or —(CH₂)₂-phenyl, preferably —CH₂-phenyl, wherein the phenyl ring in —CH₂-phenyl and —(CH₂)₂-phenyl is substituted at the meta or para position to the carbon atom of the phenyl ring that is attached to the —CH₂— group of the —CH₂-phenyl and —(CH₂)₂-phenyl ring with haloC$_{1-6}$alkoxy or haloC$_{1-6}$alkyl and the R⁵ phenyl ring is additionally optionally substituted with one or two substituents independently selected from —C$_{1-6}$alkyl, —C$_{1-6}$ alkyl (wherein alkyl is substituted with one to five fluoro), —O—C$_{1-6}$alkyl, —OC$_{1-6}$alkyl (wherein alkyl is substituted with one to five fluoro), halo, CN, —NH₂, and hydroxy.

Embodiment 11

In embodiment 11, the compounds of embodiment 1 or 2 and subembodiments contained therein are those wherein R⁵ is —CH₂-phenyl or —(CH₂)₂-phenyl, preferably —CH₂-phenyl, wherein phenyl is substituted with a substituent at the meta or para position, preferably para position, to the carbon atom of the phenyl ring that is attached to —CH₂— or —(CH₂)₂— in —CH₂-phenyl or —(CH₂)₂-phenyl, which substituent is selected from —CONR$^e$R$^f$ (where R$^e$ is hydrogen or —C$_{1-6}$alkyl and R$^f$ is —C$_{1-6}$alkylene-substituted with one or two substituents independently selected from hydroxyl, NH₂, —NHC$_{1-6}$alkyl or —N(C$_{1-6}$alkyl)₂), —OR$^i$, —C$_{1-6}$alkylene-R$^i$, —OC$_{1-6}$alkylene-R$^i$, —SR$^i$, —SC$_{1-6}$alkylene-R$^i$, —CON$^m$R$^i$, —CONR$^m$C$_{1-6}$alkylene-R$^i$ [where each R$^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, halo, CN, —COOC$_{1-6}$ alkyl, —C$_{1-6}$alkyl, —OC$_{1-6}$alkyl, —C$_{1-6}$alkyl (wherein alkyl is substituted with one to five fluoro), or —OC$_{1-6}$alkyl (wherein alkyl is substituted with one to five fluoro), heterocyclyl, —C$_{1-6}$alkyleneheterocyclyl, —OC$_{1-6}$alkyleneheterocyclyl, —SC$_{1-6}$alkyleneheterocyclyl, —CONR$^m$C$_{1-6}$alkyleneheterocyclyl, —NR$^m$COheterocyclyl, —COheterocyclyl, —NR$^m$COC$_{1-6}$alkyleneheterocyclyl [wherein each R$^m$ is hydrogen or —C$_{1-6}$alkyl and the heterocyclyl ring by itself or as part of —C$_{1-6}$alkyleneheterocyclyl, —OC$_{1-6}$alkyleneheterocyclyl, —SC$_{1-6}$alkyleneheterocyclyl, —CONR$^m$C$_{1-6}$alkyleneheterocyclyl, —COheterocyclyl, —NR$^m$COheterocyclyl, and —NR$^m$COC$_{1-6}$alkyleneheterocyclyl is optionally substituted with one, two, or three substituents independently selected from hydroxy, halo, —COOC$_{1-6}$alkyl, —C$_{1-6}$alkyl, —OC$_{1-6}$alkyl, or —C$_{1-6}$ alkyl (wherein alkyl is substituted with hydroxy or —OC$_{1-6}$ alkyl)], and —NR$^m$COC$_{1-6}$alkyleneNR$^o$R$^p$ (where R$^m$, R$^o$ and R$^p$ are independently hydrogen or C$_{1-6}$alkyl); and the R⁵ phenyl ring is additionally optionally substituted with one or two substituents independently selected from —C$_{1-6}$alkyl, —C$_{1-6}$alkyl (wherein alkyl is substituted with one to five fluoro), —O—C$_{1-6}$alkyl, —OC$_{1-6}$alkyl (wherein alkyl is substituted with one to five fluoro), halo, CN, —NH₂, and hydroxy.

Embodiment 12

In embodiment 12, the compounds of embodiment 1 or 2 and subembodiments contained therein are those wherein R⁵ is —CH₂-phenyl or —(CH₂)₂-phenyl, preferably —CH₂-phenyl, wherein phenyl is substituted with —CH=CHCO₂H, —CH₂CO₂H or CH₂CH₂CO₂ at the meta or para position, preferably para, to the carbon atom of the phenyl ring that is attached to —CH₂— or —(CH₂)₂— in —CH₂-phenyl or —(CH₂)₂-phenyl; and the phenyl ring is additionally optionally substituted with one or two substituents independently selected from —C$_{1-6}$ alkyl, —C$_{1-6}$alkyl (wherein alkyl is substituted with one to five fluoro), —O—C$_{1-6}$alkyl, —OC$_{1-6}$alkyl (wherein alkyl is substituted with one to five fluoro), halo, CN, —NH₂, and hydroxy.

Embodiment 13

In embodiment 13, the compounds of embodiment 1 or 2 and subembodiments contained therein are those wherein R⁵ is —CH₂-phenyl or —(CH₂)₂-phenyl, preferably —CH₂-phenyl, wherein phenyl is substituted —CH₂CO₂CH₃, —CH₂CH₂CO₂CH₃, —CH₂CO₂ethyl, or —CH₂CH₂CO₂ethyl at the meta or para position, preferably para, to the carbon atom of the phenyl ring that is attached to —$CH_2$— or —$(CH_2)_2$— in —$CH_2$-phenyl or —$(CH_2)_2$-phenyl; and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 14

In embodiment 14, the compounds of embodiment 1 or 2 and subembodiments contained therein are those wherein $R^5$ is —$CH_2$-phenyl or —$(CH_2)_2$-phenyl, preferably —$CH_2$-phenyl (benzyl), wherein phenyl is substituted with $CO_2H$ at the meta or para position, preferably para, to the carbon atom of the phenyl ring that is attached to —$CH_2$— or —$(CH_2)_2$— in —$CH_2$-phenyl (benzyl) or —$(CH_2)_2$-phenyl and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 15

In embodiment 15, the compounds of embodiment 1 or 2 and subembodiments contained therein are those wherein $R^5$ is —$CH_2$-phenyl (benzyl) or —$(CH_2)_2$-phenyl, preferably —$CH_2$-phenyl (benzyl), wherein phenyl is substituted with —COOmethyl or —COOethyl at the meta or para position, preferably para, to the carbon atom of the phenyl ring that is attached to —$CH_2$— or —$(CH_2)_2$— in —$CH_2$-phenyl (benzyl) or —$(CH_2)_2$-phenyl and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 16

In embodiment 16, the compounds of embodiment 1 or 2 and subembodiments contained therein are those wherein $R^5$ is —$CH_2$-phenyl or —$(CH_2)_2$-phenyl, preferably —$CH_2$-phenyl, wherein phenyl is substituted with fluoro, chloro, or cyano at the meta or para position, preferably para, to the carbon atom of the phenyl ring that is attached to —$CH_2$— or —$(CH_2)_2$— in —$CH_2$-phenyl or —$(CH_2)_2$-phenyl and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy Embodiment 17

In embodiment 17, the compounds of embodiment for 2 and subembodiments contained therein are those wherein $R^5$ is —$CH_2$-phenyl or —$(CH_2)_2$-phenyl, preferably —$CH_2$-phenyl, wherein phenyl is substituted with —$CONR^eR^f$ (where $R^e$ is hydrogen, methyl, ethyl, or propyl and $R^f$ is hydrogen, methyl, ethyl, propyl, —$(CH_2)_2$—$CO_2H$, —$(CH_2)_3$—$CO_2H$, —$(CH_2)_2$—$CO_2Me$, —$(CH_2)_3$—$CO_2Me$, —$(CH_2)_2$—$CO_2$ethyl, —$(CH_2)_3$—$CO_2$ethyl, —$(CH_2)_2$—$NH_2$, —$(CH_2)_3$—$NH_2$, —$(CH_2)_2$—NHMe, —$(CH_2)_3$—NHMe, —$(CH_2)_2$—$NHCH_3$, —$(CH_2)_3$—N$(CH_3)_2$) or —$CONHSO_2R^z$ where $R^z$ is —$C_{1-6}$alkyl, —$NHC_{1-6}$alkyl, or —$N(C_{1-6}$alkyl$)_2$ at the meta or para position, preferably para, to the carbon atom of the phenyl ring that is attached to —$CH_2$— or —$(CH_2)_2$— in —$CH_2$-phenyl or —$(CH_2)_2$-phenyl; and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 18

In embodiment 18, the compounds of embodiment 1 or 2 and subembodiments contained therein are those wherein $R^5$ is —$CH_2$-phenyl or —$(CH_2)_2$-phenyl, preferably —$CH_2$-phenyl, wherein phenyl is substituted —$SO_2NR^gR^h$ (where $R^g$ is hydrogen, methyl, ethyl, or propyl and $R^h$ is hydrogen, methyl, ethyl, propyl, —$(CH_2)_2$—$CO_2H$, —$(CH_2)_3$—$CO_2H$, —$(CH_2)_2$—$CO_2Me$, —$(CH_2)_3$—$CO_2Me$, —$(CH_2)_2$—$CO_2$ethyl, or —$(CH_2)_3$—$CO_2$ethyl) or —$SO_2NHCOR^j$ (where $R^j$ is —$C_{1-6}$alkyl, —$NHC_{1-6}$alkyl, or —$N(C_{1-6}$alkyl$)_2$) at the meta or para position, preferably para, to the carbon atom of the phenyl ring that is attached to —$CH_2$— or —$(CH_2)_2$— in —$CH_2$-phenyl or —$(CH_2)_2$-phenyl; and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 19

In embodiment 19, the compounds of embodiment 1 or 2 and subembodiments contained therein are those wherein $R^5$ is —$CH_2$-phenyl or —$(CH_2)_2$-phenyl, preferably —$CH_2$-phenyl, wherein phenyl is substituted with tetrazol-5-yl at the meta or para position, preferably para, to the carbon atom of the phenyl ring that is attached to —$CH_2$— or —$(CH_2)_2$— in —$CH_2$-phenyl or —$(CH_2)_2$-phenyl; and the $R^5$ phenyl ring is additionally optionally substituted with one or two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 20

In embodiment 20, the compounds of embodiment 1 and subembodiments contained therein are those wherein $R^5$ is 5-10 membered heteroaryl$C_{1-6}$alkyl (also referred to below as $R^5$ heteroaryl), preferably —$CH_2$— or —$(CH_2)_2$-5-10 membered heteroaryl, having one to three heteroatoms independently selected from N, O, or S and is optionally substituted, preferably substituted, with one or two substituents, more preferably one substituent, independently selected from —$C_{1-6}$alkyl, —$OC_{1-6}$alkyl, —$C_{1-6}$alkyl substituted with one to five fluoro, —$OC_{1-6}$alkyl substituted with one to five fluoro, —$C_{1-6}$alkylene-$CO_2H$, —$C_{1-6}$alkylene-$CO_2C_{1-6}$alkyl, —$C_{2-6}$alkenylene-$CO_2H$, —$C_{1-6}$alkyl substituted with one or two substituents independently selected from hydroxy, —$OC_{1-6}$alkyl substituted with hydroxy, —$C_{1-6}$alkyl substituted with one or two —OC$_{1-6}$alkyl, —OC$_{1-6}$alkyl (substituted with one or two —OC$_{1-6}$alkyl), —CO$_2$H, —COOC$_{1-6}$alkyl, hydroxy, halo, nitro, —PO$_3$H$_2$, cyano, —NH$_2$, —NH(C$_{1-6}$alkyl), —N(C$_{1-6}$alkyl)$_2$, —CONR$^e$R$^f$ (where R$^e$ and R$^f$ are independently hydrogen, —C$_{1-6}$alkyl, —C$_{1-6}$alkylene-CO$_2$H, —C$_{1-6}$alkylene-CO$_2$C$_{1-6}$alkyl, or —C$_{1-6}$alkyl substituted with one or two substituents independently selected from hydroxyl, —NHC$_{1-6}$alkyl or —N(C$_{1-6}$alkyl)$_2$), —SO$_2$(C$_{1-6}$alkyl), —SO$_2$NR$^g$R$^h$ (where R$^g$ and R$^h$ are independently hydrogen, —C$_{1-6}$alkyl, —C$_{1-6}$alkylene-CO$_2$H, or —C$_{1-6}$alkylene-CO$_2$C$_{1-6}$alkyl), —SC$_{1-6}$alkyl, —SOC$_{1-6}$alkyl, —SO$_2$NHCOR$^j$ (where R$^j$ is —C$_{1-6}$alkyl, —NH$_2$, —NHC$_{1-6}$alkyl, or —N(C$_{1-6}$alkyl)$_2$), phenyl, —C$_{1-6}$alkylenephenyl, phenoxy, —OC$_{1-6}$alkylenephenyl, 5- or 6-membered monocyclic heteroaryl containing one to four heteroatoms independently selected from O, N, and S [wherein the heteroaryl ring is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl (substituted with one to five fluoro), —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$], —OR$^i$, —C$_{1-6}$alkylene-R$^i$, —OC$_{1-6}$alkylene-R$^i$, —SR$^i$, —SC$_{1-6}$alkylene-R$^i$, heterocyclyl, —C$_{1-6}$alkyleneheterocyclyl, —OC$_{1-6}$alkyleneheterocyclyl, —SC$_{1-6}$ alkyleneheterocyclyl, —CONR$^m$C$_{1-6}$alkyleneheterocyclyl, —NR$^m$COC$_{1-6}$alkyleneNR$^o$R$^p$, —NR$^m$COheterocyclyl, —NR$^m$COC$_{1-6}$alkyleneheterocyclyl, —COheterocyclyl, —CONR$^m$R$^i$, —CONR$^m$alkylene-R$^i$, —OCONR$^m$R$^m$, —NR$^m$—COR$^y$, —NR$^m$—CO—NR$^m$R$^y$, —NR$^m$—SO$_2$—R$^y$, —NR$^m$—SO$_2$—NR$^m$R$^y$, and —CONHSO$_2$R$^z$; and the R$^5$ heteroaryl ring is additionally optionally substituted with an additional substituent selected from —C$_{1-6}$alkyl, —C$_{1-6}$alkyl (wherein alkyl is substituted with one to five fluoro), —O—C$_{1-6}$alkyl, —OC$_{1-6}$alkyl (wherein alkyl is substituted with one to five fluoro), halo, CN, —NH$_2$, and hydroxy; wherein:

each R$^m$ is hydrogen or —C$_{1-6}$alkyl;

R$^o$, R$^p$, and R$^y$ are independently hydrogen or —C$_{1-6}$alkyl;

R$^z$ is —C$_{1-6}$alkyl, —NHC$_{1-6}$alkyl, or —N(C$_{1-6}$alkyl)$_2$;

phenyl by itself or as part of —C$_{1-6}$alkylenephenyl, phenoxy, or —OC$_{1-6}$alkylenephenyl is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$;

each R$^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, and —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$;

heterocyclyl by itself or as part of —C$_{1-6}$alkyleneheterocyclyl, —OC$_{1-6}$alkyleneheterocyclyl, —SC$_{1-6}$alkyleneheterocyclyl, —CONR$^m$C$_{1-6}$alkyleneheterocyclyl, —NR$^m$CO-heterocyclyl, —COheterocyclyl, and —NR$^m$COC$_{1-6}$alkyleneheterocyclyl is optionally substituted with one, two, or three substituents independently selected from hydroxy, halo, —COOC$_{1-6}$alkyl, —C$_{1-6}$alkyl, —OC$_{1-6}$alkyl, or —C$_{1-6}$alkyl (substituted with hydroxy or —OC$_{1-6}$alkyl).

Embodiment 21

In embodiment 21, the compounds of embodiment 1 or 20 and subembodiments contained therein are those wherein R$^5$ is —CH$_2$— or —(CH$_2$)$_2$-(5-9 membered heteroaryl ring) which heteroaryl ring is optionally substituted with one or two substituents, preferably one substituent, independently selected from difluoromethyl, trifluoromethyl, difluoromethoxy, trifluoromethoxy, —CH$_2$CO$_2$H, —CH$_2$CH$_2$CO$_2$H, —CH$_2$CO$_2$CH$_3$, —CH$_2$CH$_2$CO$_2$CH$_3$, —CH$_2$CO$_2$ethyl, —CH$_2$CH$_2$CO$_2$ethyl, —CH$_2$OH, —CH$_2$CH$_2$OH, —OCH$_2$CH$_2$OH, —OCH$_2$OCH$_3$, —OCH$_2$CH$_2$OCH$_3$, —CO$_2$H, —COOmethyl, —CO$_2$ethyl, hydroxy, nitro, PO$_3$H$_2$, methylthio, ethylthio, methylsulfoxide, ethylsulfoxide, methylcarbonylaminosulfonyl, ethylcarbonylaminosulfonyl, fluoro, chloro, cyano, —NH$_2$, —NHCH$_3$, —NHethyl, —N(methyl)$_2$, —N(ethyl)$_2$, —CONR$^e$R$^f$ (where R$^e$ is hydrogen, methyl, ethyl, or propyl and R$^f$ is hydrogen, methyl, ethyl, propyl, —(CH$_2$)$_2$—CO$_2$H, —(CH$_2$)$_3$—CO$_2$H, —(CH$_2$)$_2$—CO$_2$Me, —(CH$_2$)$_3$—CO$_2$Me, —(CH$_2$)$_2$—CO$_2$ethyl, —(CH$_2$)$_3$—CO$_2$ethyl, —(CH$_2$)$_2$—NH$_2$, —(CH$_2$)$_3$—NH$_2$, —(CH$_2$)$_2$—NHMe, —(CH$_2$)$_3$—NHMe, —(CH$_2$)$_2$—N(CH$_3$)$_2$, or —(CH$_2$)$_3$—N(CH$_3$)$_2$), —SO$_2$Me, —SO$_2$NR$^g$R$^h$ (where R$^g$ is hydrogen, methyl, ethyl, or propyl and R$^h$ is hydrogen, methyl, ethyl, propyl, —(CH$_2$)$_2$—CO$_2$H, —(CH$_2$)$_3$—CO$_2$H, —(CH$_2$)$_2$—CO$_2$Me, —(CH$_2$)$_3$—CO$_2$Me, —(CH$_2$)$_2$—CO$_2$ethyl, or —(CH$_2$)$_3$—CO$_2$ethyl), phenyl, phenoxy, —CH$_2$-phenyl, —CH$_2$—CH$_2$-phenyl, —OCH$_2$-phenyl or —OCH$_2$—CH$_2$-phenyl [wherein the phenyl ring by itself or as part of phenoxy, —CH$_2$-phenyl, —CH$_2$—CH$_2$-phenyl, —OCH$_2$-phenyl, and —OCH$_2$—CH$_2$-phenyl is optionally substituted with one, two, or three substituents independently selected from hydroxyl, chloro, fluoro, —CO$_2$H, CN, —CO$_2$Me, —CO$_2$ethyl, methyl, ethyl, methoxy, ethoxy, difluoromethoxy, trifluoromethoxy, difluoromethyl, trifluoromethyl, —CH$_2$—CO$_2$H, —CH$_2$—CO$_2$methyl, —CH$_2$—CO$_2$ethyl, tetrazolyl, —SO$_2$CH$_3$, —SO$_2$NH$_2$, —SO$_2$NHCH$_3$, —SO$_2$N(CH$_3$)$_2$, —CONH$_2$, —CONHCH$_3$, and —CON(CH$_3$)$_2$], 5- or 6-membered monocyclic heteroaryl containing one to four heteroatoms independently selected from O, N, and S [wherein the heteroaryl ring is optionally substituted with one, two, or three substituents independently selected from hydroxyl, chloro, fluoro, CN, —CO$_2$H, —CO$_2$Me, —CO$_2$ethyl, methyl, ethyl, methoxy, ethoxy, difluoromethoxy, trifluoromethoxy, difluoromethyl, trifluoromethyl, —CH$_2$—CO$_2$H, —CH$_2$—CO$_2$methyl, —CH$_2$—CO$_2$ethyl, tetrazolyl, —SO$_2$CH$_3$, —SO$_2$NH$_2$, —SO$_2$NHCH$_3$, —SO$_2$N(CH$_3$)$_2$, —CONH$_2$, —CONHCH$_3$, and —CON(CH$_3$)$_2$], —OR$^i$, —SR$^i$, —OCH$_2$R$^i$, —O(CH$_2$)$_2$—R$^i$, —CH$_2$R$^i$ and —(CH$_2$)$_2$—R$^i$ [where each R$^i$, is independently 5- or 6-membered monocyclic heteroaryl containing one to four heteroatoms independently selected from O, N, and S and wherein the heteroaryl ring is optionally substituted with one, two, or three substituents independently selected from hydroxyl, chloro, fluoro, CN, —CO$_2$H, —CO$_2$Me, —CO$_2$ethyl, methyl, ethyl, methoxy, ethoxy, difluoromethoxy, trifluoromethoxy, difluoromethyl, trifluoromethyl, —CH$_2$—CO$_2$H, —CH$_2$—CO$_2$methyl, and —CH$_2$—CO$_2$ethyl]; and

Embodiment 22

In embodiment 22, the compounds of embodiment 1 or 20 and subembodiments contained therein are those wherein $R^5$ is —$(CH_2)_{1-2}$-(5-10 membered heteroaryl ring) having one to three heteroatoms independently selected from N, O, or S, preferably —$CH_2$-(5-9 membered heteroaryl ring) having one to 3 heteroatoms independently selected from N, O, or S, wherein the heteroaryl ring is substituted with one or two substituents independently selected from —$OC_{1-6}$alkyl, —$C_{1-6}$alkyl substituted with one to five fluoro, —$OC_{1-6}$alkyl (wherein alkyl is substituted with one to five fluoro), —$C_{1-6}$alkylene-$CO_2H$, —$C_{1-6}$alkylene-$CO_2C_{1-6}$alkyl, —$CO_2H$, nitro, —$COOC_{1-6}$alkyl, halo, hydroxy, cyano, —$CONR^eR^f$ (where $R^e$ is hydrogen or —$C_{1-6}$alkyl and $R^f$ is —$C_{1-6}$alkyl, —$C_{1-6}$alkylene-$CO_2H$, or —$C_{1-6}$alkylene-$CO_2C_{1-6}$alkyl), —$SO_2(C_{1-6}$alkyl), —$SO_2NR^gR^h$ (where $R^g$ is hydrogen or —$C_{1-6}$alkyl and $R^h$ is hydrogen, —$C_{1-6}$alkyl, —$C_{1-6}$alkylene-$CO_2H$, or —$C_{1-6}$alkylene-$CO_2C_{1-6}$alkyl), tetrazolyl, pyridinyl, pyrimidinyl, pyrazinyl, pyridazinyl, pyrazolyl, imidazolyl, oxazolyl, thiazolyl, oxadiazolyl, thiadiazolyl, furanyl, thienyl, pyrrolyl or isoxazolyl, (wherein each of the aforementioned heteroaryl rings is optionally substituted with one or two substituents independently selected from $C_{1-6}$alkyl, halo, CN, —$CO_2H$, —$COOC_{1-6}$alkyl, —$C_{1-6}$alkyl, —$OC_{1-6}$alkyl, —$C_{1-6}$alkyl substituted with one to five fluoro, —$OC_{1-6}$alkyl (substituted with one to five fluoro, tetrazolyl, —$SO_2C_{1-6}$alkyl, —$SO_2NH_2$, —$SO_2NHC_{1-6}$alkyl, —$SO_2N(C_{1-6}$alkyl$)_2$, —$CONH_2$, —$CONHC_{1-6}$alkyl, and —$CON(C_{1-6}$alkyl$)_2$); and the $R^5$ heteroaryl ring is additionally optionally substituted with one or two substituents, independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 23

In embodiment 23, the compounds of embodiment 1 or 20 and subembodiments contained therein are those wherein $R^5$ is 5-10 membered heteroaryl$C_{1-6}$alkyl having one to 3 heteroatoms independently selected from N, O, or S wherein the heteroaryl ring is substituted with phenyl [wherein the phenyl ring is optionally substituted with one, two, or three substituents independently selected from hydroxyl, halo, CN, —$CO_2H$, —$COOC_{1-6}$alkyl, —$C_{1-6}$alkyl, —$OC_{1-6}$alkyl, —$C_{1-6}$alkyl (wherein alkyl is substituted with one to five fluoro), —$OC_{1-6}$alkyl (wherein alkyl is substituted with one to five fluoro), —$C_{1-6}$alkylene-$CO_2H$, —$C_{1-6}$alkylene-$CO_2C_{1-6}$alkyl, tetrazolyl, —$SO_2C_{1-6}$alkyl, —$SO_2NH_2$, —$SO_2NHC_{1-6}$alkyl, —$SO_2N(C_{1-6}$alkyl$)_2$, —$CONH_2$, —$CONHC_{1-6}$alkyl, and —$CON(C_{1-6}$alkyl$)_2$]; and the $R^5$ heteroaryl ring is further optionally substituted with two substituents independently selected from —$C_{1-6}$alkyl, —$C_{1-6}$alkyl (wherein alkyl is substituted with one to five fluoro), —O—$C_{1-6}$alkyl, —$OC_{1-6}$alkyl (wherein alkyl is substituted with one to five fluoro), halo, CN, —$NH_2$, and hydroxy.

Embodiment 24

In embodiment 24, the compounds of embodiment 1, 20, 21, 22, or 23 and subembodiments contained therein are those wherein the heteroaryl ring in the —$CH_2$-(5-10 membered heteroaryl ring) of $R^5$ is selected from thienyl, furanyl, pyrazolyl, imidazolyl, triazolyl, pyridinyl, pyrazinyl, pyridazinyl, pyrimidinyl, oxazolyl, oxadiazolyl, isoxazolyl, thiazolyl, thiadiazolyl, benzimidazolyl, benzofuranyl, benzoxazolyl, indolyl, and benzothienyl. In one subembodiment of embodiment 24, the heteroaryl ring is a 9- or 10-membered heteroaryl ring selected from benzimidazol-5-yl, benzoxazol-5-yl, indol-5-yl, benzimidazol-2-yl, benzoxazol-2-yl, benzofuran-5-yl, indol-2-yl, quinolinyl, or isoquinolinyl. In one subembodiment of embodiment 24, the heteroaryl ring is 5-membered heteroaryl ring that is preferably substituted at the 3-position to the ring atom of the 5-membered ring that is attached to —$CH_2$—, and the 6-membered heteroaryl ring is substituted at a meta or para position to the ring atom that is attached to the —$CH_2$— and furthermore, the above rings are optionally substituted, preferably substituted, with one or more substituent(s) as indicated in embodiments 20, 21, 22, or 23 above.

Embodiment 25

In embodiment 25, the compounds of any one of embodiments 1-24 and subembodiments contained therein are those wherein $R^3$ is hydrogen, X is O, and Y is O.

Embodiment 26

In embodiment 26, the compounds of any one of embodiments 1-24 and subembodiments contained therein are those wherein $R^3$ is hydrogen, $C_{1-6}$alkyl, or benzyl, X is $CH_2$, and Y is O. In one group of compounds within embodiment 26, $R^3$ is hydrogen, X is $CH_2$, and Y is O.

Embodiment 27

In embodiment 27, the compounds of any one of embodiments 1-24 and subembodiments contained therein are those wherein $R^3$ is hydrogen, X is N. Within embodiment 27, in one group of compounds Y is O. Within embodiment 27, in another group of compounds Y is S.

Embodiment 28

In embodiment 28, the compounds of any one of embodiments 1-24 and subembodiments contained therein are those wherein $R^3$ is hydrogen, X is O, and Y is S.

Embodiment 29

In embodiment 29, the compounds of any one of embodiments 1-24 and subembodiments contained therein and groups contained therein are those wherein $R^3$ is hydrogen, X is $CH_2$, and Y is S.

Embodiment 30

In embodiment 30, the compounds of any one of embodiments 1-29 and subembodiments contained therein and groups contained therein are those wherein:

$R^{1a}$ is hydroxy, halo, $C_{1-6}$alkyl, cyano, azido, $NH_2$, $C_{1-6}$alkylcarbonyloxy, ethynyl, or vinyl; preferably hydroxy, fluoro, chloro, cyano, azido, $NH_2$, or methyl;

$R^{1b}$ is hydrogen;

$R^{2a}$ is hydrogen, hydroxy, halo, $C_{1-6}$alkyl, $NH_2$, cyano, azido, ethynyl, or vinyl; and $R^{2b}$ is hydrogen.

Embodiment 31

In embodiment 31, the compounds of embodiment 30 are those wherein:

$R^{1a}$ is hydroxy, fluoro, or methyl;
$R^{1b}$ is hydrogen;
$R^{2a}$ is hydroxy, fluoro, or methyl; and
$R^{2b}$ is hydrogen.

Embodiment 32

In embodiment 32, the compounds of embodiment 30 are those wherein:

$R^{1a}$ is fluoro;
$R^{1b}$ is hydrogen;
$R^{2a}$ is hydroxy, hydrogen, methyl or $NH_2$; and
$R^{2b}$ is hydrogen.

Within embodiment 32, in one group of compounds $R^{2a}$ is hydrogen.

Within embodiment 32, in another group of compounds $R^{2a}$ is hydroxy.

Within embodiment 32, in yet another group of compounds $R^{2a}$ is methyl.

Within embodiment 32, in yet another group of compounds $R^{2a}$ is $NH_2$.

Embodiment 33

In embodiment 33, the compounds of embodiment 30, 31 and 32 and groups contained therein are those wherein:

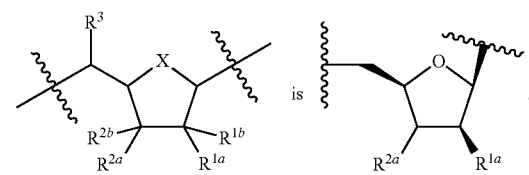

Embodiment 34

In embodiment 34, the compounds of embodiment 30, 31 and 32 and groups contained therein are those wherein:

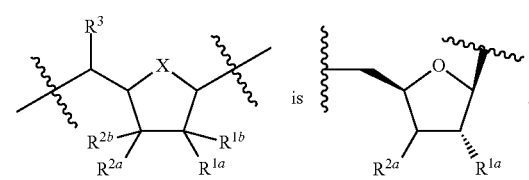

Embodiment 35

In embodiment 35, the compounds of embodiment 30, 31 and 32 and groups contained therein are those wherein:

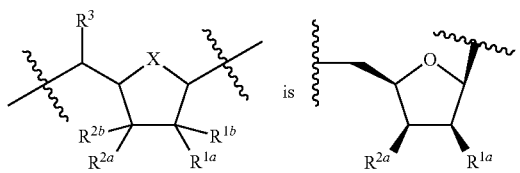

Embodiment 36

In embodiment 36, the compounds of embodiment 30, 31 and 32 and groups contained therein are those wherein:

Embodiment 37

In embodiment 37, the compounds of embodiment 30, 31 and 32 and groups contained therein are those wherein:

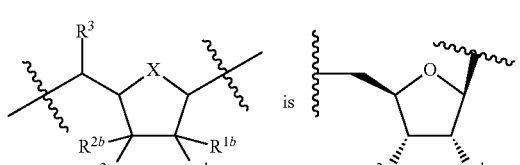

Embodiment 38

In embodiment 38, the compounds of embodiment 30, 31 and 32 and groups contained therein are those wherein:

Embodiment 39

In embodiment 39, the compounds of any one of embodiments 1-29 are those wherein:

$R^{1a}$ is halo, $C_{1-6}$alkyl, cyano, azido, $NH_2$, $C_{1-6}$alkylcarbonyloxy, ethynyl, or vinyl;
$R^{1b}$ is hydroxy or fluoro;
$R^{2a}$ is hydrogen, halo, hydroxy, $C_{1-6}$alkyl, $C_{1-6}$alkyloxy, $NH_2$, ethynyl, or vinyl; and
$R^{2b}$ is hydrogen.

Embodiment 40

In embodiment 40, the compounds of embodiment 39 are those wherein:
$R^{1a}$ is fluoro or methyl;
$R^{1b}$ is fluoro or hydroxy;
$R^{2a}$ is hydrogen, hydroxy, $NH_2$, methyl, methoxy, ethoxy, or propoxy; and
$R^{2b}$ is hydrogen.

Embodiment 41

In embodiment 41, the compounds of embodiments any one of embodiments 1-29 are those wherein:
$R^{1a}$ is hydroxy, halo, $C_{1-6}$alkyl, or cyano;
$R^{1b}$ is hydrogen;
$R^{2a}$ is hydroxy, halo, $C_{1-6}$alkyl, cyano, ethynyl, or vinyl; and
$R^{2b}$ is halo, hydroxy, or $C_{1-6}$alkyl.

Embodiment 42

In embodiment 42, the compound of embodiment 42 are those wherein:
$R^{1a}$ is hydroxy, fluoro, or methyl;
$R^{1b}$ is hydrogen;
$R^{2a}$ is methyl, fluoro, cyano, or hydroxy; and
$R^{2b}$ is fluoro, hydroxyl, or methyl.

Embodiment 43

In embodiment 43, the compound of embodiment 42 are those wherein:
$R^{1a}$ is fluoro or methyl;
$R^{1b}$ is hydrogen;
$R^{2a}$ is methyl; and
$R^{2b}$ is fluoro, hydroxy, or methyl.

Embodiment 44

In embodiment 44, the compound of any one of embodiments 1-29 and subembodiments and groups of compounds contained therein are those wherein:
$R^{1a}$ is halo, $C_{1-6}$alkyl, cyano, azido, $NH_2$, $C_{1-6}$alkylcarbonyloxy, ethynyl, or vinyl;
$R^{1b}$ is hydroxy or fluoro;
$R^{2a}$ is hydroxy, halo, $C_{1-6}$alkyl, or cyano; and
$R^{2b}$ is halo, hydroxy, or $C_{1-6}$alkyl.

Embodiment 45

In embodiment 45, the compounds of any one of embodiments 1 to 45 and subembodiments and groups of compounds contained therein are those wherein:
$R^4$ is selected from —C(O)$OR^9$, —C(O)$NR^{11}R^{12}$, —S(O)$_2$ $R^{10}$, —P(O)(O$R^{11}$)(O$R^{12}$), and —P(O)(O$R^{11}$)(N$R^{13}R^{15}$); and
$R^6$ is selected from —C(O)$OR^9$ and —P(O)(O$R^{11}$)(O$R^{12}$); wherein: $R^9$, $R^{10}$, $R^{11}$, $R^{12}$, $R^{13}$ and $R^{15}$ are independently hydrogen or $C_{1-6}$ alkyl.

Within the groups of compounds in embodiment 46, in one group of compounds, $R^4$ and $R^6$ are —C(O)$OR^9$ where $R^9$ is as defined above, preferably $R^9$ is hydrogen or $C_{1-6}$ alkyl.

Within the groups of compounds in embodiment 46, in another group of compounds, $R^4$ and $R^6$ are —C(O)OH.

Within the groups of compounds in embodiment 46, in yet another group of compounds, $R^4$ is selected from —C(O)$NR^{11}R^{12}$ or —S(O)$_2R^{11}$; and
$R^6$ is selected from —C(O)$OR^9$ and —P(O)(O$R^{11}$)(O$R^{12}$); wherein: $R^9$, $R^{11}$, and $R^{12}$ are independently hydrogen or $C_{1-6}$ alkyl. In one subembodiment, the compounds are those wherein $R^9$, $R^{11}$, and $R^{12}$ are independently hydrogen, methyl, or ethyl.

Within the groups of compounds in embodiment 46, in yet another group of compounds, $R^4$ is P(O)(O$R^{11}$)(O$R^{12}$); and
$R^6$ is —P(O)(O$R^{11}$)(O$R^{12}$); wherein:
$R^{11}$ and $R^{12}$ are independently hydrogen or $C_{1-6}$ alkyl, preferably $R^{11}$ and $R^{12}$ are independently hydrogen, methyl, or ethyl.

Embodiment 46

In embodiment 46, the compounds of embodiments 1 to 46 and subembodiments and groups of compounds contained therein are those wherein:

Het is a group selected from a group of formula (i) through (xiv) below:

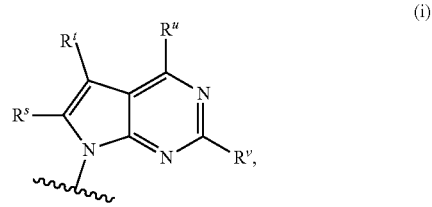

(i)

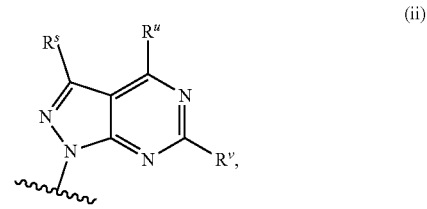

(ii)

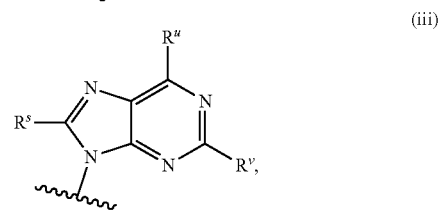

(iii)

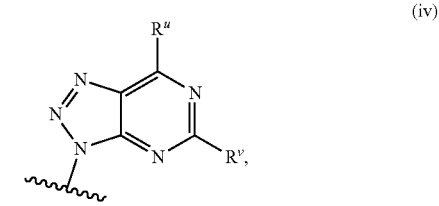

(iv)

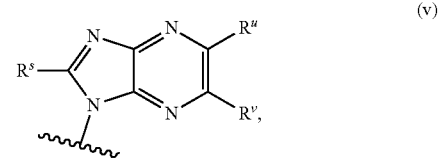

(v)

-continued (vi) 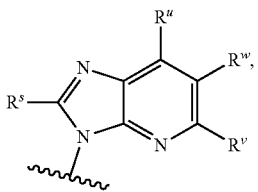

(vii) 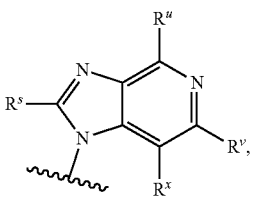

(viii) 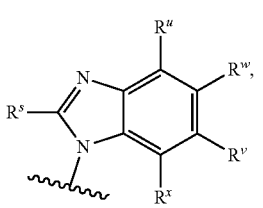

(ix) 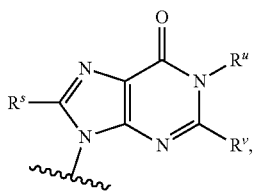

(x) 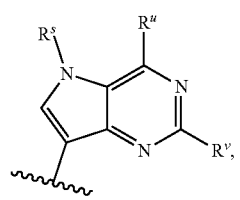

(xi) 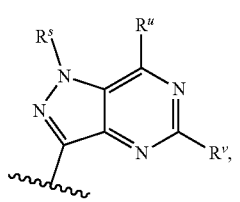

(xii) 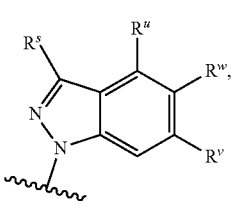

(xiii) 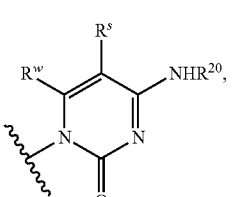

-continued (xiv) 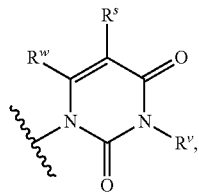

(xv) 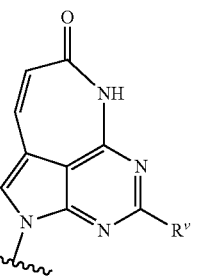 or (xvi) 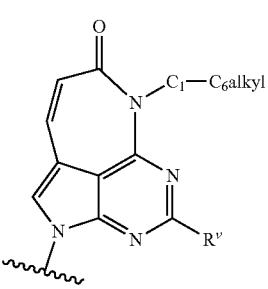

wherein:

$R^u$ is hydrogen, halo, cyano, —NH$_2$, —NHR$^{20}$, —NH-COR$^{20}$, —NHCOR$^{20}$, —NR$^{20}$R$^{21}$, —R$^{20}$, —SR$^{20}$, —OH, and —OR$^{20}$;

$R^w$ is hydrogen, halo, —NHR$^{22}$, —NR$^{22}$R$^{23}$, —R$^{22}$, —OH, and —OR$^{22}$;

$R^v$ and $R^x$ are independently hydrogen, halo, haloC$_{1-6}$alkyl, —NH$_2$, —NHR$^{24}$, —NR$^{24}$R$^{25}$, —R$^{24}$, —SR$^{24}$, cyano, —OH, —OR$^{24}$, —SO$_2$R$^{24}$, —C$_{1-6}$ alkyleneNH$_2$, —C$_{1-6}$alkyleneNHR$^{24}$, —C$_{1-6}$alkyleneNR$^{24}$R$^{25}$, —R$^{24}$, —C$_{1-6}$alkyleneSR$^{24}$, —C$_{1-6}$alkyleneOH, —C$_{1-6}$alkyleneOR$^{24}$, —C$_{1-6}$alkyleneSO$_2$R$^{24}$, $R^s$ and $R^t$ are independently hydrogen, halo, or C$_{1-6}$alkyl; and wherein:

$R^{20}$, $R^{21}$, $R^{22}$, $R^{23}$, $R^{24}$ and $R^{25}$ are independently optionally substituted C$_{1-6}$alkyl, —C$_2$-C$_6$alkenyl, —C$_2$-C$_6$alkynyl, optionally substituted cycloalkyl, optionally substituted cycloalkylC$_{1-6}$alkyl, optionally substituted heterocyclyl, optionally substituted heterocyclylC$_{1-6}$alkyl, optionally substituted aryl, optionally substituted arylC$_{1-6}$alkyl, optionally substituted heteroaryl, or optionally substituted heteroarylC$_{1-6}$alkyl; or $R^{20}$ and $R^{21}$, $R^{22}$ and $R^{23}$ and $R^{24}$ and $R^{25}$ together with the nitrogen to which they are attached form an optionally substituted nitrogen-containing heterocyclyl.

Embodiment 47

In embodiment 47, the compounds of embodiment 47 are those wherein Het is a group of formula (i).

Embodiment 48

In embodiment 48, the compounds of embodiment 47 are those wherein Het is a group of formula (ii).

Embodiment 49

In embodiment 49, the compounds of embodiment 47 are those wherein Het is a group of formula (iii).

Embodiment 50

In embodiment 50, the compounds of embodiment 47 are those wherein Het is a group of formula (iv).

Embodiment 51

In embodiment 51, the compounds of embodiment 47 are those wherein Het is a group of formula (vi).

Embodiment 52

In embodiment 52, the compounds of embodiment 47 are those wherein Het is a group of formula (vii).

Embodiment 53

In embodiment 53, the compounds of embodiment 47 are those wherein Het is a group of formula (viii).

Embodiment 54

In embodiment 54, the compounds of any one of embodiments 47-54 and subembodiments and groups of compounds contained therein are those wherein $R^s$ is hydrogen.

Embodiment 55

In embodiment 55, the compounds of any one of embodiments 47-55 and subembodiments and groups of compounds contained therein are those wherein $R^w$ and $R^d$ are hydrogen.

Embodiment 56

In embodiment 56, the compounds of any one of embodiments 47-56 and embodiments and groups of compounds contained therein are those wherein:
$R^u$ is hydrogen, halo, cyano, —NH$_2$, —NHR$^{20}$, —NH-COR$^{20}$, —NR$^{20}$R$^{21}$, —R$^{20}$, —SR$^{20}$, or —OR$^{20}$ wherein R$^{20}$ and R$^{21}$ are independently optionally substituted C$_{1-6}$alkyl, optionally substituted cycloalkyl, optionally substituted cycloalkylC$_{1-6}$alkyl, optionally substituted heterocyclyl, optionally substituted heterocyclylC$_{1-6}$alkyl, optionally substituted aryl, optionally substituted arylC$_{1-6}$alkyl, optionally substituted heteroaryl, or optionally substituted heteroarylC$_{1-6}$alkyl; or R$^{20}$ and R$^{21}$ together with the nitrogen to which they are attached form an optionally substituted nitrogen-containing heterocyclyl;
$R^v$ is hydrogen, halo, haloC$_{1-6}$alkyl, cyano, —R$^{24}$, —SR$^{24}$, —OR$^{24}$, or —SO$_2$R$^{24}$; wherein:
$R^{24}$ is optionally substituted C$_{1-6}$alkyl, —C$_2$-C$_6$alkenyl, —C$_2$-C$_6$alkynyl, optionally substituted cycloalkyl, optionally substituted cycloalkylC$_{1-6}$alkyl, optionally substituted heterocyclyl, optionally substituted heterocyclylC$_{1-6}$alkyl, optionally substituted aryl, optionally substituted arylC$_{1-6}$alkyl, optionally substituted heteroaryl, or optionally substituted heteroarylC$_{1-6}$alkyl.

Embodiment 57

In embodiment 57, the compounds of any one of embodiments 47-56 and subembodiments and groups of compounds contained therein are those wherein:
$R^u$ is —NH$_2$, —NHR$^2$, or —NR$^{20}$R$^{21}$ wherein R$^{20}$ and R$^{21}$ are independently optionally substituted C$_{1-6}$alkyl, optionally substituted cycloalkyl, optionally substituted cycloalkylC$_{1-6}$alkyl, optionally substituted heterocyclyl, optionally substituted heterocyclylC$_{1-6}$alkyl, optionally substituted aryl, optionally substituted arylC$_{1-6}$alkyl, optionally substituted heteroaryl, or optionally substituted heteroarylC$_{1-6}$alkyl; or R$^{20}$ and R$^{21}$ together with the nitrogen to which they are attached form an optionally substituted nitrogen-containing heterocyclyl; preferably —NH$_2$, and $R^v$ is halo, preferably chloro.

In some embodiments, the following compounds are included in the compound of Formula (I). In certain preferred embodiments of Embodiments 1-57, the compound of Formula (I) is not:

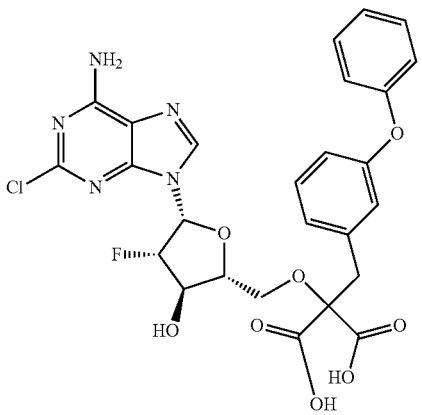 [SMILES: Nc1nc(Cl)nc2c1ncn2[C@@H]1O[C@H](COC(Cc2cccc(Oc3ccccc3)c2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonic acid;

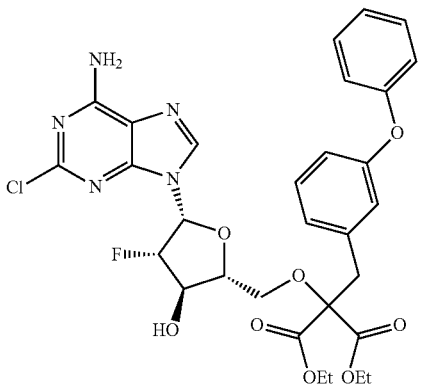 [SMILES: CCOC(=O)C(Cc1cccc(Oc2ccccc2)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonate;

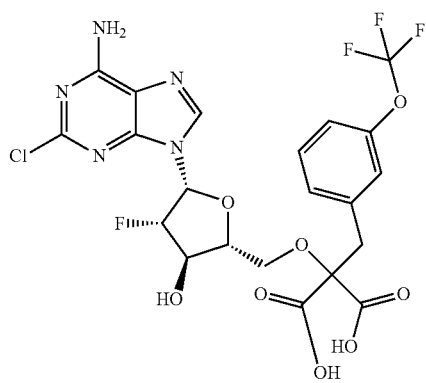 [SMILES: Nc1nc(Cl)nc2c1ncn2[C@@H]1O[C@H](COC(Cc2cccc(OC(F)(F)F)c2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonic acid;

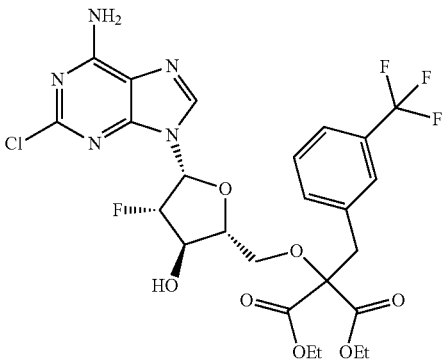

diethyl 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonate;

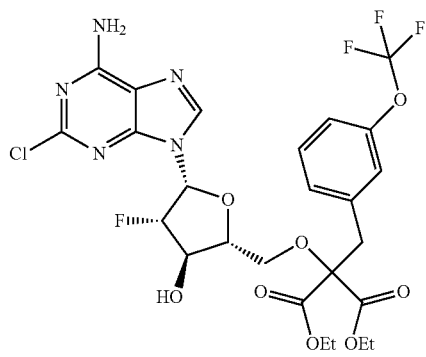 [SMILES: CCOC(=O)C(Cc1cccc(OC(F)(F)F)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonate;

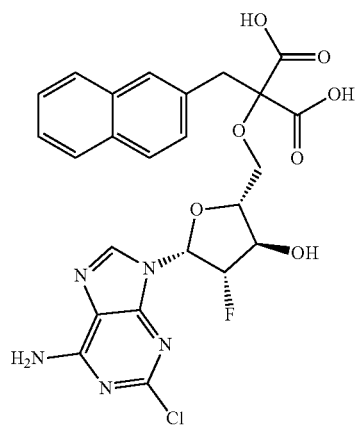

2-(((2R,3R,4S,5R)-5-(6-amino-2-chloro-9H-purin-9-yl)-4-fluoro-3-hydroxytetrahydrofuran-2-yl)methoxy)-2-(naphthalen-2-ylmethyl)malonic acid;

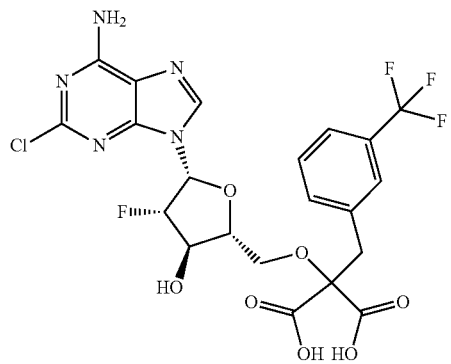 [SMILES: Nc1nc(Cl)nc2c1ncn2[C@@H]1O[C@H](COC(Cc2cccc(C(F)(F)F)c2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonic acid;

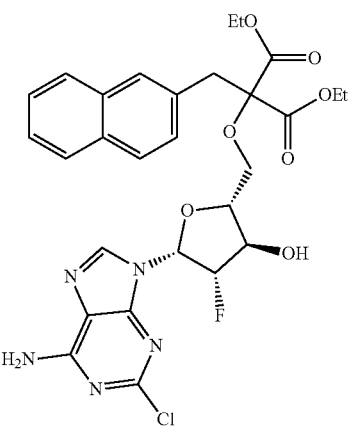 [SMILES: CCOC(=O)C(Cc1ccc2ccccc2c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(naphthalen-2-ylmethyl)malonate;

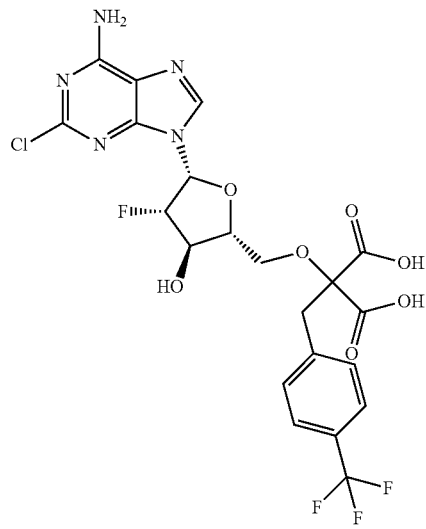 [SMILES: Nc1nc(Cl)nc2c1ncn2[C@@H]1O[C@H](COC(Cc2ccc(C(F)(F)F)cc2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonic acid;

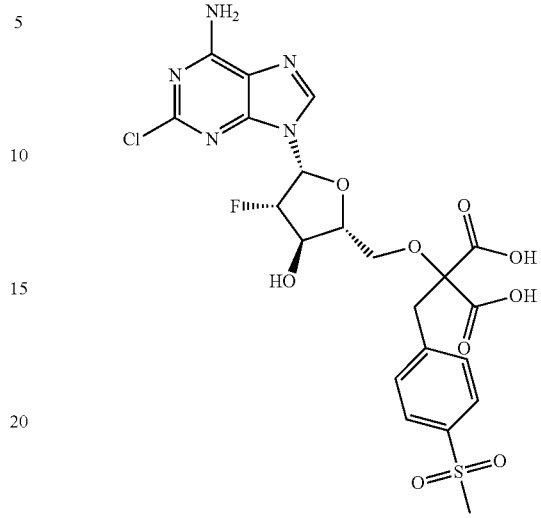

2-(((2R,3R,4S,5R)-5-(6-amino-2-chloro-9H-purin-9-yl)-4-fluoro-3-hydroxytetrahydrofuran-2-yl)methoxy)-2-(4-(methyl sulfonyl)benzyl)malonic acid;

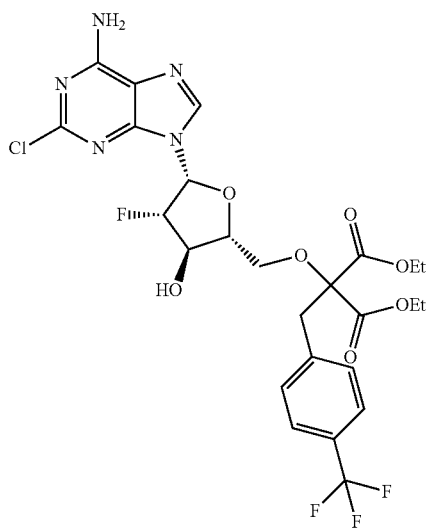 [SMILES: CCOC(=O)C(Cc1ccc(C(F)(F)F)cc1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonate;

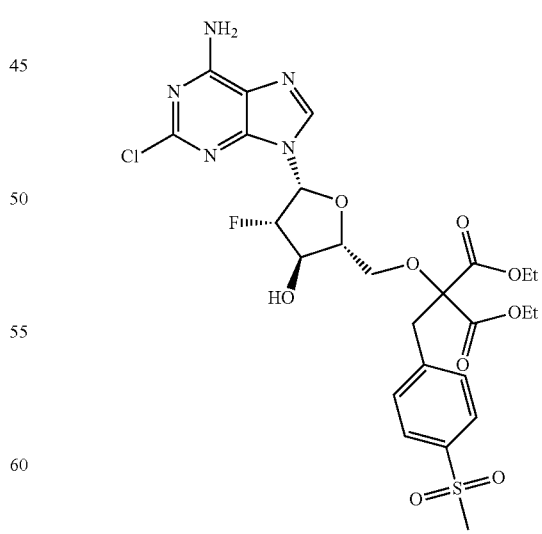

diethyl 2-(((2R,3R,4S,5R)-5-(6-amino-2-chloro-9H-purin-9-yl)-4-fluoro-3-hydroxytetrahydrofuran-2-yl)methoxy)-2-(4-(methylsulfonyl)benzyl)malonate;

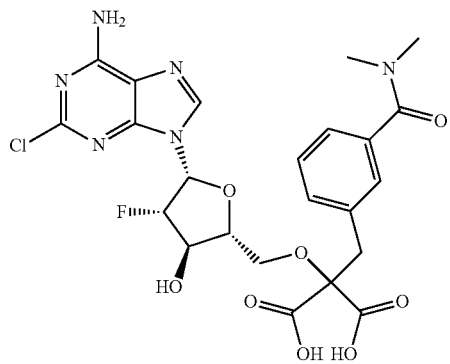 [SMILES: CN(C)C(=O)c1cccc(CC(OC[C@H]2O[C@@H](n3cnc4c(N)nc(Cl)nc43)[C@@H](F)[C@@H]2O)(C(=O)O)C(=O)O)c1]

2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonic acid;

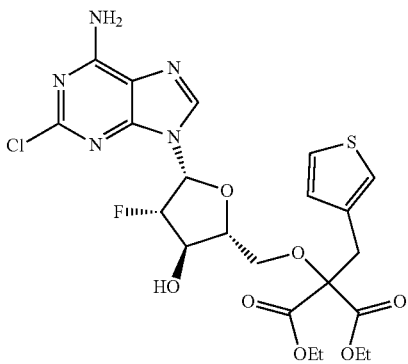

diethyl 2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonate;

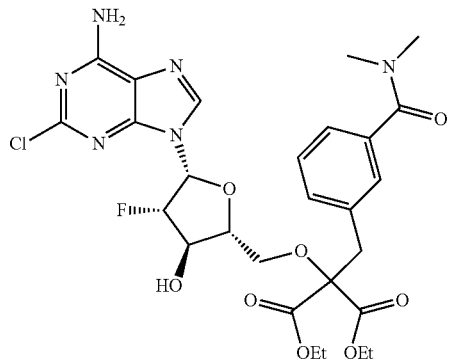 [SMILES: CCOC(=O)C(Cc1cccc(C(=O)N(C)C)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonate;

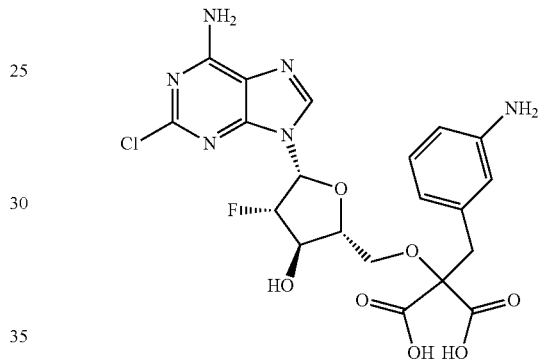

2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonic acid;

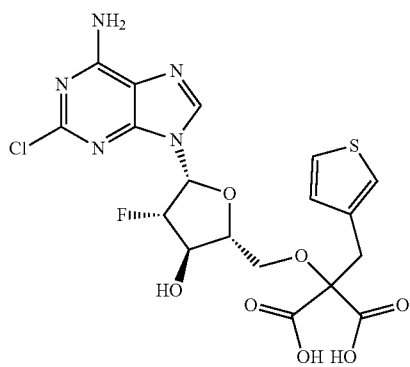 [SMILES: Nc1nc(Cl)nc2c1ncn2[C@@H]1O[C@H](COC(Cc2ccsc2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonic acid;

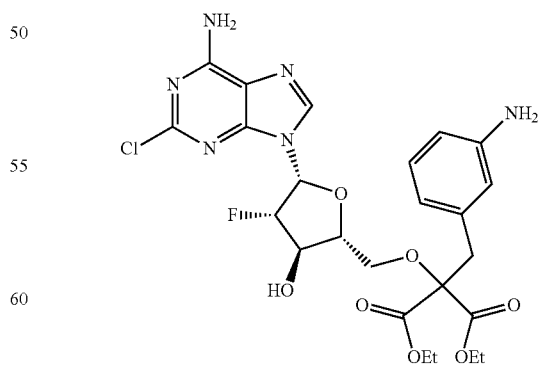

diethyl 2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonate;

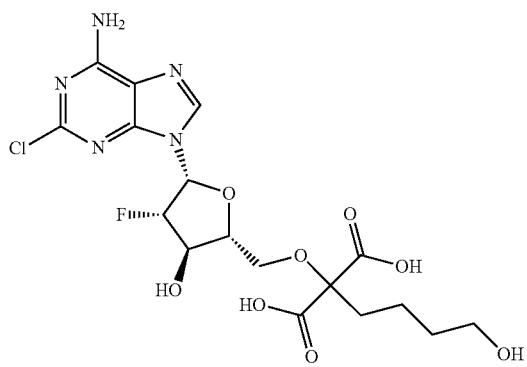 [SMILES: Nc1nc(Cl)nc2c1ncn2[C@@H]1O[C@H](COC(CCCCO)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonic acid;

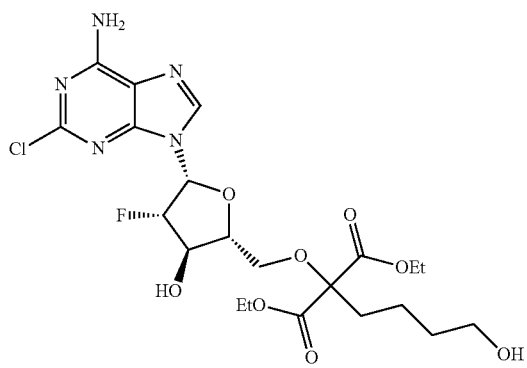 [SMILES: CCOC(=O)C(CCCCO)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonate;

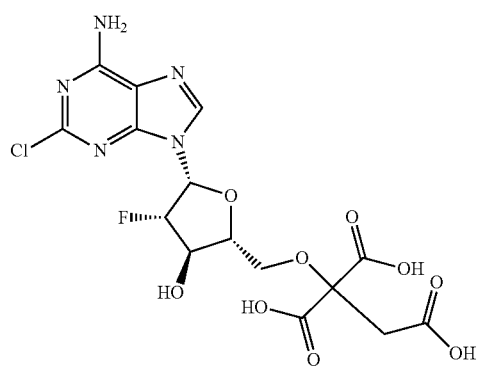 [SMILES: Nc1nc(Cl)nc2c1ncn2[C@@H]1O[C@H](COC(CC(=O)O)(C(=O)O)C(=O)O)[C@@H](O)[C@@H]1F]

1-(((2R,3R,4S,5R)-5-(6-amino-2-chloro-9H-purin-9-yl)-4-fluoro-3-hydroxytetrahydrofuran-2-yl)methoxy)ethane-1,1,2-tricarboxylic acid;

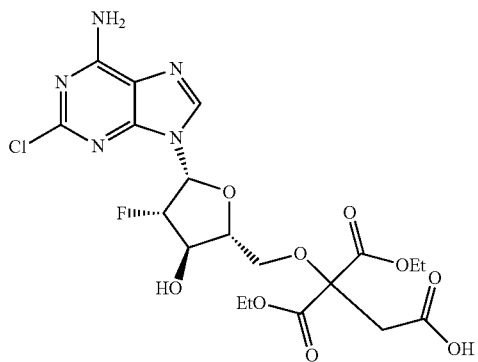 [SMILES: CCOC(=O)C(CC(=O)O)(OC[C@H]1O[C@@H](n2cnc3c(N)nc(Cl)nc32)[C@@H](F)[C@@H]1O)C(=O)OCC]

3-(((2R,3R,4S,5R)-5-(6-amino-2-chloro-9H-purin-9-yl)-4-fluoro-3-hydroxytetrahydrofuran-2-yl)methoxy)-4-ethoxy-3-(ethoxycarbonyl)-4-oxobutanoic acid;

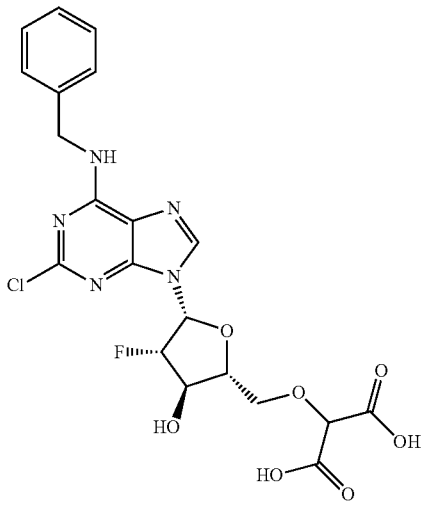 [SMILES: O=C(O)C(OC[C@H]1O[C@@H](n2cnc3c(NCc4ccccc4)nc(Cl)nc32)[C@@H](F)[C@@H]1O)C(=O)O]

2-(((2R,3R,4S,5R)-5-(6-(benzylamino)-2-chloro-9H-purin-9-yl)-4-fluoro-3-hydroxytetrahydrofuran-2-yl)methoxy)malonic acid;

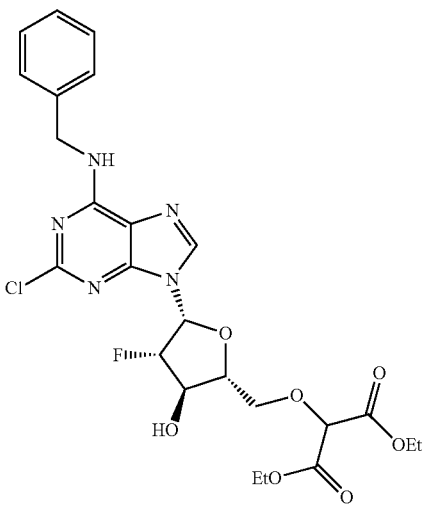 [SMILES: CCOC(=O)C(OC[C@H]1O[C@@H](n2cnc3c(NCc4ccccc4)nc(Cl)nc32)[C@@H](F)[C@@H]1O)C(=O)OCC]

diethyl 2-(((2R,3R,4S,5R)-5-(6-(benzylamino)-2-chloro-9H-purin-9-yl)-4-fluoro-3-hydroxytetrahydrofuran-2-yl)methoxy)malonate;

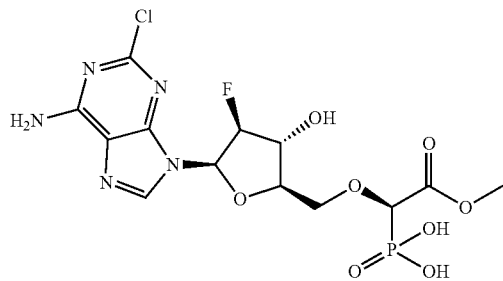 [SMILES: COC(=O)[C@H](OC[C@H]1O[C@@H](n2cnc3c(N)nc(Cl)nc32)[C@@H](F)[C@@H]1O)P(=O)(O)O]

((R)-1-(((2R,3R,4S,5R)-5-(6-amino-2-chloro-9H-purin-9-yl)-4-fluoro-3-hydroxytetrahydrofuran-2-yl)methoxy)-2-methoxy-2-oxoethyl)phosphonic acid;

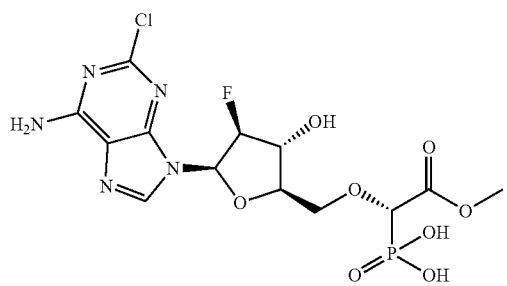 [SMILES: COC(=O)[C@@H](OC[C@H]1O[C@@H](n2cnc3c(N)nc(Cl)nc32)[C@@H](F)[C@@H]1O)P(=O)(O)O]

((S)-1-(((2R,3R,4S,5R)-5-(6-amino-2-chloro-9H-purin-9-yl)-4-fluoro-3-hydroxytetrahydrofuran-2-yl)methoxy)-2-methoxy-2-oxoethyl)phosphonic acid;

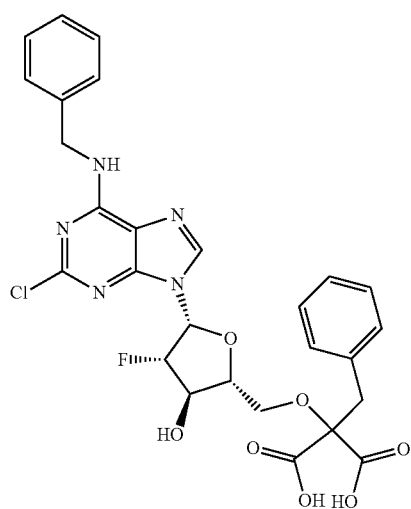 [SMILES: O=C(O)C(Cc1ccccc1)(OC[C@H]1O[C@@H](n2cnc3c(NCc4ccccc4)nc(Cl)nc32)[C@@H](F)[C@@H]1O)C(=O)O]

2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonic acid;

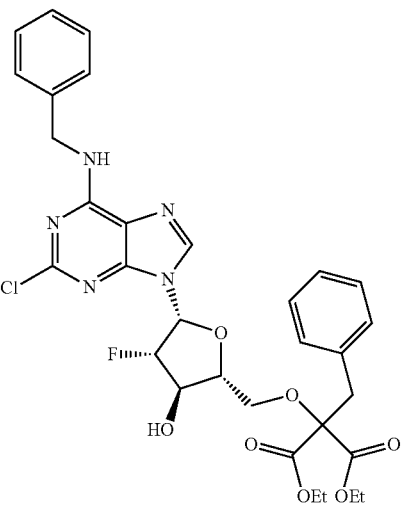 [SMILES: CCOC(=O)C(Cc1ccccc1)(OC[C@H]1O[C@@H](n2cnc3c(NCc4ccccc4)nc(Cl)nc32)[C@@H](F)[C@@H]1O)C(=O)OCC]

diethyl 2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonate;

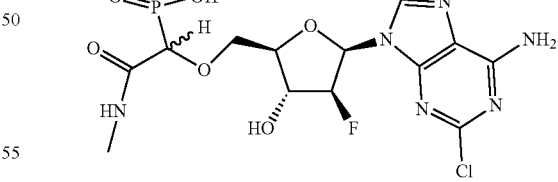

((R)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid;

((S)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid;

or a pharmaceutically acceptable salt thereof.

Representative compounds of Formula I include those in Table 1:

TABLE 1

| Cpd. # | Compound | Name |
|---|---|---|
| 1 | Isomer 1 | (1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic acid |
| 2 | Isomer 2 | (1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic acid |
| 3 | Isomer 1 | (1-(((2R,3R,4S,5R)-5-(6-((tert-butoxycarbonyl)amino)-2-chloro-9H-purin-9-yl)-4-fluoro-3-hydroxytetrahydrofuran-2-yl)methoxy)-2-ethoxy-2-oxoethyl)phosphonic acid |
| 4 | Isomer 2 | (1-(((2R,3R,4S,5R)-5-(6-((tert-butoxycarbonyl)amino)-2-chloro-9H-purin-9-yl)-4-fluoro-3-hydroxytetrahydrofuran-2-yl)methoxy)-2-ethoxy-2-oxoethyl)phosphonic acid |

TABLE 1-continued

| Cpd. # | Compound | Name |
|---|---|---|
| 5 | | 2-(((2R,3R,4S,5R)-5-(6-amino-2-chloro-9H-purin-9-yl)-4-fluoro-3-hydroxytetrahydro-furan-2-yl)methoxy)malonic acid |
| 6 | | 2-(((2R,3R,4S,5R)-5-(6-amino-2-chloro-9H-purin-9-yl)-4-fluoro-3-hydroxytetrahydro-furan-2-yl)methoxy)-2-benzylmalonic acid |
| 7 | | 2-(((2R,3R,4S,5R)-5-(6-amino-2-chloro-9H-purin-9-yl)-4-fluoro-3-hydroxytetrahydro-furan-2-yl)methoxy)-2-(4-carboxybenzyl)-malonic acid |
| 8 | | 2-(((2R,3R,4S,5R)-5-(6-amino-2-chloro-9-purin-9-yl)-4-fluoro-3-hydroxytetrahydro-furan-2-yl)methoxy)-2-((6-chloropyridin-3-yl)methyl)malonic acid |
| 9 | | 2-(((2R,3R,4R,5R)-5-(6-amino-9H-purin-9-yl)-4-fluoro-3-hydroxytetrahydrofuran-2-yl)-methoxy)malonic acid |

TABLE 1-continued

| Cpd. # | Compound | Name |
| --- | --- | --- |
| 10 | | 2-(((2R,3R,4R,5R)-5-(6-amino-9H-purin-9-yl)-4-fluoro-3-hydroxytetrahydrofuran-2-yl)methoxy)-2-benzylmalonic acid |
| 11 | | 2-(((2R,3S,5R)-5-(6-amino-2-chloro-9H-purin-9-yl)-3-hydroxytetrahydrofuran-2-yl)-methoxy)malonic acid |
| 12 | | 2-(((2R,3R,4S,5R)-5-(6-amino-2-chloro-9H-purin-9-yl)-4-fluoro-3-hydroxytetrahydrofuran-2-yl)methoxy)-2-(4-(2-carboxyethyl)benzyl)malonic acid |
| 13 | | 2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonic acid |
| 14 | | 2-(((2R,3S,5R)-3-hydroxy-5-(5-methyl-2,4-dioxo-3,4-dihydropyrimidin-1(2H)-yl)tetrahydrofuran-2-yl)methoxy)malonic acid |

TABLE 1-continued

| Cpd. # | Compound | Name |
|---|---|---|
| 15 | | 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonic acid |
| 16 | | 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonic acid |
| 17 | | 2-(((2R,3R,4S,5R)-5-(6-amino-2-chloro-9H-purin-9-yl)-4-fluoro-3-hydroxytetrahydrofuran-2-yl)methoxy)-2-(naphthalen-2-ylmethyl)malonic acid |
| 18 | | 2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonic acid |
| 19 | | 1-(((2R,3R,4S,5R)-5-(6-amino-2-chloro-9H-purin-9-yl)-4-fluoro-3-hydroxytetrahydrofuran-2-yl)methoxy)ethane-1,1,2-tricarboxylic acid |

TABLE 1-continued

| Cpd. # | Compound | Name |
| --- | --- | --- |
| 20 | | 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonic acid |
| 21 | | 2-(((2R,3R,4S,5R)-5-(6-amino-2-chloro-9H-purin-9-yl)-4-fluoro-3-hydroxytetrahydrofuran-2-yl)methoxy)-2-(4-(methylsulfonyl)benzyl)malonic acid |
| 22 | | 2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonic acid |
| 23 | | 2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonic acid |
| 24 | | (1-(((2R,3R,4S,5R)-5-(6-amino-2-chloro-9H-purin-9-yl)-4-fluoro-3-hydroxytetrahydrofuran-2-yl)methoxy)-2-methoxy-2-oxoethyl)phosphonic acid |

TABLE 1-continued

| Cpd. # | Compound | Name |
|---|---|---|
| 25 | | diethyl 2-(((2R,3R,4S,5R)-5-(6-amino-2-chloro-9H-purin-9-yl)-4-fluoro-3-(isobutyryloxy)tetrahydrofuran-2-yl)methoxy)-2-(4-(trifluoromethoxy)benzyl)malonate |
| 26 | | 2-(((2R,3R,4S,5R)-5-(6-(benzylamino)-2-chloro-9H-purin-9-yl)-4-fluoro-3-hydroxytetrahydrofuran-2-yl)methoxy)malonic acid |
| 27 | | 2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonic acid |
| 28 | | 2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonic acid |

TABLE 1-continued

| Cpd. # | Compound | Name |
|---|---|---|
| 29 | | (1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid |
| 30 | | diethyl 2-(((2R,3R,4S,5R)-5-(6-amino-2-chloro-9H-purin-9-yl)-4-fluoro-3-hydroxytetrahydrofuran-2-yl)methoxy)succinate |
| 31 | | 2-(((2R,3R,4S,5R)-5-(6-amino-2-chloro-9H-purin-9-yl)-4-fluoro-3-hydroxytetrahydrofuran-2-yl)methoxy)succinic acid |
| 32 | | 2-(((2R,3R,4S,5R)-5-(6-amino-2-chloro-9H-purin-9-yl)-4-fluoro-3-hydroxytetrahydrofuran-2-yl)methoxy)-2-((6-(trifluoromethyl)pyridin-3-yl)methyl)malonic acid |
| 33 | | 2-(((2R,3R,4S,5R)-5-(6-amino-2-chloro-9H-purin-9-yl)-4-fluoro-3-hydroxytetrahydrofuran-2-yl)methoxy)-2-(cyanomethyl)malonic acid |

TABLE 1-continued

| Cpd. # | Compound | Name |
|---|---|---|
| 34 | | 2-(((2R,3R,4S,5R)-5-(6-amino-2-chloro-9H-purin-9-yl)-4-fluoro-3-hydroxytetrahydrofuran-2-yl)methoxy)-2-(4-cyanobenzyl)malonic acid |
| 35 | | 2-(((2R,3R,4S,5R)-5-(6-amino-2-chloro-9H-purin-9-yl)-4-fluoro-3-hydroxytetrahydrofuran-2-yl)methoxy)-2-(3-cyanobenzyl)malonic acid |
| 36 | | 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)malonic acid |
| 37 | Isomer 1 | 2-(((2R,3R,4S,5R)-5-(6-amino-2-chloro-9H-purin-9-yl)-4-fluoro-3-hydroxytetrahydrofuran-2-yl)methoxy)-3-ethoxy-3-oxo-2-(4-(trifluoromethoxy)benzyl)propanoic acid |

TABLE 1-continued

| Cpd. # | Compound | Name |
|---|---|---|
| 38 | 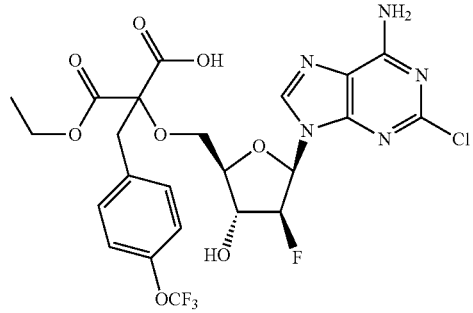 Isomer 2 | 2-(((2R,3R,4S,5R)-5-(6-amino-2-chloro-9H-purin-9-yl)-4-fluoro-3-hydroxytetrahydrofuran-2-yl)methoxy)-3-ethoxy-3-oxo-2-(4-(trifluoromethoxy)benzyl)propanoic acid |
| 39 | 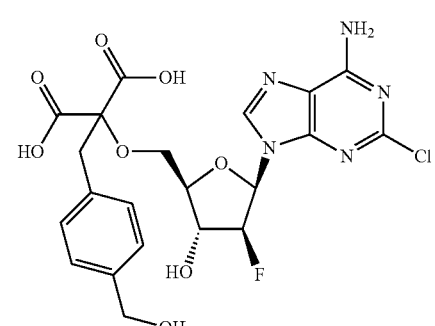 [SMILES: Nc1nc(Cl)nc2c1ncn2[C@@H]1O[C@H](COC(Cc2ccc(OC(F)(F)F)cc2)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydrofuran-2-yl)methoxy)-2-(4-(hydroxymethyl)benzyl)malonic acid |
| 40 | 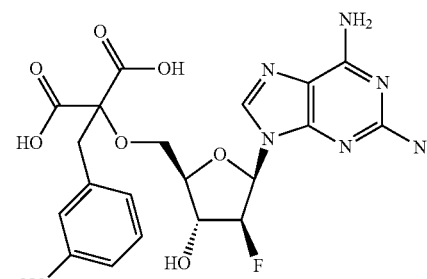 | 2-(((2R,3R,4S,5R)-5-(6-amino-2-azido-9H-purin-9-yl)-4-fluoro-3-hydroxytetrahydrofuran-2-yl)methoxy)-2-(3-cyanobenzyl)malonic acid |
| 41 | 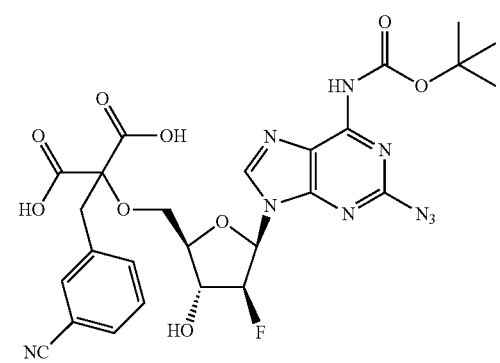 [SMILES: CC(C)(C)OC(=O)Nc1nc(N=[N+]=[N-])nc2c1ncn2[C@@H]1O[C@H](COC(Cc2cccc(C#N)c2)(C(=O)O)C(=O)O)[C@@H](O)[C@@H]1F] | 2-(((2R,3R,4S,5R)-5-(2-azido-6-((tert-butoxycarbonyl)amino)-9H-purin-9-yl)-4-fluoro-3-hydroxytetrahydrofuran-2-yl)methoxy)-2-(3-cyanobenzyl)malonic acid |

TABLE 1-continued

| Cpd. # | Compound | Name |
|---|---|---|
| 42 | | 2-(((2R,3R,4S,5R)-5-(6-amino-2-chloro-9H-purin-9-yl)-4-fluoro-3-hydroxytetrahydro-furan-2-yl)methoxy)-2-(3-carboxybenzyl)-malonic acid |
| 43 | | 2-(3-(1H-tetrazol-5-yl)benzyl)-2-(((2R,3R,4S,5R)-5-(6-amino-2-azido-9H-purin-9-yl)-4-fluoro-3-hydroxytetrahydrofuran-2-yl)methoxy)malonic acid |
| 44 | | 2-(((2R,3R,4S,5R)-5-(6-amino-2-chloro-9H-purin-9-yl)-4-fluoro-3-hydroxytetrahydrofuran-2-yl)methoxy)-2-(3-fluorobenzyl)malonic acid |
| 45 | | diethyl 2-(((2R,3R,4S,5R)-5-(6-amino-2-chloro-9H-purin-9-yl)-4-fluoro-3-hydroxytetrahydrofuran-2-yl)methoxy)-2-(3-fluorobenzyl)malonate |
| 46 | | diethyl 2-(((2R,3R,4S,5R)-5-(6-amino-2-chloro-9H-purin-9-yl)-4-fluoro-3-hydroxytetrahydrofuran-2-yl)methoxy)-2-(4-fluorobenzyl)malonate |

TABLE 1-continued

| Cpd. # | Compound | Name |
| --- | --- | --- |
| 47 | | 2-(((2R,3R,4S,5R)-5-(6-amino-2-chloro-9H-purin-9-yl)-4-fluoro-3-hydroxytetrahydrofuran-2-yl)methoxy)-2-(4-fluorobenzyl)malonic acid |
| 48 | | diethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)malonate |
| 49 | | 2-(((2R,3R,4S,5R)-5-(6-amino-2-chloro-9H-purin-9-yl)-4-fluoro-3-hydroxytetrahydrofuran-2-yl)methoxy)-2-(3-methoxybenzyl)malonic acid |
| 50 | | 2-((1H-tetrazol-5-yl)methyl)-2-(((2R,3R,4S,5R)-5-(6-amino-2-chloro-9H-purin-9-yl)-4-fluoro-3-hydroxytetrahydrofuran-2-yl)methoxy)malonic acid |
| 51 | | 2-(((2S,3S,4R,5R)-3-amino-5-(6-amino-2-chloro-9H-purin-9-yl)-4-hydroxytetrahydrofuran-2-yl)methoxy)-2-benzylmalonic acid |

TABLE 1-continued

| Cpd. # | Compound | Name |
|---|---|---|
| 52 | 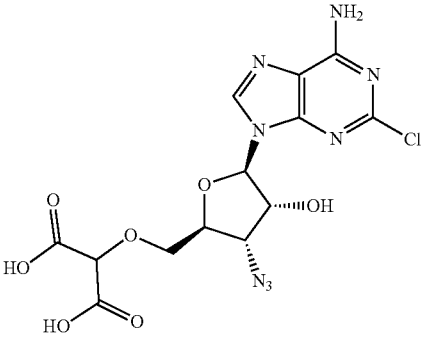 [SMILES: [N-]=[N+]=N[C@H]1[C@@H](O)[C@H](n2cnc3c(N)nc(Cl)nc32)O[C@@H]1COC(C(=O)O)C(=O)O] | 2-(((2S,3S,4R,5R)-5-(6-amino-2-chloro-9H-purin-9-yl)-3-azido-4-hydroxytetrahydrofuran-2-yl)methoxy)malonic acid |
| 53 | 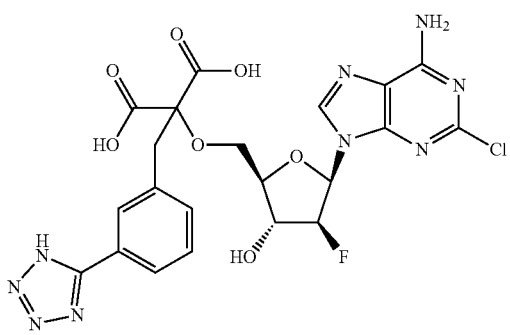 [SMILES: Nc1nc(Cl)nc2c1ncn2[C@@H]1O[C@H](COC(Cc2cccc(-c3nnn[nH]3)c2)(C(=O)O)C(=O)O)[C@@H](O)[C@@H]1F] | 2-(3-(1H-tetrazol-5-yl)benzyl)-2-(((2R,3R,4S,5R)-5-(6-amino-2-chloro-9H-purin-9-yl)-4-fluoro-3-hydroxytetrahydrofuran-2-yl)methoxy)malonic acid |
| 54 | 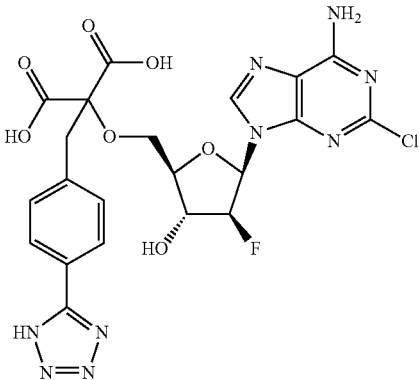 [SMILES: Nc1nc(Cl)nc2c1ncn2[C@@H]1O[C@H](COC(Cc2ccc(-c3nnn[nH]3)cc2)(C(=O)O)C(=O)O)[C@@H](O)[C@@H]1F] | 2-(4-(1H-tetrazol-5-yl)benzyl)-2-(((2R,3R,4S,5R)-5-(6-amino-2-chloro-9H-purin-9-yl)-4-fluoro-3-hydroxytetrahydro-furan-2-yl)methoxy)malonic acid |
| 55 | 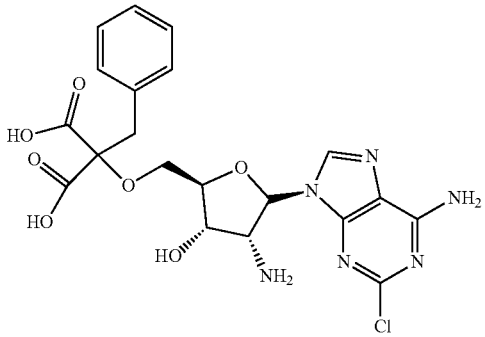 | 2-(((2R,3S,4R,5R)-4-amino-5-(6-amino-2-chloro-9H-purin-9-yl)-3-hydroxytetrahydrofuran-2-yl)methoxy)-2-benzylmalonic acid |

TABLE 1-continued

| Cpd. # | Compound | Name |
|---|---|---|
| 56 | 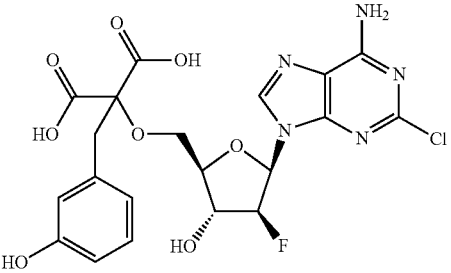 [SMILES: Nc1nc(Cl)nc2c1ncn2[C@@H]1O[C@H](COC(Cc2cccc(O)c2)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydrofuran-2-yl)methoxy)-2-(3-hydroxybenzyl)malonic acid |
| 57 | 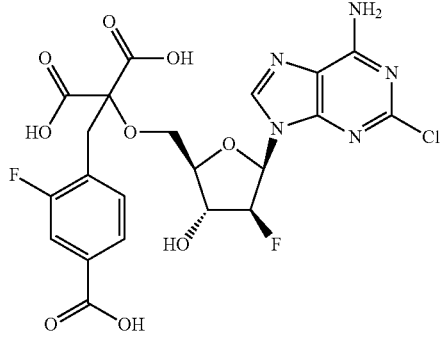 [SMILES: Nc1nc(Cl)nc2c1ncn2[C@@H]1O[C@H](COC(Cc2ccc(C(=O)O)cc2F)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydrofuran-2-yl)methoxy)-2-(4-carboxy-2-fluorobenzyl)malonic acid |
| 58 | 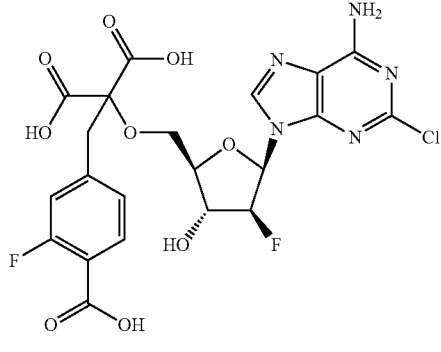 [SMILES: Nc1nc(Cl)nc2c1ncn2[C@@H]1O[C@H](COC(Cc2ccc(C(=O)O)c(F)c2)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydro-furan-2-yl)methoxy)-2-(4-carboxy-3-fluorobenzyl)malonic acid |
| 59 | 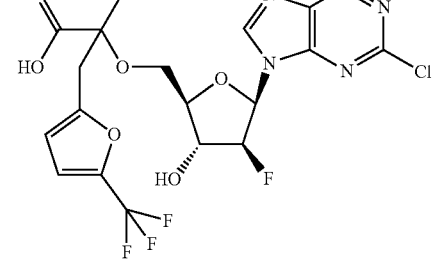 | 2-(((2R,3R,4S,5R)-5-(6-amino-2-chloro-9H-purin-9-yl)-4-fluoro-3-hydroxytetrahydro-furan-2-yl)methoxy)-2-((5-(trifluoromethyl)-furan-2-yl)methyl)malonic acid |

TABLE 1-continued

| Cpd. # | Compound | Name |
|---|---|---|
| 60 | | 2-(((2R,3R,4S,5R)-5-(6-amino-2-chloro-9H-purin-9-yl)-4-fluoro-3-hydroxytetrahydro-furan-2-yl)methoxy)-2-(3-fluoro-4-(trifluoromethyl)benzyl)malonic acid |
| 61 | | 2-(((2R,3R,4S,5R)-5-(6-amino-2-chloro-9H-purin-9-yl)-4-fluoro-3-hydroxytetrahydrofuran-2-yl)methoxy)-2-((3-phenylisoxazol-5-yl)methyl)malonic acid |
| 62 | | dimethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonate |
| 63 | | 2-(((2R,3R,4S,5R)-5-(6-amino-2-chloro-9H-purin-9-yl)-4-fluoro-3-hydroxytetrahydro-furan-2-yl)methoxy)-2-((1-benzyl-1H-pyrazol-4-yl)methyl)malonic acid |

TABLE 1-continued

| Cpd. # | Compound | Name |
|---|---|---|
| 64 | | 2-((1H-pyrazol-4-yl)methyl)-2-(((2R,3R,4S,5R)-5-(6-amino-2-chloro-9H-purin-9-yl)-4-fluoro-3-hydroxytetrahydrofuran-2-yl)methoxy)malonic acid |
| 65 | | 2-(((2R,3R,4S,5R)-5-(6-amino-2-chloro-9H-purin-9-yl)-4-fluoro-3-hydroxytetrahydrofuran-2-yl)methoxy)-2-(4-(benzyloxy)benzyl)malonic acid |
| 66 | | 2-(((2R,3R,4S,5R)-5-(6-amino-2-chloro-9H-purin-9-yl)-4-fluoro-3-hydroxytetrahydrofuran-2-yl)methoxy)-2-(4-hydroxybenzyl)malonic acid |
| 67 | | 2-(((2R,3R,4S,5R)-5-(6-amino-2-chloro-9H-purin-9-yl)-4-fluoro-3-hydroxytetrahydro-furan-2-yl)methoxy)-2-((2-carboxythiazol-5-yl)methyl)malonic acid |

TABLE 1-continued

| Cpd. # | Compound | Name |
|---|---|---|
| 68 | | 2-(((2R,3R,4S,5R)-5-(6-amino-2-chloro-9H-purin-9-yl)-4-fluoro-3-hydroxytetrahydro-furan-2-yl)methoxy)-2-((2-carboxythiazol-4-yl)methyl)malonic acid |
| 69 | Isomer 1 | 2-([1,1'-biphenyl]-4-ylmethyl)-2-(((2R,3R,4S,5R)-5-(6-amino-2-chloro-9H-purin-9-yl)-4-fluoro-3-hydroxytetrahydro-furan-2-yl)methoxy)-3-ethoxy-3-oxopropanoic acid |
| 70 | | diethyl 2-(((2R,3R,4S,5R)-5-(6-amino-2-chloro-9H-purin-9-yl)-4-fluoro-3-hydroxytetrahydrofuran-2-yl)methoxy)-2-(4-(2-methoxy-2-oxoethyl)benzyl)malonate |
| 71 | | diethyl 2-(((2R,3R,4S,5R)-5-(6-amino-2-chloro-9H-purin-9-yl)-4-fluoro-3-(isobutyryloxy)tetrahydrofuran-2-yl)methoxy)-2-((5-(methoxycarbonyl)thiophen-3-yl)methyl)malonate |

TABLE 1-continued

| Cpd. # | Compound | Name |
|---|---|---|
| 72 | | diethyl 2-(((2R,3R,4S,5R)-5-(6-amino-2-chloro-9H-purin-9-yl)-4-fluoro-3-hydroxytetrahydrofuran-2-yl)methoxy)-2-((5-(methoxycarbonyl)-1-methyl-1H-pyrazol-3-yl)methyl)malonate |
| 73 | | 2-(((2R,3R,4S,5R)-5-(6-amino-2-chloro-9H-purin-9-yl)-4-fluoro-3-hydroxytetrahydrofuran-2-yl)methoxy)-2-((5-carboxy-1-methyl-1H-pyrazol-3-yl)methyl)malonic acid |
| 74 | | 2-benzyl-2-(((2R,3R,4S,5R)-5-(2-chloro-6-hydroxy-9H-purin-9-yl)-4-fluoro-3-hydroxytetrahydrofuran-2-yl)methoxy)malonic acid |
| 75 | | 2-(((2R,3R,4S,5R)-5-(6-amino-2-chloro-9H-purin-9-yl)-4-fluoro-3-hydroxytetrahydrofuran-2-yl)methoxy)-2-(4-cyano-3-fluorobenzyl)malonic acid |

TABLE 1-continued

| Cpd. # | Compound | Name |
| --- | --- | --- |
| 76 | | 2-(((2R,3R,4S,5R)-5-(6-amino-2-chloro-9H-purin-9-yl)-4-fluoro-3-hydroxytetrahydro-furan-2-yl)methoxy)-2-((5-carboxythiophen-3-yl)methyl)malonic acid |
| 77 | | 2-(((2R,3R,4S,5R)-5-(6-amino-2-chloro-9H-purin-9-yl)-4-fluoro-3-hydroxytetrahydro-furan-2-yl)methoxy)-2-((5-carboxythiophen-2-yl)methyl)malonic acid |
| 78 | | 2-(((2R,3R,4S,5R)-5-(6-amino-2-chloro- 9H-purin-9-yl)-4-fluoro-3-hydroxytetrahydrofuran-2-yl)methoxy)-2-(4-(carboxymethyl)benzyl)malonic acid |
| 79 | | 2-([1,1'-biphenyl]-4-ylmethyl)-2-(((2R,3R,4S,5R)-5-(6-amino-2-chloro-9H-purin-9-yl)-4-fluoro-3-hydroxytetrahydro-furan-2-yl)methoxy)malonic acid |

TABLE 1-continued

| Cpd. # | Compound | Name |
|---|---|---|
| 80 | | 2-(((2R,3R,4S,5R)-5-(6-amino-2-chloro-9H-purin-9-yl)-4-fluoro-3-hydroxytetrahydrofuran-2-yl)methoxy)-2-(4-chloro-2-fluorobenzyl)malonic acid |
| 81 | Isomer 1 | 2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-methoxy-3-oxopropanoic acid |
| 82 | Isomer 2 | 2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-methoxy-3-oxopropanoic acid |
| 83 | | 2-(((2R,3R,4S,5R)-5-(6-amino-2-chloro-9H-purin-9-yl)-4-fluoro-3-hydroxytetrahydrofuran-2-yl)methoxy)-2-((3-carboxyisoxazol-5-yl)methyl)malonic acid |

TABLE 1-continued

| Cpd. # | Compound | Name |
|---|---|---|
| 84 | 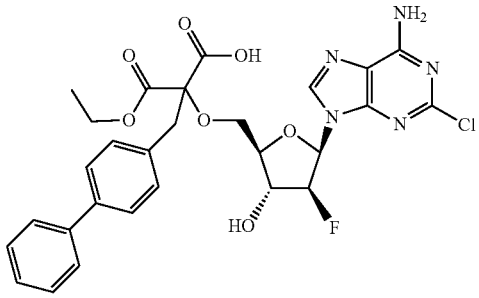 [SMILES: Nc1nc(Cl)nc2c1ncn2[C@@H]1O[C@H](COC(Cc2ccc(-c3ccccc3)cc2)(C(=O)O)C(=O)O)[C@@H](O)[C@@H]1F] Isomer 2 | 2-([1,1'-biphenyl]-4-ylmethyl)-2-((((2R,3R,4S,5R)-5-(6-amino-2-chloro-9H-purin-9-yl)-4-fluoro-3-hydroxytetrahydro-furan-2-yl)methoxy)-3-ethoxy-3-oxopropanoic acid |
| 85 | 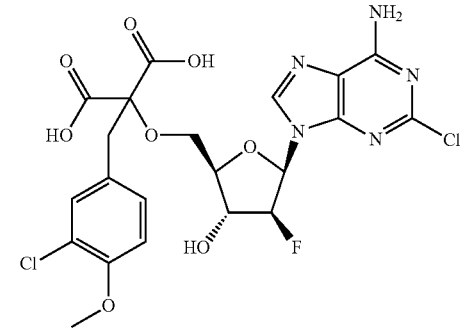 [SMILES: COc1ccc(CC(OC[C@H]2O[C@@H](n3cnc4c(N)nc(Cl)nc43)[C@@H](F)[C@@H]2O)(C(=O)O)C(=O)O)cc1Cl] | 2-(((2R,3R,4S,5R)-5-(6-amino-2-chloro-9H-purin-9-yl)-4-fluoro-3-hydroxytetrahydrofuran-2-yl)methoxy)-2-(3-chloro-4-methoxybenzyl)malonic acid |
| 86 | 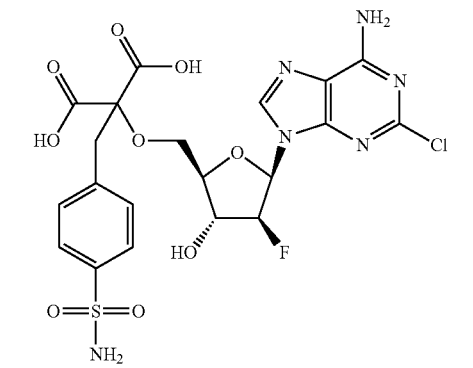 [SMILES: Nc1nc(Cl)nc2c1ncn2[C@@H]1O[C@H](COC(Cc2ccc(S(N)(=O)=O)cc2)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydrofuran-2-yl)methoxy)-2-(4-sulfamoylbenzyl)malonic acid |
| 87 | 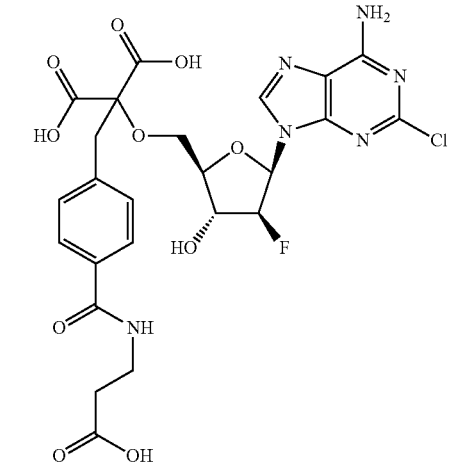 [SMILES: Nc1nc(Cl)nc2c1ncn2[C@@H]1O[C@H](COC(Cc2ccc(C(=O)NCCC(=O)O)cc2)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydro-furan-2-yl)methoxy)-2-(4-((2-carboxy-ethyl)carbamoyl)benzyl)malonic acid |

TABLE 1-continued

| Cpd. # | Compound | Name |
|---|---|---|
| 88 | | 2-(((2R,3R,4S,5R)-5-(6-amino-2-chloro-9H-purin-9-yl)-4-fluoro-3-hydroxytetrahydrofuran-2-yl)methoxy)-2-((2-carboxybenzofuran-5-yl)methyl)malonic acid |
| 89 | | 2-(((2R,3R,4S,5R)-5-(6-amino-2-chloro-9H-purin-9-yl)-4-fluoro-3-hydroxytetrahydrofuran-2-yl)methoxy)-2-(4-(2,2,2-trifluoroethoxy)benzyl)malonic acid |
| 90 | | 2-(((2R,3R,4S,5R)-5-(6-amino-2-chloro-9H-purin-9-yl)-4-fluoro-3-hydroxytetrahydrofuran-2-yl)methoxy)-2-(4-((E)-2-carboxyvinyl)benzyl)malonic acid |
| 91 | | 2-(((2R,3R,4S,5R)-5-(6-amino-2-chloro-9H-purin-9-yl)-4-fluoro-3-hydroxytetrahydrofuran-2-yl)methoxy)-2-(4-(methoxycarbonyl)benzyl)malonic acid |
| 92 | | 2-(((2R,3R,4S,5R)-5-(6-amino-2-chloro-9H-purin-9-yl)-4-fluoro-3-hydroxytetrahydrofuran-2-yl)methoxy)-2-(4-(carboxymethoxy)benzyl)malonic acid |

TABLE 1-continued

| Cpd. # | Compound | Name |
|---|---|---|
| 93 | | 2-benzyl-2-(((2R,3R,4S,5R)-5-(2-chloro-6-oxo-1H-purin-9(6H)-yl)-4-fluoro-3-hydroxytetrahydrofuran-2-yl)methoxy)malonic acid |
| 94 | | 2-(((2R,3R,4S,5R)-5-(6-amino-2-chloro-9H-purin-9-yl)-4-fluoro-3-hydroxytetrahydrofuran-2-yl)methoxy)-2-(4-(5-methyl-1,3,4-oxadiazol-2-yl)benzyl)malonic acid |
| 95 | | of 2-((2R,3R,4S,5R)-5-(6-amino-2-chloro-9H-purin-9-yl)-4-fluoro-3-hydroxytetrahydrofuran-2-yl)methoxy)-2-((2'-cyano-[1,1'-biphenyl]-4-yl)-methyl)malonic acid |
| 96 | | 2-(((2R,3R,4S,5R)-5-(6-amino-2-chloro-9H-purin-9-yl)-4-fluoro-3-hydroxytetrahydrofuran-2-yl)methoxy)-2-((5-chlorobenzo[b]thiophen-3-yl)methyl)-malonic acid |
| 97 | | 2-(((2R,3R,4S,5R)-5-(6-amino-2-chloro-9H-purin-9-yl)-4-fluoro-3-hydroxytetrahydrofuran-2-yl)methoxy)-2-(benzo[d]thiazol-2-lymethyl)malonic acid |

TABLE 1-continued

| Cpd. # | Compound | Name |
|---|---|---|
| 98 | | 2-(((2R,3R,4S,5R)-5-(6-amino-2-chloro-9H-purin-9-yl)-4-fluoro-3-hydroxytetrahydrofuran-2-yl)methoxy)-2-(4-(methylcarbamoyl)benzyl)malonic acid |

Pharmaceutical Preparations

In certain embodiments, the present invention provides a pharmaceutical preparation suitable for use in a human patient, comprising any of the compounds shown above (e.g., a compound of the invention, such as a compound of formula (I)) and one or more pharmaceutically acceptable excipients. In certain embodiments, the pharmaceutical preparations may be for use in treating or preventing a condition or disease as described herein.

Any of the disclosed compounds may be used in the manufacture of medicaments for the treatment of any diseases or conditions disclosed herein.

Methods of Use

Provided herein are methods of inhibiting CD73 in a cell, comprising contacting the cell with a compound of the invention, such as a compound of formula (I), or a pharmaceutically acceptable salt thereof. In certain embodiments, contacting the cell occurs in a subject in need thereof, thereby treating a disease or disorder mediated by adenosine.

Also, disclosed herein are methods of treating a disease or a disorder mediated by adenosine comprising administering a compound the invention, such as a compound of Formula (I), or a pharmaceutically acceptable salt thereof.

Adenosine acts on a variety of immune cells to induce immunosuppression, and the immunosuppressive effects of ectonucleotidases that enhance adenosine levels are also associated with enhanced infections of mammalian cells by parasites, fungi, bacteria, and viruses. Apart from immunosuppressive effects, adenosine also has a role in modulating the cardiovascular system (as a vasodilator and cardiac depressor), the central nervous system (CNS) (inducing sedative, anxiolytic and antiepileptic effects), the respiratory system (inducing bronchoconstriction), the kidney (having biphasic action; inducing vasoconstriction at low concentrations and vasodilation at high doses), fat cells (inhibiting lipolysis), and platelets (as an anti-aggregant). Furthermore, adenosine also promotes fibrosis (excess matrix production) in a variety of tissues. Therefore, improved treatments targeting CD73 would provide therapies for treating a wide range of conditions in addition to cancer, including cerebral and cardiac ischemic disease, fibrosis, immune and inflammatory disorders (e.g., inflammatory gut motility disorder), neurological, neurodegenerative and CNS disorders and diseases (e.g., depression, Parkinson's disease), and sleep disorders.

In some embodiments, the disease or the disorder mediated by adenosine is selected from cerebral ischemic disease, cancer, cardiac ischemic disease, depression, fibrosis, an immune disorder, an inflammatory disorder (e.g., inflammatory gut motility disorder), neurological disorder or disease, neurodegenerative disorder or disease (e.g., Parkinson's disease), CNS disorders and diseases, and sleep disorders.

The methods described herein are useful for the treatment of a wide variety of cancers, including Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Biliary Cancer, Bladder Cancer, Bone Cancer, Brain Tumor (e.g., glioblastoma), Astrocytoma, Brain and Spinal Cord Tumor, Brain Stem Glioma, Central Nervous System Atypical Teratoid/Rhabdoid Tumor, Central Nervous System Embryonal Tumor, Breast Cancer, Bronchial Tumor, Burkitt Lymphoma, Carcinoid Tumor, Cervical Cancer, Childhood Cancer, Chordoma, Chronic Lymphocytic Leukemia (CLL), Chronic Myelogenous Leukemia (CML), Chronic Myeloproliferative Disorder, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Extracranial Germ Cell Tumor, Extragonadal Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Liver Cancer, Lobular Carcinoma In Situ (LCIS), Lung Cancer, Lymphoma, AIDS-Related Lymphoma, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Multiple Myeloma, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Renal Pelvis Cancer, Ureter Cancer, Retinoblastoma, Rhabdomyosarcoma, Salivary Gland Cancer, Sézary Syndrome, Skin Cancer, Small Cell Lung Cancer, Small Intestine Cancer, Soft Tissue Sarcoma, Squamous Cell Carcinom, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Gestational Trophoblastic Tumor, Urethral Cancer, Uterine Cancer, Uterine Sarcoma, Waldenström Macroglobulinemia, or Wilms Tumor.

In some embodiments, the cancer is bladder cancer, bone cancer, brain cancer (including glioblastoma), breast cancer, cardiac cancer, cervical cancer, colon cancer, colorectal cancer, esophageal cancer, fibrosarcoma, gastric cancer, gastrointestinal cancer, head & neck cancer, Kaposi's sarcoma, kidney cancer (including renal cell adenocarcinoma), leukemia, liver cancer, lung cancer (including non-small cell lung cancer, small cell lung cancer, and mucoepidermoid pulmonary carcinoma), lymphoma, melanoma, myeloma, ovarian cancer (including ovarian adenocarcinoma), pancreatic cancer, penile cancer, prostate cancer, testicular germ-cell cancer, thymoma or thymic carcinoma.

In some embodiments, the subject has a cancer selected from breast cancer, brain cancer, colon cancer, fibrosarcoma, kidney cancer, lung cancer, melanoma, ovarian cancer, and prostate cancer. In other embodiments, the subject has a cancer selected from brain cancer, breast cancer, kidney cancer, lung cancer, melanoma, and ovarian cancer. In yet other embodiments, the subject has breast cancer. In some embodiments, the breast cancer is breast adenocarcinoma. In certain embodiments, the breast cancer is triple-negative breast cancer.

In certain embodiments, the methods for treating or preventing cancer can be demonstrated by one or more responses such as increased apoptosis, inhibition of tumor growth, reduction of tumor metastasis, inhibition of tumor metastasis, reduction of microvessel density, decreased neovascularization, inhibition of tumor migration, tumor regression, and increased survival of the subject.

In certain embodiments, the disease or the disorder mediated by adenosine is a disease or disorder mediated by CD73 activity. In some embodiments, the compounds of the invention, such as compounds of Formula (I), are useful as inhibitors of CD73.

In some embodiments, the methods described herein treat or prevent cardiovascular disease using inhibitors of CD73. Mutant genes encoding CD73 lead to extensive calcification of lower-extremity arteries and small joint capsules, which is associated with increased risk of cardiovascular disease (Hilaire et al., *N. Engl. J. Med.*, 364(5): 432-442, 2011).

In some embodiments, the methods disclosed herein treat or prevent cancer using inhibitors of CD73. A CD73 small interfering RNA and anti-CD73 monoclonal antibodies showed a significant effect in treating or preventing cancer (Antonioli et al., *Nat. Rev. Cancer,* 13: 842-857, 2013). A tight correlation exists between CD73 expression and the ability of cancer cells to migrate, invade, and adhere to the extracellular matrix (ECM) (Antonioli 2013; Antonioli et al., *Trends Cancer,* 2(2): 95-109, 2016).

In some embodiments, the treatment or prevention of cancer by inhibitors of CD73 can be demonstrated by one or more responses selected from activation, clonal expansion, and homing of tumor-specific T cells (Antonioli 2016). In other embodiments, the methods disclosed herein increase the number of effector T lymphocytes (e.g., cytolytic effector T lymphocytes).

Combination Treatments

In some embodiments, the method of treating or preventing cancer may comprise administering a CD73 inhibitor conjointly with one or more other chemotherapeutic agent(s). In one embodiment, the CD73 inhibitor is a compound of the invention, such as a compound of Formula (I). Other chemotherapeutic agents can include CD73-specific monoclonal antibodies which enhance the effects of other antibodies and therapies because of increased overall immune system activity (lower T-regulatory function and higher T-effector function, etc.) (Antonioli 2016).

In certain embodiments, the method of treating or preventing cancer may comprise administering a compound of the invention conjointly with one or more other chemotherapeutic agent(s).

Chemotherapeutic agents that may be conjointly administered with compounds of the invention include: 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, *Bacillus* Calmette-Guérin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA). In other embodiments, chemotherapeutic agents that may be conjointly administered with compounds of the invention include: ABT-263, dexamethasone, 5-fluorouracil, PF-04691502, romidepsin, and vorinostat (SAHA). In other embodiments, chemotherapeutic agents that may be conjointly administered with compounds of the invention include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, APCP, β-methylene-ADP (AOPCP), capecitabine cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Many combination therapies have been developed for the treatment of cancer. In certain embodiments, compounds of the invention (e.g., compounds of Formula (I)) may be conjointly administered with a combination therapy. Examples of combination therapies with which compounds of the invention may be conjointly administered are included in Table 2.

TABLE 2

Exemplary combinatorial therapies for the treatment of cancer

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |

TABLE 2-continued

Exemplary combinatorial therapies for the treatment of cancer

| Name | Therapeutic agents |
|---|---|
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |

TABLE 2-continued

Exemplary combinatorial therapies for the treatment of cancer

| Name | Therapeutic agents |
|---|---|
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PCV | Lomustine, Procarbazine, Vincristine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/ cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/ MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In some embodiments, the chemotherapeutic agents that may be conjointly administered with compounds of the invention, such as a compound of Formula (I), include a CD39 inhibitor. CD39 or ecto-nucleoside triphosphate diphosphohydrolase 1 (E-NTPDase1 or ENTPD 1) is a membrane-bound enzyme that catalyzes the conversion of extracellular adenosine triphosphate (ATP) and/or ADP (adenosine diphosphate) to adenosine monophosphate (AMP). In one embodiment, the CD39 inhibitor is polyoxometalate-1 (POM-1).

In other embodiments, the chemotherapeutic agents that may be conjointly administered with compounds of the invention, such as a compound of Formula (I), include known CD73 inhibitors. In some embodiments, the CD73 inhibitor is an anthraquinone derivative (Baqi et al., *J. Med. Chem.*, 53(5): 2076-2086, 2010, herein incorporated by reference). In other embodiments, the CD73 inhibitor is an sulfonic acid derivative (Raza et al., *Med. Chem.*, 8: 1133-1139, 2012, herein incorporated by reference). In yet other embodiments, the CD73 inhibitor is selected from 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, sodium 2,4-dinitrobenzenesulfonate, N-(4-sulfamoylphenylcarbamothioyl) pivalamide, APCP, β-methylene-ADP (AOPCP), PPADS, NF279, NF449, quercetin, reactive blue 2, and sumarin (Baqi 2010; Raza 2012).

In certain embodiments, the combination of a compound of the invention, such as a compound of Formula (I), with a second CD73 inhibitor or a CD39 inhibitor may have a synergistic effect in the treatment of cancer and other diseases or disorders mediated by adenosine. Without wishing to be bound by any theory, this synergy may be observed because CD39 and CD73 are often on different cell types. The hypoxic tumor microenvironment also induces greater levels of CD39 and CD73.

In some embodiments, the chemotherapeutic agents that may be conjointly administered with compounds of the invention, such as a compound of Formula (I), include an adenosine receptor inhibitor. In other embodiments, the adenosine receptor inhibitor is selected from rolofylline, tonapofylline, ATL-444, istradefylline, MSX-3, preladenant, SCH-58,261, SCH-412,348, SCH-442,416, ST-1535, VER-6623, VER-6947, VER-7835, vipadenant, and ZM-241,385. In some embodiments, the adenosine receptor inhibitor targets the $A_{2A}$ receptor as this subtype is predominantly expressed in most immune cells.

In other embodiments, the chemotherapeutic agents that may be conjointly administered with compounds of the invention, such as a compound of Formula (I), include a nucleoside-based drug. In certain embodiments, the nucleoside-based drug is selected from gemcitabine, capecitabine, cytarabine, fludarabine and cladribine.

In further embodiments, the combination therapy comprises a compound of the invention, such as a compound of Formula (I), conjointly administered with an anthracycline. In other embodiments, the combination therapy comprises a compound of the invention, such as a compound of Formula (I), conjointly administered with doxorubicin. Combination treatment with an anti-CD73 antibody and doxorubicin has demonstrated a significant chemotherapeutic effect (Young et al., Cancer Discov., 4(8): 1-10, 2014, herein incorporated by reference).

In certain embodiments, the combination therapy comprises a compound of the invention, such as a compound of Formula (I), conjointly administered with an $A_{2A}$ receptor inhibitor and an anthracycline. In some embodiments, the anthracycline is doxorubicin. Combination treatment with an anti-CD73 antibody, an $A_{2A}$ receptor inhibitor, and doxorubicin has demonstrated an increased chemotherapeutic effect (Antonioli 2013).

In certain embodiments, the conjoint therapies of the invention comprise conjoint administration with other types of chemotherapeutic agents, such as immuno-oncology agents. Cancer cells often have specific cell surface antigens that can be recognized by the immune system. Thus, immuno-oncology agents can selectively bind to cancer cell antigens and effect cell death. Other immuno-oncology agents can suppress tumor-mediated inhibition of the native immune response or otherwise activate the immune response and thus facilitate recognition of the tumor by the immune system. Exemplary immuno-oncology agents, include, but are not limited to, abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab. In some embodiments, the immune-oncology agents are selected from anti-CD73 monoclonal antibody (mAb), anti-CD39 mAb, anti-PD-1 mAb, and anti-CTLA4 mAb. Thus, in some embodiments, the methods of the invention comprise conjoint administration of one or more immuno-oncology agents, such as the agents mentioned above.

In some embodiments, the combination therapy comprises a compound of the invention, such as a compound of Formula (I), conjointly administered with anti-PD-1 therapy and anti-CTLA4 therapy. Combination treatment with an anti-CD73 monoclonal antibody (mAb), anti-PD-1 mAb, and anti-CTLA4 mAb showed a significant chemotherapeutic effect (Young 2014; Antonioli 2013).

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

In certain embodiments, compounds of the invention may be conjointly administered with one or more other compounds of the invention. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of the invention provides a synergistic effect. In certain embodiments, conjointly administering one or more additional chemotherapeutic agents provides an additive effect.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥about 33% of patients with a dose-limiting toxicity at that dose level). The recommended dose for phase II trials is conventionally defined as the dose level just below this toxic dose level.

In certain embodiments, the dosing schedule can be about 40 mg/m$^2$ to about 100 mg/m$^2$, such as about 50 mg/m$^2$ to about 80 mg/m$^2$, and further such as about 70 mg/m$^2$ to about 90 mg/m$^2$ by IV for 3 weeks of a 4 week cycle.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

General Synthesis

Compound numbers 1-45 as used in the general synthesis section below refer only to genus structures in this section and do not apply to compounds disclosed elsewhere in this application. Compounds disclosed herein can be made by methods depicted in the reaction schemes below.

The starting materials and reagents used in preparing these compounds are either available from commercial supplier such as Aldrich Chemical Co., Bachem, etc., or can be made by methods well known in the art. The schemes are merely illustrative of some methods by which the compounds disclosed herein can be synthesized and various modifications to these schemes can be made and will be suggested to POSITA having referred to this disclosure. The starting materials and the intermediates and the final products of the reaction may be isolated and purified if desired using conventional techniques, including but not limited to filtration, distillation, crystallization, chromatography, and the like and may be characterized using conventional means, including physical constants and spectral data.

Unless specified otherwise, the reactions described herein take place at atmospheric pressure over a temperature range from about −78° C. to about 150° C.

Compounds of Formula (I) having the structure:

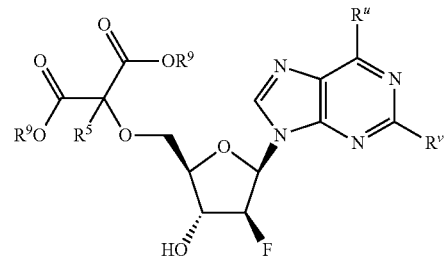

where $R^u$, $R^v$, $R^5$, and $R^9$ are as defined in the Summary can be synthesized as illustrated and described in Scheme 1 below.

Scheme 1

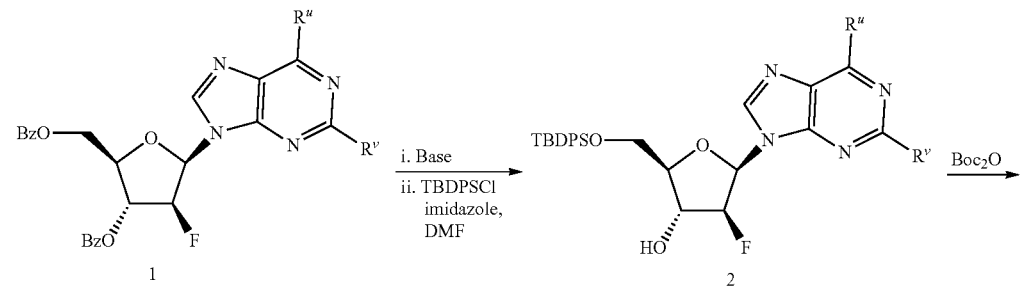

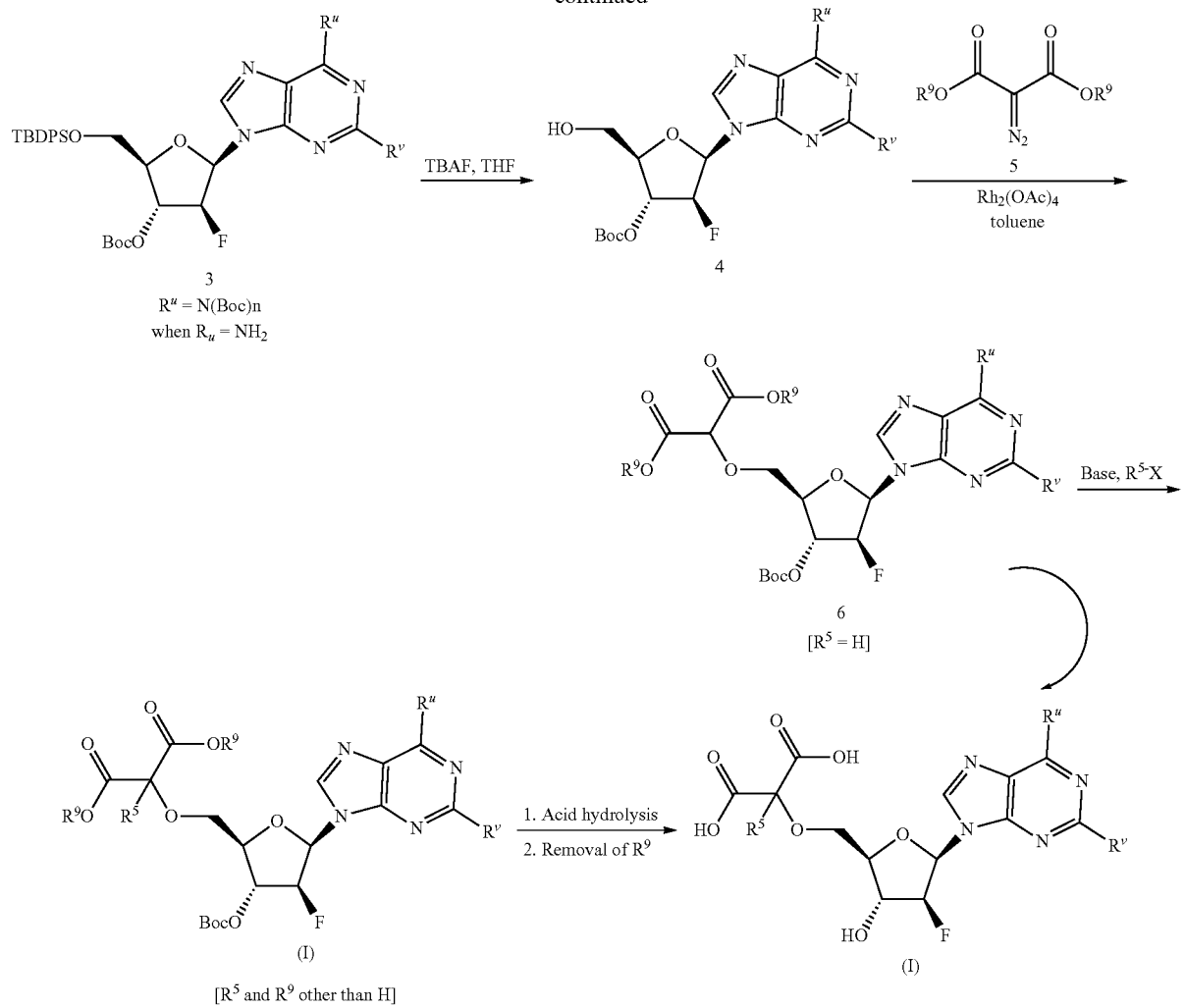

Removal of the benzoyl groups in a compound of formula 1 with a suitable base such as $NH_3$ in an organic alcohol solvent such as MeOH, or aq. LiOH or aq. NaOH, followed by selectively protecting the 5'-OH group with tert-butyldiphenylsilyl group provides a compound of formula 2.

Compounds of formula 1 are either commercially available or they can be prepared by methods well known in the art. For example, ((2R,3R,4S,5R)-3-(benzoyloxy)-5-(2,6-dichloro-9H-purin-9-yl)-4-fluorotetrahydrofuran-2-yl)methyl benzoate and ((2R,3R,4S,5R)-3-(benzoyloxy)-5-(2-amino-6-chloro-9H-purin-9-yl)-4-fluorotetrahydrofuran-2-yl)methyl benzoate are commercially available. Compounds of formula 1 where $R^u$ is other than chloro or amino and $R^v$ is other than chloro can be prepared from ((2R,3R,4S,5R)-3-(benzoyloxy)-5-(2,6-dichloro-9H-purin-9-yl)-4-fluorotetrahydrofuran-2-yl)methyl benzoate as described in PCT application publication nos. WO 2015/164573 and WO 2017/120508.

Protection of the 3'-hydroxy group in compound 2 with a suitable hydroxy protecting group such as Boc, followed by removal of the silyl group under conditions well known in the art such as TBAF in THF provides a compound of formula 4. Reaction of compound 4 with a diazo reagent of formula 5 where $R^9$ is unsubstituted alkyl or benzyl in the presence of catalyst, such as $Rh_2(OAc)_4$ or $CuOAc_2$ in a suitable organic solvent such as toluene, benzene, dichloromethane, dichloroethane, and THF, provides a compound of Formula 6 where $R^5$ is hydrogen. Compound 6 can then be converted to a compound of Formula (I) by removal of the Boc group under acidic hydrolysis conditions, followed by removal of the $R^9$ group under basic hydrolysis reaction condition e.g., aq. LiOH or NaOH (when $R^9$ is alkyl) or by hydrogenolysis with Pd/C or Pd(OH)$_2$/C (when $R^9$ is benzyl).

Alternatively, compound 6 can be reacted with a halide of formula $R^5X$ where X is halo (preferably chloro, bromo, iodo, tosylate, mesylate or triflate) and $R^5$ is as defined in the Summary except hydrogen under alkylating reaction conditions to provide a corresponding compound of Formula (I) where $R^5$ and $R^9$ are other than hydrogen which can then be converted to corresponding compound of Formula (I) where $R^9$ are hydrogen as described above.

Compounds of Formula (I) where Het is other than purine can be prepared by methods well known in the art. For example, compounds of Formula (I) where is a group of formula (i), (ii), or (vii) can be prepared from 2,4-dichloro-7H-pyrrolo[2,3-d]pyrimidine, 4,6-dichloro-1H-pyrazolo[3,4-d]pyrimidine and 4,6-dichloro-1H-imidazo[4,5-c]pyridine respectively, by synthetic procedures disclosed in PCT application publication no. WO 2017/120508 and Scheme 1 above.

Proceeding as described above but substituting compound of formula 1, with (2R,3R,4S,5R)-5-(6-amino-2-chloro-9H-purin-9-yl)-4-chloro-2-(hydroxymethyl)-tetrahydrofuran-3-ol (prepared according to the procedures reported by Secrist, John A., III et al, Journal of Medicinal Chemistry, 31(2), 405-10; 1988 and by Anderson, Bruce G. et al., Organic Process Research & Development, 12(6), 1229-1237; 2008), compounds of Formula (I) where $R^{1a}$ is chloro, $R^{1b}$ and $R^{2b}$ are hydrogen, and $R^{2a}$ is hydroxy and Het is 2-chloro-9H-purin-6-amine can be prepared. It will be apparent to a person skilled that analogs of such compounds i.e, Het is other than 2-chloro-9H-purin-6-amine can also be prepared based on the disclosure of this Application and methods known in the art.

Proceeding as described above but substituting compound of formula 1, with (2R,3S,4S,5R)-2-(6-amino-2-chloro-9H-purin-9-yl)-4-fluoro-5-(hydroxymethyl)-tetrahydrofuran-3-ol (prepared according to procedures reported by Ren, Hang et al Beilstein Journal of Organic Chemistry, 11, 2509-2520; 2015, and by Schinazi, Raymond F. et al., Heterocyclic Communications, 21(5), 315-327; 2015) compounds of Formula (I) where $R^{1a}$ is hydroxy, $R^{1b}$ and $R^{2b}$ are hydrogen, and $R^{2a}$ is fluoro and Het is 2-chloro-9H-purin-6-amine can be prepared. It will be apparent to a person skilled that analogs of such compounds i.e, Het is other than 2-chloro-9H-purin-6-amine can also be prepared based on the disclosure of this Application and methods known in the art.

Proceeding as described above but substituting compound of formula 1, with ((2R,3R,4R,5R)-5-(6-amino-2-chloro-9H-purin-9-yl)-3,4-difluorotetrahydrofuran-2-yl)methanol (prepared according to procedures reported by Schinazi, Raymond F. et al., Heterocyclic Communications, 21(5), 315-327; 2015 and by Sivets, Grigorii G. et al., Nucleosides, Nucleotides & Nucleic Acids, 28(5-7), 519-536; 2009) compounds of Formula (I) where $R^{1b}$ is fluoro, $R^{1a}$ and $R^{2a}$ are hydrogen, and $R^{2b}$ is fluoro and Het is 2-chloro-9H-purin-6-amine can be prepared. It will be apparent to a person skilled that analogs of such compounds i.e, Het is other than 2-chloro-9H-purin-6-amine can also be prepared based on the disclosure of this Application and methods known in the art.

Proceeding as described above but substituting compound of formula 1, with (2R,3S,4R,5R)-5-(6-amino-2-chloro-9H-purin-9-yl)-2-(hydroxymethyl)-3-methyltetrahydrofuran-3,4-diol (prepared according to the procedures reported by Franchetti, Palmarisa, et al., J. Med. Chem., 48(15), 4983-4989, 2005), or (2R,3S,4R,5R)-5-(6-amino-2-chloro-9H-purin-9-yl)-3-ethynyl-2-(hydroxymethyl)tetrahydrofuran-3,4-diol (prepared according to the procedures reported by Hulpia, Fabian et al., Bioorganic & Medicinal Chemistry Letters, 26(8), 1970-1972; 2016) compounds of Formula (I) where $R^{1a}$ and $R^{2a}$ are hydroxy, $R^{1b}$ is hydrogen, and $R^{2b}$ is methyl or ethynyl respectively, and Het is 2-chloro-9H-purin-6-amine can be prepared. It will be apparent to a person skilled that analogs of such compounds i.e, Het is other than 2-chloro-9H-purin-6-amine can also be prepared based on the disclosure of this Application and methods known in the art.

Compounds of Formula (I) having the structure:

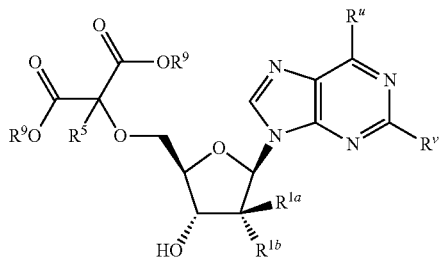

where $R^{1a}$ is halo, alkyl, alkynyl, alkenyl, or cyano, $R^{1b}$ is halo or hydroxy, or $R^{1a}$ and $R^{1b}$ are fluoro, Het is a ring of formula (iii) where $R^s$ is hydrogen, and $R^u$ and $R^v$ are as defined in the Summary and $R^5$ and $R^9$ are as defined in the Summary can be synthesized by proceeding as described in Scheme 2 below.

Scheme 2

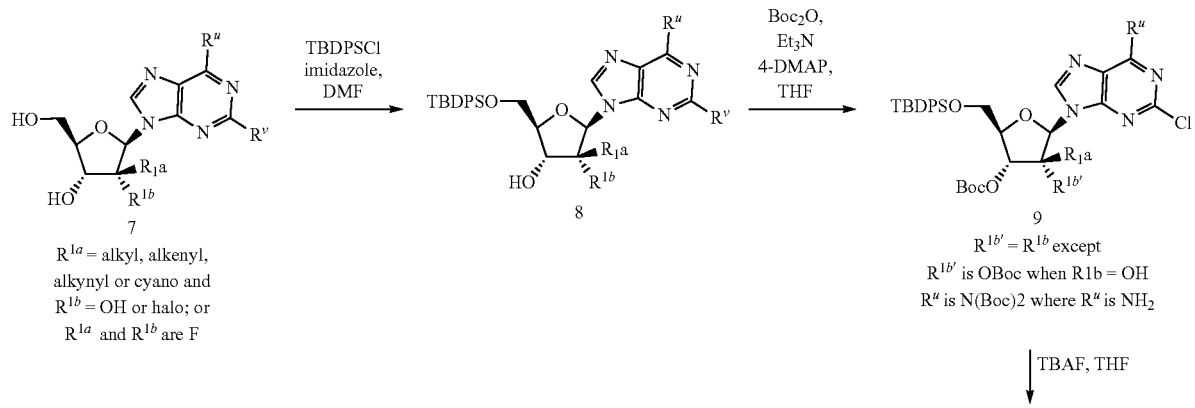

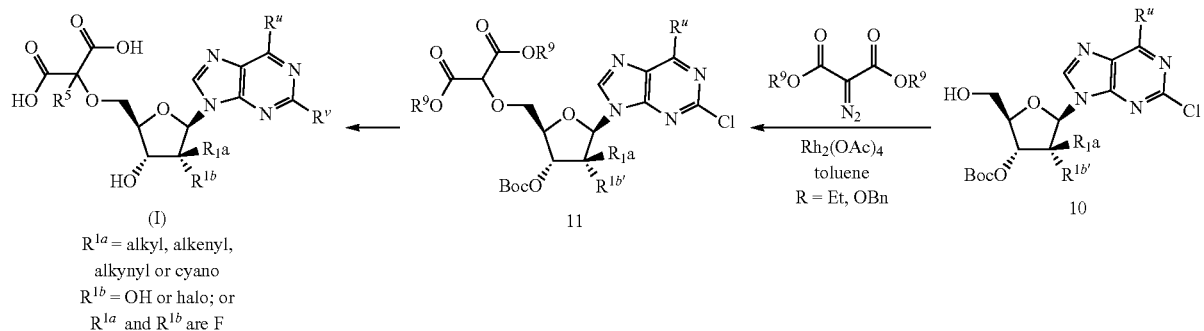

(I)
$R^{1a}$ = alkyl, alkenyl, alkynyl or cyano
$R^{1b}$ = OH or halo; or
$R^{1a}$ and $R^{1b}$ are F Compounds of Formula (I) where $R^{1a}$ is halo, alkyl, alkynyl, alkenyl, or cyano, $R^{1b}$ is halo or hydroxy, or $R^{1a}$ and $R^{1b}$ are fluoro, Het is a ring of formula (iii) where $R^s$ is hydrogen, and $R^u$ and $R^v$ are as defined in the Summary and $R^5$ and $R^9$ are as defined in the Summary can prepared from compounds of formula 7 as illustrated in Scheme 2 above by proceeding under the reaction conditions described in Scheme 1 above.

Compounds of formula 1 are either commercially available or they can be prepared by methods known in the art. For example, compound of formula 7 (2R,3R,4R,5R)-2-(6-amino-2-chloro-9H-purin-9-yl)-5-(hydroxymethyl)-3-methyltetrahydrofuran-3,4-diol is commercially available or can be prepared according to procedure reported by Caballero, Gerado et al., Helvetica Chimica Acta, 85(5), 1284-1294; 2002 and by Li, Nan-Sheng et al., J. Org. Chem., 74(5), 2227-2230, 2009). (2R,3R,4R,5R)-2-(6-Amino-2-chloro-9H-purin-9-yl)-3-ethynyl-5-(hydroxymethyl)tetrahydrofuran-3,4-diol can be prepared according to procedures reported by Nadler, Andre and Diedrerichsen, Ulf, European Journal of Organic Chemistry, 9, 1544-1549; 2008. (2R,3R,4R,5R)-2-(6-Amino-2-chloro-9H-purin-9-yl)-5-(hydroxymethyl)-3-vinyltetrahydrofuran-3,4-diol can be prepared according to procedures reported by Blatt, Lawrence M. et al., U.S. Pat. Appl. Publ. No. 20150366888, and by Carroll, Steven S. et al., PCT Int. Appl., publication no. WO 2004000858. (2R,3R,4R,5R)-2-(6-Amino-2-chloro-9H-purin-9-yl)-3,4-dihydroxy-5-(hydroxymethyl)tetrahydrofuran-3-carbonitrile can be prepared according to procedures reported by Ohtawa, Masaki et al., J. Med. Chem, 50(9), 2007-2009; 2007.

(2R,3R,4R,5R)-5-(6-Amino-2-chloro-9H-purin-9-yl)-4-fluoro-2-(hydroxymethyl)-4-methyltetrahydrofuran-3-ol is commercially available. (2R,3R,5R)-5-(6-Amino-2-chloro-9H-purin-9-yl)-2-((benzoyloxy)methyl)-4,4-difluorotetrahydrofuran-3-yl benzoate can be prepared by reacting ((2R,3R)-3-(benzoyloxy)-4,4-difluoro-5-iodotetrahydrofuran-2-yl)methyl benzoate and 2-chloroadenine under the Vorbrueggen conditions [(i) $(CH_3Si)_2NH$, $(NH_4)_2SO_4$ or $Me_3SiN=CMeOSiMe_3$, (ii) TMSOTf, refluxing] according to the procedure reported by Vorbrueggen, Helmut & Ruh-Polenz, Carmen, Organic Reactions, 55, 2000 and by Beigelman, Leonid, et al., US patent application, publication No. US 2013/0165400, followed by removal of the benzoyl groups in the resulting compound (2R,3R,5R)-5-(6-amino-2-chloro-9H-purin-9-yl)-2-((benzoyloxy)methyl)-4,4-difluorotetrahydrofuran-3-yl benzoate as described below.

Compounds of Formula (I) where Het is other than purine can be prepared from commercially available starting materials as described in Scheme 1 above.

Compounds of Formula (I) having the structure:

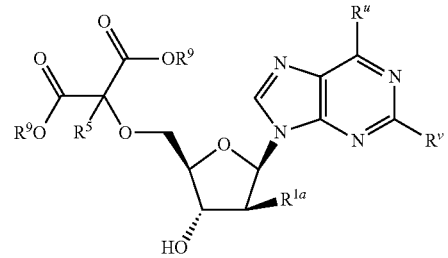

where $R^{1a}$ is alkyl, alkynyl, vinyl, or cyano, Het is a ring of formula (iii) where $R^s$ is hydrogen, and $R^u$ and $R^v$ are as defined in the Summary and $R^5$ and $R^9$ are as defined in the Summary can be synthesized by proceeding as illustrated and described in a representative example in Scheme 3 below.

Scheme 3

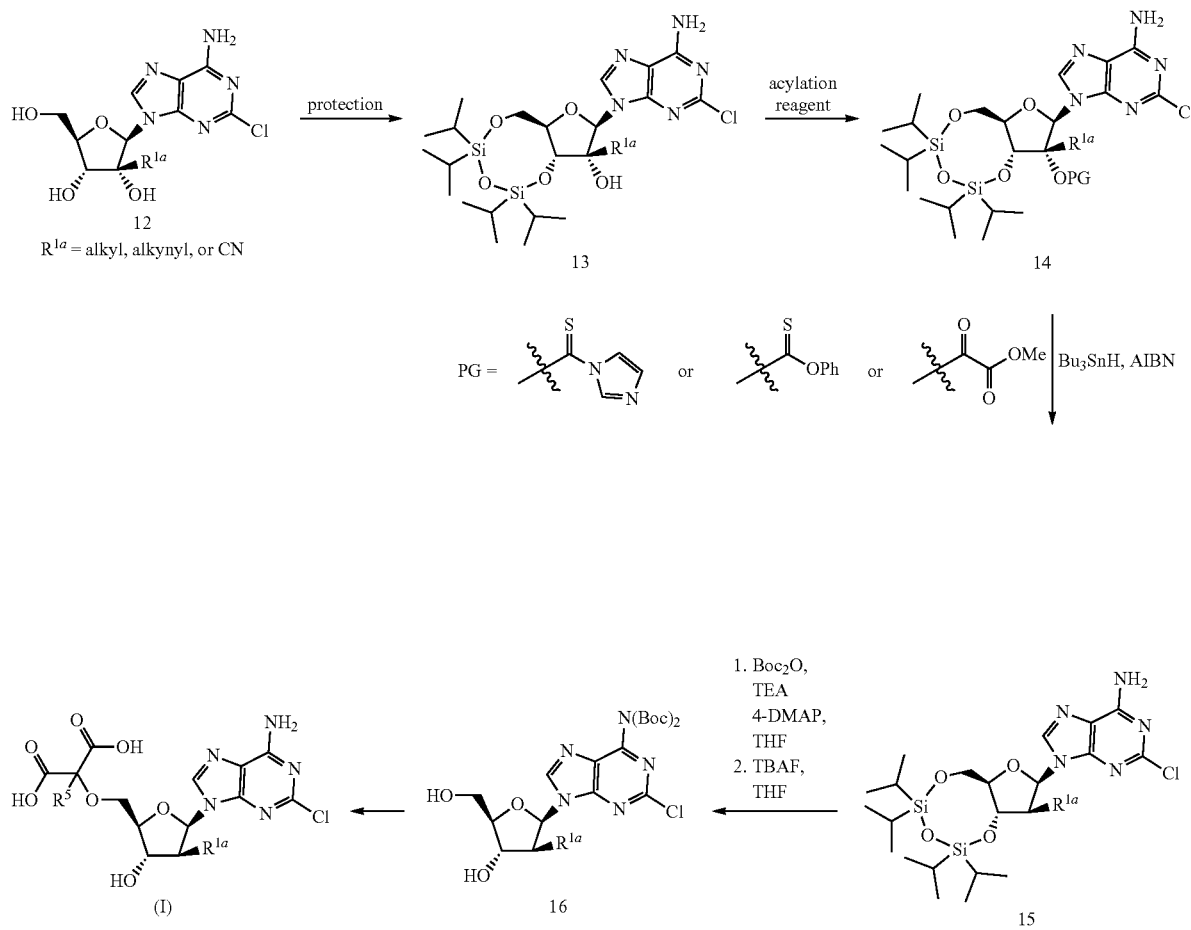

Selective protection of the 4',5'-diol in a compound of formula 12 with 1,3-dichloro-1,1,3,3-tetraisopropyldisiloxane, followed by acylation of 2'-OH in the resulting compound 13 with a suitable reagent such as 1,1'-thiocarbonyldiimidazole, O-phenyl chloro thioformate, or methyl chloro oxoacetate provides a compound of formula 14. Compound 14 is converted to a compound of formula 15 where $R^{1b}$ is hydrogen via deoxygenation of 2'-OH. The deoxygenation reaction is carried out by heating 14 in the presence of Bu$_3$SnH and AIBN at high temperature e.g., in refluxing toluene. Protection of amino group in compound 15, followed by removal of the silyl protecting group provides a compound of formula 16 which is then converted into a compound of Formula (I) as described in Scheme 1 above.

Compound of formula (I) where $R^{1a}$ is ethynyl can be converted to the corresponding compound of formula (I) where $R^{1a}$ is vinyl via reduction of the ethynyl group with Lindlar catalyst in the presence of hydrogen.

Compounds of formula 12 such as (2R,3R,4R,5R)-2-(6-amino-2-chloro-9H-purin-9-yl)-5-(hydroxymethyl)-3-methyltetrahydrofuran-3,4-diol is commercially available. (2R,3R,4R,5R)-2-(6-Amino-2-chloro-9H-purin-9-yl)-5-(hydroxymethyl)-3-vinyltetrahydrofuran-3,4-diol can be prepared according to procedures reported by Blatt, Lawrence M. et al., U.S. Pat. Appl. Publ., No. 20150366888; or by Carroll, Steven S. et al., PCT Int. Appl., publication No. 2004000858; and (2R,3R,4R,5R)-2-(6-amino-2-chloro-9H-purin-9-yl)-3,4-dihydroxy-5-(hydroxyl-methyl)tetrahydrofuran-3-carbonitrile can be prepared according to procedures reported by Ohtawa, Masaki et al., J. Med. Chem, 50(9), 2007-2009; 2007.

Compounds of Formula (I) having the structure:

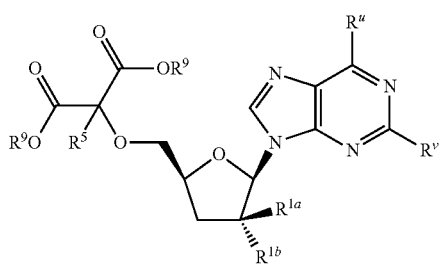

where $R^{1a}$ is alkyl, alkynyl, vinyl, or cyano, $R^{1b}$ is hydroxy or halo; or $R^{1a}$ and $R^{1b}$ are fluoro; Het is a ring of formula (iii) and $R^u$, $R^v$, $R^5$ and $R^9$ are as defined in the Summary can be synthesized by proceeding as illustrated and described in a representative example in Scheme 4 below.

Scheme 4

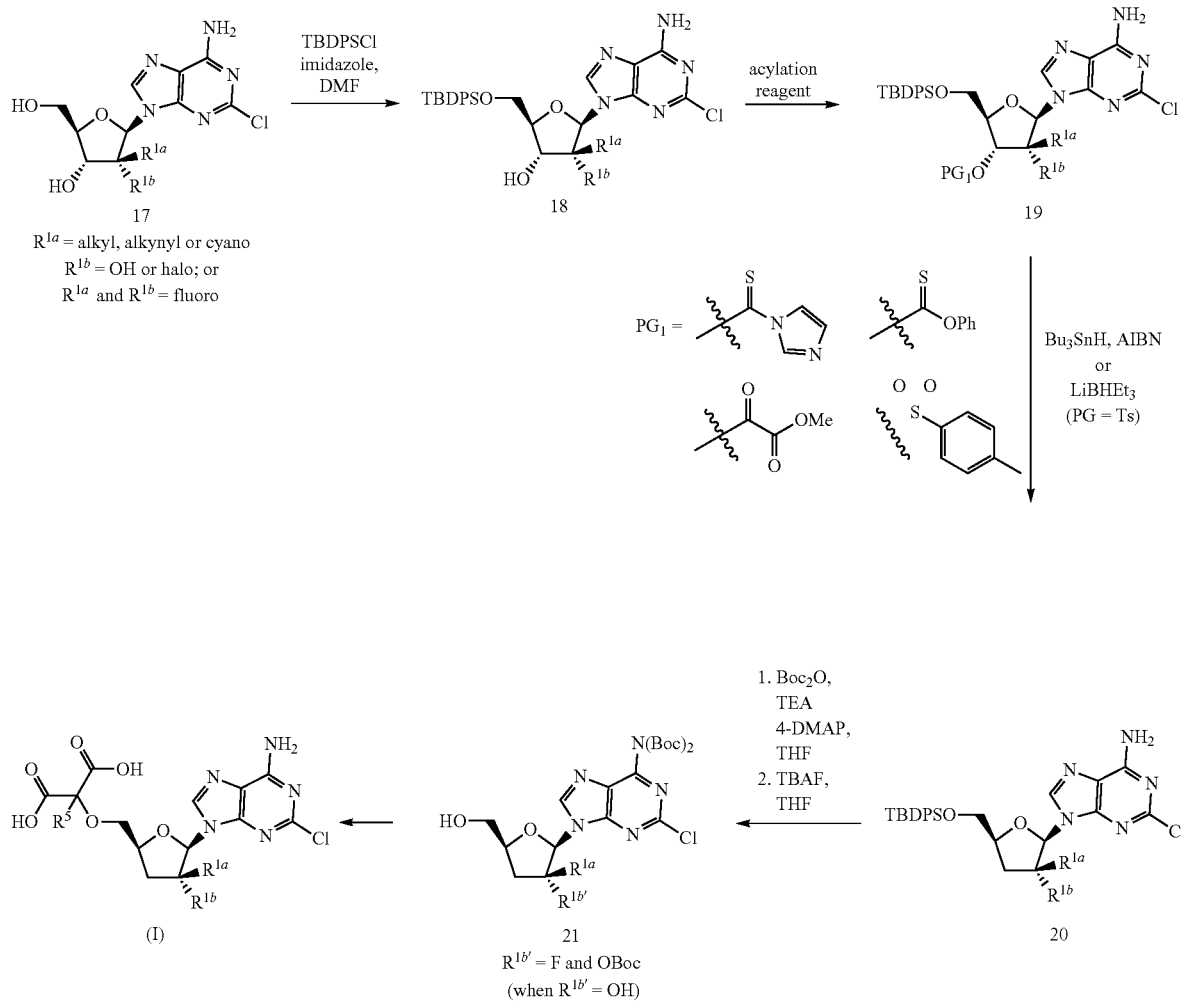

Selective protection of the primary alcohol in compound 17 with a silyl protecting group such as TBDPSCl, followed by acylation and removal of the 3'-OH in resulting compound 18 as described in Scheme 3 above provides a compound of formula 20. Treatment of compound 20 with Boc₂O, followed by removal of the silyl group provides a compound of formula 21 which is then converted to a compound of Formula (I) as described in Scheme 1 above. Compound of formula (I) where $R^{1a}$ is ethynyl can be converted to the corresponding compound of formula (I) where $R^{1a}$ is vinyl via reduction of the ethynyl group with Lindlar catalyst in the presence of hydrogen.

Compounds of formula 17 are either commercially available or they can be prepared by methods known in the art. For example, (2R,3R,4R,5R)-2-(6-amino-2-chloro-9H-purin-9-yl)-5-(hydroxymethyl)-3-methyltetrahydrofuran-3,4-diol is commercially available. (2R,3R,4R,5R)-2-(6-Amino-2-chloro-9H-purin-9-yl)-5-(hydroxymethyl)-3-vinyltetrahydrofuran-3,4-diol can be prepared according to procedures reported by Blatt, Lawrence M. et. al in U.S. Pat. Appl. Publ. No. 20150366888 or by Carroll, Steven S. et al, in PCT Int. Appl., Publication No., WO2004000858; and (2R,3R,4R,5R)-2-(6-amino-2-chloro-9H-purin-9-yl)-3,4-dihydroxy-5-(hydroxymethyl)tetrahydro-furan-3-carbonitrile can be prepared according to procedures reported by Ohtawa, Masaki et al., J. Med. Chem, 50(9), 2007-2009; 2007.

Compounds of Formula (I) having the structure:

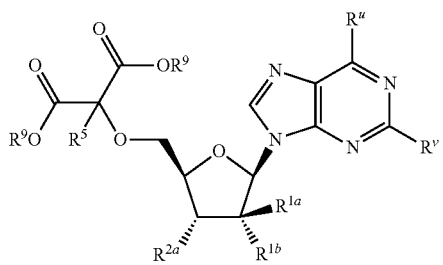

where $R^{1a}$ is hydrogen or alkyl, $R^{1b}$ is hydroxy or halo; $R^{2a}$ is azido or $NH_2$ and $R^{2b}$ is hydrogen, $R^3$ is hydrogen, Het is a ring of formula (iii), and $R^u$, $R^v$, $R^5$ and $R^9$ are as defined in the Summary can be synthesized by proceeding as illustrated and described in a representative example in Scheme 5 below.

Scheme 5

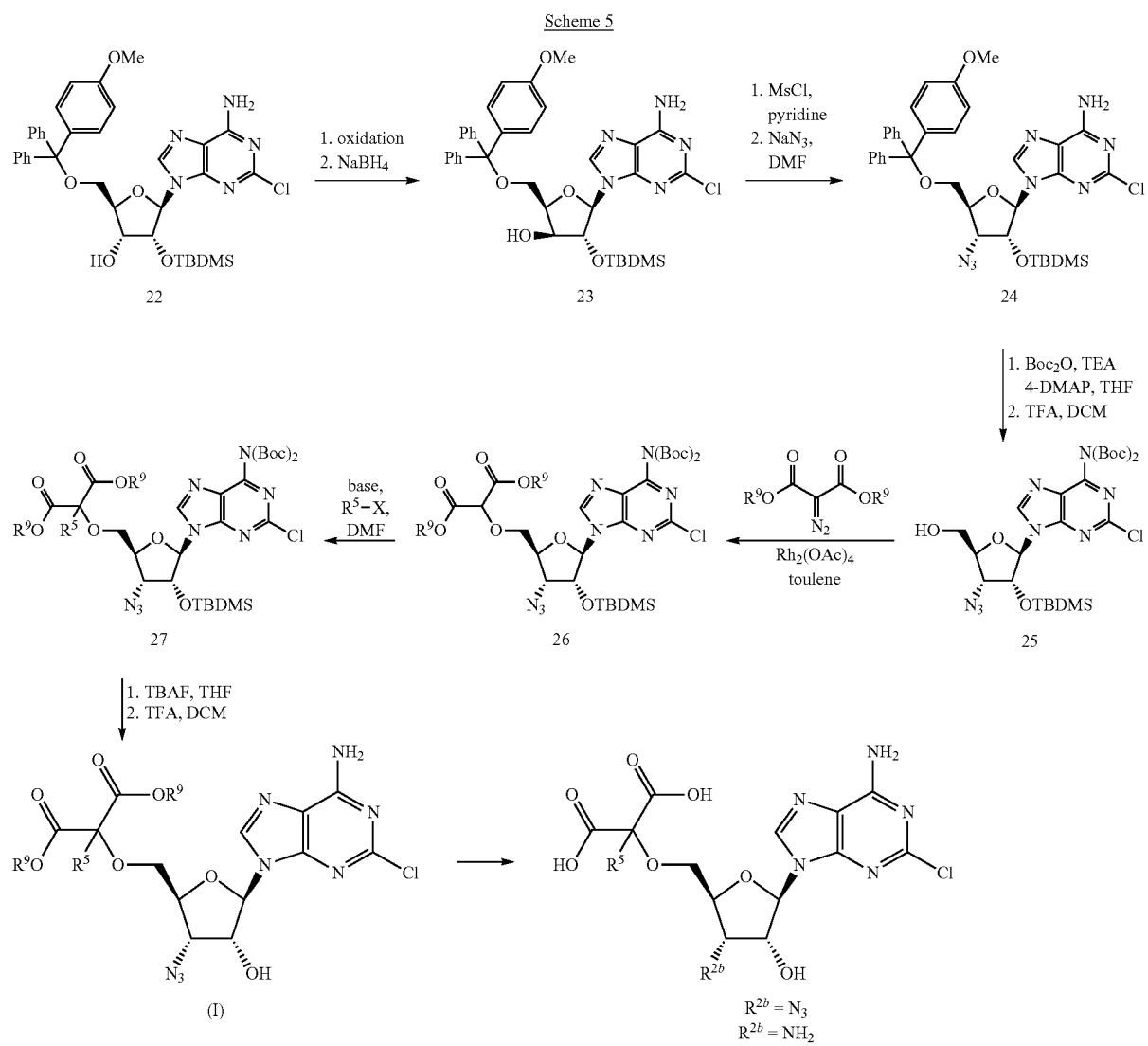

Compound 23 is synthesized by first converting the 3'-OH group in compound 22 to a ketone with a suitable oxidizing agent such as Dess-Martine periodinane, Swern, Moffet, PDC, or $SO_3$•pyridine, followed by reduction of the keto group with a suitable reducing agent such as sodium borohydride. Compound 22 can be prepared according to the procedure reported by Koole, L. H. et al., Acta Chemica Scandinavica, 43, 665-669, 1989. The 3'-OH group in compound 23 is then converted to the corresponding azide compound 24 by first converting 3'-OH to a suitable leaving group such as mesylate, tosylate or triflate under reaction conditions well known in the art, followed by displacement of the leaving group with sodium azide.

After protecting the 6-amino group in compound 24 with suitable protecting group such as tert-butoxycarbonyl, the 4-methoxytrityl group is selectively removed with an acid such as TFA to provide compound 25. Compound 25 is then converted to compound of formula 27 as described in Scheme 1 above. Sequential removal of the TBDMS and Boc groups in compound 27 is achieved with treatment with TBAF, followed by treatment with TFA to give a compound of Formula (I) where $R^{2a}$ is azido and $R^9$ is alkyl group which can then be converted to corresponding compounds of Formula (I) where $R^9$ is hydrogen as described in Scheme 1 above. Compounds of Formula (I) where $R^{2a}$ is azido can also be converted to corresponding compounds of Formula (I) where $R^{2a}$ is amino under suitable hydrogenation reaction conditions such as $H_2$, Pd/C, Pd(OH)$_2$/C or Lindlar catalyst.

Compounds of Formula (I) having the structure:

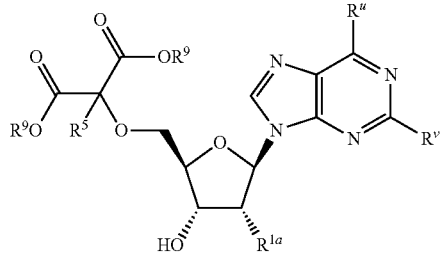

where $R^{1a}$ is azido or $NH_2$; Het is a ring of formula (iii) and $R^u$, $R^v$, $R^5$ and $R^9$ are as defined in the Summary can be synthesized by proceeding as illustrated and described in a representative example in Scheme 6 below.

Scheme 6

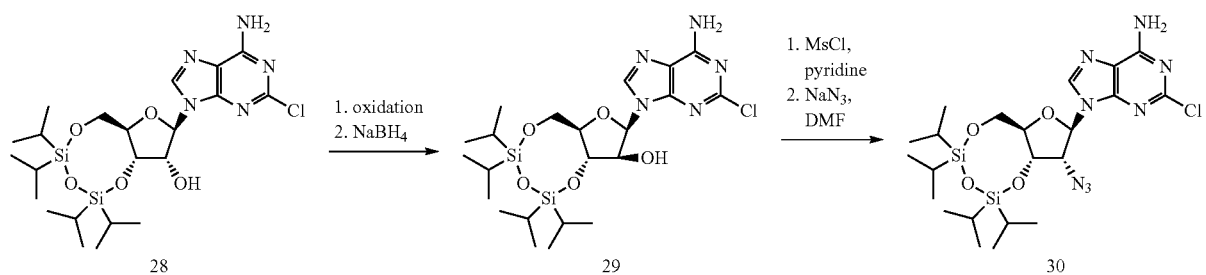

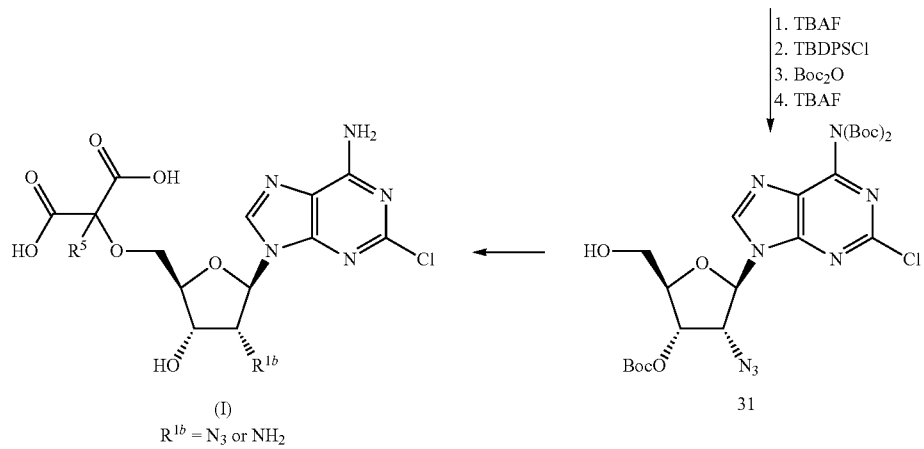

Compound 28 is first converted to compound 30 according to the procedure described in Scheme 5 above. Compound 28 can be prepared according to the procedure reported by Secrist, John A., III et al., Journal of Medicinal Chemistry, 31(2), 405-10; 1988. Compound 31 is obtained from compound 30 via a 4-step process. The bis-silyl protecting group on the 3',5'-diol of compound 30 is first removed by treatment of TBAF and then the primary alcohol is protected as a TBDPS ether. Further protection of the 3'-OH and 6-$NH_2$ groups with $Boc_2O$, followed by removal of the TBDPS ether with TBAF affords compound 31. Compound 31 is converted to a compound of Formula (I) as described in Schemes 1 and 5 above.

Compounds of Formula (I) having the structure:

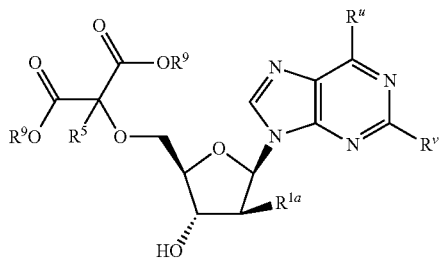

where $R^{1a}$ is azido or $NH_2$, Het is a ring of formula (iii) where $R^s$ is hydrogen, and $R^u$, $R^v$, $R^5$ and $R^9$ are as defined in the Summary can be synthesized by proceeding as illustrated and described in a representative example in Scheme 7 below.

Scheme 7

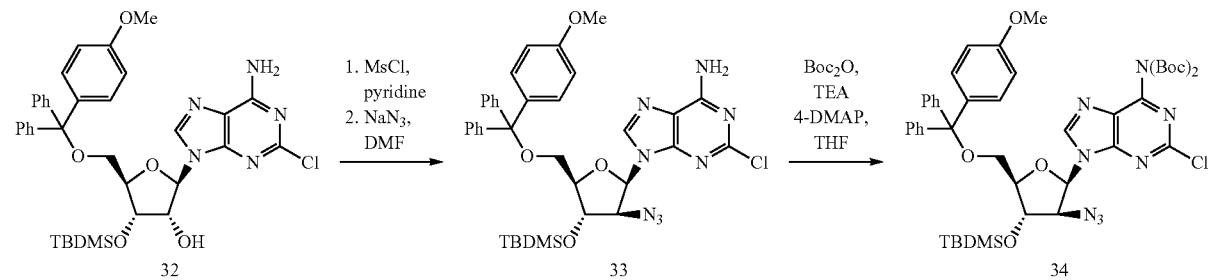

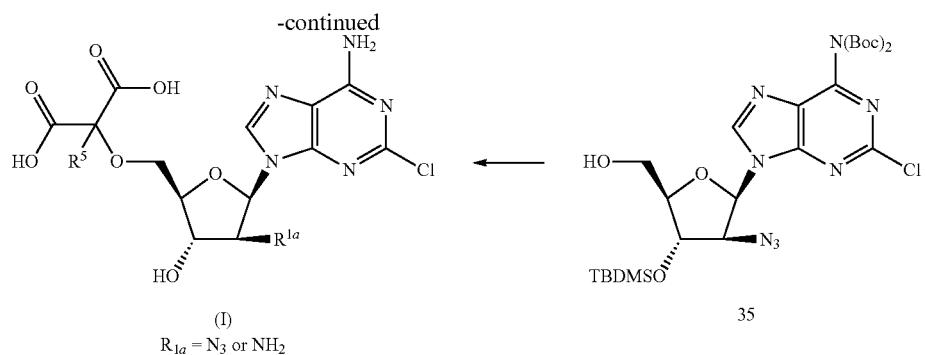

(I)

$R_{1a}$ = $N_3$ or $NH_2$

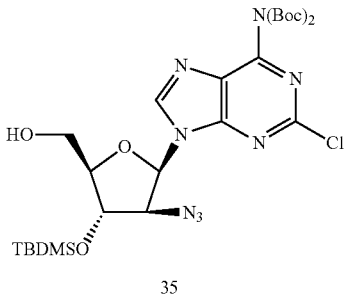

35

Compounds of Formula (I) as shown above, from compound 32 by first converting it into compound 35 as described in Scheme 7. Compound 35 is then converted to a compound of Formula (I) by following the reaction conditions described in Scheme 1. Compound 32 can be prepared according to the procedure reported by Koole, L. H. et al., Acta Chemica Scandinavica, 43, 665-669, 1989.

Proceeding as described in Scheme 7 above, but substituting compound 32 with compounds (2R,3R,4R,5R)-5-(6-amino-2-chloro-9H-purin-9-yl)-4-((tert-butyldimethylsilyl)-oxy)-2-(((4-methoxyphenyl)diphenylmethoxy)methyl)-tetrahydrofuran-3-ol,

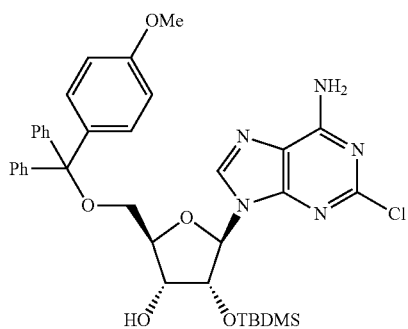 [SMILES: COc1ccc(C(OC[C@H]2O[C@@H](n3cnc4c(N)nc(Cl)nc43)[C@H](O[Si](C)(C)C(C)(C)C)[C@@H]2O)(c2ccccc2)c2ccccc2)cc1]

and (2R,3R,4S,5R)-5-(6-amino-2-chloro-9H-purin-9-yl)-4-fluoro-2-(((4-methoxyphenyl)diphenylmethoxy)methyl)-tetrahydrofuran-3-ol,

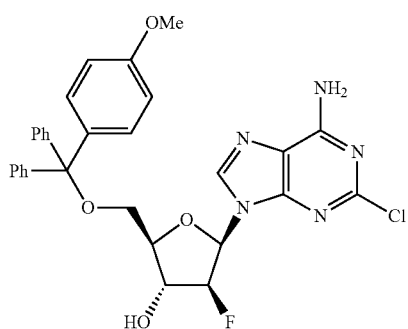 [SMILES: COc1ccc(C(OC[C@H]2O[C@@H](n3cnc4c(N)nc(Cl)nc43)[C@@H](F)[C@@H]2O)(c2ccccc2)c2ccccc2)cc1]

compounds of Formula (I) where

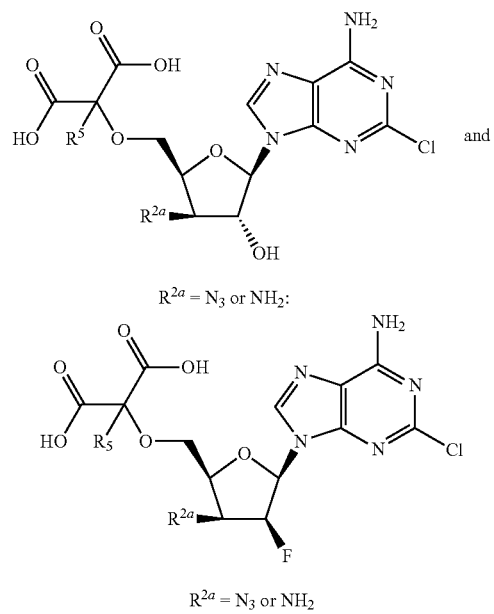

$R^{2a}$ = $N_3$ or $NH_2$:

$R^{2a}$ = $N_3$ or $NH_2$ where $R^5$ is as defined in the Summary respectively, can be synthesized.

(2R,3R,4R,5R)-5-(6-Amino-2-chloro-9H-purin-9-yl)-4-((tert-butyldimethylsilyl)oxy)-2-(((4-methoxyphenyl)diphenylmethoxy)methyl)-tetrahydrofuran-3-ol and (2R,3R,4S,5R)-5-(6-amino-2-chloro-9H-purin-9-yl)-4-fluoro-2-(((4-methoxyphenyl)diphenylmethoxy)methyl)-tetrahydrofuran-3-ol which can be prepared according to reported procedure described in Koole, L. H. et al, Acta Chemica Scandinavica, 43, 665-669, 1989.

Compounds of Formula (I) having the structure:

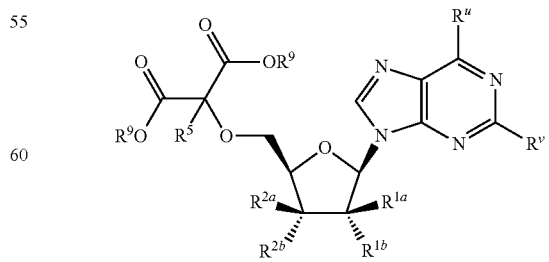

where $R^{1a}$ and $R^{2a}$, or $R^{1a}$ and $R^{2b}$, or $R^{1b}$ and $R^{2b}$, or $R^{1a}$, $R^{2a}$, $R^{1b}$ and $R^{2b}$ are fluoro, Het is a ring of formula (iii), and $R^u$, $R^v$, $R^5$ and $R^9$ are as defined in the Summary can be synthesized by proceeding as illustrated and described in a representative example in Scheme 8 below.
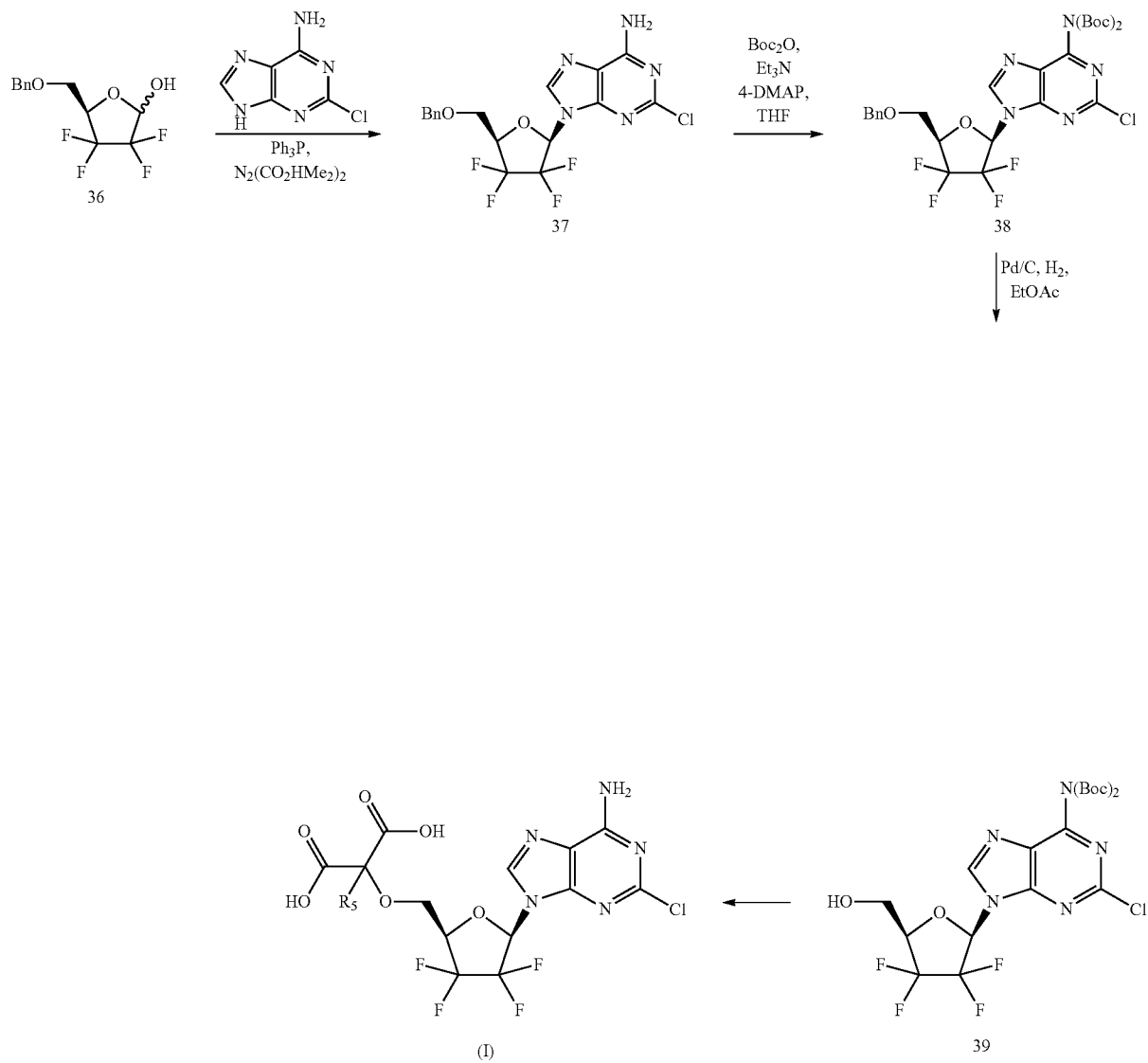

Treatment of compound 36 with 2-chloro-6H-purin-6-amine according to the procedure reported by Sari, Ozkan. et al., Tetrahedron Letters, 58(7), 642-644; 2017 provides compound 37. Protection of the amino group with tert-butoxycarbonyl, followed by removal of the benzyl group provide primary alcohol compound 39 which is converted to a compound of Formula (I) as described in Scheme 1 above.

Compounds of Formula (I) having the structure:

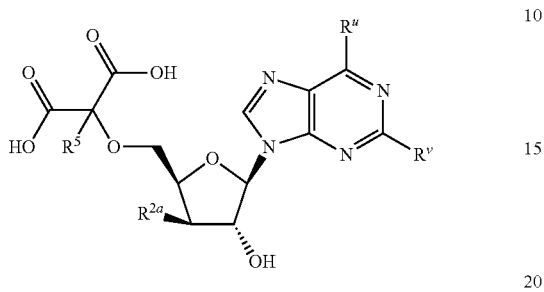

where $R^{2a}$ is alkyl, alkynyl, or cyano, Het is a ring of formula (iii) where $R^s$ is hydrogen, and $R^u$ and $R^v$ and $R^5$ is as defined in the Summary can be synthesized by proceeding as illustrated and described in a representative example in Scheme 9 below.

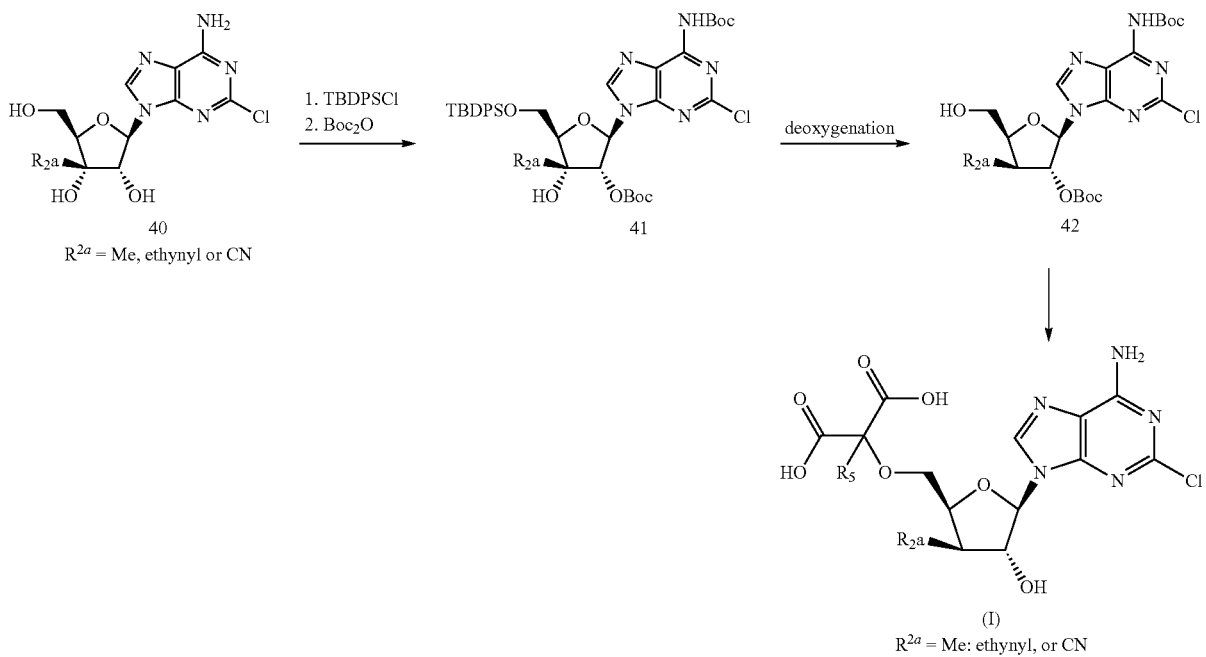

Selective protection of the primary alcohol in a compound of formula 40 with a suitable protecting group such tributyl diphenylsilyl, followed by treatment of the resulting silyl compound with Boc$_2$O under reaction conditions described above provides a compound of formula 41. Deoxygenation of the 3'-hydroxy under conditions described in Scheme 4 above provides a compound of formula 42 which is then converted into a compound of Formula (I) as described in Scheme 1 above.

Compound of formula 40 can be prepared by methods well known in the art. (2R,3 S,4R,5R)-5-(6-Amino-2-chloro-9H-purin-9-yl)-2-(hydroxymethyl)-3-methyl-tetrahydrofuran-3,4-diol can be prepared according to the procedure reported by Franchetti, Palmarisa, et al., J. Med. Chem., 48(15), 4983-4989, 2005). (2R,3S,4R,5R)-5-(6-Amino-2-chloro-9H-purin-9-yl)-3-ethynyl-2-(hydroxymethyl)-tetrahydrofuran-3,4-diol can be prepared according to the procedure reported by Hulpia, Fabian et al., Bioorganic & Medicinal Chemistry Letters, 26(8), 1970-1972; 2016.

(2R,3S,4R,5R)-5-(6-Amino-2-chloro-9H-purin-9-yl)-3,4-dihydroxy-2-(hydroxymethyl)tetrahydrofuran-3-carbonitrile can be prepared from (2R,4S,5R)-5-(6-amino-2-chloro-9H-purin-9-yl)-4-((tert-butyldimethylsilyl)-oxy)-2-(((tert-butyldimethylsilyl)oxy)-methyl)dihydrofuran-3(2H)-one and NaCN according to the similar procedure reported by Camarasa, Maria Jose et al., Journal of Medicinal Chemistry, 32(8), 1732-8; 1989 or from 2-chloro-2'-arabino-fluoro-2'-deoxyadenosine according to the procedure reported by Ohtawa, Masaki et al., *J. Med. Chem.*, 50(9), 2007-2010, 2007.

A compound of Formula (I):

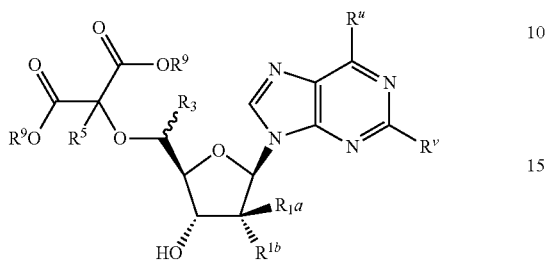

where $R^{1a}$ is hydrogen and $R^{1b}$ is hydroxyl or $R^{1a}$ is fluoro and $R^{1b}$ is hydrogen, $R^3$ is alkyl or aralkyl, Het is a ring of formula (iii) where $R^s$ is hydrogen, and $R^u$, $R^v$, $R^5$ and $R^9$ are as defined in the Summary can be synthesized as illustrated and described in Scheme 10 below.

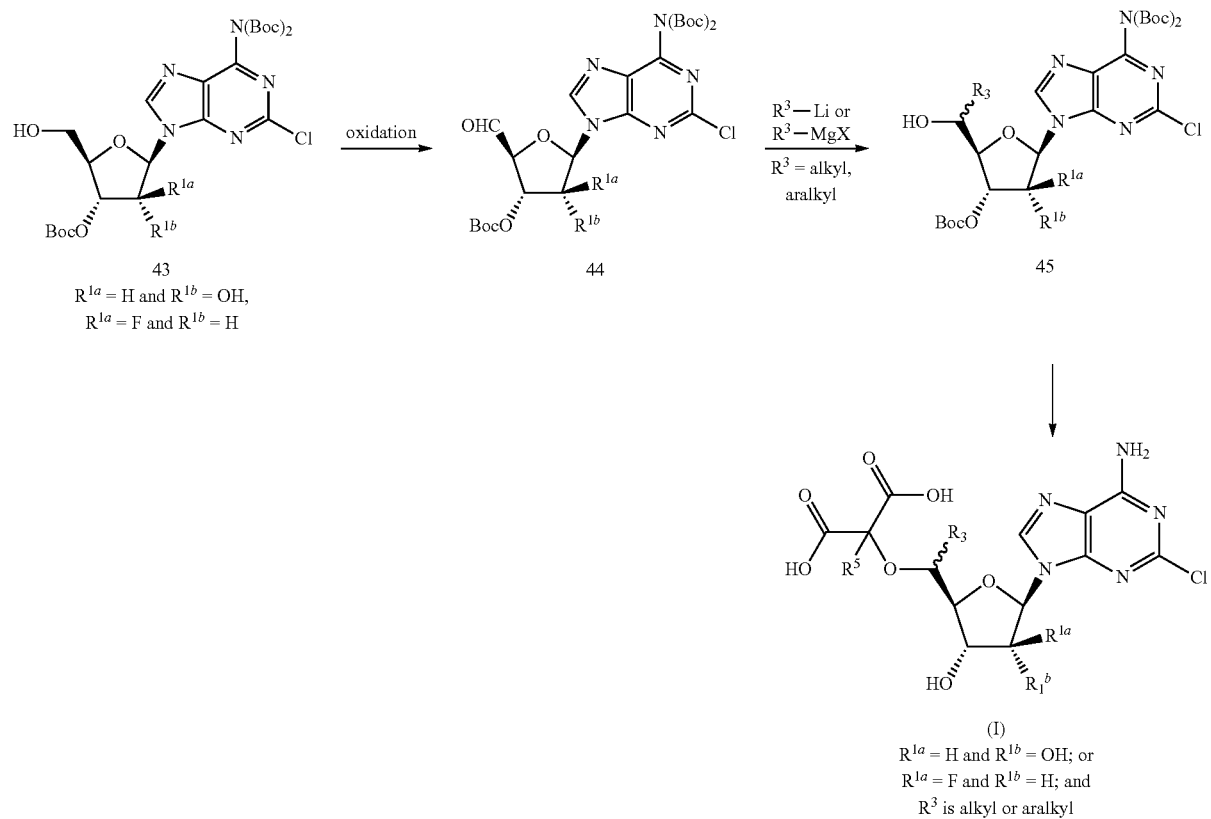

Conversion of primary alcohol group in a compound of formula 43 with a suitable oxidizing reagent such as Dess-Martin periodinane, Swern, Moffet, or PDC provides an aldehyde compound of formula 44. Compound 44 is reacted with a lithium or Grignard reagent of formula $R^3Li$ or $R^3MgX$ where $R^3$ is alkyl or aralkyl and X is halo under conditions well known in the art to provide a compound of formula 45. Compound 45 is then converted to a compound of Formula (I) as described in Scheme 1 above.

The foregoing compound numbers refer solely to the genus structures in the above general synthesis section and not to the compounds disclosed elsewhere in the application.

SYNTHETIC EXAMPLES

Example 1

Synthesis of 2-(((2R,3R,4S,5R)-5-(6-amino-2-chloro-9H-purin-9-yl)-4-fluoro-3-hydroxytetrahydrofuran-2-yl)methoxy)malonic Acid

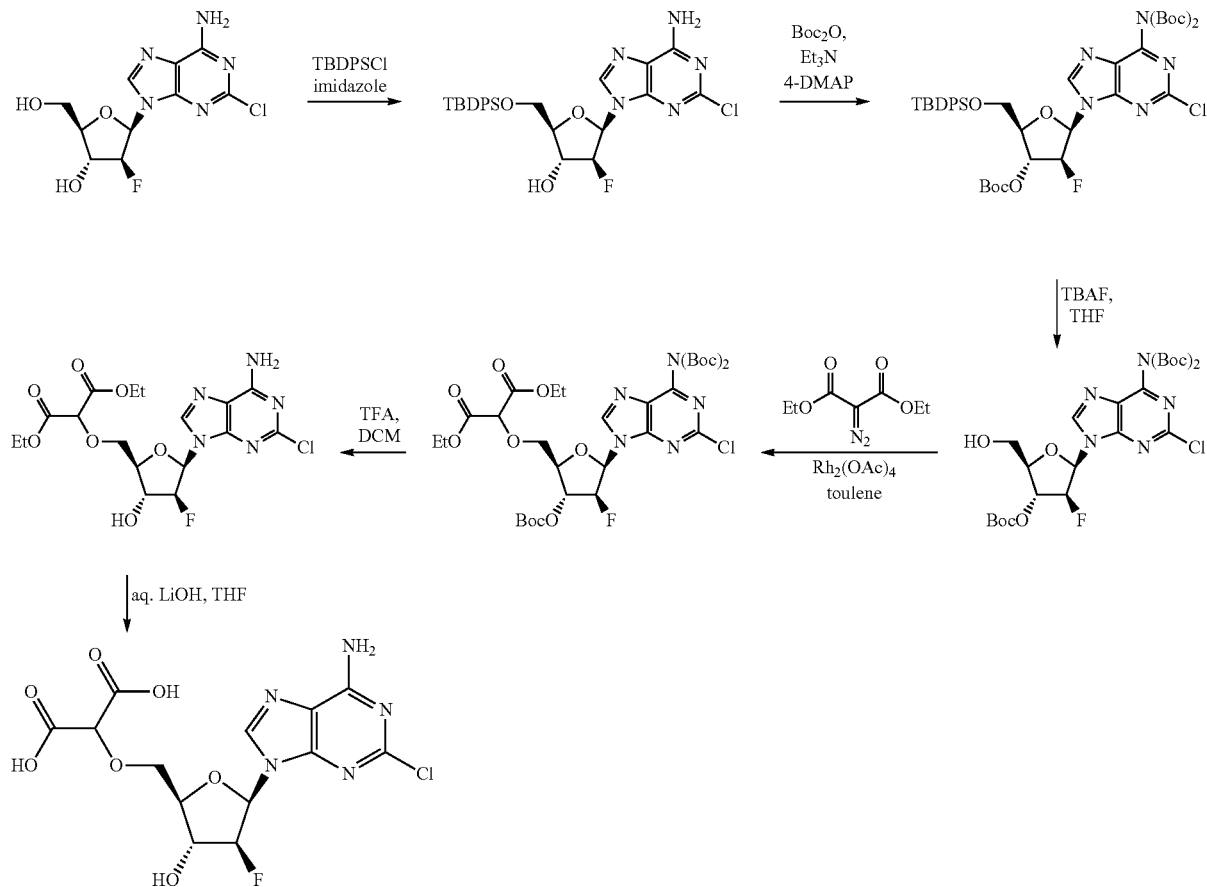

Step 1:

To a solution of 2-chloro-2'-arabino-fluoro-2'-deoxyadenosine (3.00 g, 9.9 mmol) in DMF (10 mL) at 0° C. was added imidazole (1.68 g, 24.7 mmol) and followed by TBDPSCl (3.00 mL, 11.7 mmol) dropwise. The reaction mixture was allowed to warm up to room temperature and stirred further for 8 h before it was quenched with $H_2O$ (50 mL) and extracted with EtOAc (3×50 mL). The combined organic layer was washed further with $H_2O$ (2×100 mL), brine, dried over $Na_2SO_4$ and concentrated. The residue was purified by silica gel column chromatography (0-20% EtOAc in hexanes) to provide (2R,3R,4S,5R)-5-(6-amino-2-chloro-9H-purin-9-yl)-2-(((tert-butyldiphenylsilyl)oxy)methyl)-4-fluorotetrahydrofuran-3-ol (4.10 g).

Step 2:

To a solution of (2R,3R,4S,5R)-5-(6-amino-2-chloro-9H-purin-9-yl)-2-(((tert-butyldiphenylsilyl)oxy)methyl)-4-fluorotetrahydrofuran-3-ol (4.10 g, 7.56 mmol) in DMF (10 mL) at room temperature was added $Et_3N$ (3.48 mL, 25.0 mmol), 4-DMAP (150 mg, 1.2 mmol) and $Boc_2O$ (5.20 g, 23.8 mmol). The reaction mixture was stirred for 16 h before it was diluted with EtOAc (200 mL) and $H_2O$ (100 mL). The organic layer was separated, washed with $H_2O$ (2×100 mL), brine, dried over $Na_2SO_4$ and concentrated. The residue was purified by silica gel column chromatography (0-20% EtOAc in hexanes) to provide N6,N6-bis-(tert-butoxycarbonyl)-5'-O-(tert-butyldiphenylsilyl)-2'-arabino-fluoro-2'-deoxy-3'-O-(tert-butoxycarbonyl)-2-chloro-adenosine (5.58 g).

Step 3:

N6,N6-Bis-(tert-butoxycarbonyl)-5'-O-(tert-butyldiphenylsilyl)-2'-arabino-fluoro-2'-deoxy-3'-O-(tert-butoxycarbonyl)-2-chloro-adenosine (5.58 g, 6.6 mmol) was dissolved in THF (10 mL) at 0° C. and followed by addition of a solution of TBAF (10 mL, 10 mmol, 1 M in THF) dropwise. The reaction mixture was stirred from 0° C. to room temperature over 2.5 h before it was evaporated to dryness. The residue was purified by silica gel column chromatography (0-20% EtOAc in hexanes) to provide N6,N6-bis-(tert-butoxycarbonyl)-5'-O-(tert-butyldiphenylsilyl)-2'-arabino-fluoro-2'-deoxy-3'-O-(tert-butoxycarbonyl)-2-chloro-adenosine-fluoro-2'-deoxy-3'-O-(tert-butoxycarbonyl)-2-chloro-adenosine (3.15 g).

Step 4:

To a solution of N6,N6-bis-(tert-butoxycarbonyl)-2'-fluoro-2'-deoxy-3'-O-(tert-butoxycarbonyl)-2-chloro-adenosine (800 mg, 1.32 mmol) in toluene (2 mL) was added diethyl 2-diazomalonate (321 mg, 1.72 mmol) and $Rh_2(OAc)_4$ (59 mg, 0.13 mmol) under argon atmosphere. The resulting mixture was stirred at 95° C. for 2 h before it was allowed to cool to room temperature. The organic volatile was removed under reduced pressure. The resulting crude was purified by silica gel column chromatography (0-20% EtOAc in hexanes) to provide diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)malonate as a foam (770 mg).

Step 5:

To a solution of diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-malonate (300 mg, 0.394 mmol) in $CH_2Cl_2$ (2 mL) at 0° C. was added TFA (3 mL). The resulting mixture was allowed to warm up to room temperature and stirred for 2 h before it was concentrated under reduced pressure to provide crude diethyl 2-(((2R,3R,4S,5R)-5-(6-amino-2-chloro-9H-purin-9-yl)-4-fluoro-3-hydroxytetrahydrofuran-2-yl)methoxy)malonate.

Step 6:

To a solution of crude diethyl 2-(((2R,3R,4S,5R)-5-(6-amino-2-chloro-9H-purin-9-yl)-4-fluoro-3-hydroxytetrahydrofuran-2-yl)methoxy)malonate (0.394 mmol) in THF (2 mL) and $H_2O$ (2 mL) at room temperature was added LiOH monohydrate (200 mg). The resulting mixture was stirred overnight before it was cooled to 0° C. and acidified to pH ~6 with 1N HCl(aq) solution and concentrated under reduced pressure. The crude residue was purified by preparative reversed-phase HPLC to provide 2-(((2R,3R,4S,5R)-5-(6-amino-2-chloro-9H-purin-9-yl)-4-fluoro-3-hydroxytetrahydrofuran-2-yl)methoxy)malonic acid as a white solid.

$^1$H NMR ($D_2O$, 300 MHz) δ 8.47 (d, J=1.8 Hz, 1H), 6.46 (dd, J=4.4, 13.1 Hz, 1H), 5.27 (t, J=8.5 Hz, 1H), 4.60-4.72 (m, 2H), 4.15 (q, J=4.6 Hz, 1H), 3.86-4.03 (m, 2H); LC/MS [M+H]=406.

Example 2

Synthesis of 2-(((2R,3R,4S,5R)-5-(6-amino-2-chloro-9H-purin-9-yl)-4-fluoro-3-hydroxytetrahydrofuran-2-yl)methoxy)-2-benzylmalonic Acid

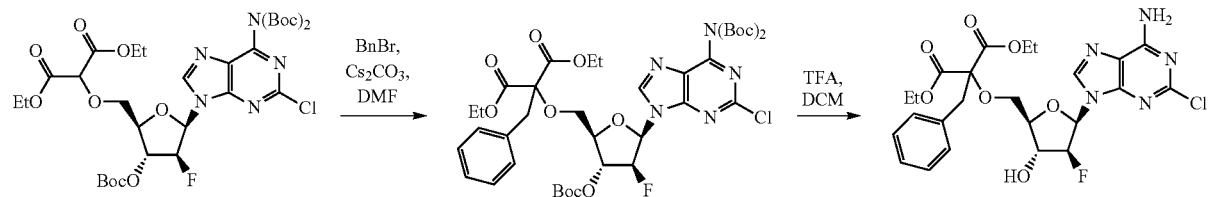

aq. LiOH, THF

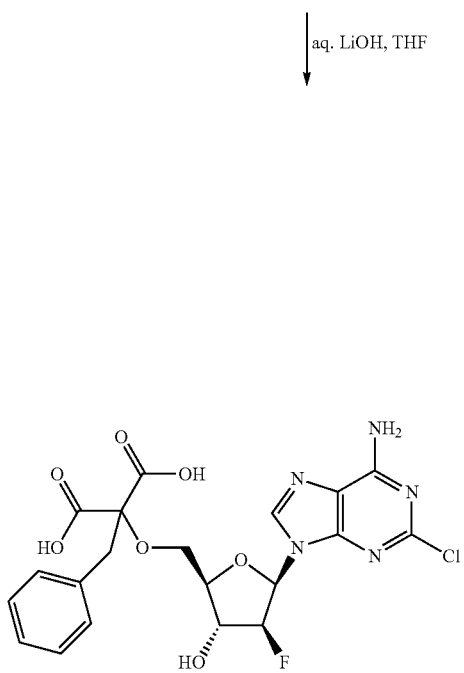

Step 1:

To a solution of diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)malonate (170 mg, 0.223 mmol) in DMF (2 mL) at 25° C. was added $Cs_2CO_3$ (145 mg, 0.446 mmol). The reaction mixture was stirred for 30 min and followed by addition of BnBr (53 uL, 0.446 mmol). The reaction mixture was stirred for 3.5 h before it was diluted with $H_2O$ (20 mL) and extracted with EtOAc (3×30 mL). The combined organic layer was washed further with $H_2O$ (2×40 mL), brine, dried over $Na_2SO_4$ and concentrated. The resulting crude was purified by silica gel column chromatography (0-16% EtOAc in hexanes) to provide diethyl 24(2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluoro-tetrahydrofuran-2-yl)methoxy)-2-benzylmalonate as a foam.

Step 2:

To a solution of diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-benzylmalonate (200 mg, 0.235 mmol) in $CH_2Cl_2$ (2 mL) at 0° C. was added TFA (2 mL). The resulting mixture was stirred at room temperature for 2.5 h before it was concentrated under reduced pressure to provide diethyl diethyl 2-(((2R,3R,4S,5R)-5-(6-amino-2-chloro-9H-purin-9-yl)-4-fluoro-3-hydroxytetrahydrofuran-2-yl)methoxy)-2-benzylmalonate.

Step 3:

To a solution of crude 2-(((2R,3R,4S,5R)-5-(6-amino-2-chloro-9H-purin-9-yl)-4-fluoro-3-hydroxytetrahydrofuran-2-yl)methoxy)-2-benzylmalonate in THF (2 mL) and $H_2O$ (2 mL) at 0° C. was added LiOH monohydrate (150 mg). The resulting mixture was stirred at room temperature overnight before it was cooled to 0° C. and acidified to pH ~6 with 1N HCl (aq) solution and concentrated under reduced pressure. The crude residue was purified by preparative reversed-phase HPLC to provide 2-(((2R,3R,4S,5R)-5-(6-amino-2-chloro-9H-purin-9-yl)-4-fluoro-3-hydroxy-tetrahydrofuran-2-yl)methoxy)-2-benzylmalonic acid as a white solid.

$^1$H NMR ($D_2O$, 300 MHz) δ 8.27 (bs, 1H), 8.16 (s, 1H), 7.11 (bs, 5H), 6.35 (dd, J=4.3, 13.5 Hz, 1H), 5.17-5.36 (m, 1H), 4.53-4.56 (m, 1H), 4.18-4.28 (m, 1H), 3.70-3.85 (m, 2H), 3.24 (s, 2H); LC/MS [M+H]=496.

Example 3

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-carboxybenzyl)malonic Acid

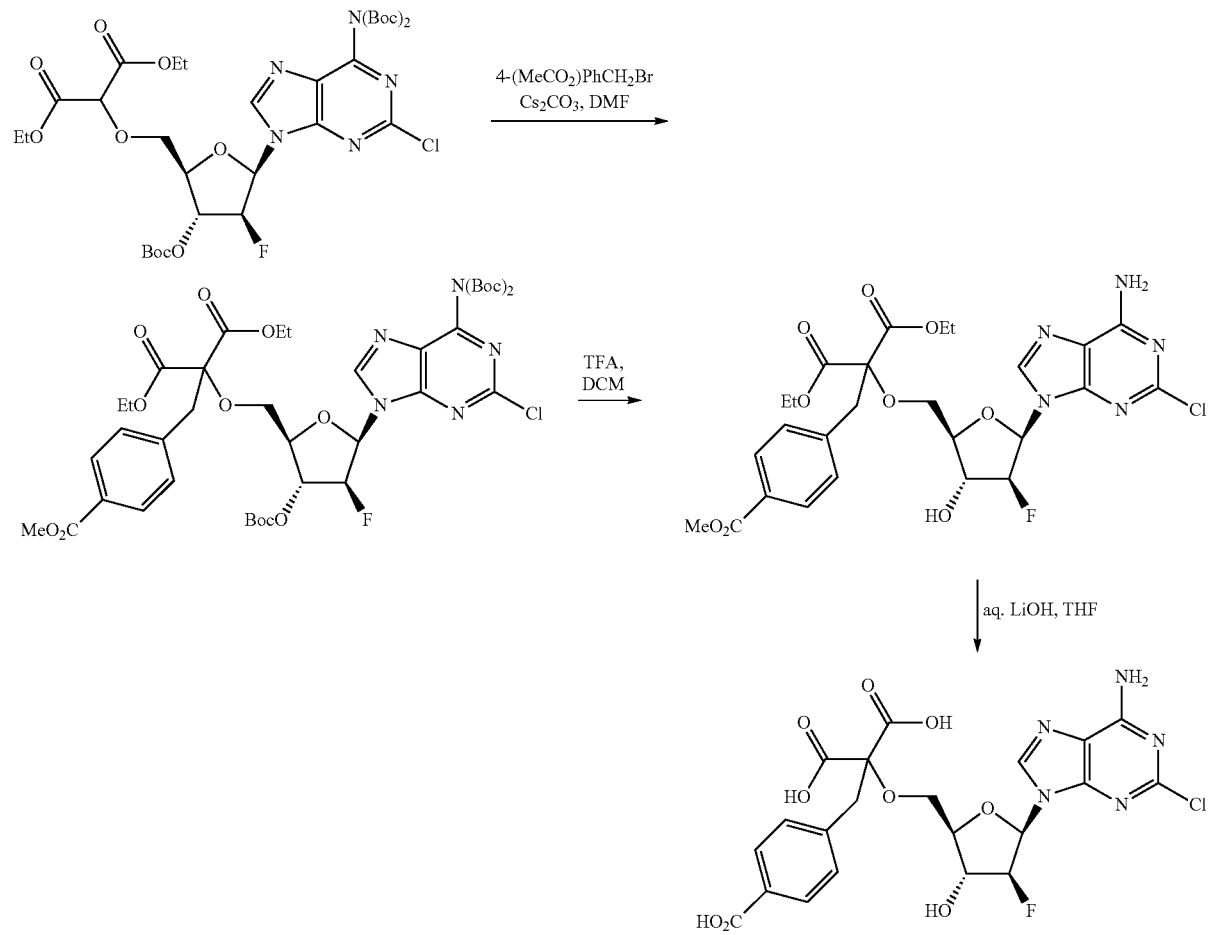

Proceeding as described in Example 2 above but substituting benzyl bromide with methyl 4-(bromomethyl)benzoate provided 2-(((2R,3R,4S,5R)-5-(6-amino-2-chloro-9H-purin-9-yl)-4-fluoro-3-hydroxytetrahydrofuran-2-yl)methoxy)-2-(4-carboxybenzyl)malonic acid as a white solid.
$^1$H NMR (CD$_3$OD, 300 MHz) δ 8.33 (d, J=2 Hz, 1H), 7.78-7.81 (d, J=8.3 Hz, 2H), 7.38-7.41 (d, J=8.3 Hz, 2H), 6.41-6.47 (dd, J=4.5, 13.6 Hz, 1H), 5.07-5.28 (dt, J=4.1, 52 Hz, 1H), 4.64-4.73 (dt, J=4.2, 18.0 Hz, 1H), 4.15-4.19 (q, J=4.6 Hz, 1H), 3.93-4.10 (m, 2H), 3.42-3.55 (m, 2H); LC/MS [M−H]=538.

Example 4

Synthesis of 2-(((2R,3R,4S,5R)-5-(6-amino-2-chloro-9H-purin-9-yl)-4-fluoro-3-hydroxytetrahydrofuran-2-yl)methoxy)-2-((6-chloropyridin-3-yl)methyl)malonic Acid

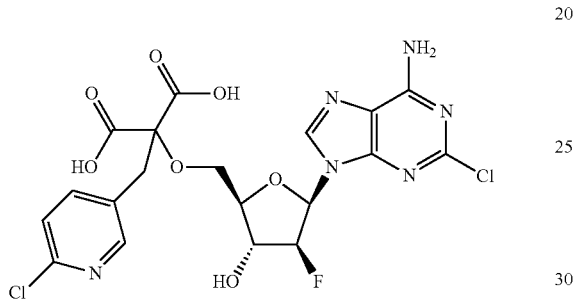

Proceeding as described in Example 2 above but substituting benzyl bromide with 5-(bromomethyl)-2-chloropyridine, the title compound was obtained as a white solid.
$^1$H NMR (CD$_3$OD, 300 MHz) δ 8.27 (s, 1H), 8.24 (d, J=2.5 Hz, 1H), 7.74 (dd, J=2.3, 8.4 Hz, 1H), 7.22 (d, J=8.3 Hz, 2H), 6.43 (dd, J=4.3, 13.7 Hz, 1H), 5.15 (dt, J=4.8, 51.7 Hz, 1H), 4.60-4.70 (m, 1H), 4.15-4.18 (m, 1H), 3.97-4.09 (m, 2H), 3.35-3.42 (m, 2H); LC/MS [M+H]=531.

Example 5

Synthesis of 2-(((2R,3S,5R)-5-(6-amino-2-chloro-9H-purin-9-yl)-3-hydroxytetrahydrofuran-2-yl)methoxy)malonic Acid

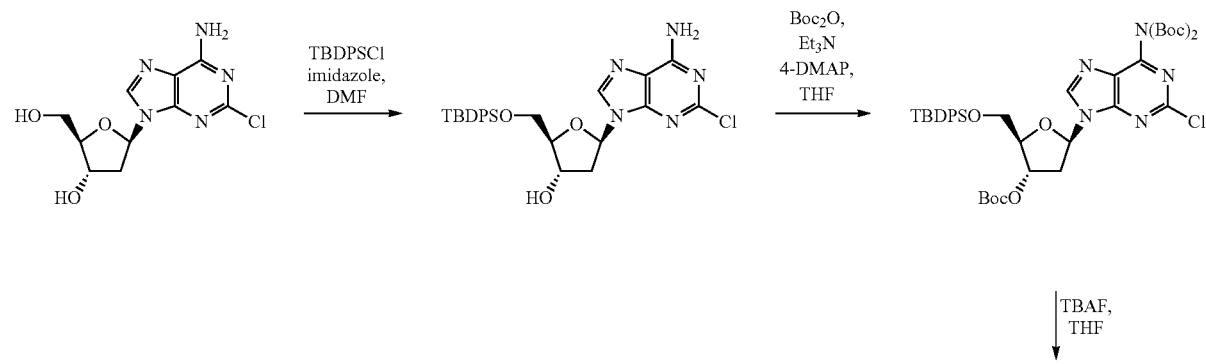

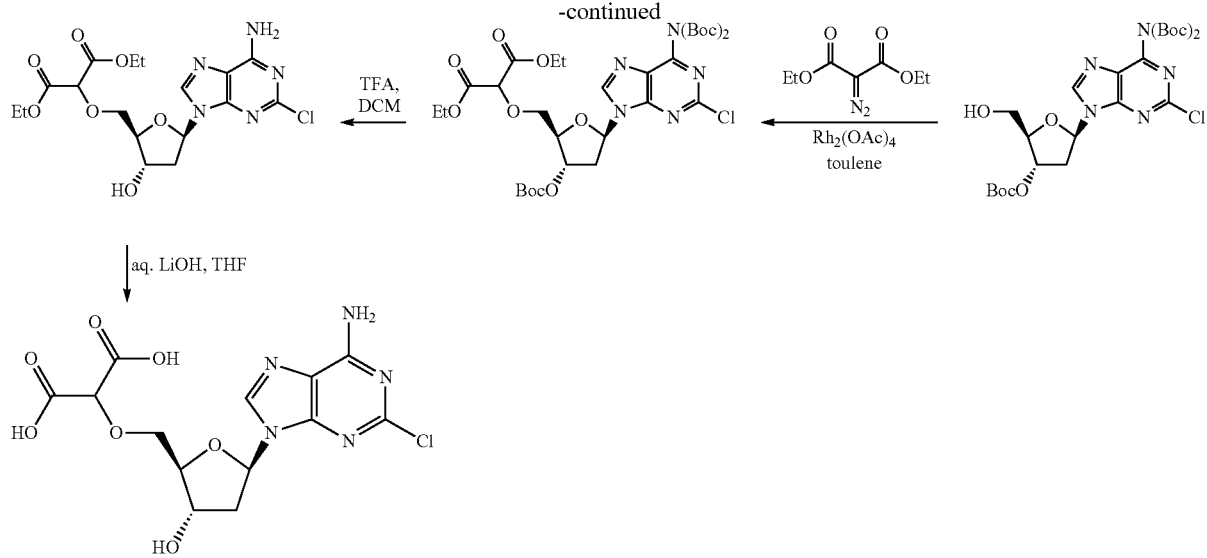
Proceeding as described in Example 1 above but substituting 2-chloro-2'-arabino-fluoro-2'-deoxyadenosine with 2-chloro-2'-deoxyadenosine, the title compound was obtained as a white solid.
$^1$H NMR (D$_2$O, 300 MHz) δ 8.40 (bs, 1H), 6.32 (t, J=6.4 Hz, 1H), 4.63-4.70 (m, 1H), 4.28 (s, 1H), 4.18-4.20 (m, 1H), 3.66 (d, J=4.5 Hz, 2H), 2.72-2.85 (m, 1H), 1.90-2.54 (m, 1H); LC/MS [M+H]=388.
Example 6
Synthesis of 2-(((2R,3R,4R,5R)-5-(6-amino-9H-purin-9-yl)-4-fluoro-3-hydroxytetrahydrofuran-2-yl)methoxy)malonic Acid
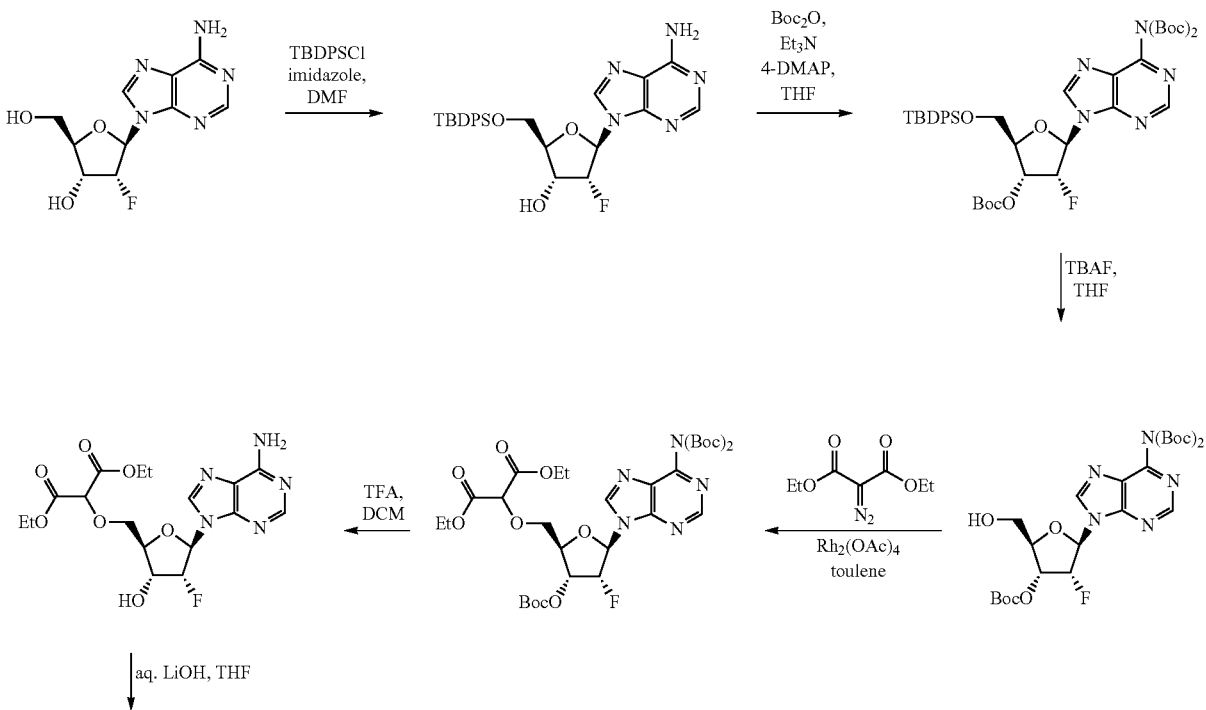

149
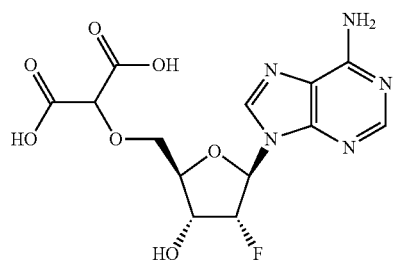
Proceeding as described in Example 1 above but substituting 2-chloro-2'-arabino-fluoro-2'-deoxyadenosine with 2'-fluoro-2'-deoxyadenosine according to the procedure for Example 1, the title compound was obtained as a white solid.
LC/MS [M+H]=372.
150
Example 7
Synthesis of 2-(((2R,3R,4R,5R)-5-(6-amino-9H-purin-9-yl)-4-fluoro-3-hydroxytetrahydrofuran-2-yl)methoxy)-2-benzylmalonic Acid
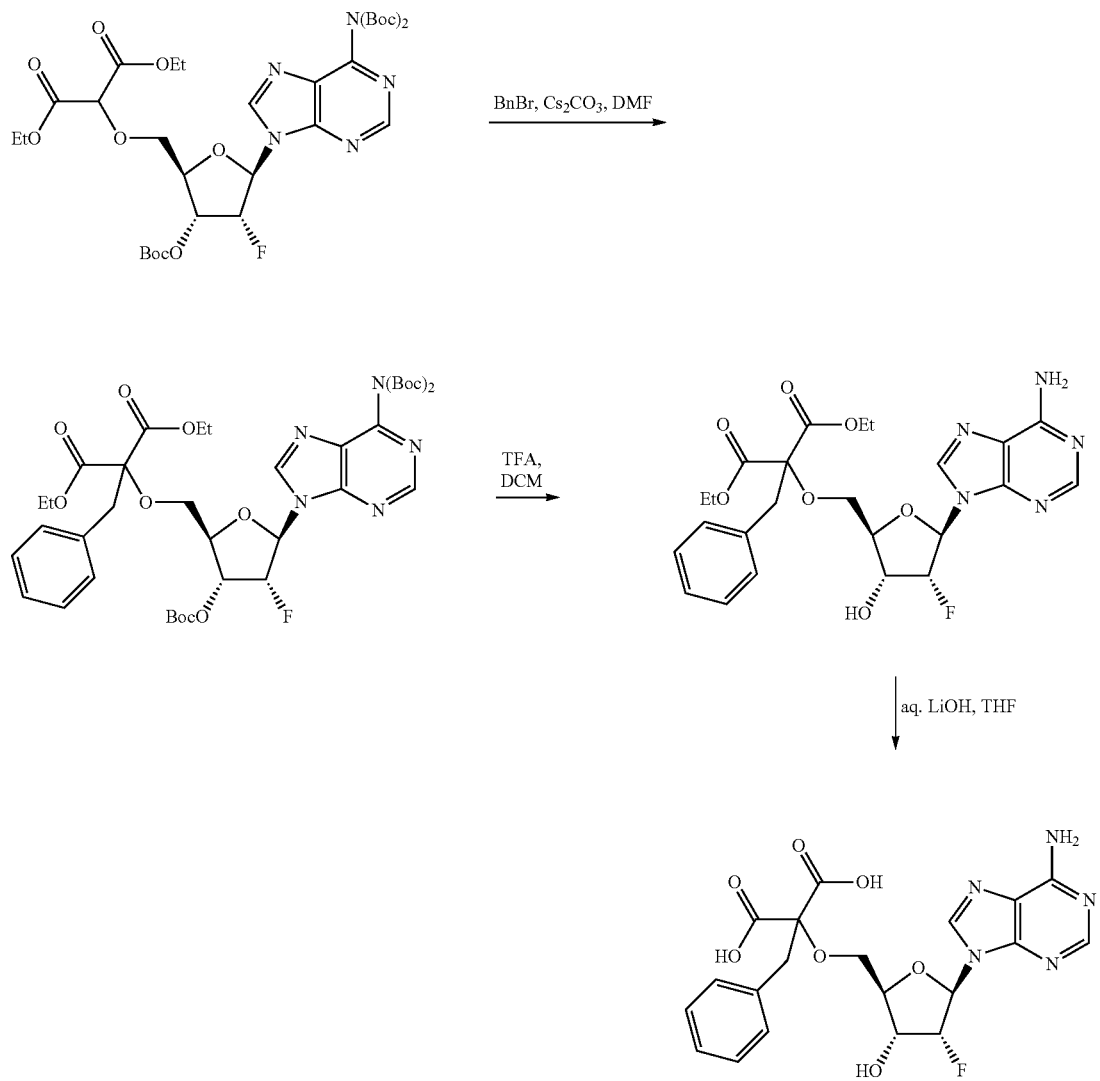

2-(((2R,3R,4R,5R)-5-(6-Amino-9H-purin-9-yl)-4-fluoro-3-hydroxy-tetrahydrofuran-2-yl)methoxy)-2-benzylmalonic acid was prepared from diethyl 2-(((2R,3R,4R,5R)-5-(6-(N-(tert-butoxycarbonyl)(tert-butoxycarbonyl)amino)-9H-purin-9-yl)-3-((tert-butoxycarbonyl)oxy)-4-fluorotetrahydrofuran-2-yl)methoxy)-malonate according to the procedure for Example 2. The title compound was isolated as a white solid.

LC/MS [M+H]=462.

Examples 8a, 8b, 8c and 8d

Synthesis of ((R)-1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic Acid ((S)-1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic Acid ((R)-1-(((2R,3R,4S,5R)-5-(6-((tert-butoxycarbonyl)amino)-2-chloro-9H-purin-9-yl)-4-fluoro-3-hydroxytetrahydrofuran-2-yl)methoxy)-2-ethoxy-2-oxoethyl)phosphonic Acid; and ((S)-1-(((2R,3R,4S,5R)-5-(6-((tert-butoxycarbonyl)amino)-2-chloro-9H-purin-9-yl)-4-fluoro-3-hydroxytetrahydrofuran-2-yl)methoxy)-2-ethoxy-2-oxoethyl)phosphonic Acid

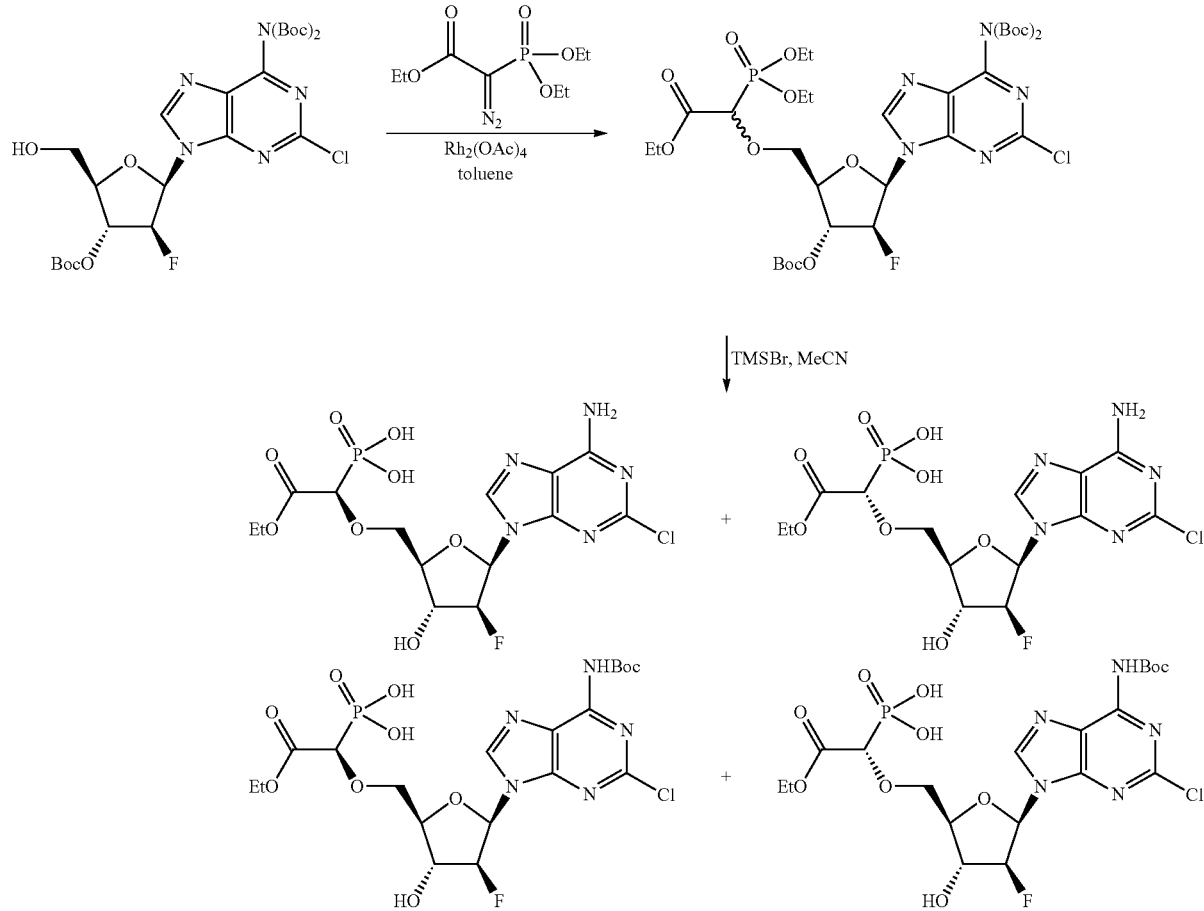

Step 1:
To a solution of N6,N6-bis-(tert-butoxycarbonyl)-2'-arabino-fluoro-2'-deoxy-3'-O-(tert-butoxycarbonyl)-2-chloro-adenosine (512 mg, 0.85 mmol) in toluene (5 mL) was added ethyl 2-diazo-2-(diethoxyphosphoryl)acetate (37 mg, 1.10 mmol) and Rh$_2$(OAc)$_4$ (37 mg, 0.08 mmol) under argon atmosphere. The resulting mixture was stirred at 95° C. for 3 h before it was allowed to cool to room temperature. The organic volatile was removed under reduced pressure. The resulting crude was purified by silica gel column chromatography (5-100% EtOAc in hexanes) to provide ethyl 2-(((2R,3R,4S,5R)-5-(6-(N-(tert-butoxy carbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-(diethoxyphosphoryl)acetate (557 mg) as a mixture of diastereomers.

Step 2:
To a solution of ethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-(diethoxyphosphoryl)acetate (345 mg, 0.42 mmol) in MeCN (6 mL) at −20° C. was added TMSBr (441 mL, 3.34 mmol) dropwise. The resulting mixture was stirred from −20 to 0° C. over 26 h before it was quenched with H$_2$O (4 mL). The resulting mixture was stirred at 0° C. for 20 h before it was quenched with NH$_4$OH (6 mL) and concentrated under reduced pressure. The crude residue was purified by preparative reversed-phase HPLC to provide the title compounds as white solids.

((R)-1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic acid (diastereisomer 1)

$^1$H NMR (CD$_3$OD, 300 MHz) δ 8.54 (bs, 1H), 6.42 (dd, J=4.1, 10.1 Hz, 1H), 5.09-5.31 (m, 1H), 4.55-4.74 (m, 1H), 4.37-4.53 (m, 1H), 4.27 (q, J=7.1 Hz, 2H), 4.10-4.20 (m, 1H), 3.84-4.01 (m, 2H), 1.28 (t, J=6.9 Hz, 3H); LC/MS [M+H]=470.

((S)-1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic acid (diastereisomer 2)

$^1$H NMR (CD$_3$OD, 300 MHz) 8.52 (bs, 1H), 6.42 (dd, J=4.6, 12.9 Hz, 1H), 5.21 (dt, J=4.6, 52.3 Hz, 1H), 4.72 (dt, J=4.9, 13.1 Hz, 1H), 4.45 (d, J=18.4 Hz, 1H), 4.27 (q, J=7.1 Hz, 2H), 4.10-4.20 (m, 1H), 3.85-4.01 (m, 2H), 1.29 (t, J=7.0 Hz, 3H); LC/MS [M+H]=470.

((R)-1-(((2R,3R,4S,5R)-5-(6-((tert-butoxy carbonyl)amino)-2-chloro-9H-purin-9-yl)-4-fluoro-3-hydroxytetrahydrofuran-2-yl)methoxy)-2-ethoxy-2-oxoethyl)phosphonic acid (NHBoc diastereisomer 1)

$^1$H NMR (CD$_3$OD, 300 MHz) δ 8.93 (bs, 1H), 8.46 (bs, 1H), 6.56 (m, 1H), 5.07-5.32 (m, 1H), 4.65-4.74 (m, 1H), 4.40 (d, J=23 Hz, 1H), 4.27 (q, J=6.9 Hz, 2H), 4.11-4.20 (m, 1H), 3.85-4.05 (m, 2H), 1.59 (bs, 9H), 1.26-1.35 (m, 3H); LC/MS [M+H]=571.

((S)-1-(((2R,3R,4S,5R)-5-(6-((tert-butoxy carbonyl)amino)-2-chloro-9H-purin-9-yl)-4-fluoro-3-hydroxytetrahydrofuran-2-yl)methoxy)-2-ethoxy-2-oxoethyl)phosphonic acid (NHBoc diastereisomer 1)

$^1$H NMR (CD$_3$OD, 300 MHz) δ 8.95 (bs, 1H), 8.46 (bs, 1H), 6.53 (m, 1H), 5.15-5.39 (m, 1H), 4.65-4.74 (m, 1H), 4.40 (m, 1H), 4.17-4.42 (m, 2H), 4.11-4.17 (m, 1H), 3.85-3.95 (m, 2H), 1.59 (bs, 9H), 1.26-1.35 (m, 3H); LC/MS [M+H]=571.

Example 9

Synthesis of 2-(((2R,3R,4S,5R)-5-(6-amino-2-chloro-9H-purin-9-yl)-4-fluoro-3-hydroxytetrahydrofuran-2-yl)methoxy)succinic Acid

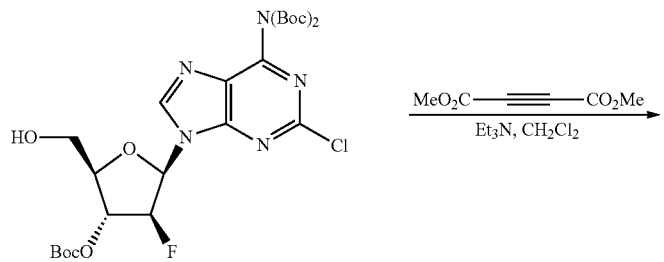

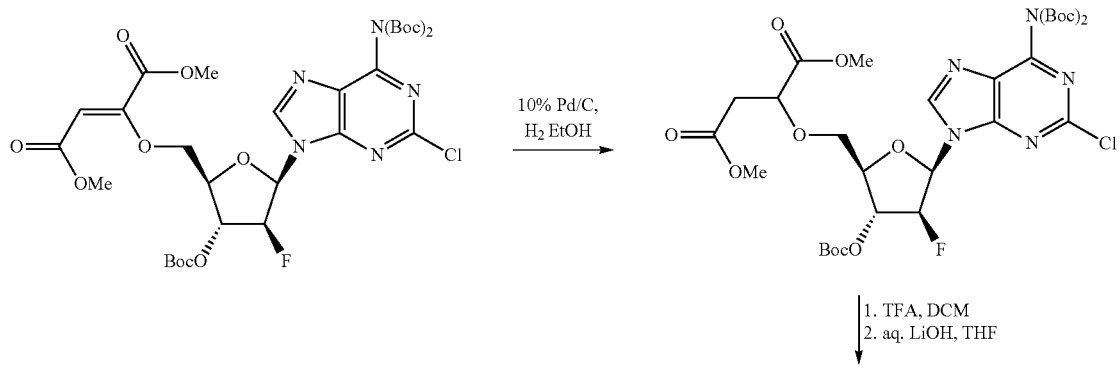

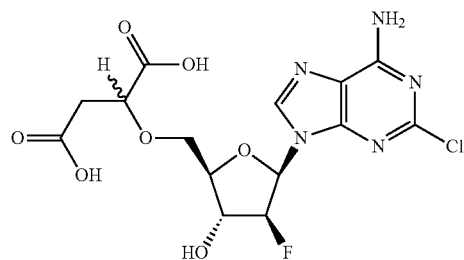

Step 1:

To a solution of N6,N6-bis-(tert-butoxycarbonyl)-2'-arabino-fluoro-2'-deoxy-3'-O-(tert-butoxycarbonyl)-2-chloro-adenosine (1.2 g, 1.99 mmol) and dimethyl acetylene dicarboxylate (1.22 mL, 9.93 mmol) in DCM (10 mL) was added Et₃N (2.52 mL, 18.1 mmol) at room temperature. The resulting mixture was stirred for 3 days before it was concentrated under reduced pressure. The crude was purified by SiO₂ column chromatography (0-24% EtOAc in hexanes) to provide dimethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydro-furan-2-yl)methoxy)fumarate.

Step 2:

To a solution of dimethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydro-furan-2-yl)methoxy)fumarate in EtOH (6 mL) at room temperature was added Pd/C (60 mg, 10% wt). The resulting mixture was stirred under 1 atmosphere of H₂ for 20 minutes before the catalyst was filtered off and the filtrate was concentrated. The crude was purified by SiO₂ column chromatography (0-24% EtOAc in hexanes) to provide dimethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydro-furan-2-yl)methoxy) as the desired product.

Step 3:

To a solution of dimethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydro-furan-2-yl)methoxy) (400 mg, 0.53 mmol) in DCM (4 mL) at room temperature was added TFA (1.5 mL). The reaction mixture was stirred for 4 h before it was concentrated under reduced pressure. The crude was re-dissolved in DCM (5 mL) and concentrated again. The crude material was purified by reversed-phase HPLC to give the product. This product was dissolved in THF (3 mL) and H₂O (1 mL) followed by addition of LiOH.H₂O (50 mg). The reaction mixture was stirred at room temperature for 2 days before the organic volatile was removed under reduced pressure. The crude was acidified to pH 6 with 1N aq. HCl solution before it was concentrated under reduced pressure. The crude was purified by reversed-phase HPLC to provide the title compound (a major isomer) as a white solid.

¹H NMR (CD₃OD, 300 MHz) δ 8.31 (s, 1H), 6.38-6.45 (dd, J=4, 15 Hz, 1H), 5.03-5.24 (m, 1H), 4.54-4.64 (m, 1H), 4.39-4.44 (q, J=4 Hz, 1H), 4.00-4.13 (m, 2H), 3.77-3.84 (m, 1H), 2.68-2.90 (m, 2H); LC/MS [M+H]=420.

Example 10

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-cyanobenzyl)malonic Acid

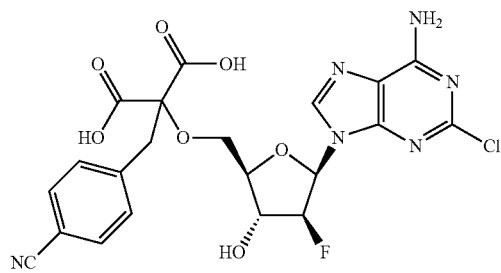 [SMILES: N#Cc1ccc(CC(OC[C@H]2O[C@@H](n3cnc4c(N)nc(Cl)nc43)[C@@H](F)[C@@H]2O)(C(=O)O)C(=O)O)cc1]

Proceeding as described in Example 2 above, but substituting benzyl bromide with 4-(bromomethyl)-benzonitrile the title compound was prepared.

¹H NMR (CD₃OD, 300 MHz) δ 8.27 (s, 1H), 7.48 (s, 4H), 6.43-6.46 (m, 1H), 5.09-5.26 (m, 1H), 4.63-4.69 (m, 1H), 3.97-4.17 (m, 3H), 3.42-3.49 (m, 2H); LC/MS [M+H]=521.

Example 11

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-cyanobenzyl)malonic Acid

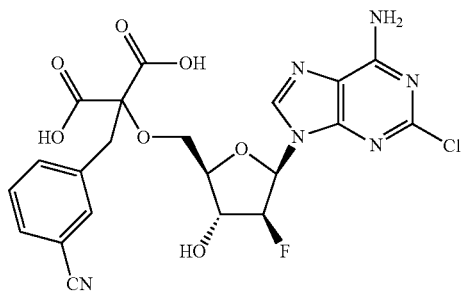 [SMILES: N#Cc1cccc(CC(OC[C@H]2O[C@@H](n3cnc4c(N)nc(Cl)nc43)[C@@H](F)[C@@H]2O)(C(=O)O)C(=O)O)c1]

Proceeding as described in Example 2 above, but substituting benzyl bromide with 3-(bromomethyl)benzonitrile- the, the title compound was obtained as a white solid.

¹H NMR (CD₃OD, 300 MHz) δ 8.27 (s, 1H), 7.67 (bs, 1H), 7.57-7.60 (d, J=8 Hz, 1H), 7.46-7.49 (d, J=8 Hz, 1H), 7.30-7.35 (t, J=8 Hz, 1H), 6.43-6.49 (dd, J=4, 13 Hz, 1H), 5.08-5.28 (dt, J=4, 50 Hz, 1H), 4.62-4.71 (dt, J=4, 17 Hz, 1H), 4.17-4.21 (q, J=4 Hz, 1H), 4.00-4.12 (m, 2H), 3.40-3.52 (m, 2H); LC/MS [M+H]=521.

Example 12

Synthesis of diethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)malonate

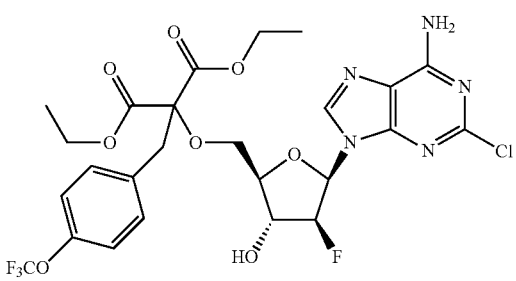

Proceeding as described in Example 2 above, but substituting benzyl bromide with 1-(bromomethyl)-4-(trifluoromethoxy)benzene, the title compound was isolated as a white solid.

$^1$H NMR (CDCl$_3$, 300 MHz) δ 8.13 (bs, 1H), 7.25-7.28 (d, J=9 Hz, 2H), 7.09-7.12 (d, J=8 Hz, 1H), 6.43-6.50 (dd, J=4, 16 Hz, 1H), 6.10 (bs, NH$_2$), 5.05-5.24 (dt, J=3, 52 Hz, 1H), 4.68-4.77 (dt, J=5, 19 Hz, 1H), 4.22-4.28 (m, 4H), 3.98-4.10 (m, 3H), 3.41 (bs, 2H), 1.25-1.30 (dd, J=1, 7 Hz, 6H); LC/MS [M+H]=636.

Example 13

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)malonic Acid, (R)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxo-2-(4-(trifluoromethoxy)-benzyl)propanoic Acid and (S)-2-(((2R,3R,4S,5R)-5-(6-amino-2-chloro-9H-purin-9-yl)-4-fluoro-3-hydroxy-tetrahydrofuran-2-yl)methoxy)-3-ethoxy-3-oxo-2-(4-(trifluoromethoxy)-benzyl)propanoic Acid

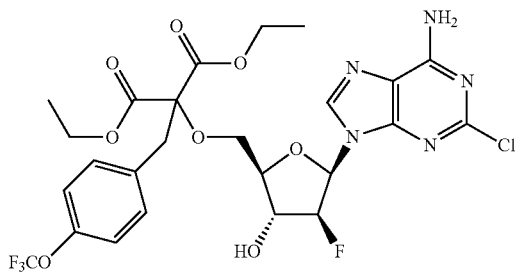 [SMILES: CCOC(=O)C(Cc1ccc(OC(F)(F)F)cc1)(OC[C@H]1O[C@@H](n2cnc3c(N)nc(Cl)nc32)[C@@H](F)[C@@H]1O)C(=O)OCC]

aq. LiOH, THF

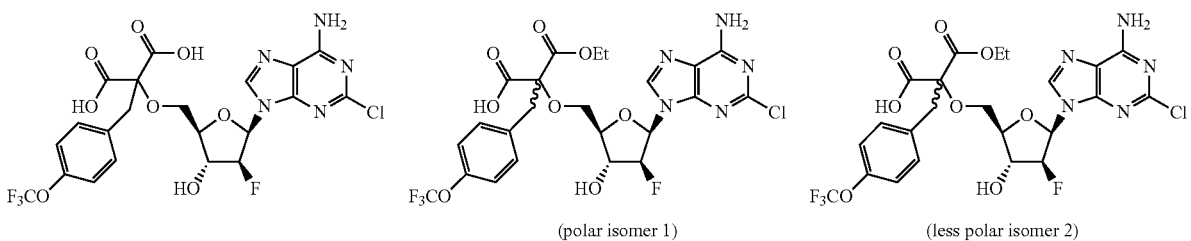

(polar isomer 1)     (less polar isomer 2)

2-(((2R,3R,4S,5R)-5-(6-Amino-2-chloro-9H-purin-9-yl)-4-fluoro-3-hydroxytetrahydrofuran-2-yl)methoxy)-2-(4-(trifluoromethoxy)benzyl)malonic acid was prepared from diethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)-malonate via base hydrolysis with aq. LiOH in THF according to the procedure described in Example 2 as a white solid.

$^1$H NMR (CD$_3$OD, 300 MHz) δ 8.38 (s, 1H), 7.37-7.34 (d, J=8 Hz, 2H), 7.07-7.09 (d, J=8 Hz, 2H), 6.39-6.46 (dd, J=4, 15 Hz, 1H), 5.05-5.25 (dt, J=4, 52 Hz, 1H), 4.63-4.80 (m, 1H), 4.15-4.20 (m, 1H), 3.91-3.99 (m, 2H), 3.37 (bs, 2H); LC/MS [M+H]=580.

A pair of diastereoisomer of mono-ethyl ester: (R)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxo-2-(4-(trifluoromethoxy)benzyl)propanoic acid and (S)-2-(((2R,3R,4S,5R)-5-(6-amino-2-chloro-9H-purin-9-yl)-4-fluoro-3-hydroxy-tetrahydrofuran-2-yl)methoxy)-3-ethoxy-3-oxo-2-(4-(trifluoromethoxy)benzyl)-propanoic acid was prepared from the partial hydrolysis of compound of Example 12. The title compounds were purified by reversed-phase HPLC and isolated as white solids.

Polar diastereomer 1: $^1$H NMR (CD$_3$OD, 300 MHz) δ 8.30 (s, 1H), 7.36-7.38 (d, J=8 Hz, 2H), 7.05-7.08 (d, J=8 Hz, 2H), 6.40-6.46 (dd, J=4, 14 Hz, 1H), 5.08-5.27 (dt, J=4, 52 Hz, 1H), 4.63-4.78 (m, 1H), 4.15-4.26 (m, 3H), 3.99-4.06 (m, 2H), 3.42-3.44 (m, 2H), 1.22-1.27 (t, J=7 Hz, 3H); LC/MS [M+H]=608.

Less polar diastereomer 2: $^1$H NMR (CD$_3$OD, 300 MHz) δ 8.37 (s, 1H), 7.35-7.38 (d, J=8 Hz, 2H), 7.05-7.08 (d, J=8 Hz, 2H), 6.42-6.48 (dd, J=4, 14 Hz, 1H), 5.10-5.30 (dt, J=4, 52 Hz, 1H), 4.64-4.71 (m, 1H), 4.15-4.25 (m, 3H), 4.02-4.04 (d, J=4 Hz, 2H), 3.44 (s, 2H), 1.22-1.25 (t, J=7 Hz, 3H); LC/MS [M+H]=608.

Example 14

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(hydroxymethyl)benzyl)malonic Acid Step 1:

To a solution of 2-(((2R,3R,4S,5R)-5-(6-amino-2-chloro-9H-purin-9-yl)-4-fluoro-3-hydroxytetrahydrofuran-2-yl)methoxy)-2-(4-formylbenzyl)malonic acid (200 mg, 0.23 mmol), prepared from diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)malonate and 4-(bromomethyl)benzaldehyde according to the procedure described for Example 2, in EtOH at 0° C. was added NaBH$_4$ (11 mg, 0.29 mmol). The resulting mixture was stirred for 15 min before it was quenched with 1N HCl(aq) solution. The organic volatile was removed under reduced pressure and the aq. layer was extracted with EtOAc. The organic layer was washed with brine, dried (Na2SO4) and concentrated. The crude residue was purified by silica gel column chromatography (0-20% EtOAc in hexanes) to provide the corresponding benzyl alcohol.

Step 2-3:

The benzyl alcohol from the last step was converted to 2-(((2R,3R,4S,5R)-5-(6-amino-2-chloro-9H-purin-9-yl)-4-fluoro-3-hydroxytetrahydrofuran-2-yl)methoxy)-2-(4-(hydroxymethyl)benzyl)malonic acid according to the procedure described for Example 2. The title compound was isolated as white solid.

$^1$H NMR (CD$_3$OD, 300 MHz) δ 8.29 (s, 1H), 7.26-7.29 (d, J=8 Hz, 2H), 7.14-7.29 (d, J=8 Hz, 2H), 6.40-6.46 (dd, J=4, 13 Hz, 1H), 5.08-5.28 (dt, J=4, 52 Hz, 1H), 4.63-4.72 (dt, J=4, 18 Hz, 1H), 4.49 (s, 2H), 4.14-4.18 (q, J=4 Hz, 1H), 3.96-4.08 (m, 2H), 3.33-3.42 (m, 2H); LC/MS [M+H]=526.

Example 15

Synthesis of 2-(((2R,3R,4S,5R)-5-(6-amino-2-chloro-9H-purin-9-yl)-4-fluoro-3-hydroxytetrahydrofuran-2-yl)methoxy)-2-(cyanomethyl)malonic Acid

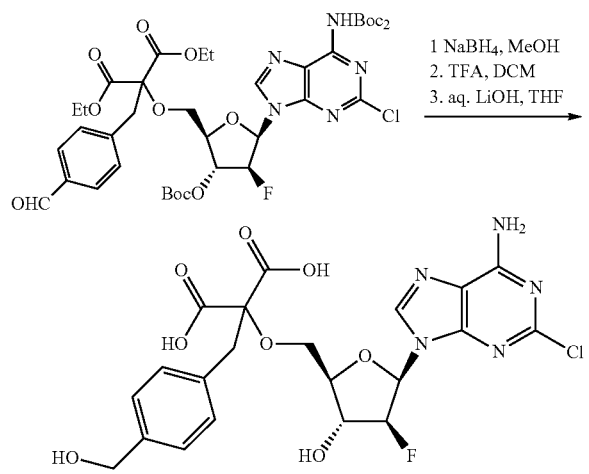

Proceeding as described in Example 2 above, but substituting benzyl with 2-bromoacetonitrile, the title compound was isolated as a white solid.

$^1$H NMR (CD$_3$OD, 300 MHz) δ 8.43 (bs, 1H), 6.41-6.48 (dd, J=4, 15 Hz, 1H), 5.07-5.27 (dt, J=4, 52 Hz, 1H), 4.66-4.75 (m, 1H), 4.14-4.20 (m, 1H), 3.98-4.10 (m, 2H), 3.15 (s, 2H); LC/MS [M+H]=445.

Example 16

Synthesis of 2-(((2R,3R,4S,5R)-((1H-tetrazol-5-yl)methyl)-2-(((2R,3R,4S,5R)-5-(6-amino-2-chloro-9H-purin-9-yl)-4-fluoro-3-hydroxytetrahydrofuran-2-yl)methoxy)malonic Acid

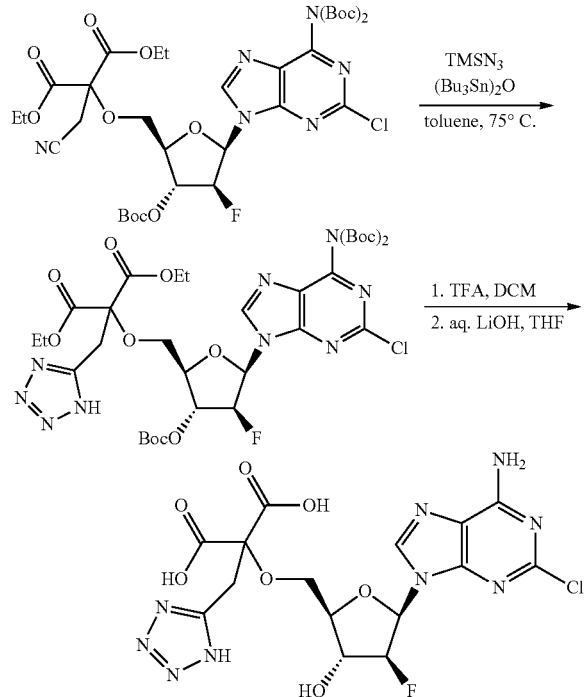

Step 1:

To a solution of diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-(cyanomethyl) (103 mg, 0.129 mmol) from the synthesis of Example 15 in toluene (5 mL) was added azidotrimethylsilane (234 uL, 1.8 mmol) in portions over period of 3 days followed by bis(tributyltin) oxide (20 uL, 0.0386 mmol), the reaction mixture was heated at 75° C. for three days before it was concentrated under reduced pressure. The crude was purified by silica gel column chromatography (0-4% MeOH in DCM) to provide diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-(1H-tetrazol-5-ylmethyl)malonate.

Step 2:

Diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-(1H-tetrazol-5-ylmethyl)malonate was converted to the title compound as a white solid by proceeding as described for Example 2 above.

$^1$H NMR (CD$_3$OD, 300 MHz) δ 8.58 (s, 1H), 6.44-6.50 (dd, J=4, 14 Hz, 1H), 5.09-5.29 (dt, J=4, 52 Hz, 1H), 4.59-4.68 (dt, J=4, 17 Hz, 1H), 4.19-4.22 (q, J=5 Hz, 1H), 4.10-4.12 (m, 2H), 3.83 (s, 2H); LC/MS [M+H]=488.

Example 17

Synthesis of 2-(3-(1H-tetrazol-5-yl)benzyl)-2-(((2R,3R,4S,5R)-5-(6-amino-2-azido-9H-purin-9-yl)-4-fluoro-3-hydroxytetrahydrofuran-2-yl)methoxy)malonic Acid 2-(((2R,3R,4S,5R)-5-(6-amino-2-azido-9H-purin-9-yl)-4-fluoro-3-hydroxytetrahydrofuran-2-yl)methoxy)-2-(3-cyanobenzyl)malonic Acid; and 2-(((2R,3R,4S,5R)-5-(2-azido-6-((tert-butoxycarbonyl)amino)-9H-purin-9-yl)-4-fluoro-3-hydroxytetrahydrofuran-2-yl)methoxy)-2-(3-cyanobenzyl)malonic Acid

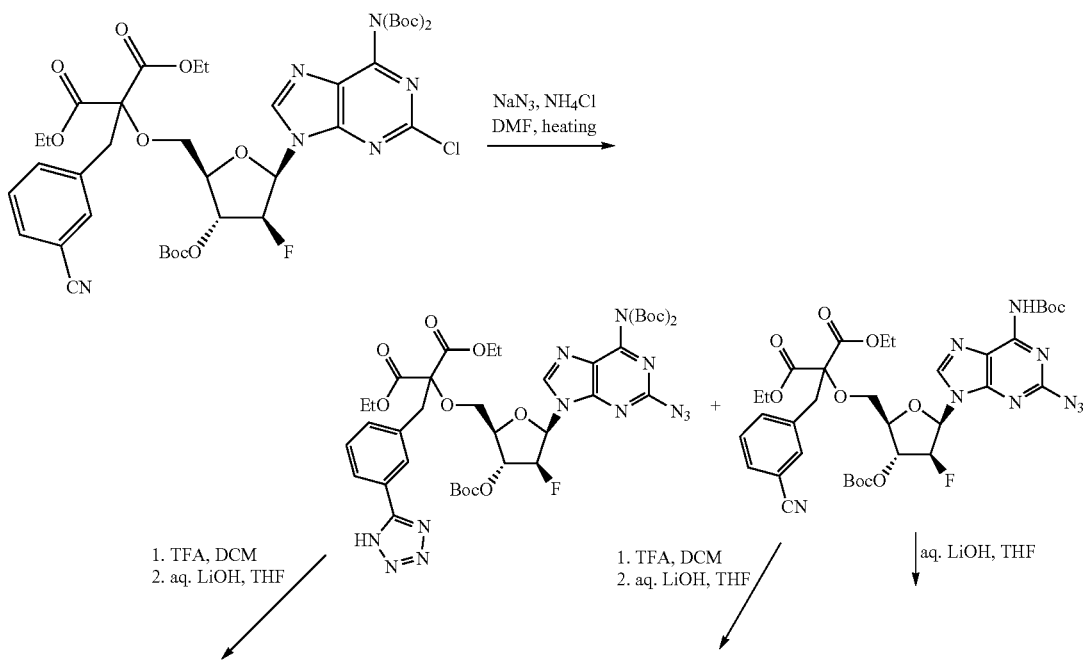

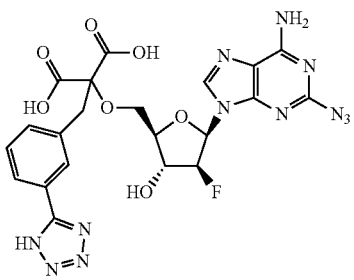
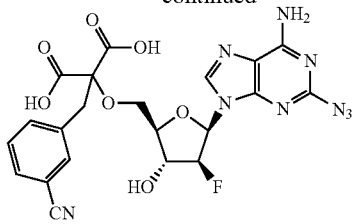
-continued
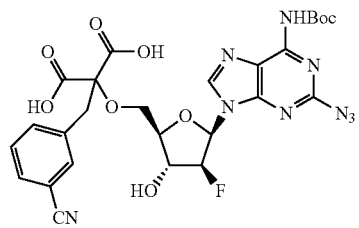

Step 1:

A mixture of diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluoro-tetrahydrofuran-2-yl)methoxy)-2-(3-cyanobenzyl)malonate (230 mg, 0.26 mmol) (prepared as described in Example 2 above, by reacting diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)malonate with 3-(bromomethyl)benzonitrile), NaN$_3$ (26 mg, 0.39 mmol) and NH$_4$Cl (18 mg, 0.34 mmol) in DMF (1.5 mL) was heated at 100° C. for 5 h before it was allowed to cool to room temperature. The crude reaction mixture was diluted with EtOAc and water. The aqueous layer was further extracted (2×) with EtOAc. The combined organic layer was washed with brine, dried (MgSO$_4$) and concentrated. The crude was purified by reversed-phase HPLC to provide diethyl 2-(3-(1H-tetrazol-5-yl)benzyl)-2-(((2R,3R,4S,5R)-5-(6-(N-(tert-butoxycarbonyl)(tert-butoxycarbonyl)-amino)-2-azido-9H-purin-9-yl)-3-((tert-butoxycarbonyl)oxy)-4-fluoro-tetrahydrofuran-2-yl)methoxy)malonate and diethyl 2-(((2R,3R,4S,5R)-5-(2-azido-6-((tert-butoxycarbonyl)amino)-9H-purin-9-yl)-3-((tert-butoxycarbonyl)oxy)-4-fluorotetrahydrofuran-2-yl)methoxy)-2-(3-cyanobenzyl)malonate.

Step 2:

Diethyl 2-(3(1H-tetrazol-5-yl)benzyl)-2-(((2R,3R,4S,5R)-5-(6-(N-(tert-butoxycarbonyl)(tert-butoxycarbonyl)amino)-2-azido-9H-purin-9-yl)-3-((tert-butoxycarbonyl)oxy)-4-fluorotetrahydrofuran-2-yl)methoxy)malonate and diethyl 2-(((2R,3R,4S,5R)-5-(2-azido-6-((tert-butoxy carbonyl)amino)-9H-purin-9-yl)-3-((tert-butoxycarbonyl)oxy)-4-fluorotetrahydrofuran-2-yl)methoxy)-2-(3-cyanobenzyl)malonate were then converted to the corresponding title compounds according to the procedure described for Example 2.

2-(((2R,3R,4S,5R)-5-(6-amino-2-azido-9H-purin-9-yl)-4-fluoro-3-hydroxytetrahydrofuran-2-yl)methoxy)-2-(3-cyanobenzyl)malonic Acid $^1$H NMR (CD$_3$OD, 300 MHz) δ 8.66 (s, 1H), 7.66 (s, 1H), 7.56-7.59 (d, J=8 Hz, 1H), 7.46-7.48 (d, J=7 Hz, 1H), 7.33-7.35 (t, J=7 Hz, 1H), 6.52-6.57 (dd, J=5, 11 Hz, 1H), 5.17-5.38 (dt, J=5, 52 Hz, 1H), 4.64-4.75 (dt, J=4, 17 Hz, 1H), 4.21-4.25 (m, 1H), 3.97-4.16 (m, 2H), 3.41-3.54 (m, 2H); LC/MS [M+H]=528.

2-(((2R,3R,4S,5R)-5-(2-azido-6-((tert-butoxycarbonyl)amino)-9H-purin-9-yl)-4-fluoro-3-hydroxytetrahydrofuran-2-yl)methoxy)-2-(3-cyanobenzyl)malonic Acid $^1$H NMR (CD$_3$OD, 300 MHz) δ 8.72 (s, 1H), 7.67 (s, 1H), 7.56-7.59 (d, J=8 Hz, 1H), 7.46-7.49 (d, J=8 Hz, 1H), 7.31-7.36 (t, J=8 Hz, 1H), 6.57-6.62 (dd, J=4, 13 Hz, 1H), 5.16-5.36 (dt, J=4, 52 Hz, 1H), 4.63-4.87 (dt, J=4, 17 Hz, 1H), 4.22-4.25 (m, 1H), 4.00-4.14 (m, 2H), 3.41-3.53 (m, 2H), 1.60 (s, 9H); LC/MS [M+H]=628.

2-(3-(1H-tetrazol-5-yl)benzyl)-2-(((2R,3R,4S,5R)-5-(6-amino-2-azido-9H-purin-9-yl)-4-fluoro-3-hydroxytetrahydrofuran-2-yl)methoxy)malonic Acid $^1$H NMR (CD$_3$OD, 300 MHz) δ 8.19 (bs, 1H), 7.99 (bs, 1H), 7.77-7.79 (d, J=8 Hz, 1H), 7.49-7.52 (d, J=8 Hz, 1H), 7.36-7.41 (t, J=8 Hz, 1H), 6.32-6.38 (dd, J=5, 13 Hz, 1H), 5.05-5.25 (dt, J=4, 52 Hz, 1H), 4.66-4.75 (dt, J=4, 18 Hz, 1H), 4.17-4.22 (m, 1H), 3.98-4.14 (m, 2H), 3.45-3.57 (m, 2H); LC/MS [M+H]=564.

Example 18

Synthesis of 2-(((2S,3S,4R,5R)-5-(6-amino-2-chloro-9H-purin-9-yl)-3-azido-4-hydroxytetrahydrofuran-2-yl)methoxy)-2-benzylmalonic Acid and 2-(((2S,3S,4R,5R)-3-amino-5-(6-amino-2-chloro-9H-purin-9-yl)-4-hydroxytetrahydrofuran-2-yl)methoxy)-2-benzylmalonic Acid

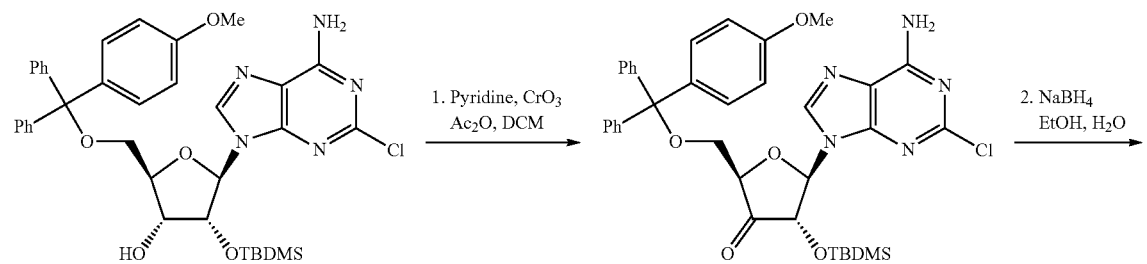

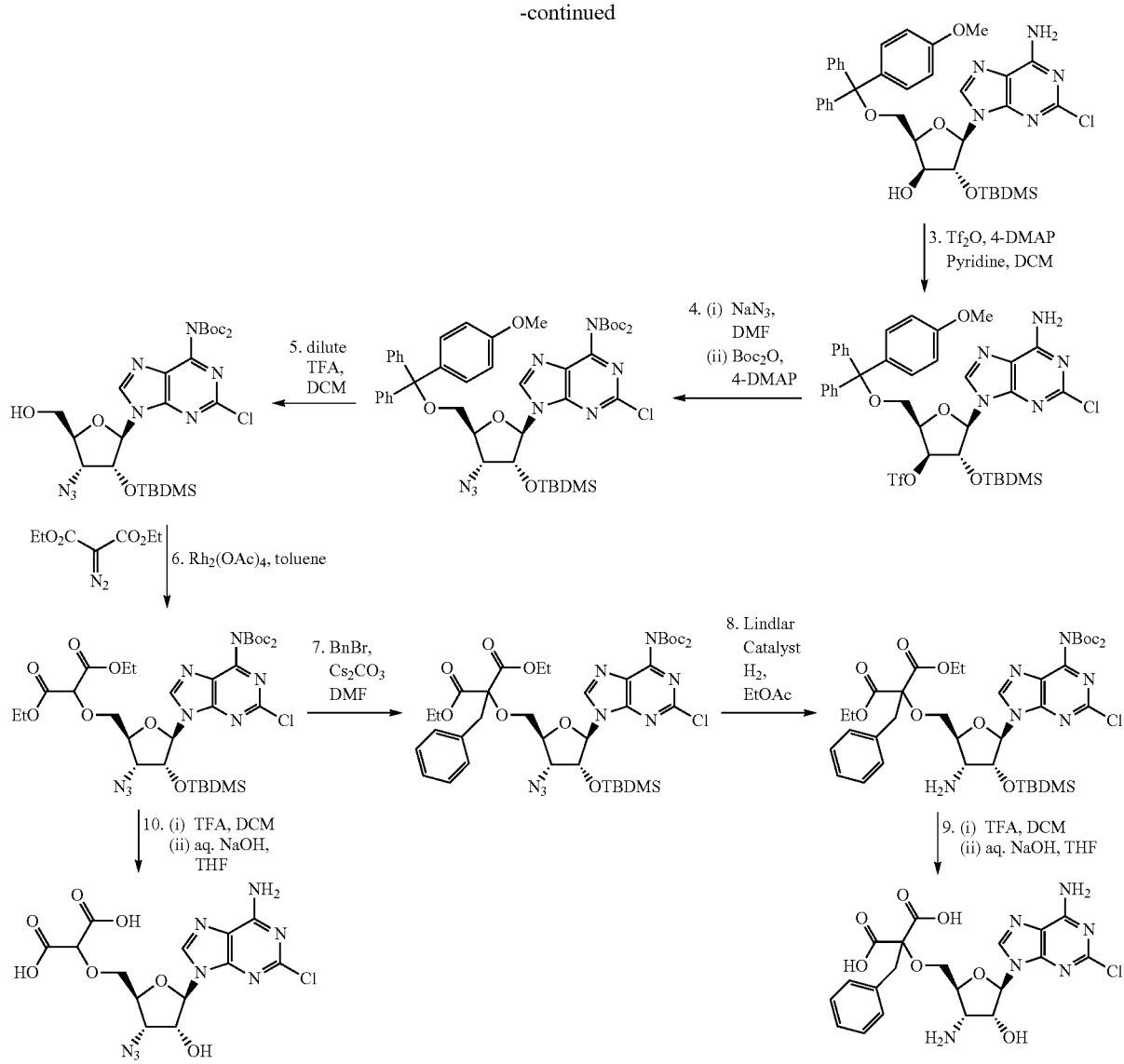

Step 1:

To a stirred suspension of chromium trioxide (2.59 g, 25.9 mmol) in CH$_2$Cl$_2$ (60 mL) was added pyridine (4.19 mL, 51.8 mmol) dropwise and followed by immediately addition of acetic anhydride (2.45 mL, 25.9 mmol). This brown slurry was allowed to stir at room temperature for 10 minutes. To this mixture was added a solution of (2R,3R,4R,5R)-5-(6-amino-2-chloro-9H-purin-9-yl)-4-((tert-butyldimethylsilyl)oxy)-2-((4-methoxyphenyl)diphenylmethoxy)methyl)-tetrahydrofuran-3-ol (synthesized from 2-chloroadenosin according to the procedure reported by Koole, L. H. et al., *Acta Chemica Scandinavica*, 43, 665-669, 1989) (5.95 g, 8.64 mmol) in CH$_2$Cl$_2$ (36 mL). The resulting mixture was stirred at room temperature for 18 h before it was passed through a short silica plug using EtOAc as eluent. The filtrate was washed with EDTA (2×100 mL) and brine (100 mL). The organic layer was separated and concentrated. The residue was purified by column chromatography on silica gel to give (2R,4S,5R)-5-(6-amino-2-chloro-9H-purin-9-yl)-4-((tert-butyldimethylsilyl)oxy)-2-(((4-methoxyphenyl)diphenylmethoxy)methyl)-dihydrofuran-3(2H)-one (4.19 g, 71% yield).

Step 2:

A solution of (2R,4S,5R)-5-(6-amino-2-chloro-9H-purin-9-yl)-4-((tert-butyldimethylsilyl)oxy)-2-(((4-methoxyphenyl)diphenylmethoxy)methyl)-dihydrofuran-3(2H)-one (4.19 g, 6.11 mmol) in a mixture of EtOH (42 mL) and water (2.1 mL) was stirred for 20 minute at −5° C. before the addition of sodium borohydride (324 mg, 8.55 mmol). The reaction was stirred for 5 h before it was carefully quenched with 1N aq. HCl until its pH reached 5. The reaction mixture was partitioned with EtOAc (100 mL). The organic layer was separated and washed with water (3×50 mL), brine, dried (MgSO$_4$) and concentrated. The crude residue was purified by column chromatography on silica gel to give (2R,3S,4R,5R)-5-(6-amino-2-chloro-9H-purin-9-yl)-4-((tert-butyldimethylsilyl)oxy)-2-(((4-methoxy-phenyl)diphenylmethoxy)methyl)tetrahydrofuran-3-ol (2.19 g, 52% yield).

Step 3:

To a solution of (2R,3S,4R,5R)-5-(6-amino-2-chloro-9H-purin-9-yl)-4-((tert-butyldimethylsilyl)oxy)-2-(((4-methoxy-phenyl)diphenylmethoxy)methyl)-tetrahydrofuran-3-ol (2.19 g, 3.18 mmol) in $CH_2Cl_2$ (33 mL) at 0° C. under argon atmosphere was added pyridine (2.3 mL, 28.6 mmol) and 4-dimethylaminopyridine (1.13 g, 9.22 mmol). The reaction mixture was stirred for 15 minutes before addition of $Tf_2O$ (0.803 mL, 4.77 mmol). The reaction was stirred at 0° C. for 15 minutes before it was allowed to warm up to ambient temperature and stirred further for 4 hours. The reaction mixture was quenched by addition of water (22 mL). The organic layer was separated, dried ($MgSO_4$) and concentrated. The crude residue was purified by column chromatography on silica gel to give (2R,3R,4R,5R)-5-(6-amino-2-chloro-9H-purin-9-yl)-4-((tert-butyldimethylsilyl)oxy)-2-(((4-methoxyphenyl)diphenylmethoxy)methyl)tetrahydrofuran-3-yl trifluoromethanesulfonate (2.00 g, 76% yield).

Step 4:

To a solution of (2R,3R,4R,5R)-5-(6-amino-2-chloro-9H-purin-9-yl)-4-((tert-butyldimethylsilyl)oxy)-2-(((4-methoxyphenyl)diphenylmethoxy)methyl)-tetrahydrofuran-3-yl trifluoromethanesulfonate (1.65 g, 2.01 mmol) in DMF (33 mL) at 0° C. was carefully added sodium azide (1.31 g, 20.1 mmol). The reaction was allowed to warm to ambient temperature and stirred for 6 hours before it was partitioned with EtOAc (100 mL). The organic layer was separated, washed with water (2×22 mL), brine, dried over $MgSO_4$ and concentrated. To the crude oil in THF (5 mL) was added $Boc_2O$ (1.70 g, 7.64 mmol) and 4-DMAP (24 mg, 0.20 mmol). The reaction was stirred under argon for 13 h before it was concentrated and the crude residue was purified by column chromatography on $SiO_2$ to give tert-butyl (tert-butoxycarbonyl)(9-((2R,3R,4R,5S)-4-azido-3-((tert-butyldimethylsilyl)oxy)-5-(((4-methoxyphenyl)diphenylmethoxy)methyl)-tetrahydrofuran-2-yl)-2-chloro-9H-purin-6-yl)carbamate (1.19 g, 65% yield for 2 steps).

Step 5:

To a solution of tert-butyl (tert-butoxycarbonyl)(9-((2R,3R,4R,5S)-4-azido-3-((tert-butyldimethylsilyl)oxy)-5-(((4-methoxyphenyl)diphenylmethoxy)methyl)-tetrahydrofuran-2-yl)-2-chloro-9H-purin-6-yl)carbamate (1.19 g, 1.30 mmol) was in DCM (30 mL) under argon atmosphere at room temperature was added trifluoroacetic acid (0.483 mL, 6.50 mmol) dropwise. The reaction was stirred for 7 h before it was concentrated. The crude residue was purified by column chromatography on $SiO_2$ to give tert-butyl (tert-butoxycarbonyl)(9-((2R,3R,4R,5S)-4-azido-3-((tert-butyldimethylsilyl)oxy)-5-(hydroxymethyl)tetrahydrofuran-2-yl)-2-chloro-9H-purin-6-yl)carbamate (548 mg, 69% yield).

Step 6:

A mixture of tert-butyl (tert-butoxycarbonyl)(9-((2R,3R,4R,5S)-4-azido-3-((tert-butyldimethylsilyl)oxy)-5-(hydroxymethyl)tetrahydrofuran-2-yl)-2-chloro-9H-purin-6-yl)carbamate (385 mg, 0.60 mmol) and diethyl 2-diazomalonate (145 mg, 0.78 mmol) were charged into a 25 mL round bottom flask and azeotroped twice with toluene. The resulting oil was dissolved in toluene (3.9 mL) and followed by addition of rhodium(II) acetate dimer (27 mg, 0.06) mmol under argon atmosphere. The reaction mixture was heated at 75° C. for 3 h before it was concentrated. The crude residue was purified by column chromatography on $SiO_2$ to give diethyl 2-(((2S,3R,4R,5R)-3-azido-5-(6-(N-(tert-butoxycarbonyl)(tert-butoxycarbonyl)amino)-2-chloro-9H-purin-9-yl)-4-((tert-butyldimethylsilyl)oxy)-tetrahydrofuran-2-yl)methoxy)malonate (234 mg, 48% yield).

Step 7:

To a solution of diethyl 2-(((2S,3R,4R,5R)-3-azido-5-(6-(N-(tert-butoxycarbonyl)(tert-butoxycarbonyl)amino)-2-chloro-9H-purin-9-yl)-4-((tert-butyldimethylsilyl)oxy)-tetrahydrofuran-2-yl)methoxy)malonate (234 mg, 0.29 mmol) in DMF (2.3 mL) at 0° C. was added oven dried cesium carbonate (191 mg, 0.59 mmol). The resulting suspension was stirred for 30 minutes and followed by dropwise addition of benzyl bromide (70 µL, 0.59 mmol). The reaction was allowed to warm to ambient temperature and stirred for 14 h before it was partitioned between EtOAc (25 mL) and water (22 mL). The organic layer was separated and washed water (22 mL), brine, dried over magnesium sulfate and concentrated. The crude residue was purified by column chromatography on $SiO_2$ to give diethyl 2-(((2S,3R,4R,5R)-3-azido-5-(6-(N-(tert-butoxycarbonyl)(tert-butoxycarbonyl)amino)-2-chloro-9H-purin-9-yl)-4-((tert-butyldimethylsilyl)oxy)tetrahydrofuran-2-yl)methoxy)-2-benzylmalonate (100 mg, 38% yield).

Step 8:

A solution of diethyl 2-(((2S,3R,4R,5R)-3-azido-5-(6-(N-(tert-butoxycarbonyl)(tert-butoxycarbonyl)amino)-2-chloro-9H-purin-9-yl)-4-((tert-butyldimethylsilyl)oxy)tetrahydrofuran-2-yl)methoxy)-2-benzylmalonate (100 mg, 0.11 mmol) in EtOAc (2.0 mL) was purged three times with argon gas and followed by addition of Lindlar catalyst (15 mg, 15% by wt) under a blanket of argon gas. The reaction mixture was then purged (thrice) and stirred under 1 atmosphere of $H_2$ for 18 h. The reaction mixture was filtered through celite and rinsed with DCM (10 mL). The filtrate was concentrated to provide diethyl 2-(((2S,3R,4R,5R)-3-amino-5-(6-(N-(tert-butoxycarbonyl)(tert-butoxycarbonyl)-amino)-2-chloro-9H-purin-9-yl)-4-((tert-butyldimethylsilyl)oxy)tetrahydrofuran-2-yl)methoxy)-2-benzylmalonate (92 mg, 94% yield) which was used in the next step without further purification.

Step 9:

To a solution of diethyl 2-(((2S,3R,4R,5R)-3-amino-5-(6-(N-(tert-butoxycarbonyl)(tert-butoxycarbonyl)-amino)-2-chloro-9H-purin-9-yl)-4-((tert-butyldimethylsilyl)oxy)tetrahydrofuran-2-yl)methoxy)-2-benzylmalonate (92 mg, 0.11 mmol) in a mixture of DCM (2.3 mL) and water (92 µL) and followed by dropwise addition of TFA (0.92 mL). The reaction was stirred for 16 hours before it was evaporated to dryness and azeotroped with acetonitrile twice. The resulting oil was taken up in THF (1.5 mL) and 4M NaOH (106 µL, 0.42 mmol) was added at room temperature. The reaction was stirred after 10 h before it was concentrated to dryness. The crude residue was purified by reversed-phase HPLC to give 2-(((2S,3S,4R,5R)-3-amino-5-(6-amino-2-chloro-9H-purin-9-yl)-4-hydroxytetrahydrofuran-2-yl)methoxy)-2-benzylmalonic acid.

$^1$H NMR (CD$_3$OD, 300 MHz) δ 8.35 (s, 1H), 7.10-7.77 (m, 5H), 6.45-6.52 (dd, J=4, 10 Hz, 1H), 5.18-5.39 (dt, J=4.5, 52 Hz, 1H), 4.65-4.73 (dt, J=5, 17 Hz, 1H), 4.21-4.24 (m, 1H), 3.95-4.18 (m, 2H), 3.45-3.59 (m, 2H); LC/MS [M+H]=493.

Step 10:

2-(((2S,3S,4R,5R)-5-(6-Amino-2-chloro-9H-purin-9-yl)-3-azido-4-hydroxytetrahydrofuran-2-yl)methoxy)malonic acid was prepared from diethyl 2-(((2S,3R,4R,5R)-3-azido-5-(6-(N-(tert-butoxycarbonyl)(tert-butoxycarbonyl)amino)-2-chloro-9H-purin-9-yl)-4-((tert-butyldimethylsilyl)oxy)-tetrahydrofuran-2-yl)methoxy)malonate under the similar deprotection conditions described in Step 9.

$^1$H NMR (CD$_3$OD, 300 MHz) δ 8.87 (bs, 1H), 6.03 (d, J=6.4 Hz, 1H), 5.17-5.21 (t, J=5.6 Hz, 1H), 4.61 (bs, 1H), 4.50 (bs, 1H), 4.20 (bs, 1H), 3.81-3.91 (q, J=0 Hz, 2H); LC/MS [M+H]=429.

Example 19
Synthesis of 2-(((2R,3S,4R,5R)-4-amino-5-(6-amino-2-chloro-9H-purin-9-yl)-3-hydroxytetrahydrofuran-2-yl)methoxy)-2-benzylmalonic Acid
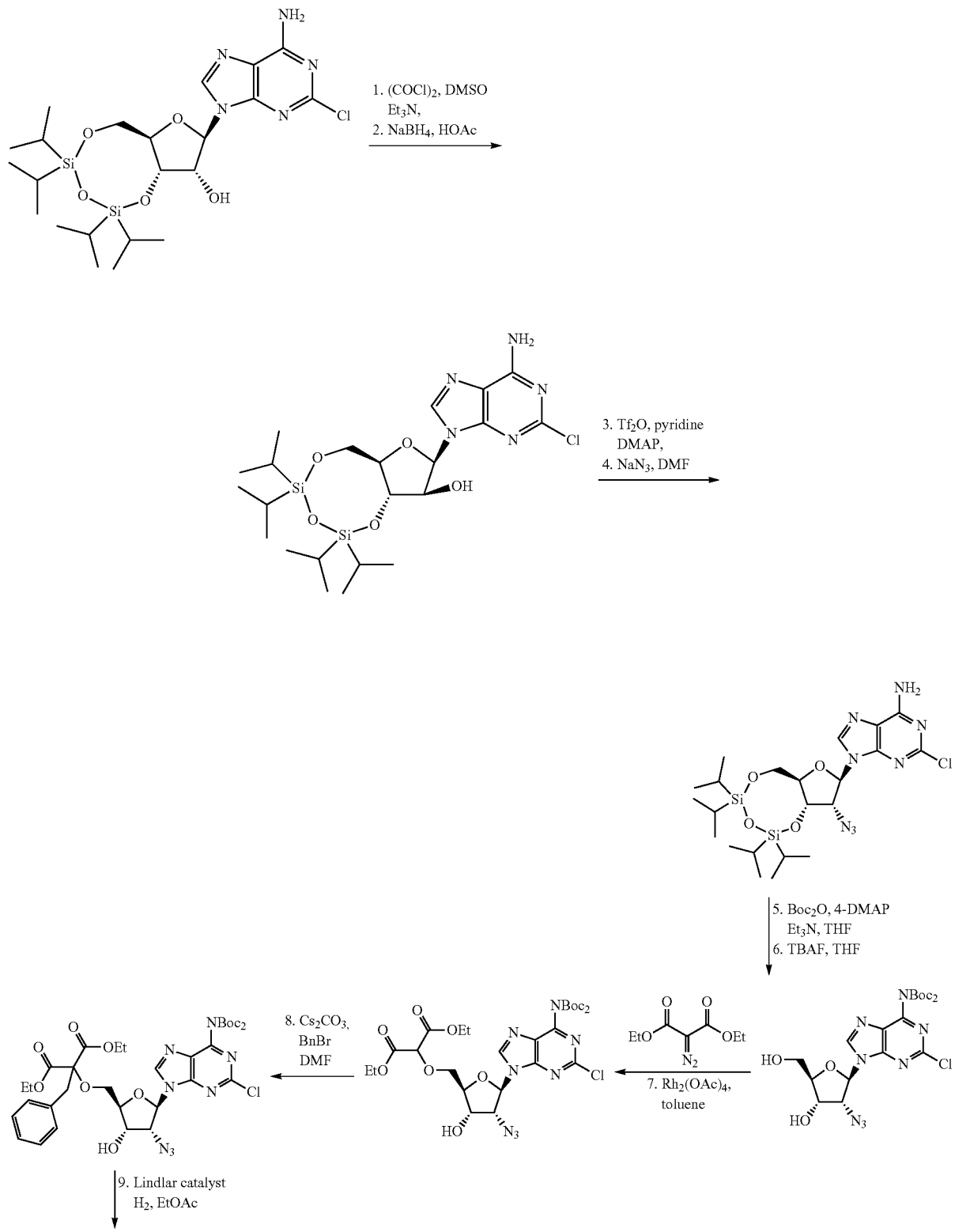

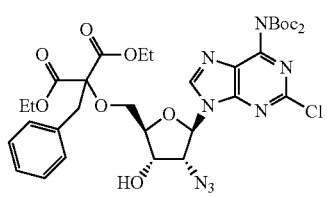 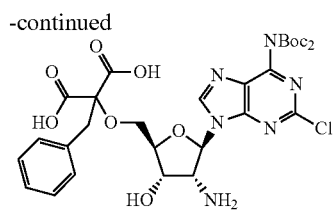

10. (i)TFA, DCM
(ii) aq. LiOH, THF

Step 1:
To a cooled (−70° C.) solution of oxalyl chloride (4.18 mL, 48.78 mmol) in dry dichloromethane (100 mL) under argon atmosphere was added a solution of dry DMSO (7.1 mL, 99.44 mmol) in dichloromethane (18 mL) dropwise. After stirring for 30 minutes, a solution of (6aR,8R,9R,9aS)-8-(6-amino-2-chloro-9H-purin-9-yl)-2,2,4,4-tetraisopropyltetrahydro-6H-furo[3,2-f][1,3,5,2,4]trioxadisilocin-9-ol (10.21 g, 18.76 mmol), synthesized from 2-chloroadenosine according to the procedure reported by Secrist, John A., III et al.; (*Journal of Medicinal Chemistry*, 31, 405-10, 1988); and by Chen, Robert H. K. (U.S. Pat. No. 5,208,327), in a mixture of dichloromethane and THF (46 mL, 1:1/v:v) was added dropwise over a period of 30 minutes and followed by triethylamine (16 mL, 114.44 mmol) via a syringe. The cooling bath was removed and the mixture was stirred at room temperature for 1.5 h before chloroform (190 mL) and water (650 mL) were added and the pH of the mixture was adjusted to neutral with 2N aq. HCl solution. The organic layer was separated and the aqueous phase was further extracted with chloroform (2×190 mL). The combined organic phase was dried (MgSO$_4$) and filtered through a short plug of celite. The filtrate was concentrated to provide (6aR,8R,9aR)-8-(6-amino-2-chloro-9H-purin-9-yl)-2,2,4,4-tetraisopropyldihydro-6H-furo[3,2-f][1,3,5,2,4]trioxadisilocin-9(6aH)-one as a solid (8.37 g) which was used without further purification in the next step.

Step 2:
To a suspension of NaBH$_4$ (2.51 g, 66.4 mmol) in dry THF (130 mL) under argon atmosphere at 0° C. was added glacial acetic acid (19.3 mL, 337 mmol) dropwise. The reaction mixture was stirred for 1.5 h and followed by addition of a solution of (6aR,8R,9aR)-8-(6-amino-2-chloro-9H-purin-9-yl)-2,2,4,4-tetraisopropyldihydro-6H-furo[3,2-f][1,3,5,2,4]trioxadisilocin-9(6aH)-one (3 g, 5.53 mmol) in tetrahydrofuran (30 mL) via a syringe. The mixture was stirred for 4 h at 0° C. The organic volatile was removed under reduced pressure and the residue was partitioned with EtOAc (115 mL) and saturated aqueous sodium bicarbonate (115 mL). The organic phase was separated and the aqueous layer was further extracted with EtOAc (2×100 mL). The combined organic phase was dried (MgSO$_4$), filtered and concentrated to provide (6aR,8R,9R,9aS)-8-(6-amino-2-chloro-9H-purin-9-yl)-2,2,4,4-tetraisopropyltetrahydro-6H-furo[3,2-f][1,3,5,2,4]trioxadisilocin-9-ol as a foam (2.69 g).

Step 3:
To a solution of (6aR,8R,9R,9aS)-8-(6-amino-2-chloro-9H-purin-9-yl)-2,2,4,4-tetraisopropyltetrahydro-6H-furo[3,2-f][1,3,5,2,4]trioxadisilocin-9-ol (2.297 g, 4.22 mmol) in anhydrous dichloromethane (90 mL) under argon atmosphere was added pyridine (3.1 mL, 38 mmol) and 4-dimethylaminopyridine (1.5 g, 12.24 mmol). The mixture was cooled to 0° C. and stirred for 15 minutes and followed by addition of trifluoromethanesulfonic anhydride (1.1 mL, 6.33 mmol) dropwise. After stirring for 5 minutes, the cooling bath was removed and the mixture was stirred at room temperature for 3 hours. The reaction was quenched with cold water (90 mL). The organic phase was separated and the aqueous phase was further extracted with DCM (2×80 mL). The combined organic phase was dried (MgSO$_4$), filtered and concentrated. The crude residue was purified by column chromatography on silica gel (25-85% EtOAc in hexanes) to provide (6aR,8R,9S,9aR)-8-(6-amino-2-chloro-9H-purin-9-yl)-2,2,4,4-tetraisopropyltetrahydro-6H-furo[3,2-f][1,3,5,2,4]-trioxadisilocin-9-yl trifluoromethanesulfonate as a white solid (1.9 g).

Step 4:
To a solution of (6aR,8R,9S,9aR)-8-(6-amino-2-chloro-9H-purin-9-yl)-2,2,4,4-tetraisopropyltetrahydro-6H-furo[3,2-f][1,3,5,2,4]trioxadisilocin-9-yl trifluoromethanesulfonate (1.9 g, 2.8 mmol) in anhydrous DMF (12 mL) under argon atmosphere was added sodium azide (1.83 g, 28.1 mmol). The mixture was stirred for 24 hours before it was partitioned with EtOAc (120 mL) and brine (120 mL). The organic phase was separated and the aqueous phase was further extracted with EtOAc (2×100 mL). The combined organic phase was dried (MgSO$_4$), filtered and concentrated to provide 9-((6aR,8R,9R,9aS)-9-azido-2,2,4,4-tetraisopropyltetrahydro-6H-furo[3,2-f][1,3,5,2,4]trioxadisilocin-8-yl)-2-chloro-9H-purin-6-amine as a solid (1.48 g).

Step 5:
To a solution of 9-((6aR,8R,9R,9aS)-9-azido-2,2,4,4-tetraisopropyltetrahydro-6H-furo[3,2-f][1,3,5,2,4]trioxadisilocin-8-yl)-2-chloro-9H-purin-6-amine (1.48 g, 2.59 mmol) in anhydrous THF (31 mL) under argon atmosphere was added 4-dimethylaminopyridine (153 mg, 1.25 mmol) and then di-tert-butyl dicarbonate (1.2 g, 5.5 mmol). The mixture was stirred at room temperature for 16 hours before it was partitioned with EtOAc (40 mL) and brine (60 mL). The organic phase was separated and the aqueous phase was further extracted with EtOAc (2×40 mL). The combined organic phase was dried (MgSO$_4$), filtered and concentrated. The crude product was purified by column chromatography on silica gel (15% EtOAc in hexanes) to provide tert-butyl (tert-butoxycarbonyl)(9-((6aR,8R,9R,9aS)-9-azido-2,2,4,4-tetraisopropyltetrahydro-6H-furo[3,2-j][1,3,5,2,4]trioxadisilocin-8-yl)-2-chloro-9H-purin-6-yl)di-carbamate as a viscous oil (1.857 g).

Step 6:
To a solution of tert-butyl (tert-butoxycarbonyl)(9-((6aR,8R,9R,9aS)-9-azido-2,2,4,4-tetraisopropyltetrahydro-6H-furo[3,2-j][1,3,5,2,4]trioxadisilocin-8-yl)-2-chloro-9H-purin-6-yl)di-carbamate (1.85 g, 2.41 mmol) in anhydrous THF (13 mL) under argon atmosphere at 0° C. was added a solution of tetrabutylammonium fluoride (6.3 mL, 1.0 M in THF, 6.3 mmol) dropwise. The flask was stirred overnight at 6° C. before it was partitioned with EtOAc (50 mL) and brine (50 mL). The organic phase was separated and the aqueous phase was further extracted with EtOAc (2×40 mL). The combined organic phase was dried (MgSO$_4$), filtered and concentrated. The crude product was purified by column chromatography on silica gel (55% EtOAc in hexanes) to provide tert-butyl (tert-butoxycarbonyl)(9-((2R,3R,4S,5R)-3-azido-4-hydroxy-5-(hydroxymethyl)tetrahydrofuran-2-yl)-2-chloro-9H-purin-6-yl)carbamate as a solid (1.117 g).

Step 7:

To a solution of tert-butyl (tert-butoxycarbonyl)(9-((2R,3R,4S,5R)-3-azido-4-hydroxy-5-(hydroxymethyl)tetrahydrofuran-2-yl)-2-chloro-9H-purin-6-yl)carbamate (408 mg, 0.77 mmol) and $Rh_2(OAc)_4$ (14 mg, 0.04 mmol) in dry toluene (2 mL) under argon atmosphere at room temperature was added diethyl 2-diazomalonate (173 mg, 0.93 mmol). The resulting mixture was stirred at 75° C. for 3 hours before it was allowed to cool to ambient temperature. The reaction mixture was then partitioned with EtOAc (20 mL) and brine (20 mL). The organic phase was separated and the aqueous phase was further extracted with EtOAc (2×20 mL). The combined organic phases was dried ($MgSO_4$), filtered and concentrated. The residue was purified by preparative thin layer chromatographic plates eluting with 60% EtOAc in hexanes to provide diethyl 2-(((2R,3S,4R,5R)-4-azido-5-(6-(N-(tert-butoxycarbonyl)(tert-butoxycarbonyl)amino)-2-chloro-9H-purin-9-yl)-3-hydroxytetrahydrofuran-2-yl)methoxy)malonate as a viscous oil (167 mg).

Step 8:

To a solution of diethyl 2-(((2R,3S,4R,5R)-4-azido-5-(6-(N-(tert-butoxycarbonyl)(tert-butoxycarbonyl)amino)-2-chloro-9H-purin-9-yl)-3-hydroxytetrahydrofuran-2-yl)methoxy)malonate (167 mg, 0.24 mmol) in dry DMF (1.5 mL) under argon atmosphere was added cesium carbonate (119 mg, 0.37 mmol) and then benzyl bromide (44 mg, 0.26 mmol). Additional amount of $Cs_2CO_3$ (60 mg) and BnBr (40 mg) were added to the reaction over 1.5 h and stirred for addition 1 h. The reaction mixture was then partitioned with EtOAc (20 mL) and brine (20 mL). The organic phase was separated and the aqueous phase was further extracted with EtOAc (2×20 mL). The combined organic phase was dried ($MgSO_4$), filtered and concentrated. The residue was purified by preparative thin layer chromatography (eluting with 40% EtOAc in hexanes) to provide diethyl 2-(((2R,3S,4R,5R)-4-azido-5-(6-(N-(tert-butoxycarbonyl)(tert-butoxycarbonyl)amino)-2-chloro-9H-purin-9-yl)-3-hydroxytetrahydrofuran-2-yl)methoxy)-2-benzylmalonate as a viscous oil.

Step 9:

To a solution of diethyl 2-(((2R,3S,4R,5R)-4-azido-5-(6-(N-(tert-butoxycarbonyl)(tert-butoxycarbonyl)amino)-2-chloro-9H-purin-9-yl)-3-hydroxytetrahydrofuran-2-yl)methoxy)-2-benzylmalonate (101 mg, 0.13 mmol) in ethanol (4 mL) was added Lindlar's catalyst (25 mg) and then stirred under 1 atmosphere of $H_2$ for 18 hours. The reaction mixture was filtered through a plug of celite and rinsed with methanol. The filtrate was concentrated to provide diethyl 2-(((2R,3S,4R,5R)-4-azido-5-(6-(N-(tert-butoxycarbonyl)(tert-butoxycarbonyl)amino)-2-chloro-9H-purin-9-yl)-3-hydroxytetrahydrofuran-2-yl)methoxy)-2-benzylmalonate as the product (100 mg).

Step 10:

To a solution of diethyl 2-(((2R,3S,4R,5R)-4-azido-5-(6-(N-(tert-butoxycarbonyl)(tert-butoxycarbonyl)amino)-2-chloro-9H-purin-9-yl)-3-hydroxytetrahydrofuran-2-yl)methoxy)-2-benzylmalonate (100 mg, 0.13 mmol) in THF (1.5 mL) and water (0.75 mL) was added lithium hydroxide mono-hydrate (65 mg, 1.56 mmol). The material was vigorously stirred for 5 hours at ambient temperature and then stirred for 66 hours at 6° C. before it was cooled to 0° C. and followed by added a solution of 1N aq. HCl (1.7 mL). The reaction mixture was concentrated to provide an off-white powder (66 mg). This material was then taken up in a solution of trifluoroacetic acid in dichloromethane (1.5 mL, 1:1/v:v) and stirred for 1 h before it was concentrated. The residue was taken up in dichloromethane (5×5 mL) and concentrated each time. The crude was purified by reversed-phase HPLC to provide 2-(((2R,3S,4R,5R)-4-amino-5-(6-amino-2-chloro-9H-purin-9-yl)-3-hydroxytetrahydrofuran-2-yl)methoxy)-2-benzylmalonic acid (18 mg) as a solid.

$^1$H NMR ($CD_3OD$, 300 MHz) δ 8.29 (s, 1H), 7.26-7.16 (m, 5H), 6.36 (d, J=9 Hz, 1H), 4.6 (d, J=5 Hz, 1H), 4.53-4.47 (m, 1H), 4.43 (bs, 1H), 4.01 (dd, J=2, 11 Hz, 1H), 3.80 (dd, J=2, 10 Hz, 2H), 3.46 (bs, 2H); LC/MS [M+H]=493.

Example 20

Synthesis of 2-(((2R,3R,4R,5R)-5-(6-amino-2-chloro-9H-purin-9-yl)-3,4-dihydroxytetrahydrofuran-2-yl)methoxy)malonic Acid

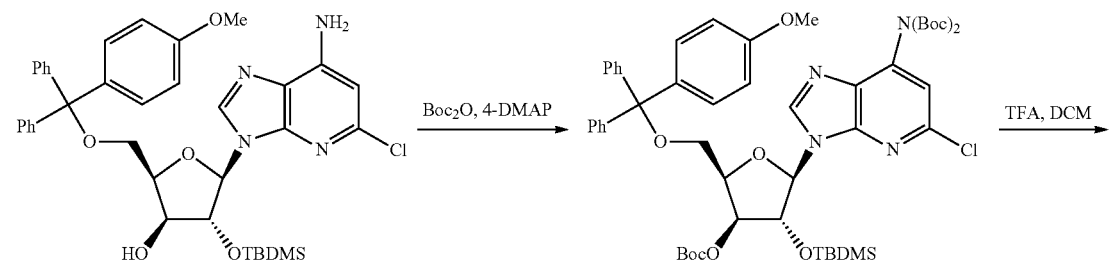

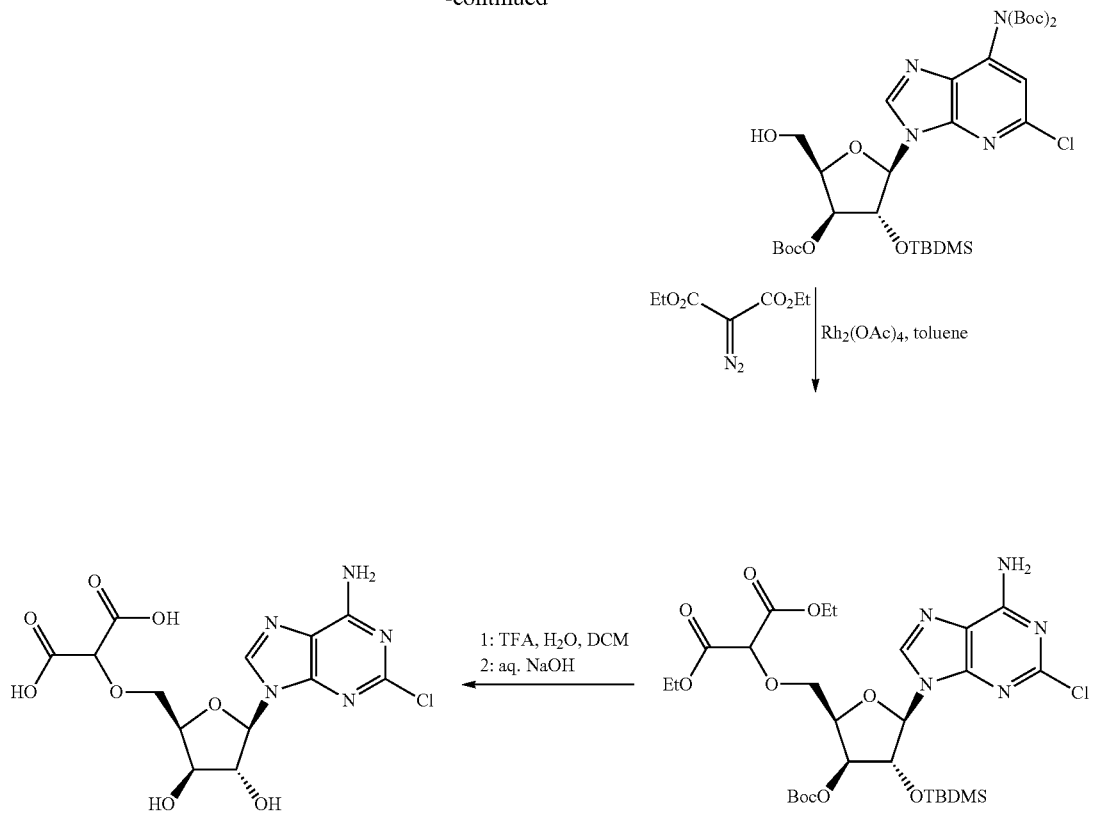

Step 1:

To a solution of (2R,3S,4R,5R)-5-(6-amino-2-chloro-9H-purin-9-yl)-4-((tert-butyldimethylsilyl)oxy)-2-(((4-methoxyphenyl)diphenylmethoxy)methyl)-tetrahydrofuran-3-ol, synthesized from 2-chloroadenosin according to the procedure reported by Koole, L. H. et al., *Acta Chemica Scandinavica*, 43, 665-669, 1989, (160 mg, 0.24 mmol) in THF (3 mL) was added $Boc_2O$ (211 mg, 0.96 mmol) and 4-DMAP (6 mg, 0.05 mmol). The reaction was stirred under argon atmosphere for 13 h before it was concentrated. The crude residue was purified by column chromatography on silica gel to give tert-butyl (tert-butoxycarbonyl)(9-((2R,3R,4S,5R)-4-((tert-butoxycarbonyl)oxy)-3-((tert-butyldimethylsilyl)oxy)-5-((4-methoxyphenyl)-diphenylmethoxy)methyl)tetrahydrofuran-2-yl)-2-chloro-9H-purin-6-yl)carbamate (190 mg, 79% yield).

Step 2:

To a solution of the above product (190 mg, 0.19 mmol) in DCM (4.8 mL) at room temperature was added TFA (71 µL, 0.95 mmol) dropwise. The reaction was stirred under argon atmosphere for 5 h before it was concentrated. The crude residue was purified by column chromatography on silica gel to give tert-butyl (tert-butoxycarbonyl)(9-((2R,3R,4S,5R)-4-((tert-butoxycarbonyl)oxy)-3-((tert-butyldimethylsilyl)oxy)-5-(hydroxymethyl)tetrahydrofuran-2-yl)-2-chloro-9H-purin-6-yl)carbamate (84 mg, 63% yield).

Step 3:

A mixture of tert-butyl (tert-butoxycarbonyl)(9-((2R,3R,4S,5R)-4-((tert-butoxycarbonyl)oxy)-3-((tert-butyldimethylsilyl)oxy)-5-(hydroxymethyl)tetrahydrofuran-2-yl)-2-chloro-9H-purin-6-yl)carbamate (84 mg, 0.12 mmol) and diethyl 2-diazomalonate (28 mg, 0.15 mmol) was charged into a 10 mL round bottom flask and azeotroped twice with toluene. The residue was dissolved in toluene (1.0 mL) under argon atmosphere and followed by addition of rhodium(II) acetate dimer (4 mg, 0.01 mmol). The reaction mixture was stirred for 3 h at 75° C. before it was allowed to cool and concentrated. The crude residue was purified by column chromatography on silica gel to give diethyl 2-(((2R,3S,4R,5R)-5-(6-(N-(tert-butoxycarbonyl)(tert-butoxycarbonyl)amino)-2-chloro-9H-purin-9-yl)-3-((tert-butoxycarbonyl)oxy)-4-((tert-butyldimethylsilyl)oxy)-tetrahydrofuran-2-yl)methoxy)malonate (40 mg, 42% yield).

Step 4:

To a solution of diethyl 2-(((2R,3S,4R,5R)-5-(6-(N-(tert-butoxycarbonyl)(tert-butoxycarbonyl)amino)-2-chloro-9H-purin-9-yl)-3-((tert-butoxycarbonyl)oxy)-4-((tert-butyldimethylsilyl)oxy)-tetrahydrofuran-2-yl)methoxy)malonate (40 mg, 0.05 mmol) in DCM (2 mL) and water (40 µL) and followed by dropwise addition of TFA (0.50 mL). The reaction was stirred for 13 h before it was evaporated to dryness and azeotroped with acetonitrile twice. The residue was taken up in THF (1.5 mL) and 4M NaOH (50 µL, 0.20 mmol) was added at room temperature. The reaction was stirred for 6 h and then concentrated. The crude residue was purified by reversed-phase HPLC gave the desired compound 2-(((2R,3R,4R,5R)-5-(6-amino-2-chloro-9H-purin-9-yl)-3,4-dihydroxytetrahydrofuran-2-yl)methoxy)malonic acid.

$^1$H NMR ($CD_3OD$, 300 MHz) δ 8.88 (s, 1H), 6.05 (d, J=6 Hz, 1H), 5.18-5.20 (t, J=5.6 Hz, 1H), 4.52-4.63 (dt, J=5, 34 Hz, 1H), 4.20 (bs, 1H), 3.80-3.90 (m, 2H); LC/MS [M+H]= 404.

Example 21

Synthesis of 2-(((2R,3R,4S,5R)-5-(4-(benzylamino)-1H-benzo[d]imidazol-1-yl)-4-fluoro-3-hydroxytetrahydrofuran-2-yl)methoxy)-2-(3-carboxybenzyl)malonic Acid

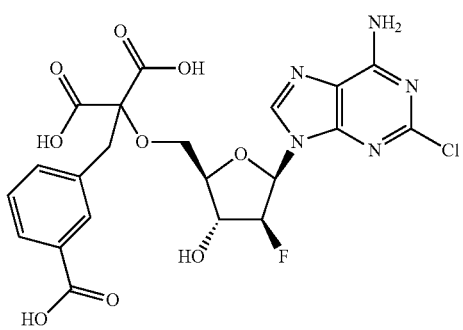 [SMILES: Nc1nc(Cl)nc2c1ncn2[C@@H]1O[C@H](COC(Cc2cccc(C(=O)O)c2)(C(=O)O)C(=O)O)[C@@H](O)[C@@H]1F]

Proceeding as described in Example 2 above but substituting benzyl bromide with methyl 3-(bromomethyl)benzoate, the title compound was isolated as a white solid.

¹H NMR (CD₃OD, 300 MHz) δ 8.31 (s, 1H), 7.99 (s, 1H), 7.81-7.84 (d, J=7 Hz, 1H), 7.52-7.55 (d, J=7 Hz, 1H), 7.25-7.30 (t, J=8 Hz, 1H), 6.40-6.46 (dd, J=4, 13 Hz, 1H), 5.07-5.27 (dt, J=4, 52 Hz, 1H), 4.66-4.73 (dt, J=5, 17 Hz, 1H), 4.16-4.20 (m, 1H), 3.99-4.11 (m, 2H), 3.40-3.55 (m, 2H); LC/MS [M+H]=540.

Example 22

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-fluorobenzyl)malonic Acid

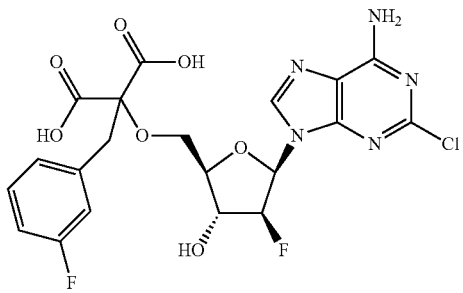 [SMILES: Nc1nc(Cl)nc2c1ncn2[C@@H]1O[C@H](COC(Cc2cccc(F)c2)(C(=O)O)C(=O)O)[C@@H](O)[C@@H]1F]

Proceeding as described in Example 2 above but substituting benzyl bromide with 3-fluorobenzyl bromide, the title compound was isolated as a white solid.

¹H NMR (CD₃OD, 300 MHz) δ 8.33 (s, 1H), 7.03-7.18 (m, 3H), 6.81-6.82 (m, 1H), 6.41-6.47 (dd, J=4, 13 Hz, 1H), 5.09-5.29 (dt, J=4, 52 Hz, 1H), 4.65-4.74 (dt, J=5, 18 Hz, 1H), 4.15-4.19 (q, J=4 Hz, 1H), 3.96-4.10 (m, 2H), 3.36-3.46 (m, 2H); LC/MS [M+H]=514.

Example 23

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-fluorobenzyl)malonic Acid

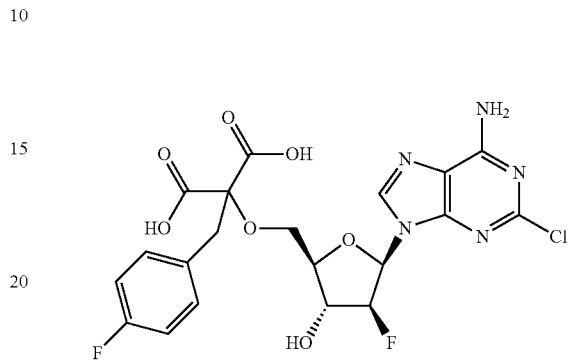

Proceeding as described in Example 2 above but substituting benzyl bromide with 4-fluorobenzyl bromide, the title compound was isolated as a white solid.

¹H NMR (CD₃OD, 300 MHz) δ 8.33 (s, 1H), 7.26-7.30 (m, 2H), 6.81-6.87 (t, J=9 Hz, 2H), 6.41-6.47 (dd, J=4, 13 Hz, 1H), 5.09-5.29 (dt, J=4, 52 Hz, 1H), 4.65-4.74 (dt, J=5, 18 Hz, 1H), 4.14-4.20 (m, 1H), 3.95-4.09 (m, 2H), 3.33-3.45 (m, 2H); LC/MS [M+H]=514.

Example 24

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-methoxybenzyl)malonic Acid

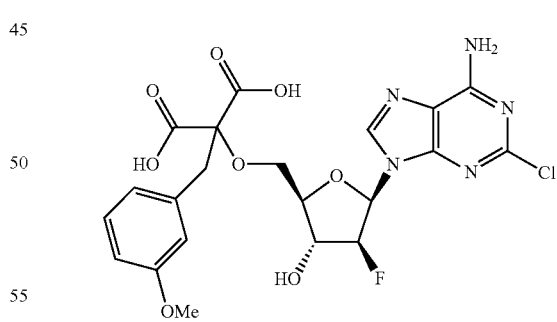

Proceeding as described in Example 2 above but substituting benzyl bromide with 3-methoxybenzyl bromide, the title compound was isolated as a white solid.

¹H NMR (CD₃OD, 300 MHz) δ 8.41 (s, 1H), 7.01-7.06 (t, J=7 Hz, 1H), 6.83-6.85 (m, 2H), 6.64-6.66 (d, J=8 Hz, 1H), 6.42-6.48 (dd, J=4, 11 Hz, 1H), 5.11-5.31 (dt, J=4, 52 Hz, 1H), 4.67-4.74 (dt, J=5, 18 Hz, 1H), 4.16-4.20 (m, 1H), 3.94-4.10 (m, 2H), 3.60 (d, J=1 Hz, 3H), 3.31-3.44 (m, 2H); LC/MS [M+H]=526.

Example 25

Synthesis of 2-(3-(1H-tetrazol-5-yl)benzyl)-2-(((2R,3R,4S,5R)-5-(6-amino-2-chloro-9H-purin-9-yl)-4-fluoro-3-hydroxytetrahydrofuran-2-yl)methoxy)malonic Acid

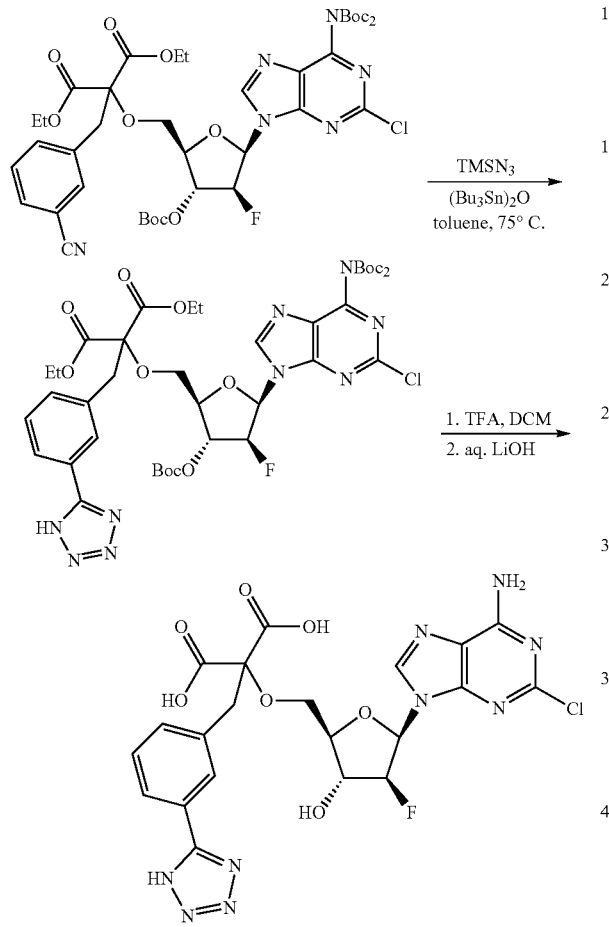

Step 1:

To a solution of diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluoro-tetrahydrofuran-2-yl)methoxy)-2-(3-cyanobenzyl)malonate, prepared from diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)malonate with 3-(bromomethyl)benzonitrile according to the procedure for Example 2, (380 mg, 0.43 mmol) in toluene (8 mL) was added azidotrimethylsilane (350 uL, 2.64 mmol) and bis(tributyltin)oxide (66 uL, 0.13 mmol) in portions over period of 4 days. The reaction mixture was then heated at 75° C. for four days before it was concentrated under reduced pressure. The crude residue was purified by column chromatography silica gel (0-4% MeOH in DCM) to provide diethyl 2-(((2R,3R,4S,5R)-5-(6-(N-(tert-butoxycarbonyl)-2-chloro-9H-purin-9-yl)-3-((tert-butoxycarbonyl)oxy)-4-fluoro-tetrahydrofuran-2-yl)methoxy)-2-(3-1-H-tetrazol-5-ylbenzyl)malonate.

Step 2:

Diethyl 2-(((2R,3R,4S,5R)-5-(6-(N-(tert-butoxy carbonyl)-2-chloro-9H-purin-9-yl)-3-((tert-butoxycarbonyl)oxy)-4-fluoro-tetrahydrofuran-2-yl)methoxy)-2-(3-1-H-tetrazol-5-ylbenzyl)malonate was then converted to the title compound as described in Example 2 above.

$^1$H NMR (CD$_3$OD, 300 MHz) δ 8.26 (s, 1H), 7.99 (s, 1H), 7.77-7.79 (d, J=7 Hz, 1H), 7.47-7.50 (d, J=8 Hz, 1H), 7.38 (t, J=7 Hz, 1H), 6.35-6.46 (m, 1H), 5.06-5.27 (m, 1H), 4.66-4.80 (m, 1H), 4.20-4.21 (m, 1H), 4.00-4.17 (m, 2H), 3.44-3.62 (m, 2H); LC/MS [M+H]=564.

Example 26

Synthesis of 2-(4-(1H-tetrazol-5-yl)benzyl)-2-(((2R,3R,4S,5R)-5-(6-amino-2-chloro-9H-purin-9-yl)-4-fluoro-3-hydroxytetrahydrofuran-2-yl)methoxy)malonic acid

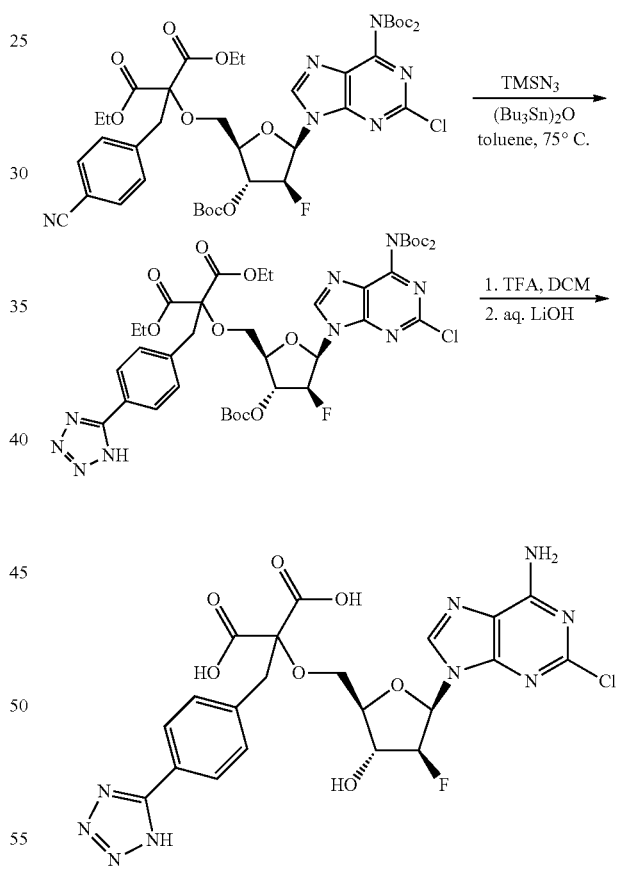

The title compound was prepared as described in Example 25 above by substituting 3-(bromomethyl)benzonitrile with 4-(bromomethyl)benzonitrile, the title compound was isolated as a white solid.

$^1$H NMR (CD$_3$OD, 300 MHz) δ 8.27 (s, 1H), 7.79-7.82 (d, J=8 Hz, 2H), 7.50-7.52 (d, J=8 Hz, 2H), 6.42-6.47 (dd, J=4, 13 Hz, 1H), 5.09-5.29 (dt, J=4, 53 Hz, 1H), 4.65-4.74 (dt, J=4, 17 Hz, 1H), 4.18-4.21 (m, 1H), 3.98-4.14 (m, 2H), 3.46-3.58 (m, 2H); LC/MS [M+H]=564.

Example 27

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(benzyloxy)benzyl)malonic Acid

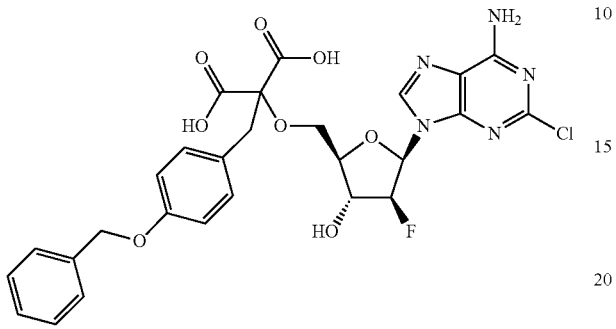

Proceeding as described in Example 2 above but substituting benzyl bromide with 1-(benzyloxy)-4-(chloromethyl)benzene, the title compound was isolated as a white solid.

$^1$H NMR (CD$_3$OD, 300 MHz) δ 8.33 (s, 1H), 7.27-7.35 (m, 5H), 7.17-7.20 (d, J=8 Hz, 2H), 6.72-6.75 (d, J=9 Hz, 2H), 6.40-6.46 (dd, J=5, 12 Hz, 1H), 5.10-5.29 (dt, J=4, 52 Hz, 1H), 4.89 (s, 2H), 4.66-4.75 (dt, J=5, 18 Hz, 1H), 4.15-4.17 (m, 1H), 3.93-4.08 (m, 2H), 3.30-3.41 (dd, J=5, 14 Hz, 2H); LC/MS [M+H]=602.

Example 28

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-hydroxybenzyl)malonic Acid

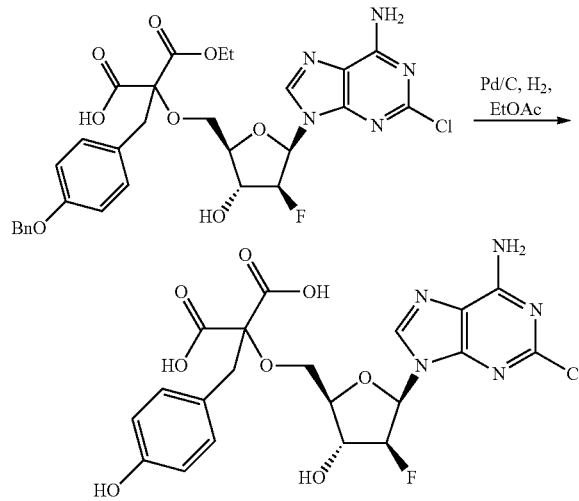

To a solution of -(((2R,3R,4S,5R)-5-(6-amino-2-chloro-9H-purin-9-yl)-4-fluoro-3-hydroxytetrahydrofuran-2-yl)methoxy)-2-(4-(benzyloxy)benzyl)malonic acid (Example 27) (280 mg) in EtOAc (10 mL) was added Pd/C (50 mg, 10% wt.). The resulting mixture was stirred under 1 atmosphere of H$_2$ for 1.5 h before it was filtered off. The filtrate was concentrated to provide the title compound as a white solid.

$^1$H NMR (CD$_3$OD, 300 MHz) δ 8.33-8.34 (d, J=2 Hz, 1H), 7.09-7.12 (d, J=9 Hz, 2H), 6.58-6.61 (d, J=8 Hz, 2H), 6.40-6.46 (dd, J=4, 14 Hz, 1H), 5.05-5.27 (dt, J=4, 52 Hz, 1H), 4.63-4.71 (dt, J=4, 33 Hz, 1H), 4.14-4.18 (q, J=5 Hz, 1H), 3.96-4.00 (m, 2H), 3.46 (bs, 2H); LC/MS [M+H]=512.

Example 29

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-hydroxybenzyl)malonic Acid

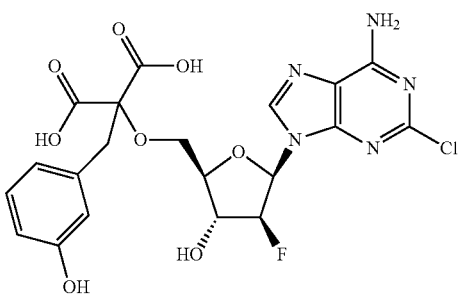 [SMILES: Nc1nc(Cl)nc2c1ncn2[C@@H]1O[C@H](COC(Cc2cccc(O)c2)(C(=O)O)C(=O)O)[C@@H](O)[C@@H]1F]

Proceeding as described in Examples 2 and 28 above, but substituting benzyl bromide with 1-(benzyloxy)-3-(chloromethyl)benzene, the title compound was isolated as white solid.

$^1$H NMR (CD$_3$OD, 300 MHz) δ 8.37 (s, 1H), 6.94-6.99 (t, J=8 Hz, 1H), 6.76-6.78 (m, 2H), 6.56-6.59 (d, J=8 Hz, 1H), 6.41-6.46 (dd, J=3, 12 Hz, 1H), 5.08-5.27 (dt, J=4, 52 Hz, 1H), 4.66-4.73 (m, 1H), 4.11-4.20 (m, 1H), 3.92-4.07 (m, 2H), 3.35 (m, 2H); LC/MS [M+H]=512.

Example 30

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-carboxy-2-fluorobenzyl)malonic Acid

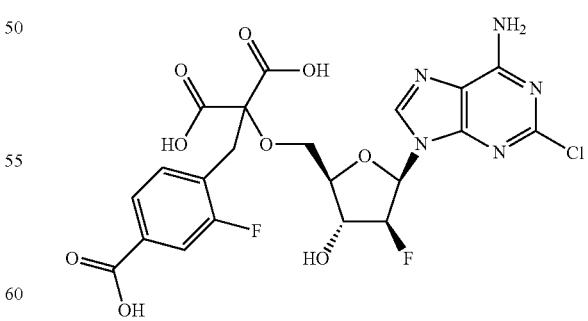

Proceeding as described in Example 2 above but substituting benzyl bromide with methyl 4-(bromomethyl)-3-fluorobenzoate, the title compound was isolated as a white solid.

$^1$H NMR (CD$_3$OD, 300 MHz) δ 8.25 (s, 1H), 7.51-7.60 (m, 3H), 6.38-6.44 (dd, J=4, 14 Hz, 1H), 5.05-5.25 (dt, J=5,

52 Hz, 1H), 4.62-4.70 (m, 1H), 4.12-4.16 (m, 1H), 3.95-4.05 (m, 2H), 3.54 (bs, 2H); LC/MS [M+H]=558.

Example 31

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-carboxy-3-fluorobenzyl)malonic Acid

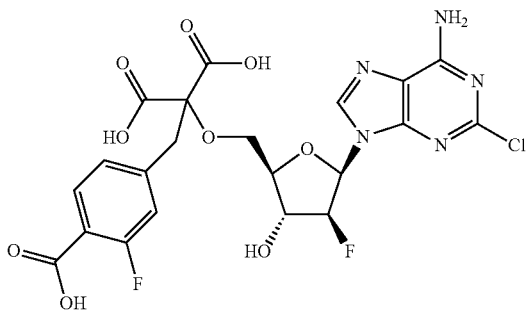 [SMILES: Nc1nc(Cl)nc2c1ncn2[C@@H]1O[C@H](COC(Cc2ccc(C(=O)O)c(F)c2)(C(=O)O)C(=O)O)[C@@H](O)[C@@H]1F]

Proceeding as described in Example 2 above but substituting benzyl bromide with methyl 4-(bromomethyl)-2-fluorobenzoate, the title compound was isolated as a white solid.

$^1$H NMR (CD$_3$OD, 300 MHz) δ 8.32 (bs, 1H), 7.69-7.74 (t, J=8 Hz, 1H), 7.12-7.16 (m, 2H), 6.41-6.47 (dd, J=5, 14 Hz, 1H), 5.06-5.28 (dt, J=5, 52 Hz, 1H), 4.65-4.73 (m, 1H), 4.14-4.19 (m, 1H), 3.92-4.04 (m, 2H), 3.44 (bs, 2H); LC/MS [M+H]=558.

Example 32

Synthesis of 2-(((2R,3R,4S,5R)-5-(6-amino-2-chloro-9H-purin-9-yl)-4-fluoro-3-hydroxytetrahydrofuran-2-yl)methoxy)-2-((5-(trifluoromethyl)furan-2-yl)methyl)-malonic Acid

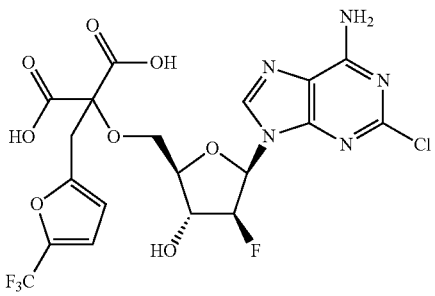 [SMILES: Nc1nc(Cl)nc2c1ncn2[C@@H]1O[C@H](COC(Cc2ccc(C(F)(F)F)o2)(C(=O)O)C(=O)O)[C@@H](O)[C@@H]1F]

Proceeding as described in Example 2 above but substituting benzyl bromide with 2-(bromomethyl)-5-(trifluoromethyl)furan, the title compound was isolated as a white solid.

$^1$H NMR (CD$_3$OD, 300 MHz) δ 8.38 (s, 1H), 6.78-6.79 (m, 4H), 6.39-6.45 (m, 2H), 5.06-5.26 (dt, J=4, 53 Hz, 1H), 4.62-4.71 (dt, J=4, 17 Hz, 1H), 4.13-4.16 (m, 1H), 3.97-4.00 (m, 2H), 3.58 (bs, 2H); LC/MS [M+H]=554.

Example 33

Synthesis of 2-(((2R,3R,4S,5R)-5-(6-amino-2-chloro-9H-purin-9-yl)-4-fluoro-3-hydroxytetrahydrofuran-2-yl)methoxy)-2-((6-(trifluoromethyl)pyridin-3-yl)methyl)malonic Acid

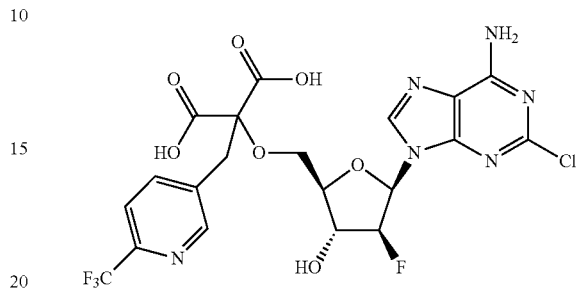

Proceeding as described in Example 2 above but substituting benzyl bromide with 5-(bromomethyl)-2-(trifluoromethyl)pyridine, the title compound was isolated as a white solid.

$^1$H NMR (CD$_3$OD, 300 MHz) δ 8.60 (bs, 1H), 8.37 (s, 1H), 7.89 (d, J=9 Hz, 1H), 7.60 (d, J=8 Hz, 1H), 6.51-6.59 (dd, J=2, 22 Hz, 1H), 5.08-5.27 (dt, J=4, 53 Hz, 1H), 4.62-4.71 (dt, J=5, 17 Hz, 1H), 4.21-4.24 (m, 1H), 3.96-4.17 (m, 2H), 3.45-3.59 (q, J=15 Hz, 2H); LC/MS [M+H]=565.

Example 34

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-fluoro-4-(trifluoromethyl)benzyl)malonic Acid

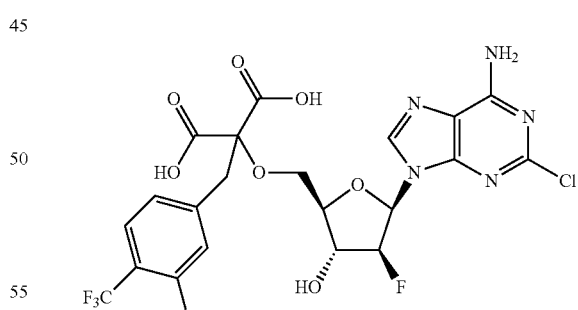

Proceeding as described in Example 2 above but substituting benzyl bromide with 4-(bromomethyl)-2-fluoro-1-(trifluoromethyl)benzene, the title compound was isolated as a white solid.

$^1$H NMR (CD$_3$OD, 300 MHz) δ 8.76 (s, 1H), 7.27-7.49 (m, 3H), 6.51-6.56 (dd, J=4, 10 Hz, 1H), 5.18-5.39 (dt, J=5, 52 Hz, 1H), 4.62-4.71 (dt, J=5, 17 Hz, 1H), 4.21-4.24 (m, 1H), 3.96-4.17 (m, 2H), 3.45-3.59 (q, J=15 Hz, 2H); LC/MS [M+H]=582.

Example 35

Synthesis of 2-(((2R,3R,4S,5R)-5-(6-amino-2-chloro-9H-purin-9-yl)-4-fluoro-3-hydroxytetrahydrofuran-2-yl)methoxy)-2-((3-phenylisoxazol-5-yl)methyl)malonic Acid

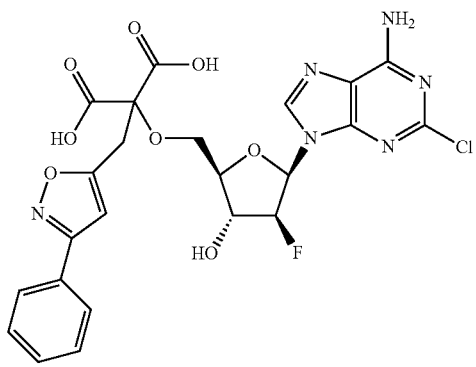 [SMILES: Nc1nc(Cl)nc2c1ncn2[C@@H]1O[C@H](COC(Cc2cc(-c3ccccc3)no2)(C(=O)O)C(=O)O)[C@@H](O)[C@@H]1F]

Proceeding as described in Example 2 above but substituting benzyl bromide with 5-(bromomethyl)-3-phenylisoxazole, the title compound was isolated as a white solid.

$^1$H NMR (CD$_3$OD, 300 MHz) δ 8.96 (s, 1H), 7.40-7.80 (m, 5H), 6.51-6.56 (dd, J=4, 10 Hz, 1H), 6.29 (s, 1H), 5.18-5.39 (dt, J=5, 52 Hz, 1H), 4.60-4.69 (dt, J=5, 17 Hz, 1H), 4.21-4.24 (m, 1H), 3.98-4.19 (m, 2H), 3.45-3.59 (q, J=15 Hz, 2H); LC/MS [M+H]=563.

Example 36

Synthesis of 2-(((2R,3R,4S,5R)-5-(6-amino-2-chloro-9H-purin-9-yl)-4-fluoro-3-hydroxytetrahydrofuran-2-yl)methoxy)-2-((1-benzyl-1H-pyrazol-4-yl)methyl)malonic Acid

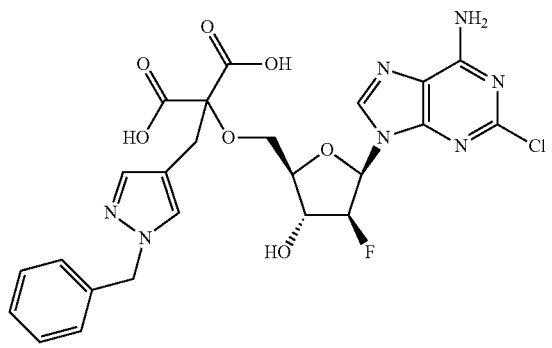 [SMILES: Nc1nc(Cl)nc2c1ncn2[C@@H]1O[C@H](COC(Cc2cnn(Cc3ccccc3)c2)(C(=O)O)C(=O)O)[C@@H](O)[C@@H]1F]

Proceeding as described in Example 2 above but substituting benzyl bromide with 1-benzyl-4-(bromomethyl)-1H-pyrazole, the title compound was isolated as a white solid.

$^1$H NMR (CD$_3$OD, 300 MHz) δ 8.45 (s, 1H), 7.56 (s, 1H), 7.414 (s, 1H), 7.17-7.23 (m, 3H), 7.00-7.03 (m, 2H), 6.39-6.45 (dd, J=4, 12 Hz, 1H), 5.10-5.31 (m, 3H), 4.65-4.75 (dt, J=5, 18 Hz, 1H), 4.14-4.17 (q, J=5 Hz, 1H), 3.93-4.02 (m, 2H), 3.30-3.36 (m, 2H); LC/MS [M+H]=576.

Example 37

Synthesis of 2-((1H-pyrazol-4-yl)methyl)-2-(((2R,3R,4S,5R)-5-(6-amino-2-chloro-9H-purin-9-yl)-4-fluoro-3-hydroxytetrahydrofuran-2-yl)methoxy)malonic Acid

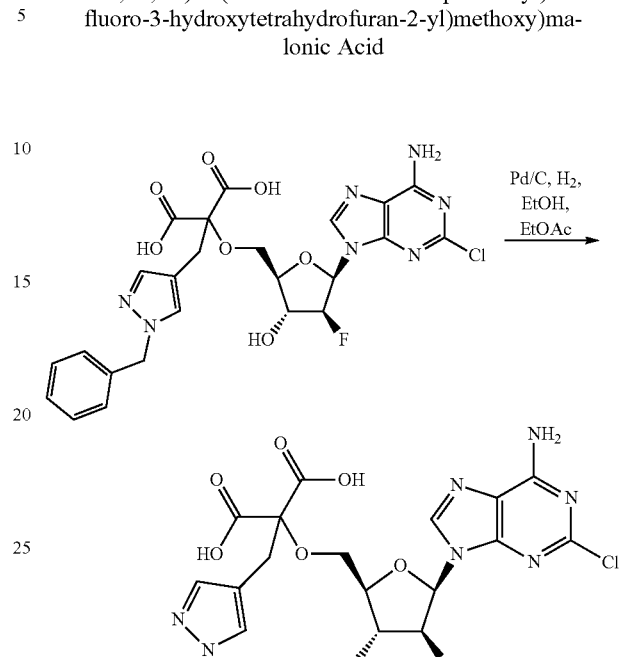

2-((1H-pyrazol-4-yl)methyl)-2-(((2R,3R,4S,5R)-5-(6-amino-2-chloro-9H-purin-9-yl)-4-fluoro-3-hydroxytetrahydrofuran-2-yl)methoxy)malonic acid was prepared from Example 36 (200 mg) via de-benzylation with Pd/C (50 mg, 10 wt %) in an mixture of EtOH (0.5 mL) and EtOAc (5 mL) under 1 atmosphere of H$_2$. The catalyst was filtered off after 1 h and the filtrate was concentrated to provide the title compound as a white solid.

$^1$H NMR (CD$_3$OD, 300 MHz) δ 8.46 (s, 1H), 7.55 (s, 2H), 6.44-6.49 (dd, J=5, 12 Hz, 1H), 5.12-5.31 (dt, J=4, 53 Hz, 1H), 4.68-4.74 (dt, J=5, 13 Hz, 1H), 4.17-4.22 (q, J=5 Hz, 1H), 3.96-4.03 (m, 2H), 3.36 (bs, 2H); LC/MS [M+H]=486.

Example 38

Synthesis of 2-(((2R,3R,4S,5R)-5-(6-amino-2-chloro-9H-purin-9-yl)-4-fluoro-3-hydroxytetrahydrofuran-2-yl)methoxy)-2-((2-carboxythiazol-5-yl)methyl)malonic Acid

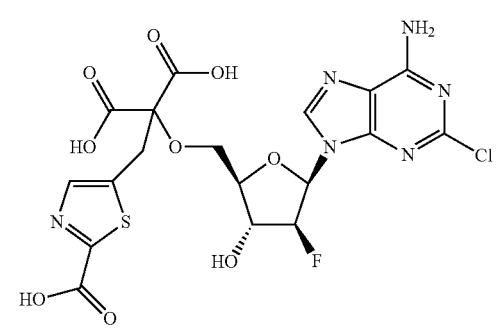 [SMILES: Nc1nc(Cl)nc2c1ncn2[C@@H]1O[C@H](COC(Cc2cnc(C(=O)O)s2)(C(=O)O)C(=O)O)[C@@H](O)[C@@H]1F]

Proceeding as described in Example 2 above but substituting benzyl bromide with methyl 4-(bromomethyl)thiazole-2-carboxylate, the title compound was isolated as a white solid. ¹H NMR (CD₃OD, 300 MHz) δ 8.38 (d, J=2 Hz, 1H), 7.37-7.59 (d, J=4 Hz, 1H), 6.41-6.48 (m, 1H), 5.05-5.25 (dt, J=3, 52 Hz, 1H), 4.65-4.74 (m, 1H), 4.22-4.24 (m, 1H), 3.98 (bs, 2H), 3.66 (bs, 2H); LC/MS [M+H]=548.

Example 39

Synthesis of 2-(((2R,3R,4S,5R)-5-(6-amino-2-chloro-9H-purin-9-yl)-4-fluoro-3-hydroxytetrahydrofuran-2-yl)methoxy)-2-((2-carboxythiazol-4-yl)methyl)malonic acid

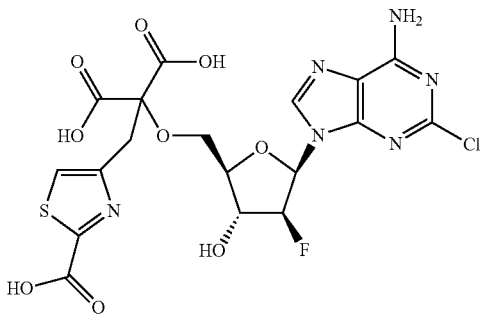

Proceeding as described in Example 2 above but substituting benzyl bromide with methyl 5-(bromomethyl)thiazole-2-carboxylate, the title compound was isolated as a white solid.

¹H NMR (CD₃OD, 300 MHz) δ 8.48 (bs, 1H), 7.64 (bs, 1H), 6.41-6.44 (dd, J=5, 8 Hz, 1H), 5.14-5.33 (dt, J=4, 52 Hz, 1H), 4.73-4.79 (m, 1H), 4.01-4.04 (m, 1H), 3.70-3.79 (m, 2H), 3.73 (bs, 2H); LC/MS [M+H]=547.

Example 40

Synthesis of 2-(((2R,3R,4S,5R)-5-(6-amino-2-chloro-9H-purin-9-yl)-4-fluoro-3-hydroxytetrahydrofuran-2-yl)methoxy)-2-((5-carboxy-1-methyl-1H-pyrazol-3-yl)methyl)malonic Acid

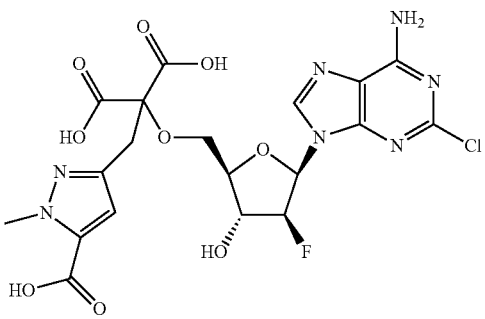 [SMILES: Cn1nc(CC(OC[C@H]2O[C@@H](n3cnc4c(N)nc(Cl)nc43)[C@@H](F)[C@@H]2O)(C(=O)O)C(=O)O)cc1C(=O)O]

Proceeding as described in Example 2 above but substituting benzyl bromide with ethyl 5-(bromomethyl)-1-methyl-1H-pyrazole-3-carboxylate, the title compound was isolated as a white solid.

¹H NMR (CD₃OD, 300 MHz) δ 8.90 (bs, 1H), 6.51-6.56 (dd, J=4, 10 Hz, 1H), 6.35 (s, 1H), 5.19-5.40 (dt, J=4.7, 52 Hz, 1H), 4.61-4.70 (dt, J=5, 17 Hz, 1H), 4.21-4.24 (m, 1H), 3.96-4.17 (m, 2H), 3.93 (s, 3H), 3.45-3.59 (q, J=15 Hz, 2H); LC/MS [M+H]=543.

Example 41

Synthesis of 2-(((2R,3R,4S,5R)-5-(6-amino-2-chloro-9H-purin-9-yl)-4-fluoro-3-hydroxytetrahydrofuran-2-yl)methoxy)-2-((3-carboxyisoxazol-5-yl)methyl)malonic Acid

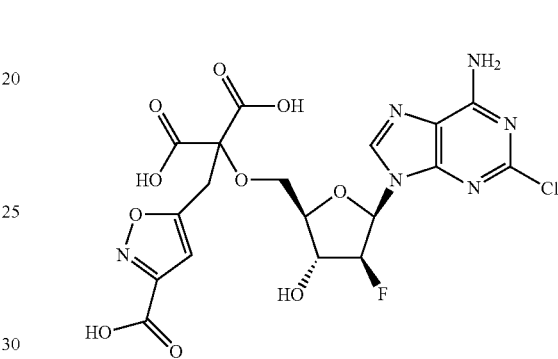

Proceeding as described in Example 2 above but substituting benzyl bromide with ethyl 5-(bromomethyl)isoxazole-3-carboxylate, the title compound was isolated as a white solid.

¹H NMR (CD₃OD, 300 MHz) δ 8.98 (bs, 1H), 6.51-6.56 (dd, J=4, 10 Hz, 1H), 6.39 (s, 1H), 5.18-5.39 (dt, J=5, 52 Hz, 1H), 4.62-4.71 (dt, J=5, 17 Hz, 1H), 4.21-4.25 (m, 1H), 3.97-4.17 (m, 2H), 3.43-3.56 (q, J=15 Hz, 2H); LC/MS [M+H]=531.

Example 42

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-cyano-3-fluorobenzyl)malonic acid

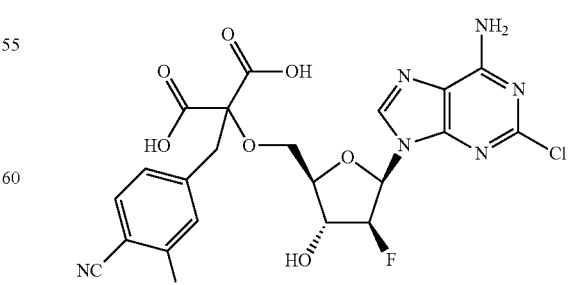

Proceeding as described in Example 2 above but substituting benzyl bromide with 4-(bromomethyl)-2-fluorobenzonitrile, the title compound was isolated as a white solid.

¹H NMR (CD₃OD, 300 MHz) δ 8.35 (bs, 1H), 7.04-7.57 (m, 3H), 6.48-6.54 (dd, J=4, 10 Hz, 1H), 5.18-5.39 (dt, J=5, 52 Hz, 1H), 4.65-4.75 (dt, J=5, 17 Hz, 1H), 4.21-4.24 (m, 1H), 3.94-4.18 (m, 2H), 3.45-3.60 (m, 2H); LC/MS [M+H]= 539.

Example 43

Synthesis of 2-(((2R,3R,4S,5R)-5-(6-amino-2-chloro-9H-purin-9-yl)-4-fluoro-3-hydroxytetrahydrofuran-2-yl)methoxy)-2-((5-carboxythiophen-3-yl)methyl)malonic Acid

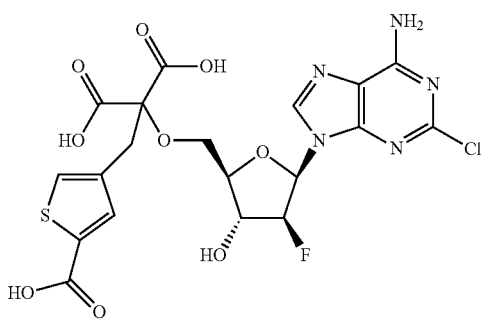 [SMILES: Nc1nc(Cl)nc2c1ncn2[C@@H]1O[C@H](COC(Cc2csc(C(=O)O)c2)(C(=O)O)C(=O)O)[C@@H](O)[C@@H]1F]

Proceeding as described in Example 2 above but substituting benzyl bromide with ethyl 4-(bromomethyl)thiophene-2-carboxylate, the title compound was isolated as a white solid.

¹H NMR (CD₃OD, 300 MHz) δ 8.40 (bs, 1H), 7.73 (s, 1H), 7.50 (s, 1H), 6.44-6.49 (dd, J=3, 11 Hz, 1H), 5.03-5.30 (m, 1H), 4.65-4.75 (m, 1H), 4.15-4.23 (m, 1H), 3.96-4.10 (m, 2H), 3.39-3.53 (m, 2H); LC/MS [M+H]=546.

Example 44

Synthesis of 2-(((2R,3R,4S,5R)-5-(6-amino-2-chloro-9H-purin-9-yl)-4-fluoro-3-hydroxytetrahydrofuran-2-yl)methoxy)-2-((5-carboxythiophen-2-yl)methyl)malonic Acid

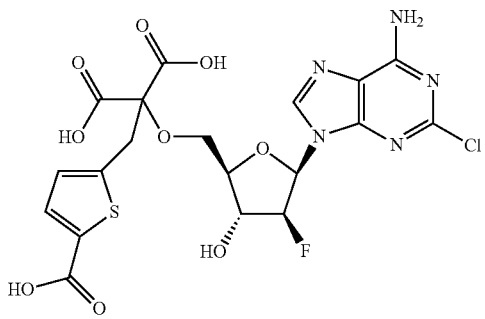

Proceeding as described in Example 2 above but substituting benzyl bromide with ethyl 5-(bromomethyl)thiophene-2-carboxylate, the title compound was isolated as a white solid.

¹H NMR (CD₃OD, 300 MHz) δ 8.36 (s, 1H), 7.52-7.53 (d, J=4 Hz, 1H), 6.99-7.00 (d, J=4 Hz, 1H), 6.41-6.47 (dd, J=4, 14 Hz, 1H), 5.07-5.26 (dt, J=3, 48 Hz, 1H), 4.68-4.76 (dt, J=4, 18 Hz, 1H), 4.18-4.21 (m, 1H), 4.01-4.11 (m, 2H), 3.66 (s, 2H); LC/MS [M+H]=546.

Example 45

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(carboxymethyl)benzyl)malonic Acid

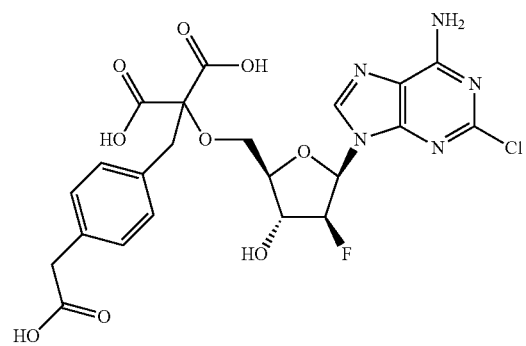 [SMILES: Nc1nc(Cl)nc2c1ncn2[C@@H]1O[C@H](COC(Cc2ccc(CC(=O)O)cc2)(C(=O)O)C(=O)O)[C@@H](O)[C@@H]1F]

Proceeding as described in Example 2 above but substituting benzyl bromide with ethyl 2-(4-(bromomethyl)phenyl)acetate, the title compound was isolated as a white solid.

¹H NMR (CD₃OD, 300 MHz) δ 8.32 (bs, 1H), 7.24-7.26 (d, J=8 Hz, 2H), 7.08-7.10 (d, J=8 Hz, 2H), 6.40-6.46 (dd, J=4, 13 Hz, 1H), 5.07-5.27 (dt, J=4, 53 Hz, 1H), 4.63-4.72 (dt, J=4, 18 Hz, 1H), 4.15-4.20 (m, 1H), 3.95-4.06 (m, 2H), 3.44-3.54 (m, 2H), 3.40 (bs, 2H); LC/MS [M+H]=554.

Example 46

Synthesis of 2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)malonic Acid (R)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-methoxy-3-oxopropanoic Acid (S)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-methoxy-3-oxopropanoic Acid (R)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxopropanoic Acid; and (S)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxopropanoic Acid

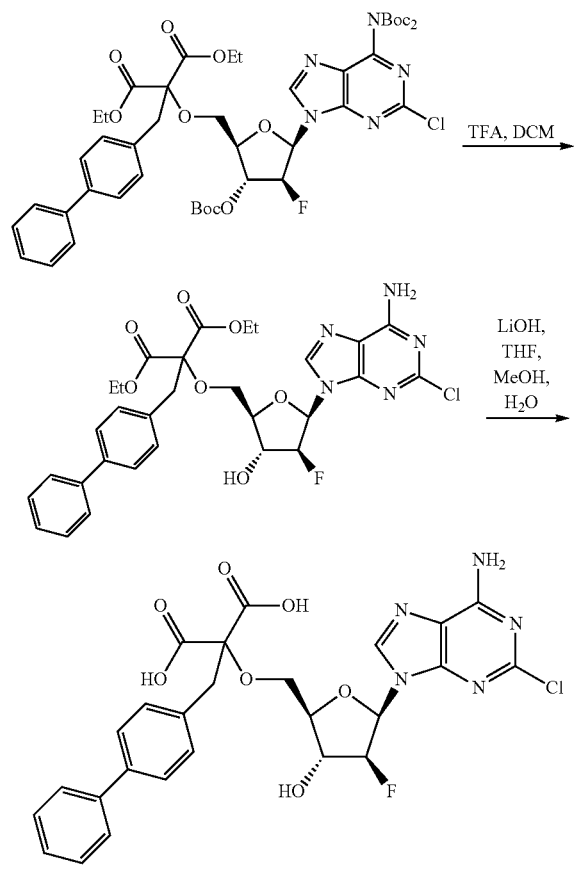

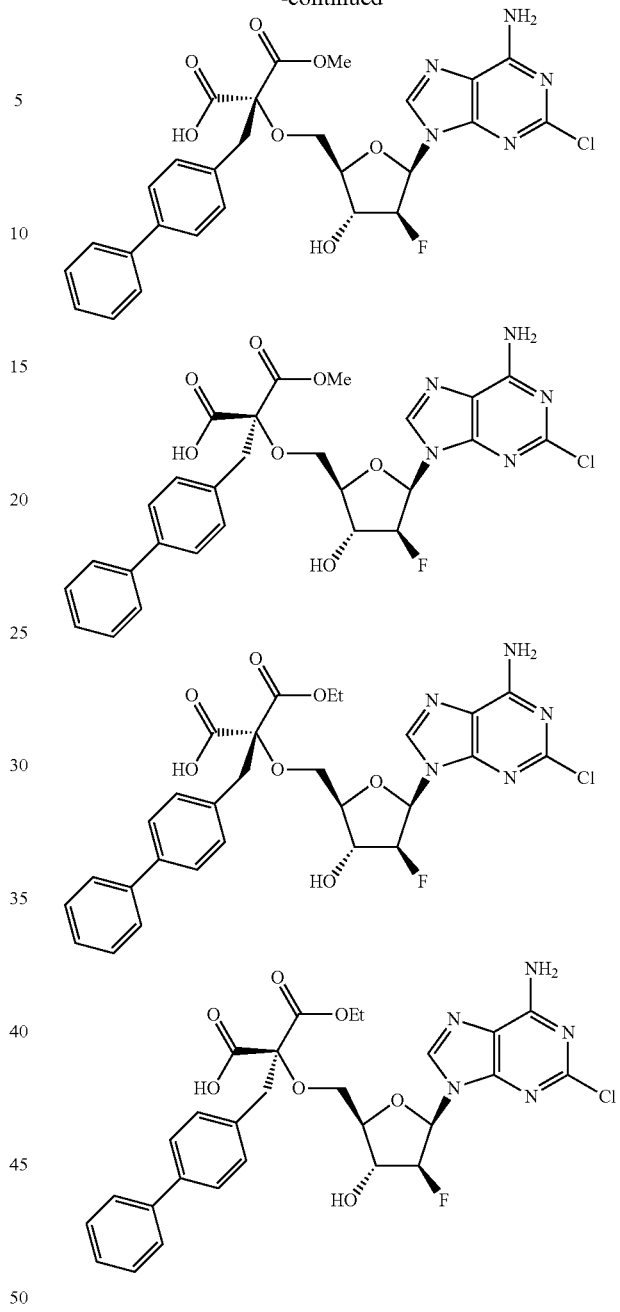

Step 1:

Diethyl 2-([1,1'-biphenyl]-4-ylmethyl)-2-(((2R,3R,4S,5R)-5-(6-N-(bis-(tert-butoxycarbonyl)amino)-2-chloro-9H-purin-9-yl)-3-((tert-butoxycarbonyl)oxy)-4-fluorotetrahydrofuran-2-yl)methoxy)malonate (200 mg, 0.22 mmol), prepared by alkylating N6,N6-bis-(tert-butoxycarbonyl)-2'-arabino-fluoro-2'-deoxy-3'-O-(tert-butoxycarbonyl)-2-chloro-adenosine with 4-phenylbenzyl bromide according to the procedure described for Example 2, was dissolved in DCM (5 mL) and followed by addition of TFA (1.5 mL) at room temperature. The resulting mixture was stirred for 7 h before it was concentrated. The residue was re-taken up in DCM (3×5 mL) and concentrated under reduced pressure each time to remove the excessive TFA to provide diethyl 2-([1,1'-biphenyl]-4-ylmethyl)-2-(((2R,3R,4S,5R)-5-(6-(N-(tert-butoxycarbonyl)(tert-butoxycarbonyl)amino)-2- chloro-9H-purin-9-yl)-3-((tert-butoxycarbonyl)oxy)-4-fluo-rotetrahydrofuran-2-yl)methoxy)malonate.

Step 2:

To a solution of diethyl 2-([1,1'-biphenyl]-4-ylmethyl)-2-(((2R,3R,4S,5R)-5-(6-(N-(tert-butoxycarbonyl)(tert-bu-toxycarbonyl)amino)-2-chloro-9H-purin-9-yl)-3-((tert-bu-toxycarbonyl)oxy)-4-fluorotetrahydrofuran-2-yl)methoxy) malonate (0.22 mmol) in a mixture of MeOH (2 mL), THF (2 mL) and H$_2$O (2 mL) was added LiOH.H$_2$O (90 mg, 2.15 mmol). The resulting mixture was stirred at room temperature for 5 h before the organic volatiles were removed under reduced pressure. The residue was re-dissolved in H$_2$O (2 mL) and acidified with 1N aq.HCl solution to pH 5 before it was concentrated under reduced pressure. The crude residue was purified by reversed-phase HPLC to provide the title compounds as white solids.

2-([1,1'-Biphenyl]-4-ylmethyl)-2-(((2R,3R,4S,5R)-5-(6-amino-2-chloro-9H-purin-9-yl)-4-fluoro-3-hy-droxytetrahydrofuran-2-yl)methoxy)malonic Acid $^1$H NMR (CD$_3$OD, 300 MHz) δ 8.34 (bs, 1H), 7.27-7.46 (m, 9H), 6.41-6.46 (dd, J=5, 12 Hz, 1H), 5.09-5.30 (dt, J=4, 52 Hz, 1H), 4.68-4.77 (dt, J=4, 18 Hz, 1H), 4.15-4.19 (m, 1H), 3.97-4.12 (m, 2H), 3.43-3.52 (m, 2H); LC/MS [M+H]=572.

2-([1,1'-Biphenyl]-4-ylmethyl)-2-(((2R,3R,4S,5R)-5-(6-amino-2-chloro-9H-purin-9-yl)-4-fluoro-3-hy-droxytetrahydrofuran-2-yl)methoxy)-3-methoxy-3-oxopropanoic Acid (Methyl diastereomer 1)

$^1$H NMR (CD$_3$OD, 300 MHz) δ 8.31 (bs, 1H), 7.26-7.48 (m, 9H), 6.42-6.47 (dd, J=5, 12 Hz, 1H), 5.10-5.31 (dt, J=4, 52 Hz, 1H), 4.67-4.77 (dt, J=5, 18 Hz, 1H), 4.15-4.19 (m, 1H), 3.98-4.10 (m, 2H), 3.78 (s, 3H), 3.40-3.52 (m, 2H); LC/MS [M+H]=586.

2-([1,1'-Biphenyl]-4-ylmethyl)-24(2R,3R,4S,5R)-5-(6-amino-2-chloro-9H-purin-9-yl)-4-fluoro-3-hy-droxytetrahydrofuran-2-yl)methoxy)-3-methoxy-3-oxopropanoic Acid (Methyl diastereomer 2)

$^1$H NMR (CD$_3$OD, 300 MHz) δ 8.31 (bs, 1H), 7.25-7.47 (m, 9H), 6.40-6.46 (dd, J=4, 12 Hz, 1H), 5.10-5.30 (dt, J=4, 53 Hz, 1H), 4.66-4.76 (dt, J=5, 18 Hz, 1H), 4.08-4.17 (m, 2H), 3.92-3.96 (m, 1H), 3.79 (s, 3H), 3.40-3.52 (m, 2H); LC/MS [M+H]=586.

2-([1,1'-Biphenyl]-4-ylmethyl)-24(2R,3R,4S,5R)-5-(6-amino-2-chloro-9H-purin-9-yl)-4-fluoro-3-hy-droxytetrahydrofuran-2-yl)methoxy)-3-ethoxy-3-oxopropanoic Acid (Ethyl diastereomer 1)

$^1$H NMR (CD$_3$OD, 300 MHz) δ 8.33 (bs, 1H), 7.26-7.48 (m, 9H), 6.44-6.49 (dd, J=5, 8 Hz, 1H), 5.11-5.31 (dt, J=4, 53 Hz, 1H), 4.71-4.77 (m, 1H), 4.17-4.25 (m, 3H), 4.00-4.09 (m, 2H), 3.44 (bs, 2H), 1.24-1.28 (t, J=7 Hz, 3H); LC/MS [M+H]=600.

2-([1,1'-Biphenyl]-4-ylmethyl)-2-(((2R,3R,4S,5R)-5-(6-amino-2-chloro-9H-purin-9-yl)-4-fluoro-3-hy-droxytetrahydrofuran-2-yl)methoxy)-3-ethoxy-3-oxopropanoic Acid (Ethyl diastereomer 2)

$^1$H NMR (CD$_3$OD, 300 MHz) δ 8.31 (bs, 1H), 7.25-7.47 (m, 9H), 6.40-6.46 (dd, J=5, 12 Hz, 1H), 5.10-5.30 (dt, J=4, 52 Hz, 1H), 4.68-4.77 (dt, J=5, 18 Hz, 1H), 4.22-4.29 (q, J=7 Hz, 2H), 4.10-4.19 (m, 2H), 3.93-3.98 (m, 1H), 3.40-3.53 (m, 2H), 1.25-1.30 (t, J=7 Hz, 3H); LC/MS [M+H]=600.

Example 47

Synthesis of 2-(((2R,3R,4S,5R)-5-(6-amino-2-chloro-9H-purin-9-yl)-4-fluoro-3-hydroxytetrahy-drofuran-2-yl)methoxy)-2-(3-chloro-4-methoxyben-zyl)malonic Acid

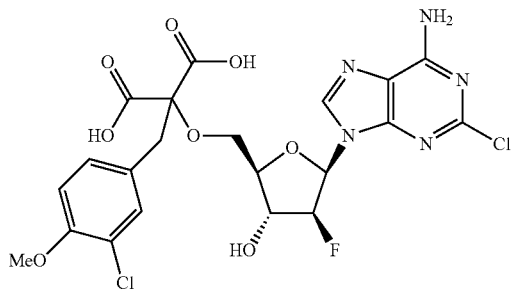 [SMILES: COc1ccc(CC(OC[C@H]2O[C@@H](n3cnc4c(N)nc(Cl)nc43)[C@@H](F)[C@@H]2O)(C(=O)O)C(=O)O)cc1Cl]

Proceeding as described in Example 2 above but substituting benzyl bromide with 4-(bromomethyl)-2-chloro-1-methoxybenzene, the title compound was isolated as a white solid.

$^1$H NMR (CD$_3$OD, 300 MHz) δ 8.34 (bs, 1H), 7.27-7.28 (d, J=2 Hz, 1H), 7.27-7.28 (dd, J=2, 8 Hz, 1H), 6.77-6.80 (d, J=8 Hz, 1H), 6.43-6.48 (dd, J=4, 11 Hz, 1H), 5.11-5.31 (dt, J=4, 52 Hz, 1H), 4.69-4.83 (dt, J=5, 17 Hz, 1H), 4.15-4.20 (m, 1H), 3.93-4.10 (m, 2H), 3.75 (s, 3H), 3.27-3.34 (m, 2H); LC/MS [M+H]=560.

Example 48

Synthesis of 2-(((2R,3R,4S,5R)-5-(6-amino-2-chloro-9H-purin-9-yl)-4-fluoro-3-hydroxytetrahy-drofuran-2-yl)methoxy)-2-(4-sulfamoylbenzyl)ma-lonic Acid

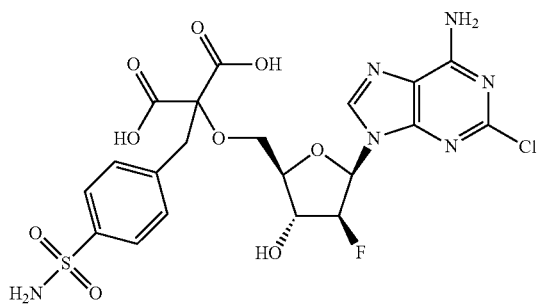 [SMILES: Nc1nc(Cl)nc2c1ncn2[C@@H]1O[C@H](COC(Cc2ccc(S(N)(=O)=O)cc2)(C(=O)O)C(=O)O)[C@@H](O)[C@@H]1F]

Proceeding as described in Example 2 above but substituting benzyl bromide with 4-(bromomethyl)benzenesulfo-namide, the title compound was isolated as a white solid.

$^1$H NMR (CD$_3$OD, 300 MHz) δ 8.27 (s, 1H), 7.70-7.73 (d, J=8 Hz, 2H), 7.47-7.49 (d, J=8 Hz, 2H), 6.40-6.46 (dd, J=4, 14 Hz, 1H), 5.07-5.27 (dt, J=4, 52 Hz, 1H), 4.62-4.70 (dt, J=5, 17 Hz, 1H), 4.16-4.20 (q, J=5 Hz, 1H), 3.99-4.10 (m, 2H), 3.34-3.52 (m, 2H); LC/MS [M+H]=575.

Example 49

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-chloro-2-fluorobenzyl) malonic Acid

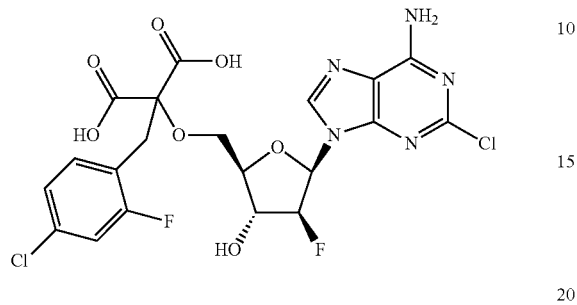

Proceeding as described in Example 2 above but substituting benzyl bromide with 4-chloro-2-fluorobenzyl bromide, the title compound was isolated as a white solid. [M+H]=548.

Example 50

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-((2-carboxyethyl)carbamoyl)-benzyl)malonic Acid

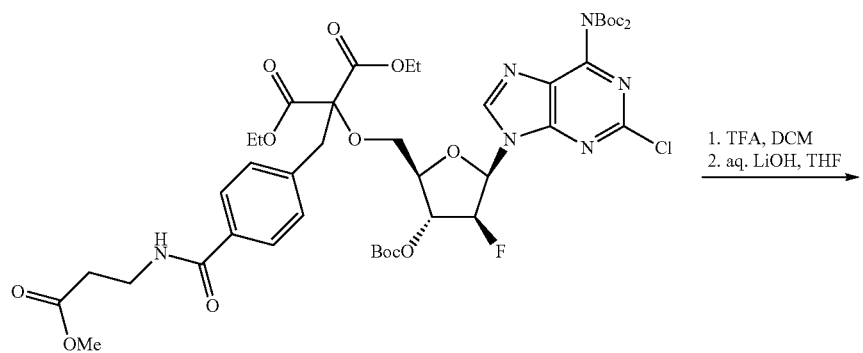

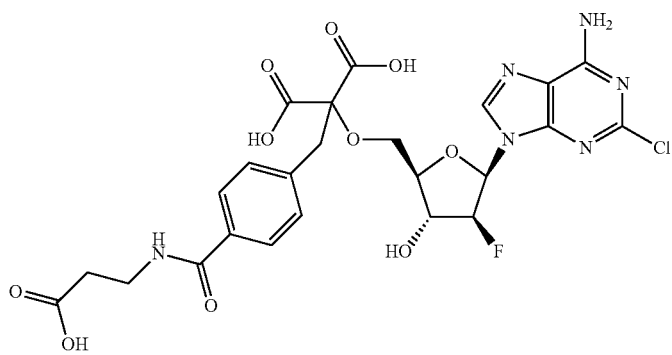

Diethyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)-2-(4-((3-methoxy-3-oxopropyl)carbamoyl)benzyl)malonate was prepared as described in Example 2 above but substituting benzyl bromide with methyl 3-(4-(bromomethyl)benzamido)propanoate. The title compound was isolated as a white solid.

$^1$H NMR (CD$_3$OD, 300 MHz) δ 8.25 (s, 1H), 7.59-7.62 (d, J=8 Hz, 2H), 7.37-7.40 (d, J=8 Hz, 1H), 6.40-6.46 (dd, J=5, 14 Hz, 1H), 5.07-5.27 (dt, J=4, 52 Hz, 1H), 4.62-4.71 (dt, J=4, 18 Hz, 1H), 4.14-4.19 (m, 1H), 3.97-4.10 (m, 2H), 3.57-3.62 (t, J=7 Hz, 2H), 3.42-3.52 (m, 2H), 2.59-2.64 (t, J=7 Hz, 3H); LC/MS [M+H]=611.

Example 51

Synthesis of -(((2R,3R,4S,5R)-5-(6-amino-2-chloro-9H-purin-9-yl)-4-fluoro-3-hydroxytetrahydrofuran-2-yl)methoxy)-2-((2-carboxybenzofuran-5-yl)methyl)-malonic Acid

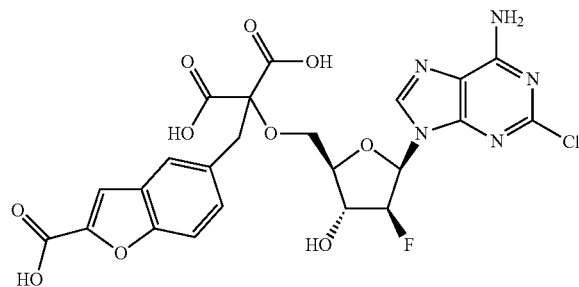 [SMILES: Nc1nc(Cl)nc2c1ncn2[C@@H]1O[C@H](COC(Cc2ccc3oc(C(=O)O)cc3c2)(C(=O)O)C(=O)O)[C@@H](O)[C@@H]1F]

Proceeding as described in Example 2 above but substituting benzyl bromide with methyl 5-(bromomethyl)benzofuran-2-carboxylate, the title compound was isolated as a white solid.

$^1$H NMR (CD$_3$OD, 300 MHz) δ 8.21 (s, 1H), 7.64-7.67 (d, J=9 Hz, 2H), 7.59 (s, 1H), 7.39-7.42 (dd, J=1, 9 Hz, 1H), 7.14 (s, 1H), 6.45-6.49 (dd, J=7, 7 Hz, 1H), 5.16-5.38 (dt, J=6, 53 Hz, 1H), 4.75-4.85 (m, 1H), 4.18-4.25 (m, 2H), 3.88-3.93 (dd, J=3, 10 Hz, 2H), 3.45-3.64 (m, 2H); LC/MS [M+H]=580.

Example 52

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(2,2,2-trifluoroethoxy)benzyl)malonic Acid

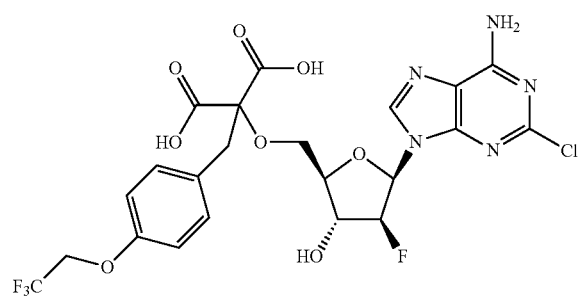 [SMILES: Nc1nc(Cl)nc2c1ncn2[C@@H]1O[C@H](COC(Cc2ccc(OCC(F)(F)F)cc2)(C(=O)O)C(=O)O)[C@@H](O)[C@@H]1F]

Proceeding as described in Example 2 above but substituting benzyl bromide with 1-(bromomethyl)-4-(2,2,2-trifluoroethoxy)benzene, the title compound was isolated as a white solid.

$^1$H NMR (CD$_3$OD, 300 MHz) δ 8.31 (s, 1H), 7.23-7.26 (d, J=9 Hz, 2H), 6.76-6.79 (d, J=8 Hz, 2H), 6.40-6.46 (dd, J=4, 13 Hz, 1H), 5.08-5.28 (dt, J=4, 52 Hz, 1H), 4.65-4.73 (dt, J=4, 17 Hz, 1H), 4.33-4.43 (m, 2H), 4.14-4.19 (m, 1H), 3.95-4.08 (m, 2H), 3.32-3.42 (m, 2H);

LC/MS [M+H]=594.

Example 53

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(carboxymethoxy)benzyl)malonic Acid

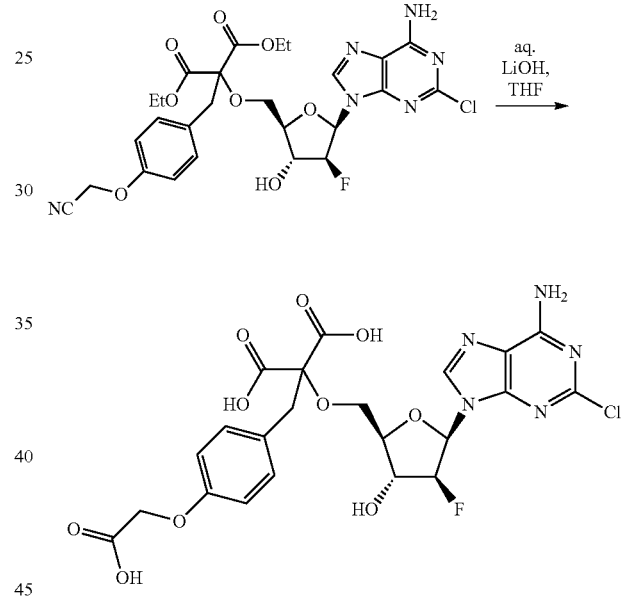

Step 1:

Diethyl 2-(((2R,3R,4S,5R)-5-(6-amino-2-chloro-9H-purin-9-yl)-4-fluoro-3-hydroxytetrahydrofuran-2-yl)methoxy)-2-(4-(cyanomethoxy)benzyl)malonate was prepared according to the procedure described in Example 2 above but substituting benzyl bromide with 2-(4-(bromomethyl)phenoxy)acetonitrile.

Step 2:

Diethyl 2-(((2R,3R,4S,5R)-5-(6-amino-2-chloro-9H-purin-9-yl)-4-fluoro-3-hydroxytetrahydrofuran-2-yl)methoxy)-2-(4-(cyanomethoxy)benzyl)malonate was then hydrolyzed to the corresponding acid with the treatment of aq. LiOH in THF. The title compound was isolated as a white solid.

$^1$H NMR (CD$_3$OD, 300 MHz) δ 8.31 (s, 1H), 7.20-7.23 (d, J=8 Hz, 2H), 6.71-6.74 (d, J=8 Hz, 2H), 6.40-6.46 (dd, J=4, 13 Hz, 1H), 5.07-5.27 (dt, J=4, 52 Hz, 1H), 4.65-4.73 (m, 1H), 4.55 (s, 2H), 4.13-4.18 (m, 1H), 3.95-4.05 (m, 2H), 3.35-3.42 (m, 2H); LC/MS [M+H]=570.

Example 54

Synthesis of 2-benzyl-2-(((2R,3R,4S,5R)-5-(2-chloro-6-hydroxy-9H-purin-9-yl)-4-fluoro-3-hydroxytetrahydrofuran-2-yl)methoxy)malonic Acid

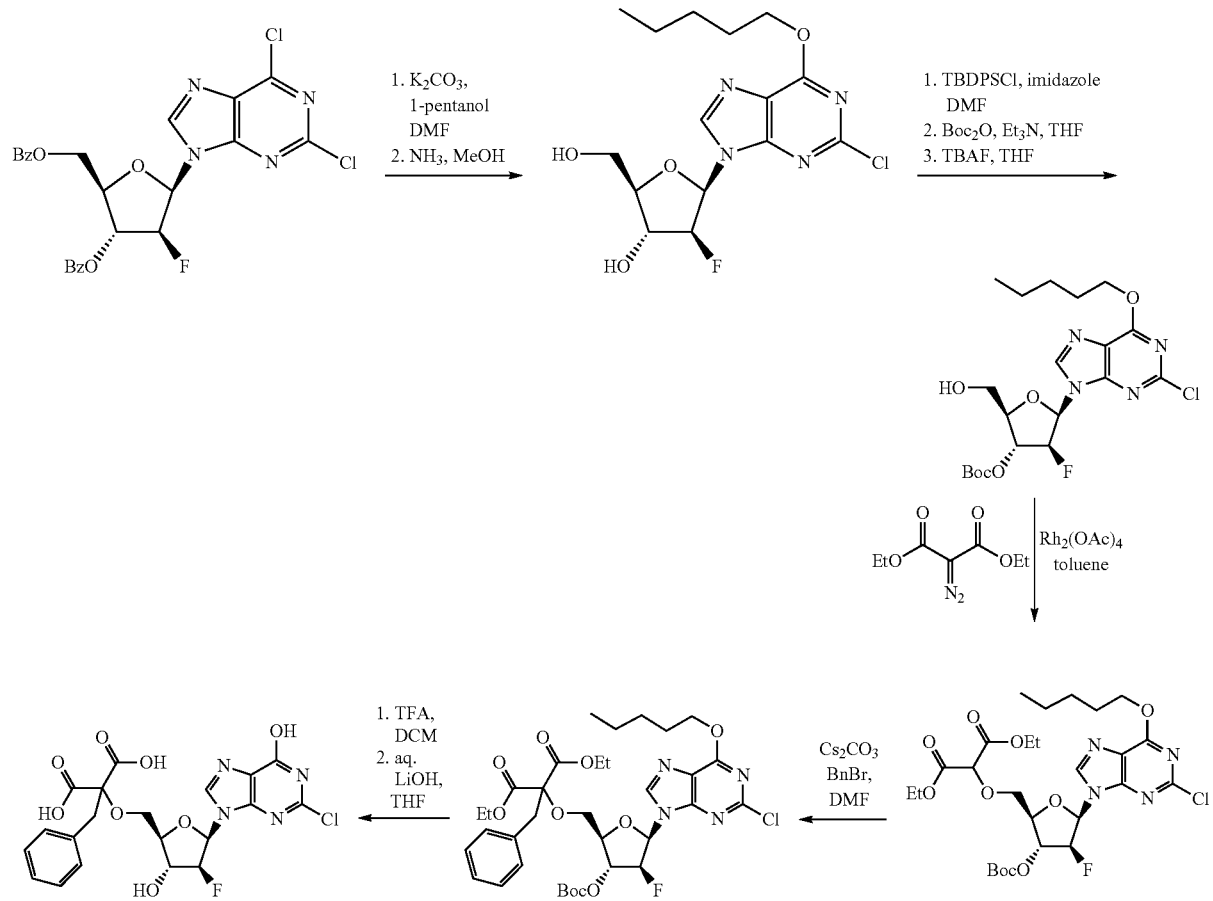

Step 1:

To a solution of ((2R,3R,4S,5R)-3-(benzoyloxy)-5-(2,6-dichloro-9H-purin-9-yl)-4-fluorotetrahydrofuran-2-yl)methyl benzoate (2.00 g, 3.77 mmol) in DMF was added $K_2CO_3$ (625 mg, 4.52 mmol) and 1-pentanol (655 μL, 6.03 mmol). The resulting mixture was stirred at 40° C. for 2 h before it was allowed to cool to room temperature and diluted with EtOAc and water. The organic layer was separated, washed with brine, dried ($MgSO_4$) and concentrated. This crude was dissolved in MeOH (20 mL) and cooled to 0° C. To this mixture was added a solution of $NH_3$ in MeOH (19 mL, 2.0 M in MeOH). The reaction mixture was stirred from 0° C. to ambient temperature over 18 h before it was concentrated under reduced pressure. The crude was purified by $SiO_2$ column chromatography (0-5% MeOH in DCM) to provide (2R,3R,4S,5R)-5-(2-chloro-6-(pentyloxy)-9H-purin-9-yl)-4-fluoro-2-(hydroxymethyl)tetrahydrofuran-3-ol.

Step 2-4:

(2R,3R,4S,5R)-5-(2-chloro-6-(pentyloxy)-9H-purin-9-yl)-4-fluoro-2-(hydroxymethyl)tetrahydrofuran-3-ol was then converted to diethyl 2-(((2R,3R,4S,5R)-3-((tert-butoxycarbonyl)oxy)-5-(2-chloro-6-(pentyloxy)-9H-purin-9-yl)-4-fluorotetrahydrofuran-2-yl)methoxy)malonate according to the procedure described for Example 1.

Step 5:

To a solution of diethyl 2-(((2R,3R,4S,5R)-3-((tert-butoxycarbonyl)oxy)-5-(2-chloro-6-(pentyloxy)-9H-purin-9-yl)-4-fluorotetrahydrofuran-2-yl)methoxy)malonate (210 mg, 0.29 mmol) in DCM (4 mL) at room temperature was added TFA (2.0 mL). The reaction mixture was then stirred for 8 h before it was concentrated under reduced pressure. The residue was re-dissolved in DCM (2×5 mL) and re-concentrated. The crude product was dissolved in a mixture of THF (3 mL) and water (3 mL) and followed by addition of $LiOH.H_2O$ (139 mg). The reaction was then stirred at room temperature for 48 h before it was concentrated under reduced pressure. The residue was re-dissolved in water (2 mL) and acidified to pH 6 with 1N aq. HCl solution before it was concentrated. The crude residue was purified by reversed-phase HPLC to provide the title compound as a white solid.

$^1$H NMR ($CD_3OD$, 300 MHz) δ 8.25 (s, 1H), 7.16-7.30 (m, 5H), 6.38-6.45 (dd, J=4, 15 Hz, 1H), 5.05-5.25 (dt, J=4, 52 Hz, 1H), 4.59-4.68 (dt, J=5, 17 Hz, 1H), 4.15-4.19 (q, J=5 Hz, 1H), 3.96-4.05 (m, 2H), 3.40 (bs, 2H); LC/MS [M+H]= 497.

Example 55

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(5-methyl-1,3,4-oxadiazol-2-yl)benzyl)malonic Acid

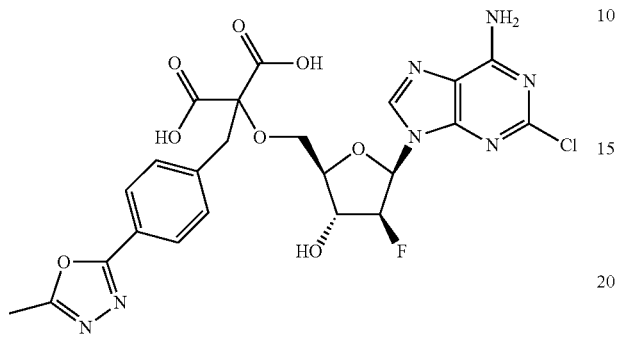

Proceeding as described in Example 2 above but substituting benzyl bromide with 2-(4-(bromomethyl)phenyl)-5-methyl-1,3,4-oxadiazole, the title compound was isolated as a white solid.

$^1$H NMR (CD$_3$OD, 300 MHz) δ 8.26 (s, 1H), 7.66-7.69 (d, J=8 Hz, 2H), 7.37-7.39 (d, J=8 Hz, 2H), 6.42-6.47 (dd, J=5, 9 Hz, 1H), 5.14-5.33 (dt, J=4, 53 Hz, 1H), 4.62-4.70 (dt, J=5, 19 Hz, 1H), 4.15-4.20 (m, 2H), 3.92-3.96 (m, 1H), 3.32-3.52 (q, J=15 Hz, 2H), 2.61 (s, 3H); LC/MS [M+H]=578.

Example 56

Synthesis of 2-(((2R,3R,4S,5R)-5-(6-amino-2-chloro-9H-purin-9-yl)-4-fluoro-3-hydroxytetrahydrofuran-2-yl)methoxy)-2-((2'-cyano-[1,1'-biphenyl]-4-yl)-methyl)malonic Acid

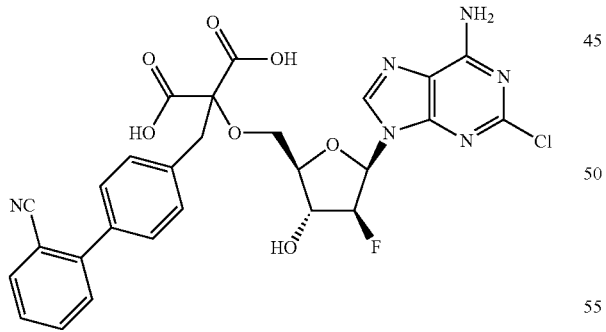

Proceeding as described in Example 2 above but substituting benzyl bromide with 4'-(bromomethyl)-[1,1'-biphenyl]-2-carbonitrile, the title compound was isolated as a white solid.

$^1$H NMR (CD$_3$OD, 300 MHz) δ 8.41 (d, J=1 Hz, 1H), 7.70-7.73 (dd, J=1, 8 Hz, 1H), 7.55-7.58 (dd, J=1, 8 Hz, 1H), 7.29-7.49 (m, 6H), 6.41-6.46 (dd, J=5, 11 Hz, 1H), 5.12-5.33 (dt, J=5, 53 Hz, 1H), 4.69-4.79 (dt, J=5, 18 Hz, 1H), 4.10-4.21 (m, 2H), 3.98-4.02 (m, 1H), 3.47-3.59 (m, 2H); LC/MS [M+H]=597.

Example 57

Synthesis of 2-(((2R,3R,4S,5R)-5-(6-amino-2-chloro-9H-purin-9-yl)-4-fluoro-3-hydroxytetrahydrofuran-2-yl)methoxy)-2-((5-chlorobenzo[b]thiophen-3-yl)methyl)-malonic Acid

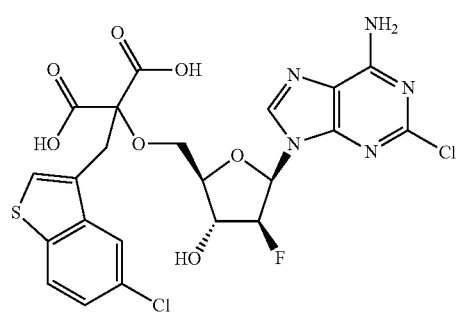 [SMILES: Nc1nc(Cl)nc2c1ncn2[C@@H]1O[C@H](COC(Cc2csc3ccc(Cl)cc23)(C(=O)O)C(=O)O)[C@@H](O)[C@@H]1F]

Proceeding as described in Example 2 above but substituting benzyl bromide with 3-(bromomethyl)-5-chlorobenzo[b]thiophene, the title compound was isolated as a white solid.

$^1$H NMR (CD$_3$OD, 300 MHz) δ 8.43 (s, 1H), 7.80 (s, 1H), 7.48-7.53 (m, 2H), 6.99-7.02 (d, J=8 Hz, 1H), 6.44-6.49 (dd, J=5, 10 Hz, 1H), 5.16-5.34 (m, 1H), 4.72-4.82 (dt, J=6, 18 Hz, 1H), 4.12-4.20 (m, 2H), 3.94-3.98 (m, 1H), 3.57-3.71 (m, 2H); LC/MS [M+H]=586.

Example 58

Synthesis of 2-(((2R,3R,4S,5R)-5-(6-amino-2-chloro-9H-purin-9-yl)-4-fluoro-3-hydroxytetrahydrofuran-2-yl)methoxy)-2-(benzo[d]thiazol-2-ylmethyl)malonic Acid

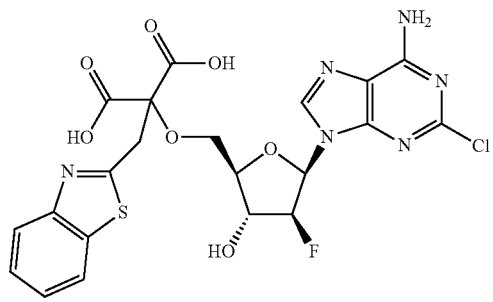 [SMILES: Nc1nc(Cl)nc2c1ncn2[C@@H]1O[C@H](COC(Cc2nc3ccccc3s2)(C(=O)O)C(=O)O)[C@@H](O)[C@@H]1F]

Proceeding as described in Example 2 above but substituting benzyl bromide with 2-(bromomethyl)benzo[d]thiazole, the title compound was isolated as a white solid.

$^1$H NMR (CD$_3$OD, 300 MHz) δ 8.35 (s, 1H), 7.80-7.86 (m, 2H), 7.28-7.41 (m, 2H), 6.37-6.42 (dd, J=4.5, 13 Hz, 1H), 5.08-5.11 (dt, J=4, 52 Hz, 1H), 4.72-4.81 (dt, J=4, 17 Hz, 1H), 4.08-4.19 (m, 3H), 3.99 (s, 2H); LC/MS [M+H]=553.

Example 59

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(methylcarbamoyl)benzyl)malonic Acid

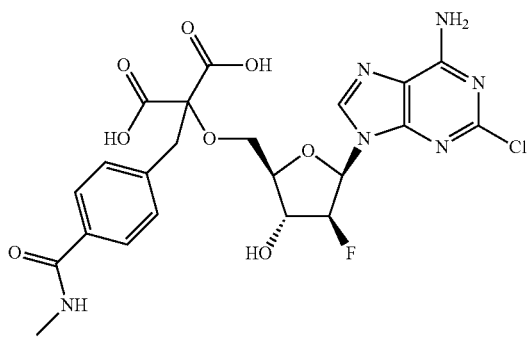 [SMILES: CNC(=O)c1ccc(CC(OC[C@H]2O[C@@H](n3cnc4c(N)nc(Cl)nc43)[C@@H](F)[C@@H]2O)(C(=O)O)C(=O)O)cc1]

Proceeding as described in Example 2 above but substituting benzyl bromide with 4-(bromomethyl)-N-methylbenzamide, the title compound was isolated as a white solid.

$^1$H NMR (CD$_3$OD, 300 MHz) δ 8.26 (s, 1H), 7.59-7.62 (d, J=8 Hz, 2H), 7.37-7.40 (d, J=8 Hz, 2H), 6.40-6.46 (dd, J=4, 13 Hz, 1H), 5.07-5.27 (dt, J=4, 52 Hz, 1H), 4.62-4.71 (dt, J=5, 18 Hz, 1H), 4.17-4.18 (q, J=4 Hz, 3H), 3.97-4.10 (m, 2H), 3.42-3.52 (m, 2H); LC/MS [M+H]=553.

Example 60

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(methoxycarbonyl)benzyl)malonic Acid

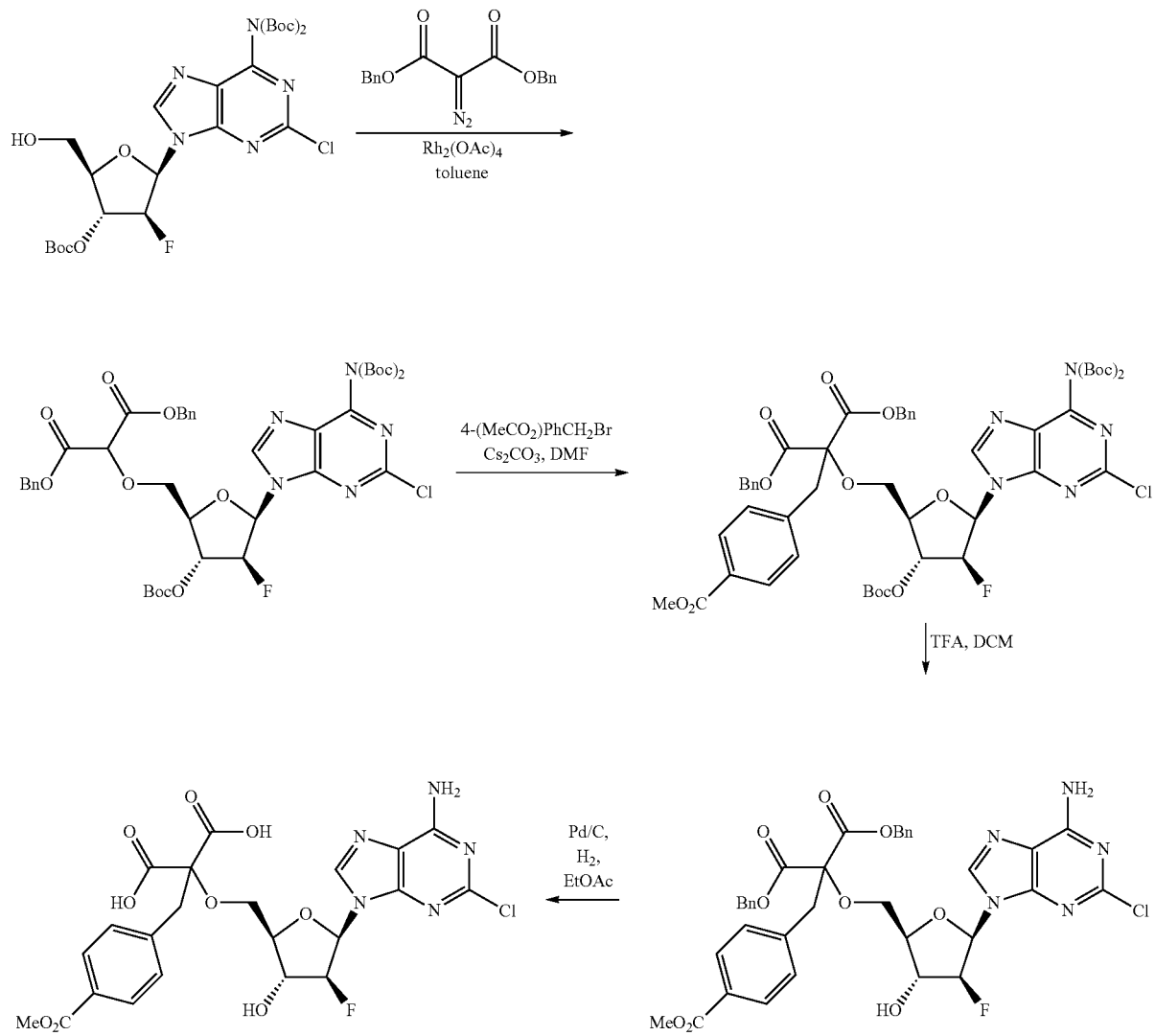

205
Step 1:

Dibenzyl 2-(((2R,3R,4S,5R)-5-(6-(N-(tert-butoxycarbonyl)(tert-butoxycarbonyl)amino)-2-chloro-9H-purin-9-yl)-3-((tert-butoxycarbonyl)oxy)-4-fluorotetrahydrofuran-2-yl)methoxy)malonate was prepared by proceeding as described in Example 1 above by, utilizing dibenzyl diazomalonate instead of diethyl diazomalonate.

Step 2:

Proceeding as described in Example 2 above, but utilizing methyl 4-(bromomethyl)benzoate in place of benzyl bromide and subsequent removal of Boc groups with treatment of TFA provided dibenzyl 2-(((2R,3R,4S,5R)-5-(6-amino-2-chloro-9H-purin-9-yl)-4-fluoro-3-hydroxy-tetrahydrofuran-2-yl)methoxy)-2-(4-(methoxycarbonyl)benzyl)-malonate.

Steps 3-4:

The title compound was isolated as a white solid from dibenzyl 2-(((2R,3R,4S,5R)-5-(6-amino-2-chloro-9H-purin-9-yl)-4-fluoro-3-hydroxy-tetrahydrofuran-2-yl)methoxy)-2-(4-(methoxycarbonyl)benzyl)malonate according to the procedure described for Example 28.

$^1$H NMR (CD$_3$OD, 300 MHz) δ 8.27 (s, 1H), 7.69-7.71 (d, J=8 Hz, 2H), 7.36-7.38 (d, J=8 Hz, 2H), 6.42-6.47 (dd, J=5, 11 Hz, 1H), 5.11-5.31 (dt, J=5, 53 Hz, 1H), 4.68-4.77 (dt, J=5, 18 Hz, 1H), 3.94-4.18 (m, 3H), 3.42-3.55 (m, 2H), 3.42-3.52 (m, 2H); LC/MS [M+H]=554.

Example 61

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-((E)-2-carboxyvinyl)benzyl)malonic Acid Proceeding as described in Example 2 above but substituting benzyl bromide with methyl 3-(4-bromomethyl)cinnamate, the title compound was isolated as a white solid.

LC/MS [M+H]=567.

206

Example 62

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(2-carboxyethyl)benzyl)malonic Acid

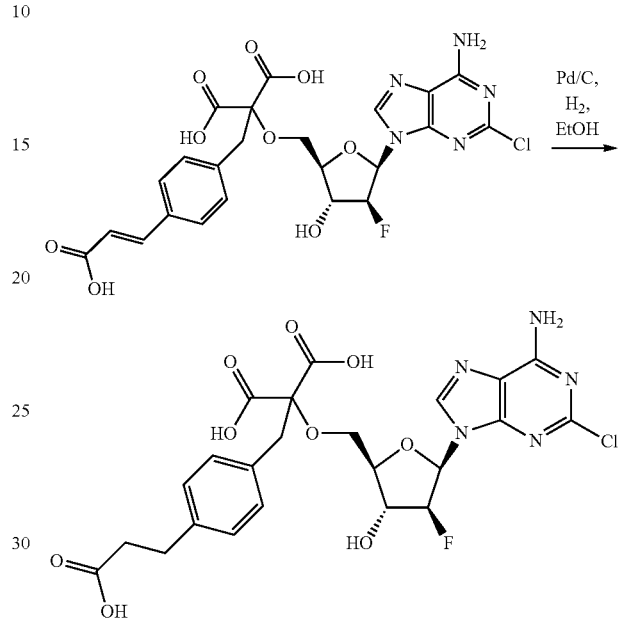

The title compound was prepared from 2-(((2R,3R,4S,5R)-5-(6-amino-2-chloro-9H-purin-9-yl)-4-fluoro-3-hydroxytetrahydrofuran-2-yl)methoxy)-2-(4-((E)-2-carboxyvinyl)benzyl)malonic acid (Example 58) by reducing the olefin bond with Pd/C in EtOH under 1 atmosphere of H$_2$. The title compound isolated as a white solid.

LC/MS [M+H]=568.

Example 63

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonic acid

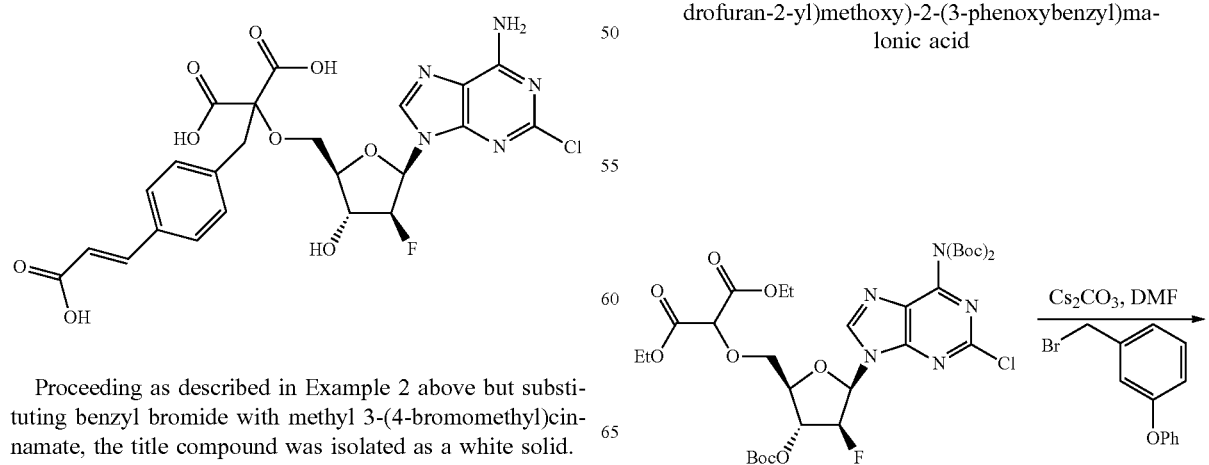

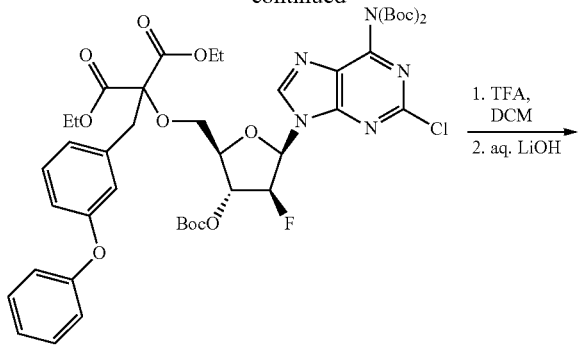

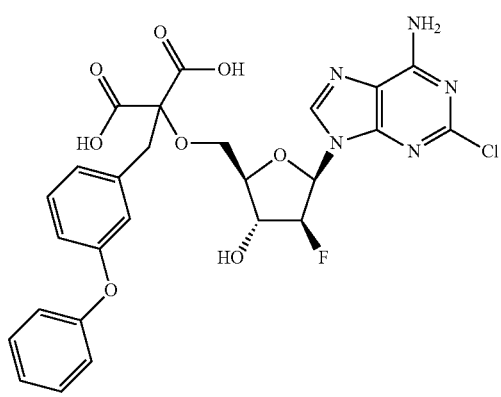

Proceeding as described in Example 2 above but substituting benzyl bromide with 3-(phenoxy)benzyl bromide, the title compound was prepared and isolated as a white solid.

$^1$H NMR (CD$_3$OD, 300 MHz) δ 8.38 (bs, 1H), 7.02-7.22 (m, 6H), 6.70-6.81 (m, 3H), 6.37-6.41 (dd, J=4.3, 13 Hz, 1H), 5.07-5.25 (m, 1H), 4.62-4.67 (m, 1H), 3.93-4.18 (m, 3H), 3.24 (m, 2H); LC/MS [M+H]=589.

Example 64

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonic Acid

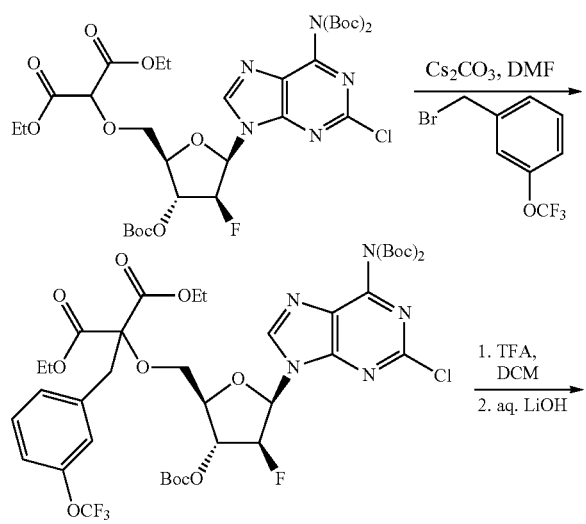

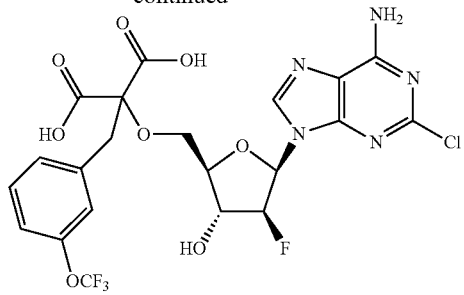

Proceeding as described in Example 2 above but substituting benzyl bromide with 3-trifluoromethoxybenzyl bromide, the title compound was prepared and isolated as a white solid.

$^1$H NMR (CD$_3$OD, 300 MHz) δ 8.34 (bs, 1H), 7.20-7.29 (m, 3H), 7.01-7.04 (d, 1H), 6.42-6.48 (dd, J=4, 13 Hz, 1H), 5.08-5.28 (dt, J=4.7, 52 Hz, 1H), 4.62-4.71 (dt, J=5, 17 Hz, 1H), 4.15-4.19 (m, 1H), 3.98-4.10 (m, 2H), 3.44-3.45 (m, 2H); LC/MS [M+H]=580.8.

Example 65

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonic acid

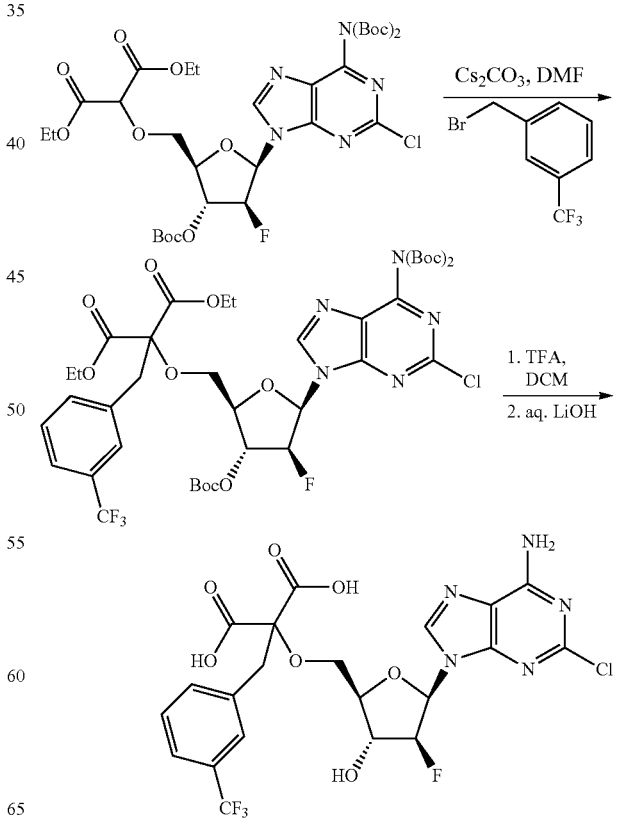

Proceeding as described in Example 2 above but substituting benzyl bromide with 3-trifluoromethylbenzyl bromide, the title compound was prepared and isolated as a white solid.

$^1$H NMR (CD$_3$OD, 300 MHz) δ 8.96 (bs, 1H), 7.37-7.59 (m, 4H), 6.51-6.56 (dd, J=4, 10 Hz, 1H), 5.18-5.39 (dt, J=4.7, 52 Hz, 1H), 4.62-4.71 (dt, J=5, 17 Hz, 1H), 4.21-4.24 (m, 1H), 3.96-4.17 (m, 2H), 3.45-3.59 (q, J=15 Hz, 2H); LC/MS [M+H]=564.8.

Example 66

Synthesis of 2-(((2R,3R,4S,5R)-5-(6-amino-2-chloro-9H-purin-9-yl)-4-fluoro-3-hydroxytetrahydrofuran-2-yl)methoxy)-2-(naphthalen-2-ylmethyl)malonic Acid

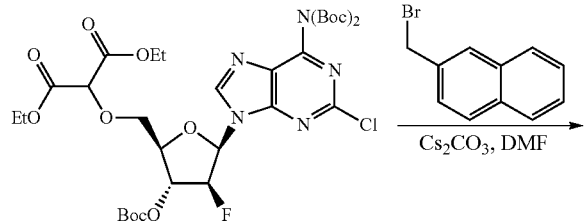

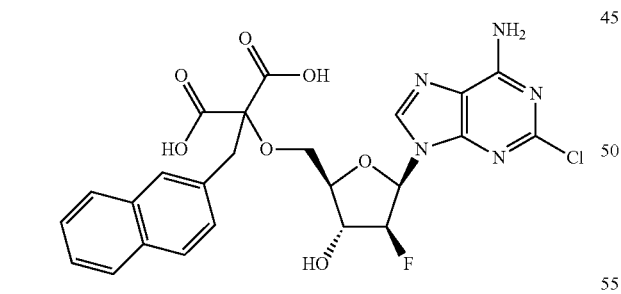

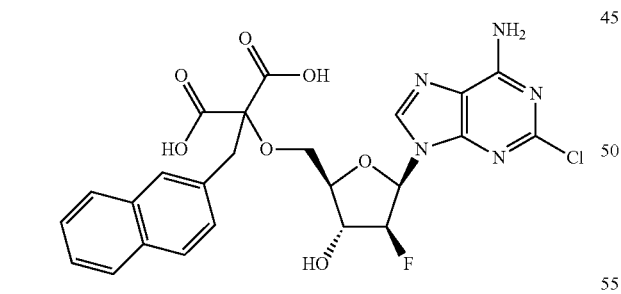

Proceeding as described in Example 2 above but substituting benzyl bromide with naphthalene-2-ylmethyl bromide, the title compound was prepared and isolated as a white solid.

$^1$H NMR (CD$_3$OD, 300 MHz) δ 8.29 (bs, 1H), 7.60-7.72 (m, 3H), 7.51-7.53 (d, J=8 Hz, 1H), 7.36-7.39 (d, J=8 Hz, 1H), 7.19-7.30 (m, 2H), 6.40-6.45 (dd, J=4.7, 10.6 Hz, 1H), 5.10-5.30 (dt, J=4.3, 53 Hz, 1H), 4.71-4.77 (m, 1H), 4.09-4.20 (m, 1H), 3.91-4.12 (m, 2H), 3.49-3.62 (q, J=11 Hz, 2H); LC/MS [M+H]=546.9.

Example 67

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonic Acid

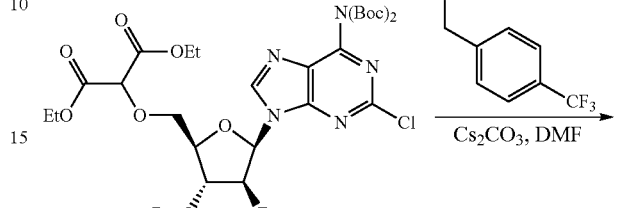

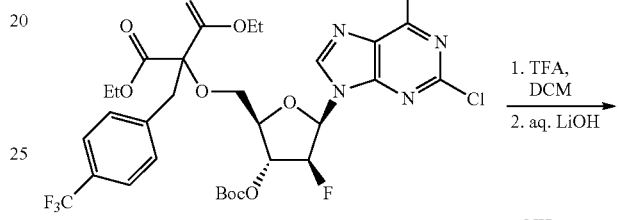

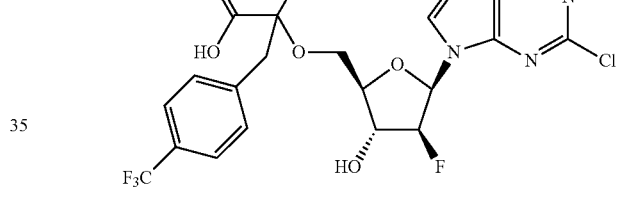

Proceeding as described in Example 2 above but substituting benzyl bromide with 4-trifluoromethylbenzyl bromide, the title compound was prepared and isolated as a white solid.

$^1$H NMR (CD$_3$OD, 300 MHz) δ 8.31 (d, J=1.6 Hz, 1H), 7.41-7.49 (m, 4H), 6.40-6.46 (dd, J=4.3, 13.4 Hz, 1H), 5.08-5.29 (dt, J=4.0, 52 Hz, 1H), 4.63-4.88 (dt, J=3.9, 17.5 Hz, 1H), 4.15-4.19 (m, 1H), 3.99-4.10 (m, 2H), 3.49 (m, 2H); LC/MS [M+H]=564.8.

Example 68

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-(methylsulfonyl)benzyl)malonic Acid

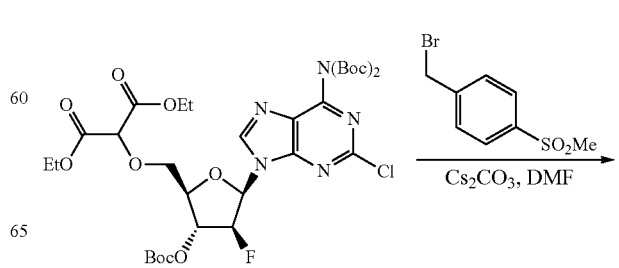

-continued

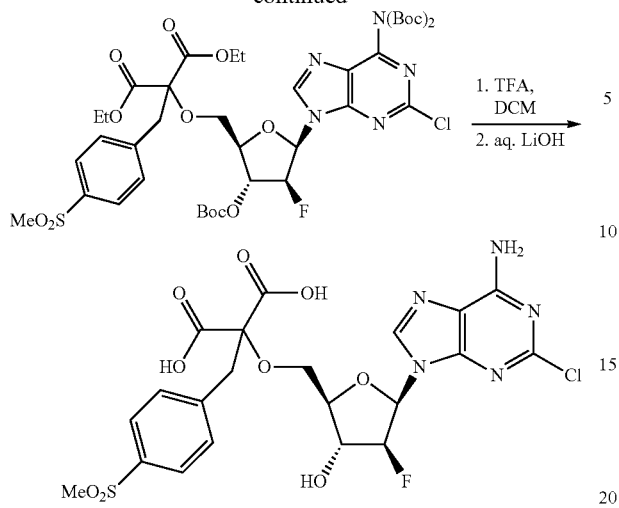

Proceeding as described in Example 2 above but substituting benzyl bromide with 4-methylsulfonylbenzyl bromide, the title compound was prepared and isolated as a white solid.

$^1$H NMR (CD$_3$OD, 300 MHz) δ 8.28 (d, J=1 Hz, 1H), 7.55-7.75 (dd, J=8.3, 50 Hz, 2H), 6.40-6.46 (dd, J=4.6, 13.3 Hz, 1H), 5.08-5.26 (dt, J=4.1, 52 Hz, 1H), 4.63-4.68 (dt, J=4.9, 17.6 Hz, 1H), 4.15-4.19 (m, 1H), 3.99-4.10 (m, 2H), 3.52-3.53 (m, 2H), 3.03 (s, 3H); LC/MS [M+H]=574.9.

Example 69

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonic Acid

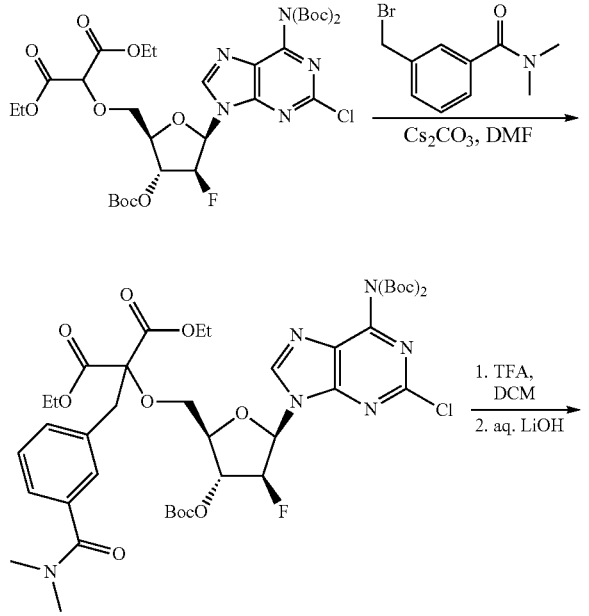

-continued

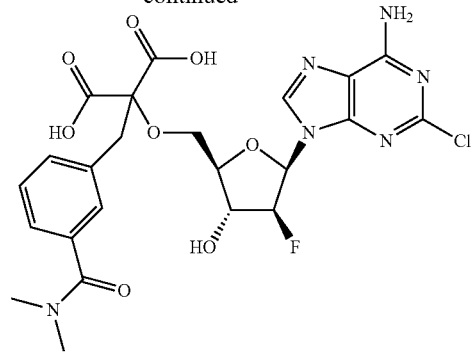

Proceeding as described in Example 2 above but substituting benzyl bromide with 3-(bromomethyl)-N,N-dimethylbenzamide, the title compound was prepared and isolated as a white solid.

$^1$H NMR (CD$_3$OD, 300 MHz) δ 8.42 (bs, 1H), 7.20-7.41 (m, 4H), 6.41-6.47 (dd, J=4.4, 13.3 Hz, 1H), 5.08-5.28 (dt, J=4, 52 Hz, 1H), 4.59-4.68 (dt, J=4.3, 17.6 Hz, 1H), 4.14-4.19 (q, J=5 Hz, 1H), 4.02-4.05 (m, 2H), 3.52-3.53 (m, 2H), 3.00 (s, 3H), 2.92 (s, 3H); LC/MS [M+H]=568.

Example 70

Synthesis of 2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonic Acid

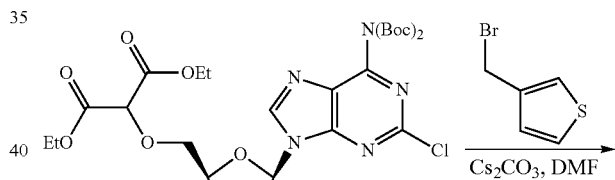

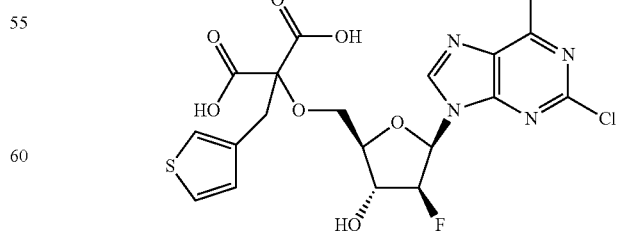

Proceeding as described in Example 2 above but substituting benzyl bromide with 3-(bromomethyl)thiophene, the title compound was prepared and isolated as a white solid.

$^1$H NMR (CD$_3$OD, 300 MHz) δ 8.38 (bs, 1H), 7.19-7.22 (m, 2H), 7.02-7.04 (m, 1H), 6.40-6.46 (dd, J=4.3, 13.4 Hz, 1H), 5.07-5.27 (dt, J=3.9, 9, 52 Hz, 1H), 4.60-4.66 (m, 1H), 4.15-4.19 (q, J=5 Hz, 1H), 3.94-3.99 (m, 2H), 3.45 (bs, 2H); LC/MS [M+H]=503.

Example 71

Synthesis of 2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonic Acid

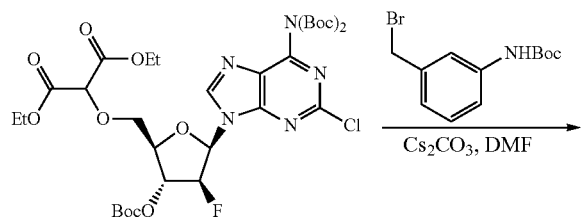

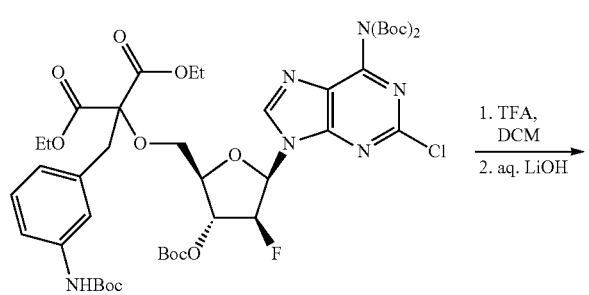

Proceeding as described in Example 2 above but substituting benzyl bromide with tert-butyl (3-(bromomethyl)phenyl)carbamate, the title compound was prepared and isolated as a white solid.

$^1$H NMR (CD$_3$OD, 300 MHz) δ 8.33 (bs, 1H), 7.09-7.25 (bs, 4H), 6.39-6.44 (d, J=15 Hz, 1H), 5.06-5.24 (m, 1H), 4.18-4.28 (d, J=18.4 Hz, 1H), 4.20 (bs, 1H), 3.90 (bs, 2H), 3.39 (s, 2H); LC/MS [M+H]=512.

Example 72

Synthesis of 2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonic Acid

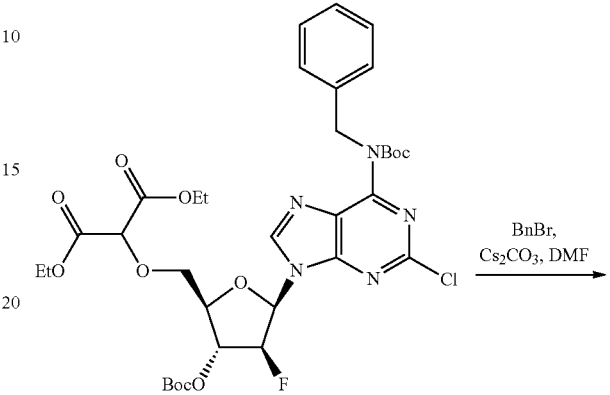

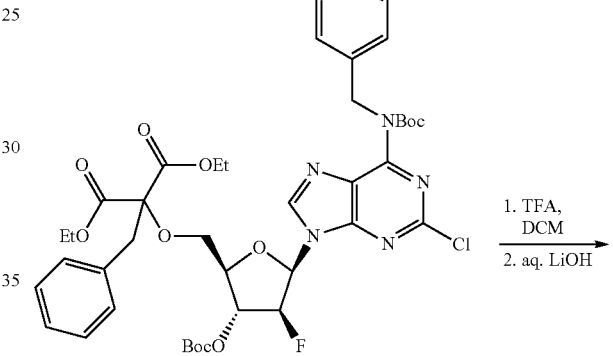

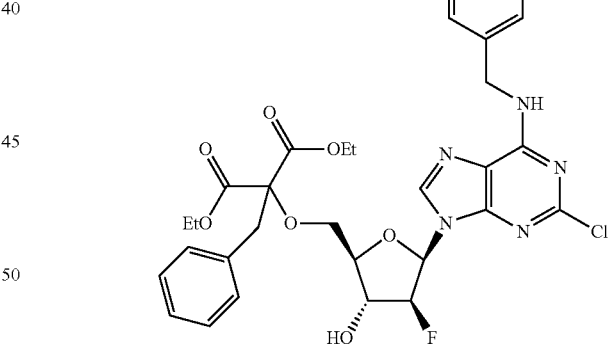

Step 1:

To a solution of diethyl 2-(((2R,3R,4S,5R)-5-(6-(benzyl(tert-butoxycarbonyl)-amino)-2-chloro-9H-purin-9-yl)-3-((tert-butoxycarbonyl)oxy)-4-fluoro-tetrahydrofuran-2-yl)methoxy)malonate (130 mg, 0.173 mmol) in DMF (2 mL) at 25° C. was added Cs$_2$CO$_3$ (113 mg, 0.346 mmol). The reaction mixture was stirred for 30 min and followed by addition of benzyl bromide (41 uL, 0.346 mmol). The reaction mixture was stirred for 3.5 h before it was diluted with H$_2$O (15 mL) and extracted with EtOAc. The combined organic layer was washed further with H$_2$O, brine, dried over Na$_2$SO$_4$ and concentrated. The resulting crude was purified by silica gel column chromatography (0-20%

EtOAc in hexanes) to provide diethyl 2-benzyl-2-(((2R,3R,4S,5R)-5-(6-(benzyl(tert-butoxycarbonyl)amino)-2-chloro-9H-purin-9-yl)-3-((tert-butoxycarbonyl)oxy)-4-fluorotetrahydrofuran-2-yl)methoxy)malonate as a foam.

Diethyl 2-benzyl-2-((2R,3R,4S,5R)-5-(6-(benzyl(tert-butoxycarbonyl)amino)-2-chloro-9H-purin-9-yl)-3-((tert-butoxycarbonyl)oxy)-4-fluorotetrahydrofuran-2-yl)methoxy)malonate was converted into the title compound according to the procedure described for Example 2.

$^1$H NMR (CD$_3$OD, 300 MHz) δ 8.23 (bs, 1H), 7.23-7.42 (m, 10H), 6.36-6.45 (dd, J=2.6, 22.6 Hz, 1H), 4.96-5.14 (dd, J=2.4, 50 Hz, 1H), 4.74-4.80 (m, 3H), 4.16-4.19 (m, 1H), 3.73-3.88 (m, 2H), 3.35-3.40 (m, 2H); LC/MS [M+H]=587.

Example 73

Synthesis of 2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonic Acid

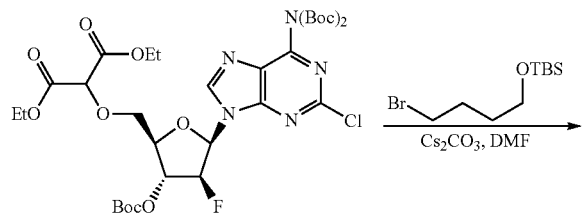

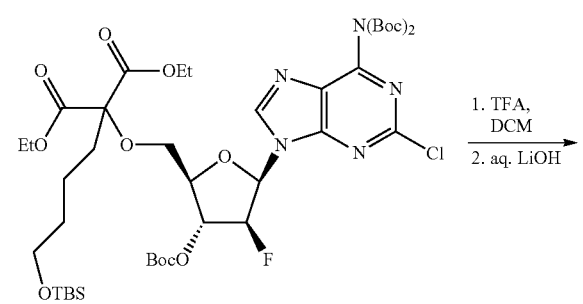

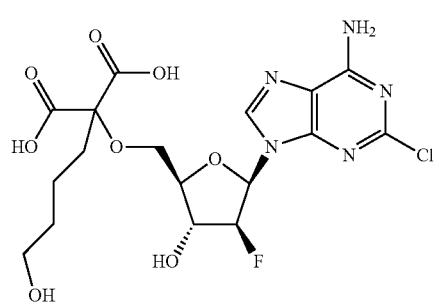

Proceeding as described in Example 2 above but substituting benzyl bromide with (4-bromobutoxy)(tert-butyl)dimethylsilane, the title compound was prepared and isolated as a white solid.

$^1$H NMR (CD$_3$OD, 300 MHz) δ 8.50-8.54 (m, 1H), 6.41-6.47 (dd, J=4.6, 12.7 Hz, 1H), 5.17-5.36 (dt, J=4.3, 52 Hz, 1H), 4.18-4.28 (dt, J=4.2, 17.3 Hz, 1H), 4.08-4.17 (m, 2H), 3.70-3.90 (m, 2H), 3.52 (t, J=6.3 Hz, 1H), 2.12-2.18 (m, 2H), 1.35-1.72 (m, 4H); LC/MS [M+H]=479.

Example 74

Synthesis of 1-(((2R,3R,4S,5R)-5-(6-amino-2-chloro-9H-purin-9-yl)-4-fluoro-3-hydroxytetrahydrofuran-2-yl)methoxy)ethane-1,1,2-tricarboxylic Acid

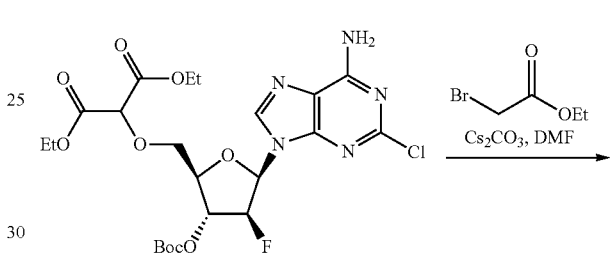

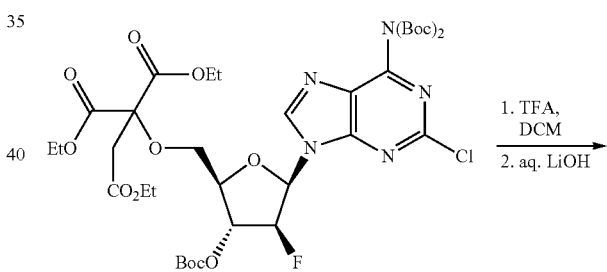

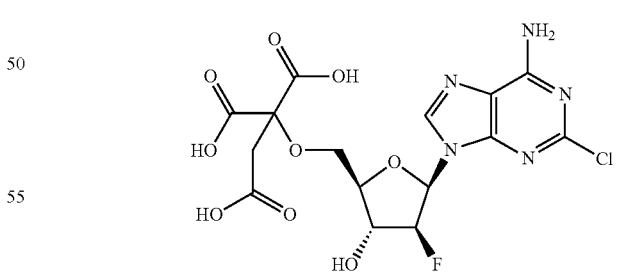

Proceeding as described in Example 2 above but substituting benzyl bromide with (ethyl 2-bromoacetate, the title compound was prepared and isolated as a white solid.

$^1$H NMR (CD$_3$OD, 300 MHz) δ 8.78 (bs, 1H), 6.44-6.49 (dd, J=4.6, 11.8 Hz, 1H), 5.12-5.32 (dt, J=4.5, 52 Hz, 1H), 4.67-4.76 (m, 1H), 4.13-4.18 (q, J=4.7 Hz, 1H), 3.93-3.99 (m, 2H), 3.23 (s, 2H); LC/MS [M+H]=464.

Example 75

Synthesis of 2-(((2R,3R,4S,5R)-5-(4-(benzylamino)-1H-benzo[d]imidazol-1-yl)-4-fluoro-3-hydroxytetrahydrofuran-2-yl)methoxy)malonic Acid

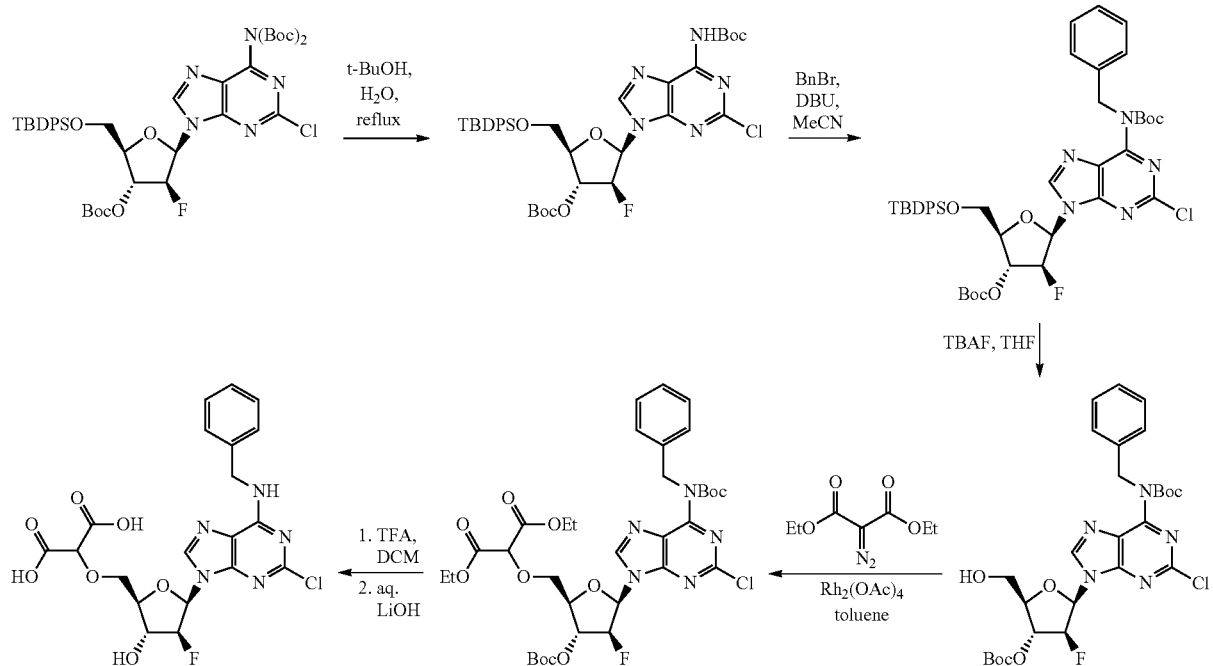

Step 1:

A suspension of N6,N6-bis-Boc-5'-O-tert-butyldiphenylsilyl-3'-O-Boc-2-chloro-adenosine (1.00 g, 1.19 mol) in a mixture of t-BuOH and H$_2$O (8 mL, 1:1/v:v) was refluxed for 13 h before it was allowed to cool to room temperature and concentrated. The crude residue was purified by silica gel column chromatography (5-20% EtOAc in hexanes) to provide tert-butyl (9-((2R,3S,4R,5R)-4-((tert-butoxycarbonyl)oxy)-5-(((tert-butyldiphenylsilyl)oxy)methyl)-3-fluorotetrahydro-furan-2-yl)-2-chloro-9H-purin-6-yl)carbamate.

Step 2:

To a solution tert-butyl (9-((2R,3S,4R,5R)-4-((tert-butoxycarbonyl)oxy)-5-(((tert-butyldiphenylsilyl)oxy)methyl)-3-fluorotetrahydrofuran-2-yl)-2-chloro-9H-purin-6-yl)carbamate (500 mg, 0.67 mmol) in MeCN (4 mL) at room temperature was added DBU (201 uL, 1.35 mmol) and followed by BnBr (119 uL, 0.996 mmol). The reaction mixture was stirred for 3 h before it was diluted with EtOAc (10 mL) and H$_2$O (10 mL). The organic layer was separated, washed with brine, dried over Na$_2$SO$_4$ and concentrated. The crude residue was purified by silica gel column chromatography (0-15% EtOAc in hexanes) to provide tert-butyl benzyl (9-((2R,3S 4R,5R)-4-((tert-butoxycarbonyl)oxy)-5-(((tert-butyldiphenylsilyl)oxy)-methyl)-3-fluorotetrahydro-furan-2-yl)-2-chloro-9H-purin-6-yl)carbamate.

Step 3:

To a solution of tert-butyl benzyl (9-((2R,3S,4R,5R)-4-((tert-butoxycarbonyl)-oxy)-5-(((tert-butyldiphenylsilyl)oxy)methyl)-3-fluorotetrahydrofuran-2-yl)-2-chloro-9H-purin-6-yl)carbamate (545 mg, 0.655 mmol) was dissolved in THF (1 mL) at 0° C. and followed by addition of a solution of TBAF (1 mL, 0.982 mmol, 1 M in THF) dropwise. The reaction mixture was stirred from 0° C. to room temperature over 2.5 h before it was evaporated to dryness. The residue was purified by silica gel column chromatography (0-20% EtOAc in hexanes) to provide tert-butyl benzyl (9-((2R,3S,4R,5R)-4-((tert-butoxycarbonyl)oxy)-3-fluoro-5-(hydroxymethyl)tetrahydro-furan-2-yl)-2-chloro-9H-purin-6-yl)carbamate.

Step 4:

To a solution of tert-butyl benzyl (9-((2R,3S,4R,5R)-4-((tert-butoxycarbonyl)-oxy)-3-fluoro-5-(hydroxymethyl)tetrahydrofuran-2-yl)-2-chloro-9H-purin-6-yl)carbamate (300 mg, 0.505 mmol) in toluene (3 mL) was added diethyl 2-diazomalonate (122 mg, 0.657 mmol) and Rh$_2$(OAc)$_4$ (22 mg, 0.051 mmol) under argon atmosphere. The resulting mixture was stirred at 80° C. for 2.5 h before it was allowed to cool to room temperature. The organic volatile was removed under reduced pressure. The resulting crude was purified by silica gel column chromatography (0-25% EtOAc in hexanes) to provide diethyl 2-(((2R,3R,4S,5R)-5-(6-(benzyl(tert-butoxycarbonyl)amino)-2-chloro-9H-purin-9-yl)-3-((tert-butoxycarbonyl)oxy)-4-fluorotetrahydrofuran-2-yl)methoxy)malonate.

Step 5:

To a solution of diethyl 2-(((2R,3R,4S,5R)-5-(6-(benzyl (tert-butoxycarbonyl)-amino)-2-chloro-9H-purin-9-yl)-3-((tert-butoxycarbonyl)oxy)-4-fluorotetrahydro-furan-2-yl) methoxy)malonate (200 mg, 0.27 mmol) in CH$_2$Cl$_2$ (2 mL) at 0° C. was added TFA (3 mL). The resulting mixture was warm up to room temperature and stirred for 2 h before it was concentrated under reduced pressure to provide crude diethyl 2-(((2R,3R,4S,5R)-5-(6-(benzylamino)-2-chloro-9H-purin-9-yl)-4-fluoro-3-hydroxytetrahydrofuran-2-yl)

methoxy)malonate as a TFA salt which was used in the next step without further purification.

Step 6:

To a solution of crude diethyl 2-(((2R,3R,4S,5R)-5-(6-(benzylamino)-2-chloro-9H-purin-9-yl)-4-fluoro-3-hydroxytetrahydrofuran-2-yl)methoxy)malonate TFA salt (0.27 mmol) in THF (3 mL) and H$_2$O (1 mL) at room temperature was added LiOH monohydrate (50 mg). The resulting mixture was stirred overnight before it was cooled to 0° C. and acidified to pH ~6 with 1N aq. HCl solution and concentrated under reduced pressure. The crude residue was purified by preparative reverse-phase HPLC to provide 2-(((2R,3R,4S,5R)-5-(4-(benzylamino)-1H-benzo[d]imidazol-1-yl)-4-fluoro-3-hydroxytetrahydrofuran-2-yl)methoxy) malonic acid as a white solid.

$^1$H NMR (CD$_3$OD, 300 MHz) δ 8.40 (bs, 1H), 7.26-7.42 (m, 5H), 6.40-6.47 (dd, J=4.5, 13.8 Hz, 1H), 5.07-5.28 (dt, J=3.9, 52 Hz, 1H), 4.77 (bs, 2H), 4.62-4.70 (m, 2H), 4.13-4.16 (q, J=5 Hz, 1H), 3.90-3.98 (m, 2H); LC/MS [M+H]=497.

Example 76

Synthesis of ((R)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid and ((S)-1-(((2R,3R,4S,5R)-5-(6-amino-2-chloro-9H-purin-9-yl)-4-fluoro-3-hydroxytetrahydrofuran-2-yl) methoxy)-2-(methylamino)-2-oxoethyl)phosphonic Acid

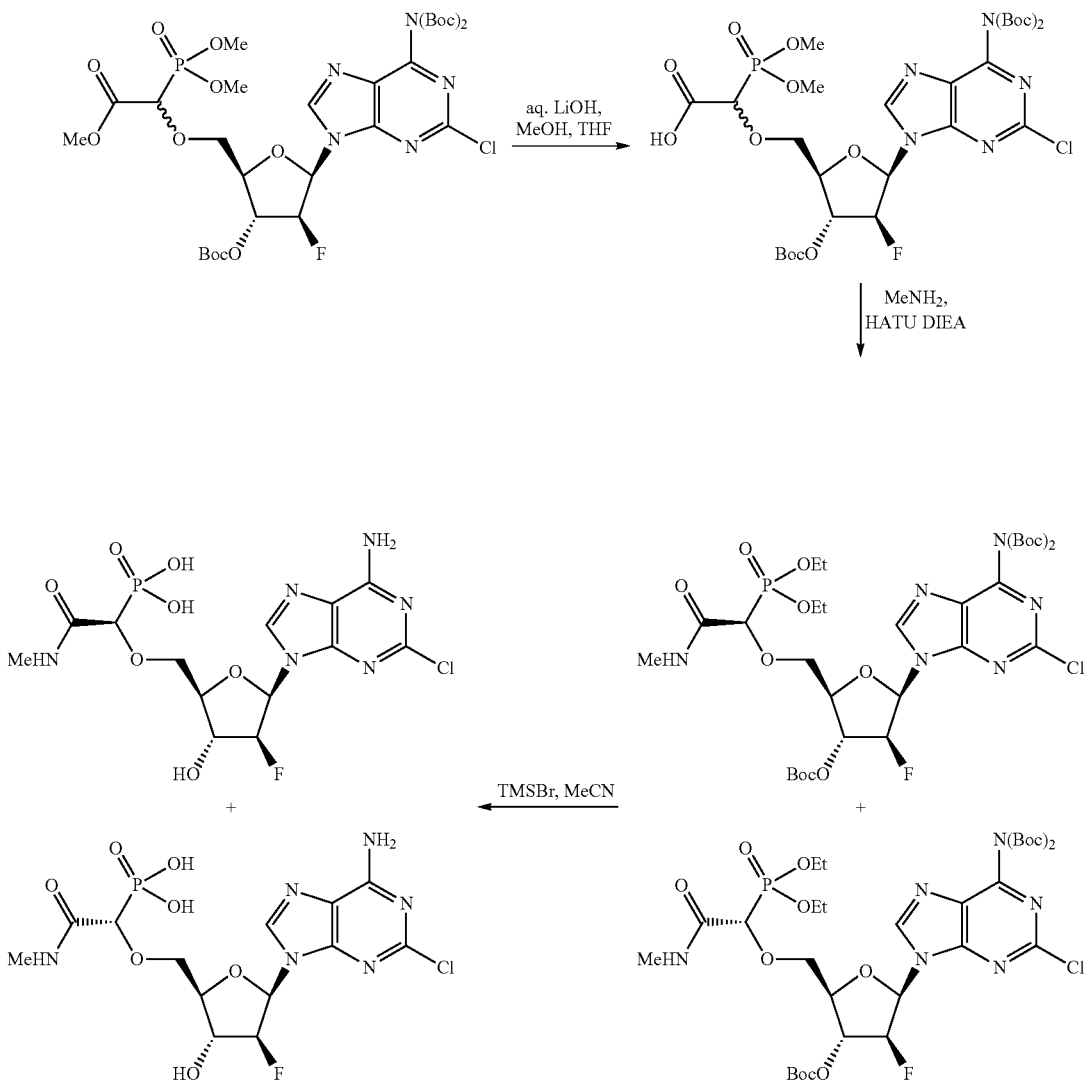

Step 1:

To a solution of diastereomeric mixture (1:1 ratio) of methyl 2-(((2R,3R,4S,5R)-5-(N6,N6-bis-Boc-2-chloro-9H-purin-9-yl)-3-((tert-butoxycarbonyl)-oxy)-4-fluorotetrahydrofuran-2-yl)methoxy)-2-(dimethoxyphosphoryl)acetate (0.352 mmol) in THF (4 mL) at room temperature was added a solution of 1N aq. LiOH (0.7 mL). The resulting mixture was stirred for 75 minutes before it was cooled to 0° C. and acidified to pH ~6 with 1N aq. HCl solution and concentrated under reduced pressure to provide a crude diastereomeric mixture of 2-(((2R,3R,4S,5R)-5-(N6,N6-bis-Boc-2-chloro-9H-purin-9-yl)-3-((tert-butoxycarbonyl)oxy)-4-fluoro-tetrahydrofuran-2-yl)methoxy)-2-(dimethoxyphosphoryl)acetic acid (280 mg) which was used in the next step without further purification.

Step 2:

To a solution of the above crude diastereomeric mixture of 2-(((2R,3R,4S,5R)-5-(N6,N6-bis-Boc-2-chloro-9H-purin-9-yl)-3-((tert-butoxycarbonyl)oxy)-4-fluorotetrahydrofuran-2-yl)methoxy)-2-(dimethoxyphosphoryl)acetic acid (140 mg, 0.182 mmol) in dry DCM (10 mL) was added methylamine hydrochloride (49 mg, 0.73 mmol) and HATU (140 mg, 0.364 mmol). To this mixture was added DIEA (0.22 mL, 1.3 mmol) and the reaction mixture was stirred overnight. Additional amounts of methylamine (25 mg), HATU (140 mg) and DIEA (0.22 mL) were added and the mixture was stirred for 20 hours before it was quenched with water (25 mL). The organic layer was separated and the aqueous was extracted with DCM (3×25 mL). The combined organic phases were dried and the crude product was purified via preparative TLC (60% ethyl acetate/hexane) to provide methyl 2-(((2R,3R,4S,5R)-5-(N6,N6-bis-Boc-2-chloro-9H-purin-9-yl)-3-((tert-butoxycarbonyl)oxy)-4-fluorotetrahydrofuran-2-yl)methoxy)-2-(diethoxyphosphoryl)acetamide (66 mg) as a mixture of diastereomers (1:1 ratio).

Step 3:

Diastereomeric mixture of methyl 2-(((2R,3R,4S,5R)-5-(N6,N6-bis-Boc-2-chloro-9H-purin-9-yl)-3-((tert-butoxycarbonyl)oxy)-4-fluorotetrahydrofuran-2-yl)methoxy)-2-(diethoxyphosphoryl)acetamide was converted to a diastereomeric mixture of ((R)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid (Example 23a) and ((S)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid (Examples 23b) as a solid (1:1 ratio) according to the procedure for Examples 8a and 8b.

$^1$H NMR (CD$_3$OD, 300 MHz) for a mixture of diastereomers (1:1 ratio) Example 23a and 23b δ 8.63-8.91 (m, 1H), 6.51 (d, 1H, diastereomeric), 5.11-5.40 (m, 1H), 4.18-4.70 (m, 3H), 4.01 (broad s, 2H), 2.78 (broad d, 3H); LC/MS [M+H]=456.

Example 77

Inhibition of the CD73 Enzyme In Vitro

For measurements of soluble CD73 enzyme activity, recombinant CD73 was obtained from R&D Systems, Cat. No. 5795-EN-010. Serial dilutions of test compounds were incubated with recombinant CD73 and AMP in reaction buffer (25 mM Tris HCl pH7.5, 5 mM MgCl2, 50 mM NaCl, 0.25 mM DTT, 0.005% Triton X-100). The final reaction volume was 25 µL and the final concentrations of recombinant CD73 and AMP were 0.5 nM and 50 µM, respectively. Reactions were allowed to proceed for 30 minutes at room temperature before the addition of 100 µL Malachite Green (Cell Signaling Technology, Cat. No. 12776). After 5 minutes at room temperature, absorbance at 630 nm was determined on a microplate spectrophotometer. The concentration of inorganic phosphate was determined using a phosphate standard curve. The IC$_{50}$ data is given below in Table 3.

TABLE 3

| Cpd. # | Compound | IC$_{50}$ (µM) |
|---|---|---|
| 1 | 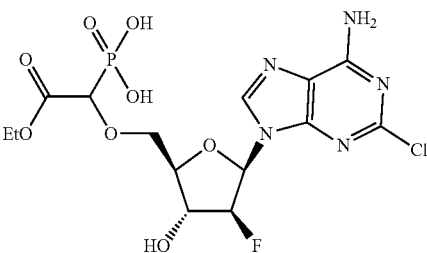 Isomer 1 | 2.79 |
| 2 | 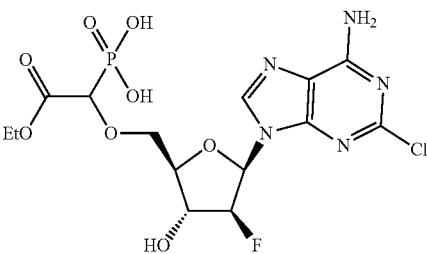 Isomer 2 | 8.91 |

TABLE 3-continued
| Cpd. # | Compound | IC$_{50}$ (μM) |
|---|---|---|
| 3 | 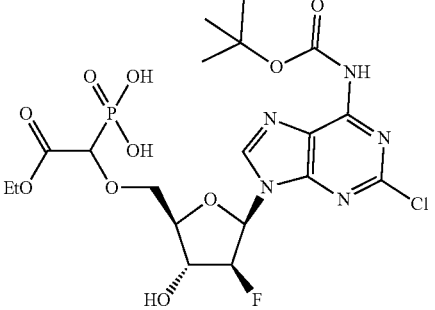<br>Isomer 1 | 2.47 |
| 4 | 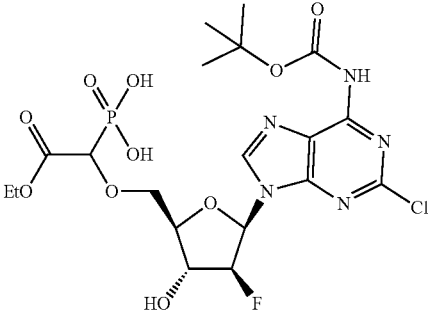<br>Isomer 2 | 2.95 |
| 5 | 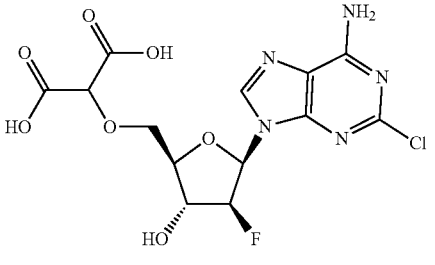 [SMILES: Nc1nc(Cl)nc2c1ncn2[C@@H]1O[C@H](COC(C(=O)O)C(=O)O)[C@@H](O)[C@@H]1F] | 13.089 |
| 6 | 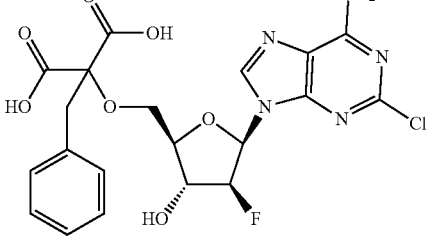 | 0.130 |
| 7 | 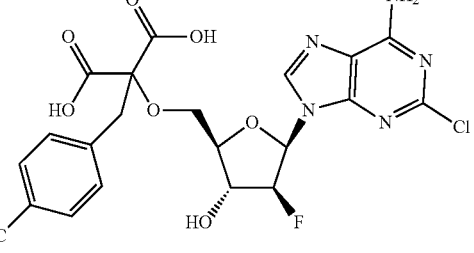 | 0.121 |

TABLE 3-continued

| Cpd. # | Compound | IC$_{50}$ (μM) |
|---|---|---|
| 8 | | 0.363 |
| 9 | | >50 |
| 10 | | 21.63 |
| 11 | | >50 |
| 13 | | 0.403 |

TABLE 3-continued

| Cpd. # | Compound | IC$_{50}$ (μM) |
|---|---|---|
| 14 | | >50 |
| 15 | | 0.308 |
| 16 | | 0.257 |
| 17 | | 0.699 |
| 18 | | 1.888 |

US 11,208,414 B2
TABLE 3-continued
| Cpd. # | Compound | IC$_{50}$ (μM) |
|---|---|---|
| 19 | 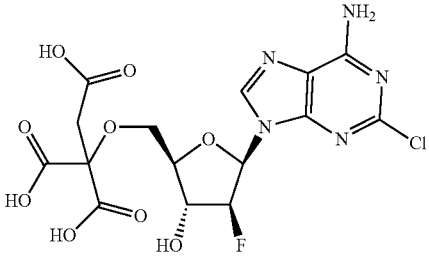 [SMILES: Nc1nc(Cl)nc2c1ncn2[C@@H]1O[C@H](COC(CC(=O)O)(C(=O)O)C(=O)O)[C@@H](O)[C@@H]1F] | 2.557 |
| 20 | 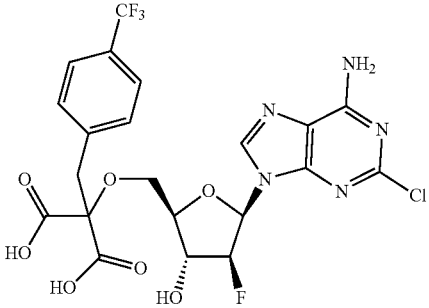 | 0.109 |
| 21 | 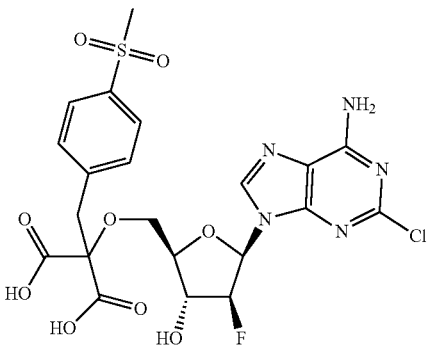 [SMILES: CS(=O)(=O)c1ccc(CC(OC[C@H]2O[C@@H](n3cnc4c(N)nc(Cl)nc43)[C@@H](F)[C@@H]2O)(C(=O)O)C(=O)O)cc1] | 0.193 |
| 22 | 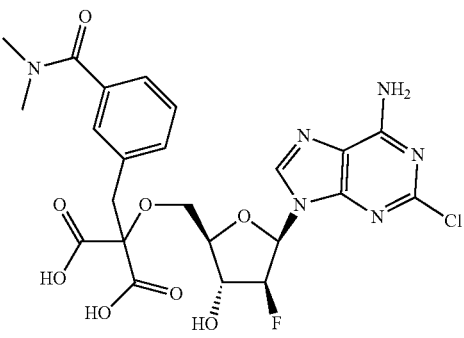 [SMILES: CN(C)C(=O)c1cccc(CC(OC[C@H]2O[C@@H](n3cnc4c(N)nc(Cl)nc43)[C@@H](F)[C@@H]2O)(C(=O)O)C(=O)O)c1] | 0.521 |
| 23 | 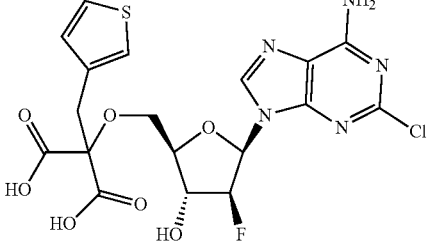 | 0.206 |

TABLE 3-continued

| Cpd. # | Compound | IC$_{50}$ (μM) |
|---|---|---|
| 24 | | 5.90 |
| 26 | | 8.778 |
| 27 | | 0.218 |
| 28 | | 2.648 |

TABLE 3-continued

| Cpd. # | Compound | IC$_{50}$ (μM) |
|---|---|---|
| 29 | | 11.972 |
| 31 | | >50 |
| 50 | | 1.911 |
| 33 | | 1.510 |
| 34 | | 0.097 |

TABLE 3-continued
| Cpd. # | Compound | IC$_{50}$ (μM) |
|---|---|---|
| 35 | 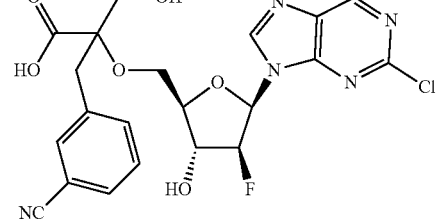 | 0.531 |
| 36 | 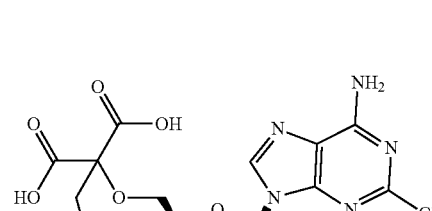 | 0.057 |
| 37 | 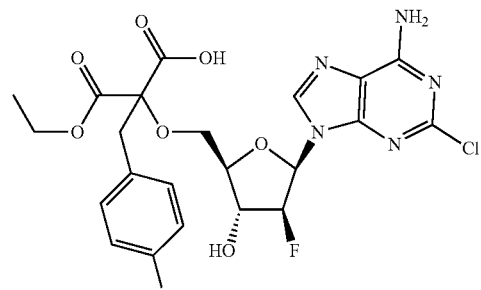
Isomer 1 | 0.718 |
| 38 | 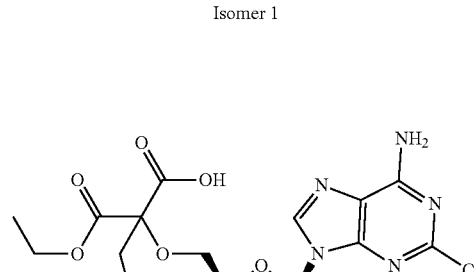
Isomer 2 | 0.686 |

TABLE 3-continued

| Cpd. # | Compound | IC$_{50}$ (μM) |
|---|---|---|
| 39 | | 0.160 |
| 40 | | 1.280 |
| 41 | | 1.790 |
| 42 | | 0.119 |

TABLE 3-continued

| Cpd. # | Compound | IC$_{50}$ (μM) |
|---|---|---|
| 43 | | 1.040 |
| 44 | | 0.273 |
| 47 | | 0.343 |
| 49 | | 0.839 |
| 32 | | 0.199 |

TABLE 3-continued

| Cpd. # | Compound | IC$_{50}$ (µM) |
|---|---|---|
| 51 | | 1.870 |
| 52 | | >50 |
| 53 | | 0.448 |
| 54 | | 0.220 |

TABLE 3-continued

| Cpd. # | Compound | IC$_{50}$ (μM) |
|---|---|---|
| 55 | | >50 |
| 56 | | 0.168 |
| 57 | | 0.142 |
| 58 | | 0.038 |

TABLE 3-continued

| Cpd. # | Compound | IC$_{50}$ (µM) |
|---|---|---|
| 59 | | 0.439 |
| 60 | | 0.051 |
| 61 | | 2.246 |
| 63 | | 1.222 |

TABLE 3-continued

| Cpd. # | Compound | IC$_{50}$ (μM) |
|---|---|---|
| 64 | | 0.860 |
| 65 | | 0.031 |
| 66 | | 0.133 |
| 67 | | 0.602 |

TABLE 3-continued
| Cpd. # | Compound | IC$_{50}$ (μM) |
|---|---|---|
| 68 | 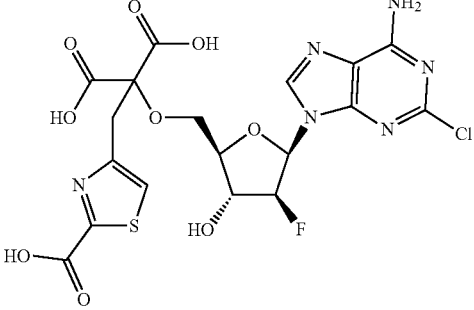 | 0.322 |
| 73 | 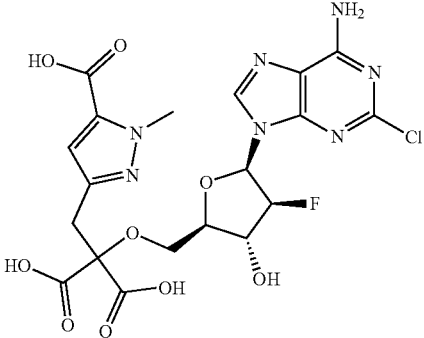 [SMILES: Cn1nc(CC(OC[C@H]2O[C@@H](n3cnc4c(N)nc(Cl)nc43)[C@@H](F)[C@@H]2O)(C(=O)O)C(=O)O)cc1C(=O)O] | 8.614 |
| 74 | 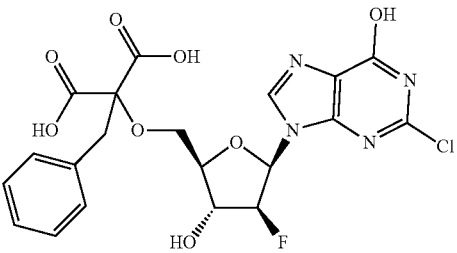 [SMILES: O=C(O)C(Cc1ccccc1)(OC[C@H]1O[C@@H](n2cnc3c(O)nc(Cl)nc32)[C@@H](F)[C@@H]1O)C(=O)O] | 1.659 |
| 75 | 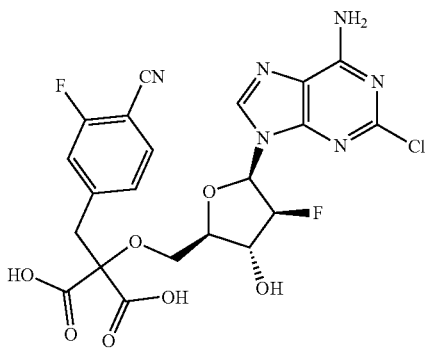 [SMILES: N#Cc1ccc(CC(OC[C@H]2O[C@@H](n3cnc4c(N)nc(Cl)nc43)[C@@H](F)[C@@H]2O)(C(=O)O)C(=O)O)cc1F] | 0.887 |

TABLE 3-continued
| Cpd. # | Compound | IC$_{50}$ (μM) |
|---|---|---|
| 76 | 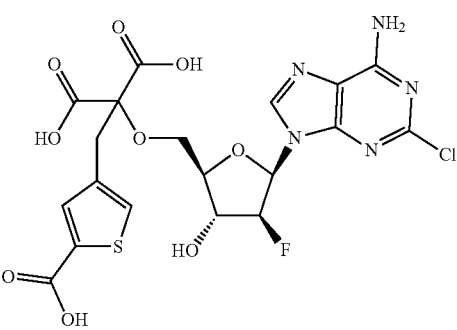 [SMILES: Nc1nc(Cl)nc2c1ncn2[C@@H]1O[C@H](COC(Cc2csc(C(=O)O)c2)(C(=O)O)C(=O)O)[C@@H](O)[C@@H]1F] | 0.074 |
| 77 | 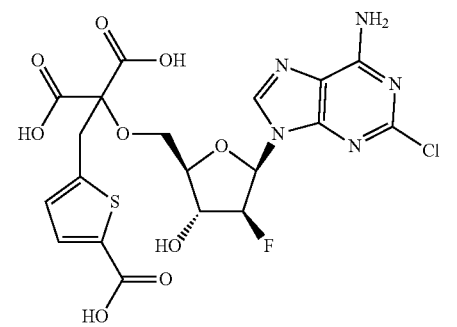 [SMILES: Nc1nc(Cl)nc2c1ncn2[C@@H]1O[C@H](COC(Cc2ccc(C(=O)O)s2)(C(=O)O)C(=O)O)[C@@H](O)[C@@H]1F] | 0.255 |
| 78 | 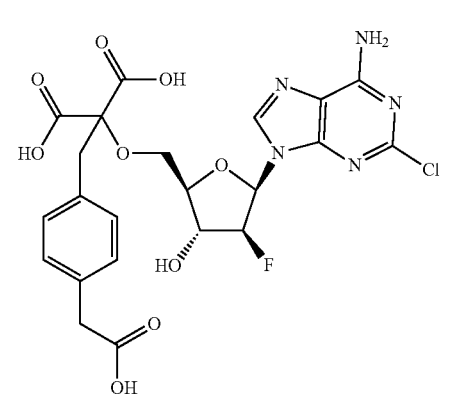 [SMILES: Nc1nc(Cl)nc2c1ncn2[C@@H]1O[C@H](COC(Cc2ccc(CC(=O)O)cc2)(C(=O)O)C(=O)O)[C@@H](O)[C@@H]1F] | 0.086 |
| 79 | 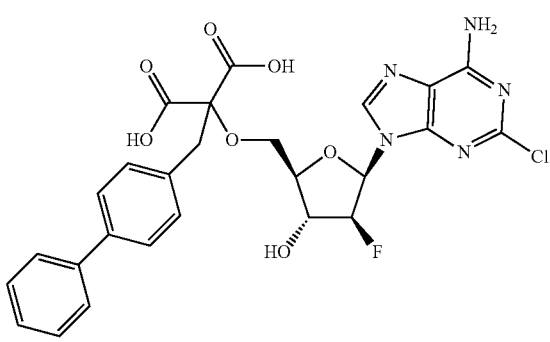 | 0.029 |

TABLE 3-continued
| Cpd. # | Compound | IC$_{50}$ (μM) |
|---|---|---|
| 80 | 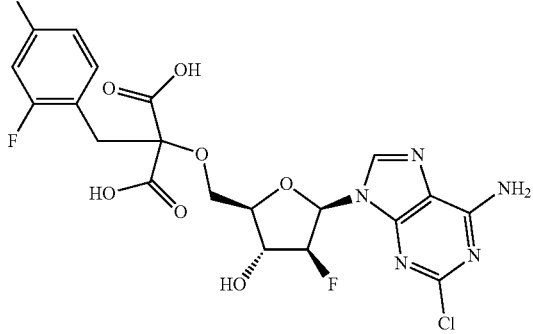 | 0.044 |
| 81 | 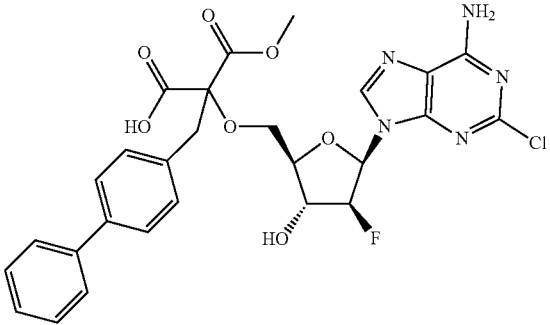<br>Isomer 1 | 2.857 |
| 82 | 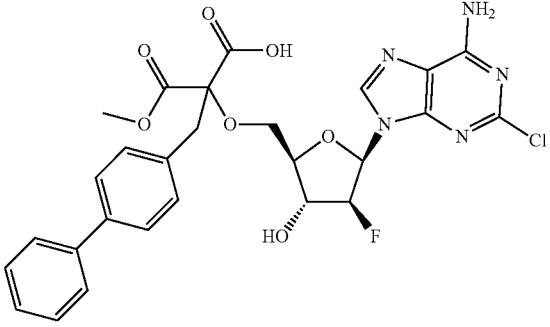 [SMILES: Nc1nc(Cl)nc2c1ncn2[C@@H]1O[C@H](COC(Cc2ccc(-c3ccccc3)cc2)(C(=O)O)C(=O)O)[C@@H](O)[C@@H]1F]<br>Isomer 2 | 3.433 |
| 83 | 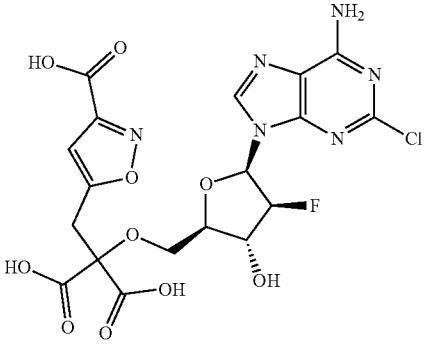 [SMILES: Nc1nc(Cl)nc2c1ncn2[C@@H]1O[C@H](COC(Cc2cc(C(=O)O)no2)(C(=O)O)C(=O)O)[C@@H](O)[C@@H]1F] | 6.443 |

TABLE 3-continued

| Cpd. # | Compound | IC$_{50}$ (μM) |
|---|---|---|
| 84 | Isomer 1 | 7.261 |
| 84 | Isomer 2 | 8.264 |
| 85 | | 0.183 |
| 86 | | 0.062 |

TABLE 3-continued

| Cpd. # | Compound | IC$_{50}$ (μM) |
|---|---|---|
| 87 | | 0.083 |
| 88 | | 0.238 |
| 89 | | 0.043 |
| 91 | | 0.322 |

TABLE 3-continued

| Cpd. # | Compound | IC$_{50}$ (μM) |
|---|---|---|
| 92 | | 0.172 |
| 94 | | 0.906 |
| 95 | | 0.105 |

TABLE 3-continued

| Cpd. # | Compound | IC$_{50}$ (μM) |
|---|---|---|
| 96 | | 0.788 |
| 97 | | 3.432 |
| 98 | | 0.512 |

Example 78

Biological Activity of Disclosed Compounds In Vitro

The ability of compounds to inhibit endogenous, cell-bound CD73 enzyme activity was demonstrated using SK-MEL-28 cells, which express CD73 on their surface. The day before the experiment, 5000 cells were plated per well in a 96-well plate. Cells were washed twice with 200 μL reaction buffer (20 mM HEPES, pH 7.4, 125 mM NaCl, 1 mM KCl, 2 mM MgCl2, 10 mM glucose) to remove residual inorganic phosphate. After washing, assays contained serial dilutions of test compounds and 100 μM of AMP in a total volume of 200 μL reaction buffer, with a final DMSO concentration ≤0.5%. After 30 minutes at room temperature, supernatant was removed from the cells. A volume of 100 μL Malachite Green (Cell Signaling Technology, Cat. No. 12776) was added to 25 μL of supernatant. After 5 minutes at room temperature, absorbance at 630 nm was determined on a microplate spectrophotometer. The concentration of inorganic phosphate was determined using a phosphate standard curve to determine IC$_{50}$. Table 4 provides the IC$_{50}$ data of a representative number of compounds.

TABLE 4

| Cpd. # | Compound | IC$_{50}$ (μM) |
|---|---|---|
| 6 | | 0.489 |
| 7 | | 0.257 |
| 8 | | 0.772 |
| 13 | | 2.19 |
| 15 | | 1.579 |

TABLE 4-continued

| Cpd. # | Compound | IC$_{50}$ (µM) |
|---|---|---|
| 16 | | 1.024 |
| 17 | | 1.814 |
| 18 | | 6.323 |
| 19 | | 5.836 |
| 20 | | 0.611 |

TABLE 4-continued

| Cpd. # | Compound | IC$_{50}$ (μM) |
|---|---|---|
| 21 | | 0.510 |
| 22 | | 1.135 |
| 23 | | 0.480 |
| 24 | | 16.382 |
| 27 | | 0.886 |

TABLE 4-continued

| Cpd. # | Compound | IC$_{50}$ (µM) |
|---|---|---|
| 29 | | 5.716 |
| 50 | | 6.368 |
| 33 | | 3.377 |
| 34 | | 0.153 |
| 35 | | 0.261 |

TABLE 4-continued
| Cpd. # | Compound | IC$_{50}$ (μM) |
|---|---|---|
| 36 | 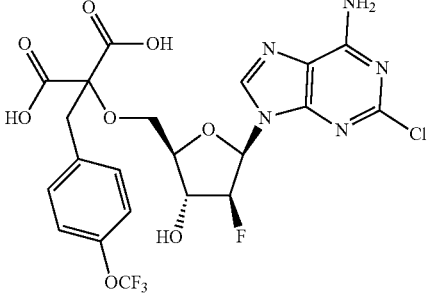 | 0.197 |
| 37 | 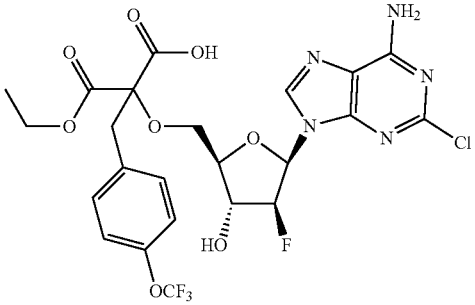<br>Isomer 1 | 0.598 |
| 38 | 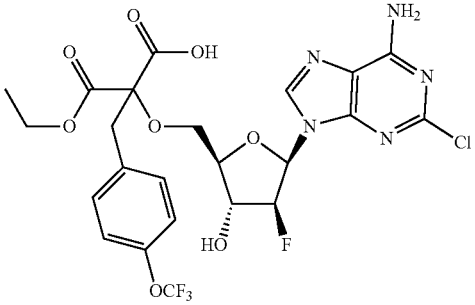<br>Isomer 2 | 1.485 |
| 39 | 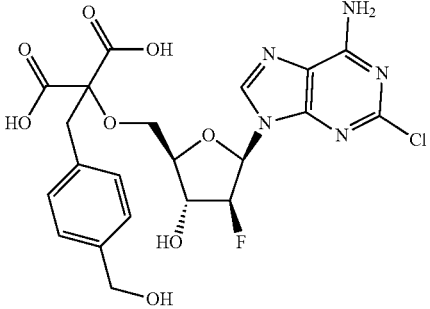 [SMILES: Nc1nc(Cl)nc2c1ncn2[C@@H]1O[C@H](COC(Cc2ccc(CO)cc2)(C(=O)O)C(=O)O)[C@@H](O)[C@@H]1F] | 0.493 |

TABLE 4-continued

| Cpd. # | Compound | IC$_{50}$ (μM) |
|---|---|---|
| 40 | | 2.411 |
| 41 | | 4.885 |
| 42 | | 0.887 |
| 43 | | 9.921 |
| 44 | | 1.006 |

TABLE 4-continued

| Cpd. # | Compound | IC$_{50}$ (μM) |
|---|---|---|
| 47 | | 0.669 |
| 49 | | 2.382 |
| 32 | | 2.317 |
| 51 | | 4.344 |

TABLE 4-continued

| Cpd. # | Compound | IC$_{50}$ (μM) |
|---|---|---|
| 53 | | 2.598 |
| 54 | | 0.973 |
| 55 | | >50 |
| 56 | | 1.250 |

TABLE 4-continued

| Cpd. # | Compound | IC$_{50}$ (μM) |
|---|---|---|
| 57 | | 0.1.250 |
| 58 | | 0.853 |
| 59 | | 6.984 |
| 60 | | 0.512 |

TABLE 4-continued

| Cpd. # | Compound | IC$_{50}$ (µM) |
|---|---|---|
| 61 | | 6.974 |
| 63 | | 2.006 |
| 64 | | 0.588 |
| 65 | | 0.196 |

TABLE 4-continued

| Cpd. # | Compound | IC$_{50}$ (μM) |
|---|---|---|
| 66 | | 0.426 |
| 67 | | 1.309 |
| 68 | | 0.924 |
| 73 | | 1.243 |
| 74 | | 2.557 |

TABLE 4-continued

| Cpd. # | Compound | IC$_{50}$ (μM) |
|---|---|---|
| 75 | | 0.990 |
| 76 | | 0.305 |
| 77 | | 1.331 |
| 78 | | 0.234 |

TABLE 4-continued

| Cpd. # | Compound | IC$_{50}$ (μM) |
|---|---|---|
| 79 | | 0.162 |
| 80 | | 0.177 |
| 81 | Isomer 1 | 2.109 |
| 82 | Isomer 2 | 4.122 |

TABLE 4-continued

| Cpd. # | Compound | IC$_{50}$ (µM) |
|---|---|---|
| 83 | | 5.196 |
| 85 | | 1.368 |
| 86 | | 0.626 |
| 87 | | 0.549 |

TABLE 4-continued

| Cpd. # | Compound | IC$_{50}$ (μM) |
|---|---|---|
| 88 | | 0.443 |
| 89 | | 0.070 |
| 92 | | 0.202 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of treating a cancer selected from colon cancer, prostate cancer, lymphoma, breast cancer, lung cancer, ovarian cancer, bladder cancer, leukemia, glioma, glioblastoma, melanoma, thyroid cancer, and esophageal cancer, comprising administering a compound of Formula (I) to a subject in need thereof, wherein the compound of Formula (I) has the structure:

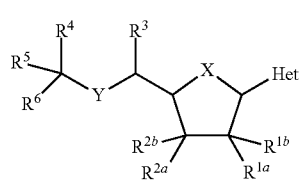

(I)

or a pharmaceutically acceptable salt thereof, wherein
X is O;
Y is O or S;

Z is $NR^{19}$, O or S;

Het is an optionally substituted purinyl ring or an optionally substituted 5-methyl-pyrimidin-2,4-dione ring;

$R^{1a}$ is selected from halo, hydroxy, cyano, azido, amino, $C_{1-6}$alkyl, hydroxy$C_{1-6}$alkyl, amino-$C_{1-6}$alkyl, $C_{1-6}$acyloxy, $C_{1-6}$alkoxy, $C_{2-6}$alkenyl, and $C_{2-6}$alkynyl; and $R^{1b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl; or $R^{1a}$ and $R^{1b}$, together with the carbon atom to which they are attached, form a C=$CH_2$ or C=C(H)$C_{1-6}$alkyl;

$R^{2a}$ is selected from H, halo, hydroxy, cyano, azido, amino, $C_{1-6}$alkyl, hydroxy-$C_{1-6}$alkyl, amino-$C_{1-6}$alkyl, $C_{1-6}$acyloxy, $C_{1-6}$alkoxy, $C_{2-6}$alkenyl, and $C_{2-6}$alkynyl;

$R^{2b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl; or $R^{2a}$ and $R^{2b}$, together with the carbon atom to which they are attached, form a C=$CH_2$ or C=C(H)$C_{1-6}$alkyl;

$R^3$ is selected from H, alkyl, cycloalkyl, cycloalkylalkyl, heterocyclyl, heterocyclylalkyl, aryl, aralkyl, heteroaryl, heteroaralkyl, and —($CH_2$)—C(O)$OR^9$;

$R^4$ is selected from alkyl, —C(O)$OR^9$, —C(O)$NR^{11}R^{12}$, —S(O)$_2R^{10}$, —P(O)($OR^{11}$)($OR^{12}$), and —P(O)($OR^{11}$)($NR^{13}R^{15}$);

$R^5$ is selected from H, cyano, alkyl, cycloalkylalkyl, heterocyclylalkyl, aralkyl, heteroaralkyl, and —C(O)$OR^9$;

$R^6$ is selected from —C(O)$OR^9$ and —P(O)($OR^{11}$)($OR^{12}$);

each $R^7$ and $R^8$ is independently selected from H, alkyl, acyloxyalkyl, alkenyl, alkynyl, cycloalkyl, cycloalkylalkyl, heterocyclyl, heterocyclylalkyl, aryl, aralkyl, heteroaryl, and heteroaralkyl;

$R^9$ is independently selected from H, alkyl, acyloxyalkyl, alkenyl, alkynyl, cycloalkyl, cycloalkylalkyl, heterocyclyl, heterocyclylalkyl, aryl, aralkyl, heteroaryl, and heteroaralkyl, and —(CHR$^{13}$)$_m$—Z—C(O)—$R^{14}$;

each $R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl, and each $R^{11}$ and $R^{12}$ is independently selected from H, alkyl, alkenyl, alkynyl, —S(O)$_2R^{10}$, cycloalkyl, cycloalkylalkyl, heterocyclyl, heterocyclylalkyl, aryl, aralkyl, heteroaryl, heteroaralkyl and —(CHR$^{13}$)$_m$—Z—C(O)—$R^{14}$, or $R^{11}$ and $R^{12}$, together with the atoms to which they are attached, form a 5- to 7-membered heterocyclyl;

each $R^{13}$ is independently H or alkyl;

each $R^{14}$ is independently selected from alkyl, aminoalkyl, heterocyclyl, and heterocyclylalkyl;

$R^{15}$ is selected from alkyl, aralkyl, and C($R^{16}$)($R^{17}$)—C(O)O—$R^{18}$;

each $R^{16}$ and $R^{17}$ are selected from H, alkyl, amino-alkyl, hydroxy-alkyl, mercapto-alkyl, sulfonyl-alkyl, cycloalkyl, aryl, aralkyl, heterocyclylalkyl, heteroaralkyl, and —($CH_2$)C(O)$OR^9$;

$R^{18}$ is selected from H, alkyl, alkoxyalkyl, aminoalkyl, haloalkyl, amido, cycloalkyl, cycloalkylalkyl, heterocyclyl, heterocyclylalkyl, aryl, aralkyl, heteroaryl, and heteroaralkyl;

$R^{19}$ is H or alkyl, preferably H; and m is 1 or 2;

provided that if $R^3$ is H and $R^{1a}$ and $R^{2a}$ are each hydroxy, then at least one of $R^{1b}$ and $R^{2b}$ is $C_{1-6}$alkyl.

2. The method of claim 1, wherein $R^{1a}$ is fluoro and $R^{1b}$ is H.

3. The method of claim 1, wherein $R^{2a}$ is fluoro and $R^{2b}$ is H.

4. The method of claim 1, wherein $R^{1a}$ and $R^{1b}$ are each fluoro.

5. The method of claim 1, wherein $R^{2a}$ and $R^{2b}$ are each fluoro.

6. The method of claim 1, wherein $R^{1a}$ is fluoro and $R^{2a}$ is $C_{1-6}$alkoxy.

7. The method of claim 1, wherein $R^{1a}$ is fluoro and $R^{2a}$ is $C_{1-6}$alkyl.

8. The method of claim 1, wherein $R^{1a}$ is fluoro and $R^{2a}$ is methyl or ethyl.

9. The method of claim 1, wherein $R^{2a}$ is hydroxy and $R^{2b}$ is methyl.

10. The method of claim 1, wherein the compound has the structure:

11. The method of claim 10, wherein $R^{1a}$ is in the α-configuration.

12. The method of claim 11, wherein the compound of Formula (I) has the structure (IA):

13. The method of claim 10, wherein $R^{1a}$ is in the β-configuration.

14. The method of claim 13, wherein the compound of Formula (I) has the structure (IB):

15. The method of claim 10, wherein $R^{2a}$ is in the α-configuration.

16. The method of claim 15, wherein the compound of Formula (I) has the structure (IC):

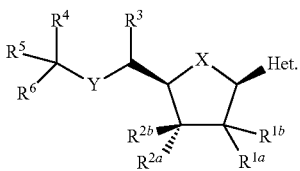

(IC)

17. The method of claim 10, wherein $R^{2a}$ is in the β-configuration.

18. The method of claim 17, wherein the compound of Formula (I) has the structure (ID):

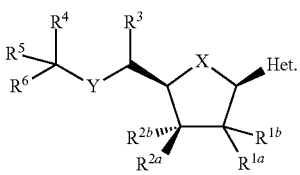

(ID)

19. The method of claim 10, wherein the compound of Formula (I) has the structure (IE):

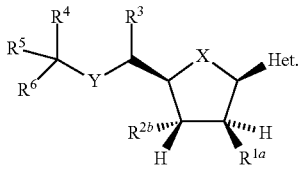

(IE)

20. The method of claim 1, wherein $R^3$ is H.

21. The method of claim 1, wherein $R^3$ is unsubstituted $C_{1-6}$alkyl.

22. The method of claim 1, wherein $R^3$ is alkyl, and the alkyl is unsubstituted or substituted with one or more substituents selected from halo, CN, $NO_2$, azido, hydroxy, alkoxy, alkylthio, thioalkoxy, carbonyl, thiocarbonyl, amidino, imino, amino, amido, alkoxycarbonyl, carbamate, urea, sulfinamido, sulfonamido, sulfinyl, sulfonyl, phosphoryl, phosphate, phosphonate, and phosphinate.

23. The method of claim 22, wherein the substituents are selected from halo, CN, azido, alkoxy, carbonyl, amino, amido, and alkoxycarbonyl.

24. The method of claim 1, wherein $R^4$ is selected from —C(O)$OR^9$, —C(O)$NR^{11}R^{12}$, —S(O)$_2R^{10}$, and —P(O)(OR$^{11}$)(OR$^{12}$).

25. The method of claim 1, wherein $R^4$ is —C(O)$OR^9$.

26. The method of claim 1, wherein $R^4$ is alkyl.

27. The method of claim 1, wherein $R^4$ is —C(O)NR$^{11}$R$^{12}$.

28. The method of claim 1, wherein $R^5$ is selected from alkyl, cycloalkylalkyl, heterocyclylalkyl, aralkyl and heteroaralkyl, and each is unsubstituted or substituted with one or more substituents.

29. The method of claim 28, wherein the substituents are selected from halo, CN, azido, alkoxy, carbonyl, amino, amido, and alkoxycarbonyl.

30. The method of claim 28, wherein $R^5$ is aralkyl or heteroaralkyl.

31. The method of claim 30, wherein $R^5$ is aralkyl, and the aryl ring is substituted or unsubstituted phenyl or naphthyl.

32. The method of claim 30, wherein $R^5$ is heteroaralkyl, wherein the heteroaryl ring is selected from benzofuranyl, benzothienyl, benzothiazolyl, pyridyl, thienyl, furanyl, pyrazolyl, thiazolyl, oxazolyl, and oxadiazolyl, each of which may be substituted or unsubstituted.

33. The method of claim 28, wherein the substituents are selected from tetrazolyl, substituted or unsubstituted phenyl, and substituted or unsubstituted benzyl.

34. The method of claim 1, wherein $R^6$ is —C(O)$OR^9$.

35. The method of claim 1, wherein $R^6$ is —P(O)(OR$^{11}$)(OR$^{12}$) and $R^{11}$ and $R^{12}$ are each H.

36. The method of claim 1, wherein $R^7$ is H or $C_{1-6}$alkyl.

37. The method of claim 1, wherein $R^8$ is H.

38. The method of claim 1, wherein $R^9$ is H or $C_{1-6}$alkyl.

39. The method of claim 1, wherein $R^{11}$ and $R^{12}$ are each H.

40. The method of claim 1, wherein $R^{11}$ and $R^{12}$ are each alkyl.

41. The method of claim 1, wherein the substituents on each $R^7$, $R^8$, $R^9$, $R^{10}$, $R^{11}$ and $R^{12}$ are selected from halo, CN, azido, alkoxy, carbonyl, amino, amido, and alkoxycarbonyl.

42. The method of claim 1, wherein Y is O.

43. The method of claim 1, wherein Z is O.

44. The method of claim 1, wherein Het is a purinyl ring or a 5-methyl-pyrimidin-2,4-dione ring unsubstituted or substituted with one or more substituents selected from halo, CN, $NO_2$, azido, hydroxy, alkoxy, alkylthio, thioalkoxy, carbonyl, thiocarbonyl, amidino, imino, amino, amido, alkoxycarbonyl, carbamate, urea, sulfinamido, sulfonamido, sulfinyl, sulfonyl, phosphoryl, phosphate, phosphonate, and phosphinate.

45. The method of claim 44, wherein the substituents are selected from halo, CN, azido, alkoxy, carbonyl, amino, amido, and alkoxycarbonyl.

46. The method of claim 1, wherein Het is purinyl.

47. The method of claim 1, wherein Het is

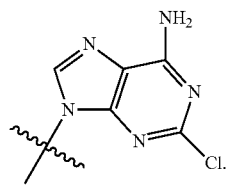 [SMILES: *n1cnc2c(N)nc(Cl)nc21]

48. The method of claim 1, wherein Het is

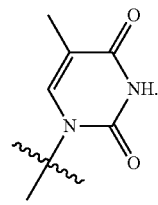 [SMILES: *n1cc(C)c(=O)[nH]c1=O]

49. The method of claim 44, wherein Het is selected from

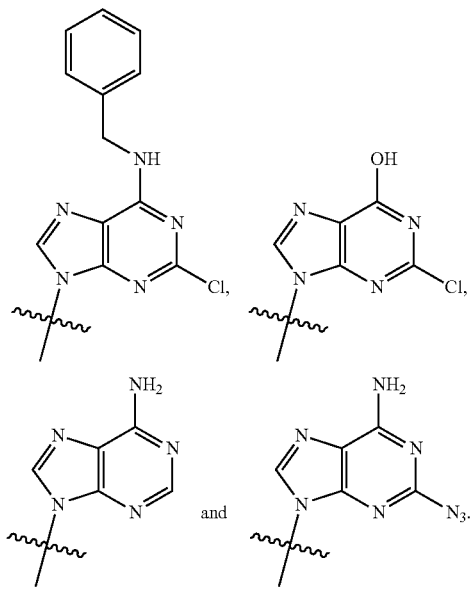

and

50. The method of claim 1, wherein

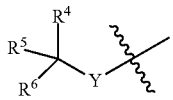

represents

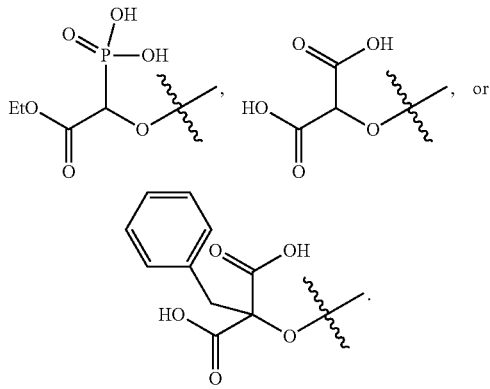

51. The method of claim 1, wherein

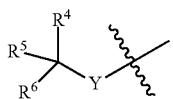

represents

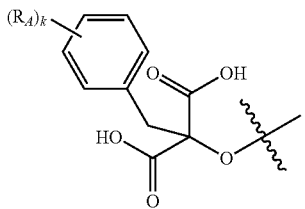

wherein:
each $R_A$ is independently selected from H, halo, CN, OH, alkyl, haloalkyl, hydroxyalkyl, alkoxy, haloalkoxy, aryloxy, aralkyloxy, alkyl sulfonyl, sulfonamido, amido, amino, hydroxycarbonyl, alkoxycarbonyl, heteroaryl, aryl, aralkyl, and heteroaralkyl; and
k is 1, 2, or 3.

52. The compound of claim 1, wherein the compound of Formula (I) has the structure:

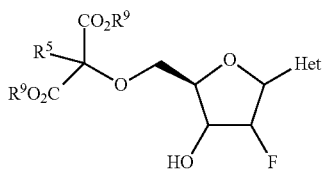

wherein:
$R^5$ is:
(i) phenyl$C_{1-6}$alkyl or naphthyl$C_{1-6}$alkyl wherein phenyl and naphthyl are optionally substituted with one, two, or three substituents independently selected from —$C_{1-6}$alkyl, —O$C_{1-6}$alkyl, —$C_{1-6}$alkyl substituted with one to five fluoro, —O$C_{1-6}$alkyl (substituted with one to five fluoro), —$C_{1-6}$alkylene-$CO_2H$, —$C_{1-6}$alkylene-$CO_2C_{1-6}$alkyl, —$C_{2-6}$alkenylene-$CO_2H$, —O$C_{1-6}$alkylene-$CO_2H$, —O$C_{1-6}$alkylene-$CO_2C_{1-6}$alkyl, —$C_{1-6}$alkyl substituted with one or two hydroxy, —O$C_{1-6}$alkyl substituted with one or two hydroxy, —$C_{1-6}$alkyl substituted with one or two —O$C_{1-6}$alkyl, —O$C_{1-6}$alkyl (substituted with one or two —O$C_{1-6}$alkyl), —$CO_2H$, —COO$C_{1-6}$alkyl, hydroxy, halo, nitro, —$PO_3H_2$, cyano, —$NH_2$, —NH($C_{1-6}$alkyl), —N($C_{1-6}$alkyl)$_2$, —CONR$^e$R$^f$ (where R$^e$ and R$^f$ are independently hydrogen, —$C_{1-6}$ alkyl, —$C_{1-6}$alkylene-$CO_2H$, —$C_{1-6}$ alkylene-$CO_2C_{1-6}$ alkyl, or —$C_{1-6}$ alkylene-substituted with one or two substituents independently selected from hydroxy, $NH_2$, —NH$C_{1-6}$alkyl or —N($C_{1-6}$alkyl)$_2$), —$SO_2$($C_{1-6}$alkyl), —$SO_2$NR$^g$R$^h$ (where R$^g$ and R$^h$ are independently hydrogen, —$C_{1-6}$ alkyl, —$C_{1-6}$alkylene-$CO_2H$, or —$C_{1-6}$alkylene-$CO_2C_{1-6}$alkyl), —S$C_{1-6}$alkyl, —SO$C_{1-6}$alkyl, —$SO_2$NHCOR$^j$ (where R$^1$ is —$C_{1-6}$alkyl, —NH$C_{1-6}$alkyl, or —N($C_{1-6}$alkyl)$_2$), phenyl, —$C_{1-6}$ alkylenephenyl, phenoxy, —O$C_{1-6}$alkylenephenyl, 5- or 6-membered monocyclic heteroaryl containing one to four heteroatoms independently selected from O, N, and S [wherein the heteroaryl ring is optionally substituted with one, two, or three substituents independently selected from hydroxyl, halo, CN, —$CO_2H$, —$CO_2C_{1-6}$alkyl, —$C_{1-6}$alkyl, —O$C_{1-6}$alkyl, —$C_{1-6}$alkyl (substituted with one to five fluoro), —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$], —OR$^i$, —C$_{1-6}$alkylene-R$^i$, —OC$_{1-6}$alkylene-R$^i$, —SR$^i$, —SC$_{1-6}$alkylene-R$^i$, heterocyclyl, —C$_{1-6}$alkyleneheterocyclyl, —OC$_{1-6}$alkylene-heterocyclyl, —SC$_{1-6}$alkyleneheterocyclyl, —CONR$^m$C$_{1-6}$alkyleneheterocyclyl, —NR$^m$COC$_{1-6}$alkyleneNR$^o$R$^p$, —NR$^m$COheterocyclyl, —NR$^m$COC$_{1-6}$alkyleneheterocyclyl, —COheterocyclyl, —CONR$^m$C$_{1-6}$alkylene-R$^i$, —OCONR$^m$R$^m$, —NR$^m$—COR$^y$, —NR$^m$—CO—NR$^m$R$^y$, —NR$^m$—SO$_2$—R$^y$, —NR$^m$—SO$_2$—NR$^m$R$^y$, and —CONHSO$_2$R$^z$; or (ii) 5-10 membered heteroarylC$_{1-6}$alkyl having one to three heteroatoms independently selected from N, O, or S and 5-10 membered heteroaryl in 5-10 membered heteroarylC$_{1-6}$alkyl is optionally substituted with one or two substituents independently selected from —C$_{1-6}$alkyl, —OC$_{1-6}$alkyl, —C$_{1-6}$alkyl substituted with one to five fluoro, —OC$_{1-6}$alkyl substituted with one to five fluoro, —C$_{1-6}$alkylene-CO$_2$H, —C$_{1-6}$alkylene-CO$_2$C$_{1-6}$alkyl, —C$_{2-6}$alkenylene-CO$_2$H, —C$_{1-6}$alkyl substituted with one or two hydroxy, —OC$_{1-6}$alkyl substituted with one or two hydroxy, —C$_{1-6}$alkyl substituted with one or two —OC$_{1-6}$alkyl, —OC$_{1-6}$alkyl (substituted with one or two —OC$_{1-6}$alkyl), —CO$_2$H, —COOC$_{1-6}$alkyl, hydroxy, halo, nitro, —PO$_3$H$_2$, cyano, —NH$_2$, —NH(C$_{1-6}$alkyl), —N(C$_{1-6}$alkyl)$_2$, —CONR$^e$R$^f$ (where R$^e$ and R$^f$ are independently hydrogen, —C$_{1-6}$ alkyl, —C$_{1-6}$alkylene-CO$_2$H, —C$_{1-6}$alkylene-CO$_2$C$_{1-6}$alkyl, or —C$_{1-6}$alkyl substituted with one or two hydroxyl, —NHC$_{1-6}$alkyl or —N(C$_{1-6}$alkyl)$_2$), —SO$_2$(C$_{1-6}$alkyl), —SO$_2$NR$^g$R$^h$ (where R$^g$ and R$^h$ are independently hydrogen, —C$_{1-6}$ alkyl, —C$_{1-6}$alkylene-CO$_2$H, or —C$_{1-6}$alkylene-CO$_2$C$_{1-6}$alkyl), —SC$_{1-6}$alkyl, —SOC$_{1-6}$alkyl, —SO$_2$NHCOR$^j$ (where is —C$_{1-6}$alkyl, —NH$_2$, —NHC$_{1-6}$alkyl, or —N(C$_{1-6}$alkyl)$_2$), phenyl, —C$_{1-6}$alkylenephenyl, phenoxy, —OC$_{1-6}$alkylenephenyl, 5- or 6-membered monocyclic heteroaryl containing one to four heteroatoms independently selected from O, N, and S [wherein the heteroaryl ring is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl (substituted with one to five fluoro), —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$], —OR$^i$, —C$_{1-6}$alkylene-R$^i$, —OC$_{1-6}$alkylene-R$^i$, —SR$^i$, —SC$_{1-6}$alkylene-R$^i$, heterocyclyl, —C$_{1-6}$alkyleneheterocyclyl, —OC$_{1-6}$ alkyleneheterocyclyl, —SC$_{1-6}$ alkyleneheterocyclyl, —CONR$^m$C$_{1-6}$alkyleneheterocyclyl, —NR$^m$COC$_{1-6}$ alkyleneNR$^o$R$^p$, —NR$^m$COheterocyclyl, —NR$^m$COC$_{1-6}$alkyleneheterocyclyl, —COheterocyclyl, —CONR$^m$R$^i$, —CONR$^m$alkylene-R$^i$, —OCONR$^m$R$^m$, —NR$^m$—COR$^y$, —NR$^m$—CO—NR$^m$R$^y$, —NR$^m$—SO$_2$—R$^y$, —NR$^m$—SO$_2$—NR$^m$R$^y$, and —CONHSO$_2$R$^z$; and the R$^5$ 5-10 membered heteroaryl ring is additionally optionally substituted with an additional substituent selected from —C$_{1-6}$alkyl, —C$_{1-6}$alkyl (wherein alkyl is substituted with one to five fluoro), —O—C$_{1-6}$alkyl, —OC$_{1-6}$alkyl (wherein alkyl is substituted with one to five fluoro), halo, CN, —NH$_2$, and hydroxy; wherein:

each R$^m$ is hydrogen or —C$_{1-6}$alkyl;

R$^o$, R$^p$, and R$^y$ are each independently hydrogen or —C$_{1-6}$alkyl;

R$^z$ is —C$_{1-6}$alkyl, —NHC$_{1-6}$alkyl, or —N(C$_{1-6}$alkyl)$_2$, phenyl by itself or as part of —C$_{1-6}$alkylenephenyl, phenoxy, or —OC$_{1-6}$alkylenephenyl is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, —C$_{1-6}$alkylene-CO$_2$C$_{1-6}$alkyl, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and —CON(C$_{1-6}$alkyl)$_2$;

each R$^i$ is independently 5- or 6-membered monocyclic heteroaryl containing one to four heteroatoms independently selected from O, N, and S and wherein the heteroaryl ring is optionally substituted with one, two, or three substituents independently selected from hydroxyl, halo, CN, —CO$_2$H, —COOC$_{1-6}$alkyl, —C$_{1-6}$alkyl, —OC$_{1-6}$alkyl, —C$_{1-6}$alkyl substituted with one to five fluoro, —OC$_{1-6}$alkyl (substituted with one to five fluoro), —C$_{1-6}$alkylene-CO$_2$H, C$_{1-6}$alkylene-CO$_2$C$_{1-6}$alky, tetrazolyl, —SO$_2$C$_{1-6}$alkyl, —SO$_2$NH$_2$, —SO$_2$NHC$_{1-6}$alkyl, —SO$_2$N(C$_{1-6}$alkyl)$_2$, —CONH$_2$, —CONHC$_{1-6}$alkyl, and CON(C$_{1-6}$alkyl)$_2$;

heterocyclyl by itself or as part of —C$_{1-6}$alkyleneheterocyclyl, —OC$_{1-6}$alkyleneheterocyclyl, —SC$_{1-6}$alkyleneheterocyclyl, —CONR$^m$C$_{1-6}$alkyleneheterocyclyl, —NR$^m$COC$_{1-6}$alkylene-heterocyclyl, —COheterocyclyl, or —NR$^m$COheterocyclyl is optionally substituted with one, two, or three substituents independently selected from hydroxy, halo, —COOC$_{1-6}$alkyl, —C$_{1-6}$alkyl, —OC$_{1-6}$alkyl, and —C$_{1-6}$alkyl (substituted with hydroxy or —OC$_{1-6}$alkyl); and Het is a group of formula (iii) or (xiv) below:

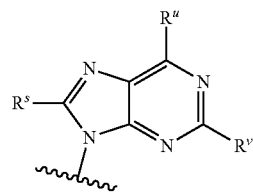

(iii)

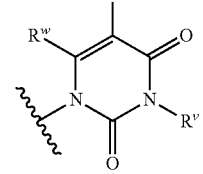

(xiv)

wherein:

R$^u$ is —NH$_2$, —NHR$^{20}$, —NHCOR$^{20}$, and —NR$^{20}$R$^{21}$;

$R^w$ is hydrogen, halo, —NHR$^{22}$, —NR$^{22}$R$^{23}$; —R$^{22}$, —OH, or —OR$^{22}$;

$R^v$ is hydrogen, halo, haloC$_{1-6}$alkyl, —NH$_2$, —NHR$^{24}$, —NR$^{24}$R$^{25}$; —R$^{24}$, —SR$^{24}$, cyano, —OH, —OR$^{24}$, —SO$_2$R$^{24}$, —C$_{1-6}$alkyleneNH$_2$, —C$_{1-6}$alkyleneNHR$^{24}$, —C$_{1-6}$alkyleneNR$^{24}$R$^{25}$, —C$_{1-6}$alkyleneSR$^{24}$, —C$_{1-6}$alkyleneOH, —C$_{1-6}$alkyleneOR$^{24}$, or —C$_{1-6}$alkyleneSO$_2$R$^{24}$, $R^s$ is hydrogen, halo, or C$_{1-6}$alkyl; and wherein:

R$^{20}$, R$^{21}$, R$^{22}$, R$^{23}$, R$^{24}$ and R$^{25}$ are independently optionally substituted C$_{1-6}$alkyl, —C$_2$-C$_6$ alkenyl, —C$_2$-C$_6$alkynyl, optionally substituted carbocyclyl, optionally substituted carbocyclyl C$_{1-6}$ alkyl, optionally substituted heterocyclyl, optionally substituted heterocyclylC$_{1-6}$alkyl, optionally substituted aryl, optionally substituted arylC$_{1-6}$alkyl, optionally substituted heteroaryl, and optionally substituted heteroarylC$_{1-6}$ alkyl; or R$^{20}$ and R$^{21}$, R$^{22}$ and R$^{23}$, and/or R$^{24}$ and R$^{25}$, together with the nitrogen to which they are attached form an optionally substituted nitrogen-containing heterocyclyl;

and further wherein, unless otherwise specified:

C$_{1-6}$alkyl is unsubstituted;

C$_{1-6}$ alkyl of C$_{1-6}$alkyloxy is unsubstituted;

haloC$_{1-6}$alkyl is C$_{1-6}$alkyl substituted with one to five halo atoms;

haloC$_{1-6}$alkyloxy is C$_{1-6}$alkyloxy substituted with one to five halo atoms;

C$_{2-6}$alkenyl is unsubstituted;

C$_{2-6}$alkynyl is unsubstituted;

C$_{1-6}$alkylene is unsubstituted;

C$_{2-6}$alkenylene is unsubstituted;

optionally substituted C$_{1-6}$alkyl is optionally substituted with one or two substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), —N(C$_{1-6}$alkyl)$_2$, optionally substituted carbocyclyl, optionally substituted aryl, optionally substituted heteroaryl, and optionally substituted heterocyclyl;

carbocyclyl is an unsubstituted saturated or partially unsaturated mono or bicyclic ring containing 3 to 10 carbon atoms;

optionally substituted carbocyclyl is optionally substituted with one, two, or three substituents independently selected from C$_{1-6}$alkyl, halo, hydroxy, and C$_{1-6}$alkoxy;

optionally substituted aryl is optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$;

aryl is phenyl or naphthyl;

optionally substituted carbocyclyl, aryl [optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$], heteroaryl [optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$], and heterocyclyl [optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(unsubstituted C$_{1-6}$ alkyl)$_2$];

heteroaryl is an unsubstituted five to ten membered or five to six membered aromatic ring containing one to four or one to three heteroatoms independently selected from N, O, and S; the remaining ring atoms being carbon;

optionally substituted heteroaryl is a five to ten membered aromatic ring containing one to four heteroatoms independently selected from N, O, and S; the remaining ring atoms being carbon, that is optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), —N(C$_{1-6}$alkyl)$_2$, optionally substituted carbocyclyl, aryl [optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$], heteroaryl [optionally substituted with one, two, or three substituents independently selected from hydroxy, unsubstituted C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$], and heterocyclyl [optionally substituted with one, two, or three substituents independently selected from hydroxy, C$_{1-6}$alkyloxy, halo, haloC$_{1-6}$ alkyl, haloC$_{1-6}$alkyloxy, cyano, —NH$_2$, —NH(C$_{1-6}$ alkyl), and —N(C$_{1-6}$alkyl)$_2$];

heterocyclyl is an unsubstituted monocyclic, saturated or partially unsaturated 4 to 8 membered ring containing one to three heteroatoms independently selected from N, O, S, SO, and SO$_2$ and optionally contains one or two CO, the remaining atoms in the ring being carbon that is optionally fused to phenyl or 5 to 6 membered carbocyclyl or 5 or 6 heteroaryl ring;

nitrogen-containing heterocyclyl is a heterocyclyl ring that has at least a nitrogen atom;

optionally substituted heterocyclyl is heterocyclyl that is optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), —N(C$_{1-6}$alkyl)$_2$, optionally substituted carbocyclyl, aryl [optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$], heteroaryl [optionally substituted with one, two, or three substituents independently selected from hydroxy, C$_{1-6}$alkyloxy, halo, haloC$_{1-6}$alkyl, haloC$_{1-6}$alkyloxy, cyano, —NH$_2$, —NH(C$_{1-6}$alkyl), and —N(C$_{1-6}$alkyl)$_2$], and heterocyclyl optionally substituted with one, two, or three substituents independently selected from hydroxy, C$_{1-6}$alkyloxy, halo, haloC$_{1-6}$ alkyl, haloC$_{1-6}$alkyloxy, cyano, —NH$_2$, —NH(C$_{1-6}$ alkyl), and —N(C$_{1-6}$alkyl)$_2$];

optionally substituted carbocyclyl C$_{1-6}$alkyl is optionally substituted carbocyclyl attached via C$_{1-6}$alkyl;

optionally substituted heterocyclylC$_{1-6}$alkyl is optionally substituted heterocyclyl attached via C$_{1-6}$alkyl;

optionally substituted arylC$_{1-6}$alkyl is optionally substituted aryl attached via C$_{1-6}$alkyl;

optionally substituted heteroarylC$_{1-6}$alkyl is optionally substituted heteroaryl attached via C$_{1-6}$alkyl;

provided that the compound of Formula (I) is not:

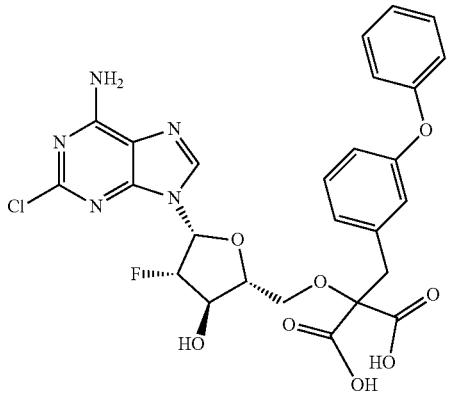 [SMILES: Nc1nc(Cl)nc2c1ncn2[C@@H]1O[C@H](COC(Cc2cccc(Oc3ccccc3)c2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonic acid;

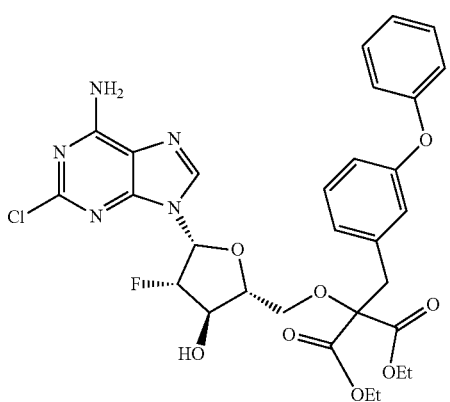 [SMILES: CCOC(=O)C(Cc1cccc(Oc2ccccc2)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonate;

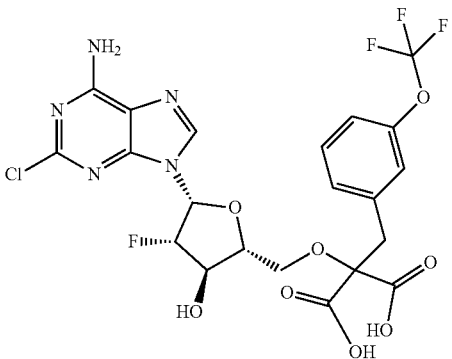 [SMILES: Nc1nc(Cl)nc2c1ncn2[C@@H]1O[C@H](COC(Cc2cccc(OC(F)(F)F)c2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonic acid;

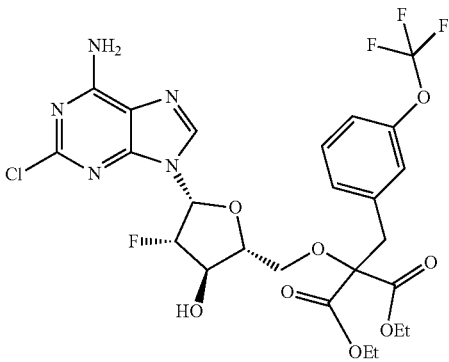 [SMILES: CCOC(=O)C(Cc1cccc(OC(F)(F)F)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonate;

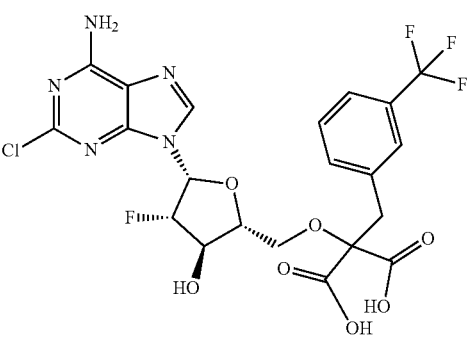 [SMILES: Nc1nc(Cl)nc2c1ncn2[C@@H]1O[C@H](COC(Cc2cccc(C(F)(F)F)c2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonic acid;

diethyl 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonate;

305

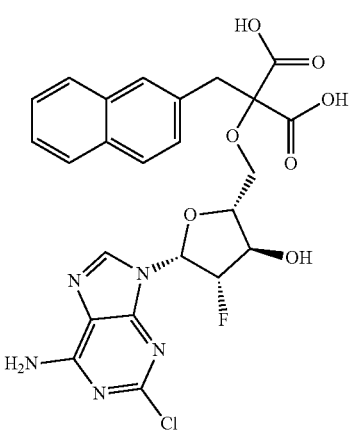 [SMILES: Nc1nc(Cl)nc2c1ncn2[C@@H]1O[C@H](COC(Cc2ccc3ccccc3c2)(C(=O)O)C(=O)O)[C@@H](O)[C@@H]1F]

2-(((2R,3R,4S,5R)-5-(6-amino-2-chloro-9H-purin-9-yl)-
4-fluoro-3-hydroxytetrahydrofuran-2-yl)methoxy)-2-
(naphthalen-2-ylmethyl)malonic acid;

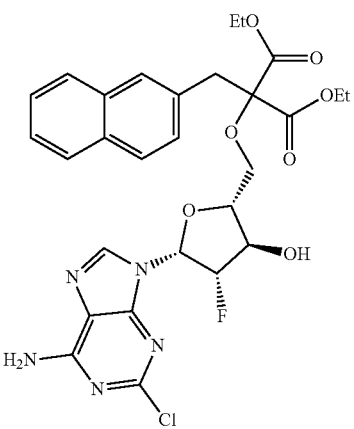 [SMILES: CCOC(=O)C(Cc1ccc2ccccc2c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(naphthalen-2-ylmethyl)malonate;

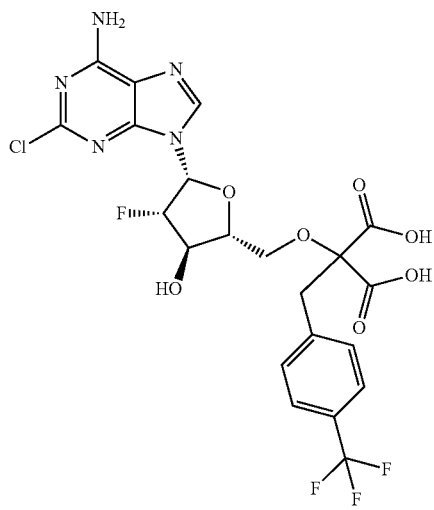 [SMILES: Nc1nc(Cl)nc2c1ncn2[C@@H]1O[C@H](COC(Cc2ccc(C(F)(F)F)cc2)(C(=O)O)C(=O)O)[C@@H](O)[C@@H]1F]

306

2-(((2R,3R,4S,5R)-5-(6-amino-2-chloro-9H-purin-9-yl)-
4-fluoro-3-hydroxytetrahydrofuran-2-yl)methoxy)-2-
(4-(trifluoromethyl)benzyl)malonic acid;

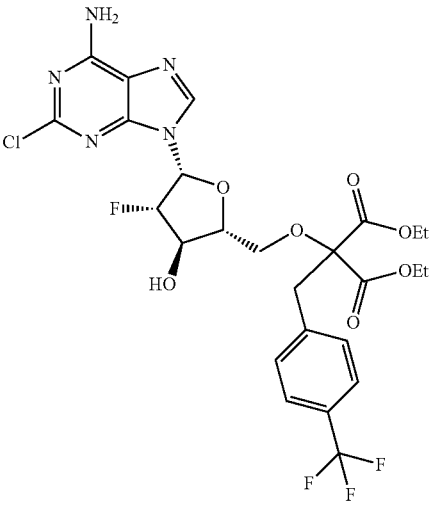 [SMILES: CCOC(=O)C(Cc1ccc(C(F)(F)F)cc1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonate;

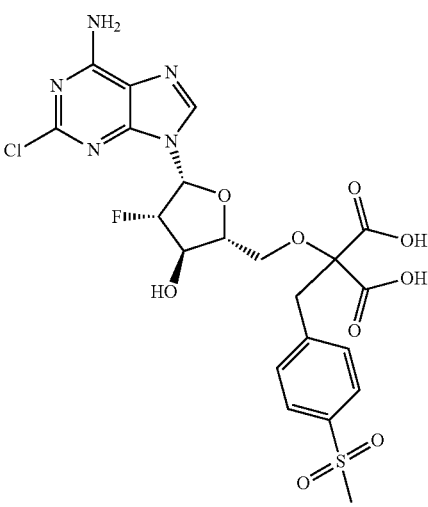 [SMILES: CS(=O)(=O)c1ccc(CC(OC[C@H]2O[C@@H](n3cnc4c(N)nc(Cl)nc43)[C@@H](F)[C@@H]2O)(C(=O)O)C(=O)O)cc1]

2-(((2R,3R,4S,5R)-5-(6-amino-2-chloro-9H-purin-9-yl)-
4-fluoro-3-hydroxytetrahydrofuran-2-yl)methoxy)-2-
(4-(methylsulfonyl)benzyl)malonic acid;

307

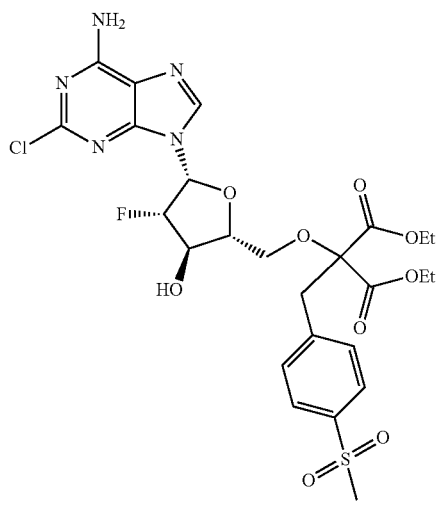 [SMILES: CCOC(=O)C(Cc1ccc(S(C)(=O)=O)cc1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(4-(methylsulfonyl)benzyl)malonate;

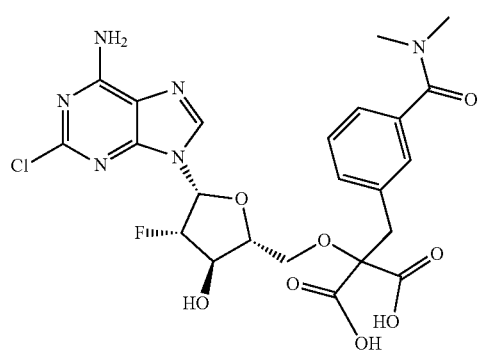 [SMILES: CN(C)C(=O)c1cccc(CC(OC[C@H]2O[C@@H](n3cnc4c(N)nc(Cl)nc43)[C@@H](F)[C@@H]2O)(C(=O)O)C(=O)O)c1]

2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonic acid;

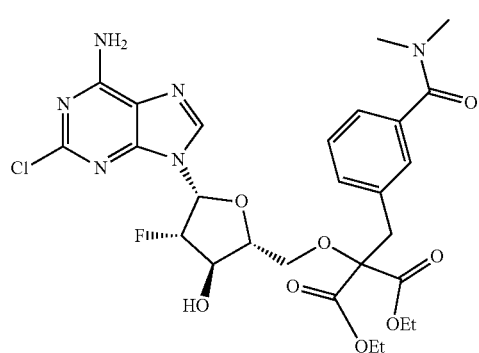 [SMILES: CCOC(=O)C(Cc1cccc(C(=O)N(C)C)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonate;

308

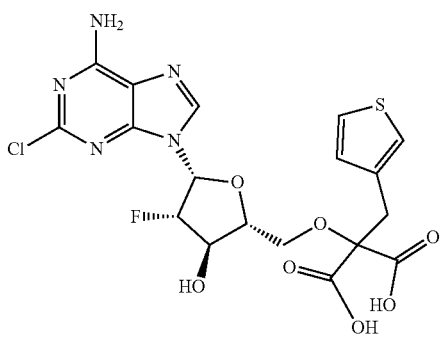 [SMILES: Nc1nc(Cl)nc2c1ncn2[C@@H]1O[C@H](COC(Cc2ccsc2)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonic acid;

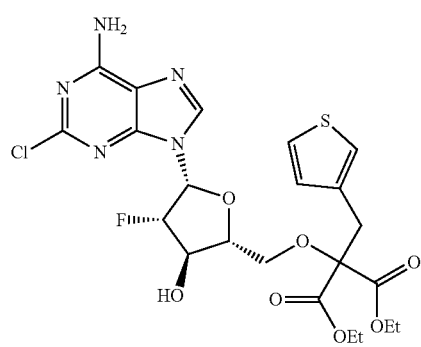 [SMILES: CCOC(=O)C(Cc1ccsc1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonate;

2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonic acid;

309

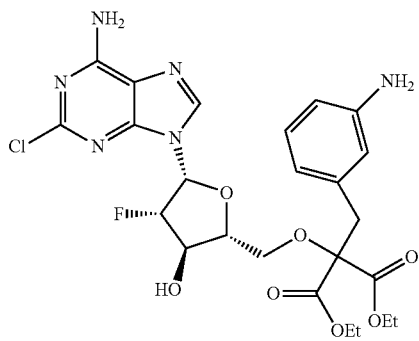 [SMILES: CCOC(=O)C(Cc1cccc(N)c1)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonate;

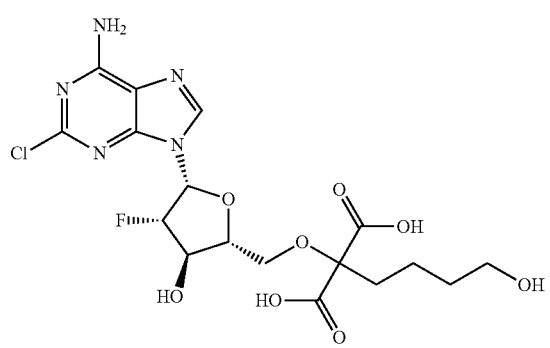 [SMILES: Nc1nc(Cl)nc2c1ncn2[C@@H]1O[C@H](COC(CCCCO)(C(=O)O)C(=O)O)[C@@H](O)[C@@H]1F]

2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonic acid;

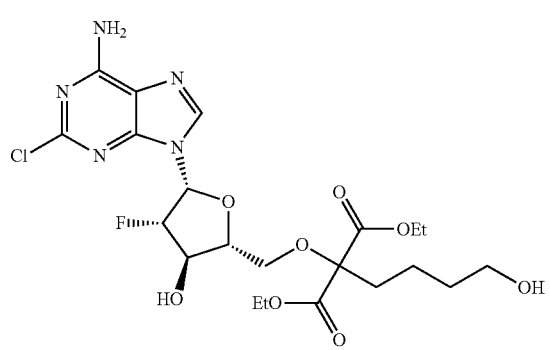 [SMILES: CCOC(=O)C(CCCCO)(OC[C@H]1O[C@@H](n2cnc3c(N)nc(Cl)nc32)[C@@H](F)[C@@H]1O)C(=O)OCC]

diethyl 2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonate;

310

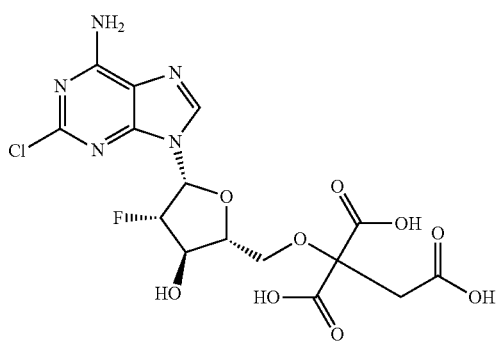 [SMILES: Nc1nc(Cl)nc2c1ncn2[C@@H]1O[C@H](COC(CC(=O)O)(C(=O)O)C(=O)O)[C@@H](O)[C@@H]1F]

1-(((2R,3R,4S,5R)-5-(6-amino-2-chloro-9H-purin-9-yl)-4-fluoro-3-hydroxytetrahydrofuran-2-yl)methoxy)ethane-1,1,2-tricarboxylic acid;

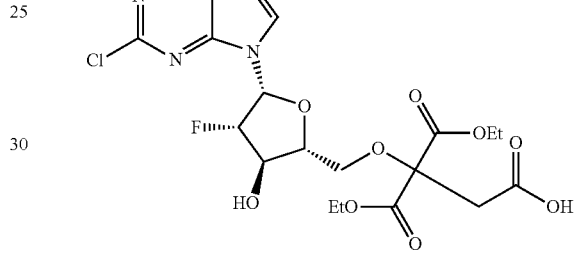

3-(((2R,3R,4S,5R)-5-(6-amino-2-chloro-9H-purin-9-yl)-4-fluoro-3-hydroxytetrahydrofuran-2-yl)methoxy)-4-ethoxy-3-(ethoxycarbonyl)-4-oxobutanoic acid;

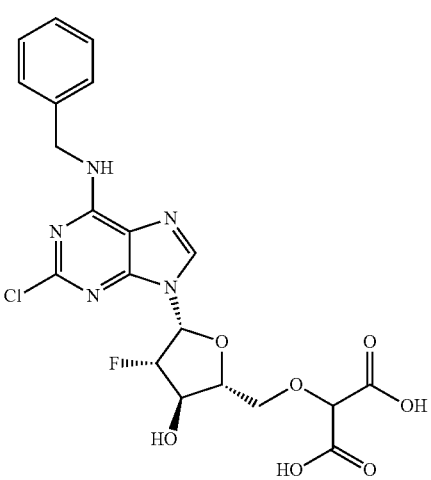 [SMILES: O=C(O)C(OC[C@H]1O[C@@H](n2cnc3c(NCc4ccccc4)nc(Cl)nc32)[C@@H](F)[C@@H]1O)C(=O)O]

2-(((2R,3R,4S,5R)-5-(6-(benzylamino)-2-chloro-9H-purin-9-yl)-4-fluoro-3-hydroxytetrahydrofuran-2-yl)methoxy)malonic acid;

311

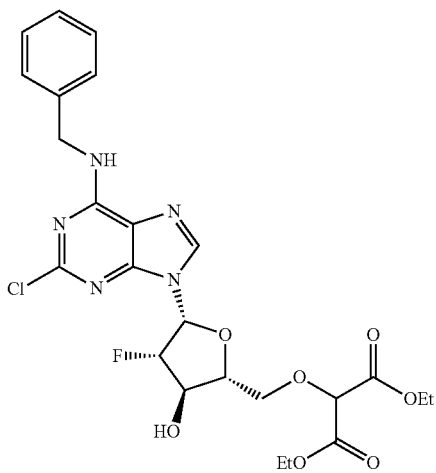 [SMILES: CCOC(=O)C(OC[C@H]1O[C@@H](n2cnc3c(NCc4ccccc4)nc(Cl)nc32)[C@@H](F)[C@@H]1O)C(=O)OCC]

diethyl 2-(((2R,3R,4S,5R)-5-(6-(benzylamino)-2-chloro-9H-purin-9-yl)-4-fluoro-3-hydroxytetrahydrofuran-2-yl)methoxy)malonate;

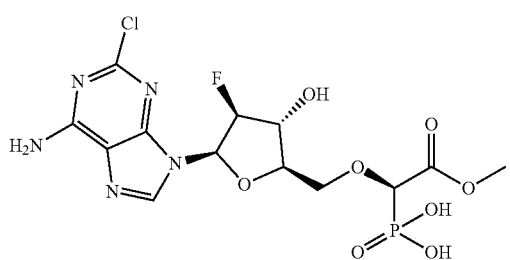 [SMILES: COC(=O)[C@H](OC[C@H]1O[C@@H](n2cnc3c(N)nc(Cl)nc32)[C@@H](F)[C@@H]1O)P(=O)(O)O]

((R)-1-(((2R,3R,4S,5R)-5-(6-amino-2-chloro-9H-purin-9-yl)-4-fluoro-3-hydroxytetrahydrofuran-2-yl)methoxy)-2-methoxy-2-oxoethyl)phosphonic acid;

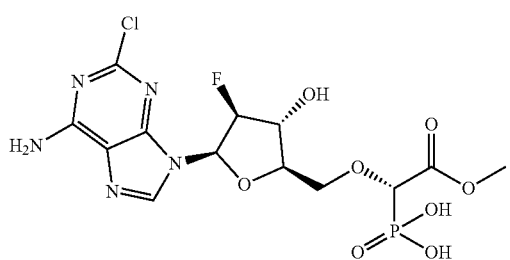 [SMILES: COC(=O)[C@@H](OC[C@H]1O[C@@H](n2cnc3c(N)nc(Cl)nc32)[C@@H](F)[C@@H]1O)P(=O)(O)O]

((S)-1-(((2R,3R,4S,5R)-5-(6-amino-2-chloro-9H-purin-9-yl)-4-fluoro-3-hydroxytetrahydrofuran-2-yl)methoxy)-2-methoxy-2-oxoethyl)phosphonic acid;

312

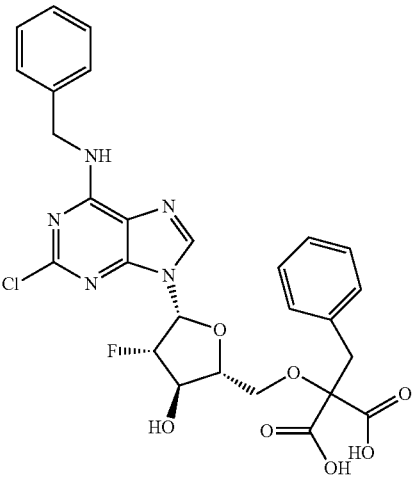 [SMILES: O=C(O)C(Cc1ccccc1)(OC[C@H]1O[C@@H](n2cnc3c(NCc4ccccc4)nc(Cl)nc32)[C@@H](F)[C@@H]1O)C(=O)O]

2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonic acid;

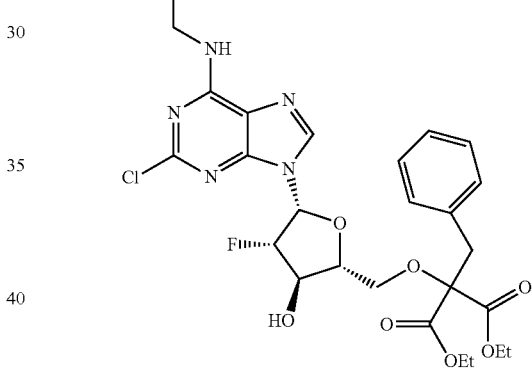

diethyl 2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonate;

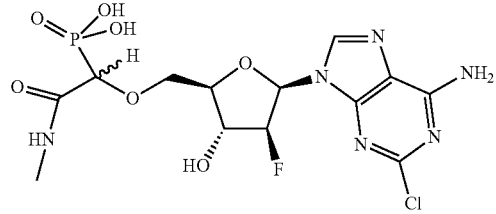 [SMILES: CNC(=O)C(OC[C@H]1O[C@@H](n2cnc3c(N)nc(Cl)nc32)[C@@H](F)[C@@H]1O)P(=O)(O)O]

((R)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid; or ((S)-1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid or a pharmaceutically acceptable salt thereof.

53. The method of claim 52, wherein the compound of Formula (I) has the structure:

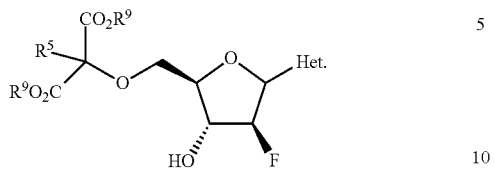

5

10

54. The method of claim 1, wherein the compound of Formula (I) is selected from:

| Cpd. # | Compound | Name |
|---|---|---|
| 1 | Isomer 1 | 1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic acid |
| 2 | Isomer 2 | (1-(((2R,3R,4S,5R)-5-(6-amino-2-chloro-9H-purin-9-yl)-4-fluoro-3-hydroxytetrahydrofuran-2-yl)methoxy)-2-ethoxy-2-oxoethyl)phosphonic acid |
| 3 | Isomer 1 | (1-(((2R,3R,4S,5R)-5-(6-((tert-butoxycarbonyl)amino)-2-chloro-9H-purin-9-yl)-4-fluoro-3-hydroxytetrahydrofuran-2-yl)methoxy)-2-ethoxy-2-oxoethyl)phosphonic acid |

| Cpd. # | Compound | Name |
|---|---|---|
| 4 | 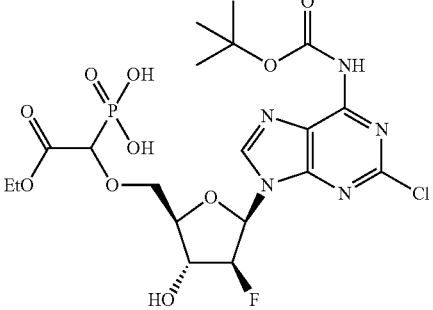 Isomer 2 | (1-(((2R,3R,4S,5R)-5-(6-((tert-butoxycarbonyl)amino)-2-chloro-9H-purin-9-yl)-4-fluoro-3-hydroxytetrahydrofuran-2-yl)methoxy)-2-ethoxy-2-oxoethyl)phosphonic acid |
| 5 | 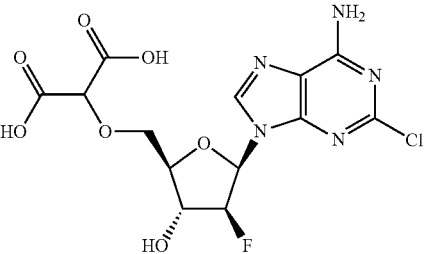 [SMILES: Nc1nc(Cl)nc2c1ncn2[C@@H]1O[C@H](COC(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydrofuran-2-yl)methoxy)malonic acid |
| 6 | 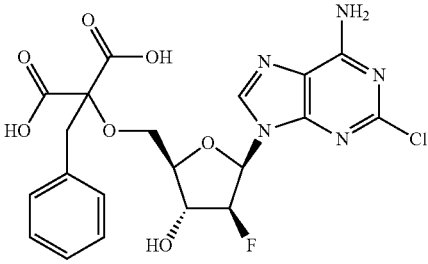 [SMILES: Nc1nc(Cl)nc2c1ncn2[C@@H]1O[C@H](COC(Cc2ccccc2)(C(=O)O)C(=O)O)[C@@H](O)[C@@H]1F] | 2-(((2R,3R,4S,5R)-5-(6-amino-2-chloro-9H-purin-9-yl)-4-fluoro-3-hydroxytetrahydrofuran-2-yl)methoxy)-2-benzylmalonic acid |
| 7 | 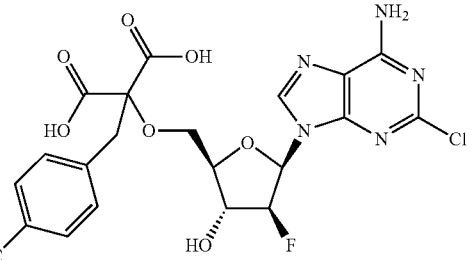 | 2-(((2R,3R,4S,5R)-5-(6-amino-2-chloro-9H-purin-9-yl)-4-fluoro-3-hydroxytetrahydrofuran-2-yl)methoxy)-2-(4-carboxybenzyl)malonic acid |
| 8 | 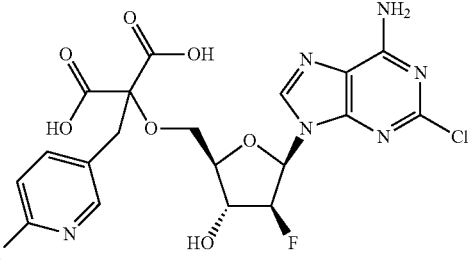 | 2-(((2R,3R,4S,5R)-5-(6-amino-2-chloro-9H-purin-9-yl)-4-fluoro-3-hydroxytetrahydrofuran-2-yl)methoxy)-2-((6-chloropyridin-3-yl)methyl)malonic acid |

-continued

| Cpd. # | Compound | Name |
|---|---|---|
| 9 | | 2-(((2R,3R,4R,5R)-5-(6-amino-9H-purin-9-yl)-4-fluoro-3-hydroxytetrahydrofuran-2-yl)methoxy)malonic acid |
| 10 | | 2-(((2R,3R,4R,5R)-5-(6-amino-9H-purin-9-yl)-4-fluoro-3-hydroxytetrahydrofuran-2-yl)methoxy)-2-benzylmalonic acid |
| 12 | | 2-(((2R,3R,4S,5R)-5-(6-amino-2-chloro-9H-purin-9-yl)-4-fluoro-3-hydroxytetrahydrofuran-2-yl)methoxy)-2-(4-(2-carboxyethyl)benzyl)malonic acid |
| 13 | | 2-(((2R,3R,4S,5R)-5-(6-amino-2-chloro-9H-purin-9-yl)-4-fluoro-3-hydroxytetrahydrofuran-2-yl)methoxy)-2-(3-phenoxybenzyl)malonic acid |
| 15 | | 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethoxy)benzyl)malonic acid |

| Cpd. # | Compound | Name |
|---|---|---|
| 16 | | 2-(((2R,3R,4S,5R)-5-(6-amino-2-chloro-9H-purin-9-yl)-4-fluoro-3-hydroxytetrahydrofuran-2-yl)methoxy)-2-(3-(trifluoromethyl)benzyl)malonic acid |
| 17 | | 2-(((2R,3R,4S,5R)-5-(6-amino-2-chloro-9H-purin-9-yl)-4-fluoro-3-hydroxytetrahydrofuran-2-yl)methoxy)-2-(naphthalen-2-ylmethyl)malonic acid |
| 18 | | 2-(((2R,3R,4S,5R)-5-(6-amino-2-chloro-9H-purin-9-yl)-4-fluoro-3-hydroxytetrahydrofuran-2-yl)methoxy)-2-(4-hydroxybutyl)malonic acid |
| 19 | | 1-(((2R,3R,4S,5R)-5-(6-amino-2-chloro-9H-purin-9-yl)-4-fluoro-3-hydroxytetrahydrofuran-2-yl)methoxy)ethane-1,1,2-tricarboxylic acid |
| 20 | | 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonic acid |

| Cpd. # | Compound | Name |
| --- | --- | --- |
| 21 | | 2-(((2R,3R,4S,5R)-5-(6-amino-2-chloro-9H-purin-9-yl)-4-fluoro-3-hydroxytetrahydrofuran-2-yl)methoxy)-2-(4-(methylsulfonyl)benzyl)malonic acid |
| 22 | | 2-(((2R,3R,4S,5R)-5-(6-amino-2-chloro-9H-purin-9-yl)-4-fluoro-3-hydroxytetrahydrofuran-2-yl)methoxy)-2-(3-(dimethylcarbamoyl)benzyl)malonic acid |
| 23 | | 2-(((2R,3R,4S,5R)-5-(6-amino-2-chloro-9H-purin-9-yl)-4-fluoro-3-hydroxytetrahydrofuran-2-yl)methoxy)-2-(thiophen-3-ylmethyl)malonic acid |
| 24 | | (1-(((2R,3R,4S,5R)-5-(6-amino-2-chloro-9H-purin-9-yl)-4-fluoro-3-hydroxytetrahydrofuran-2-yl)methoxy)-2-methoxy-2-oxoethyl)phosphonic acid |
| 25 | | diethyl 2-(((2R,3R,4S,5R)-5-(6-amino-2-chloro-9H-purin-9-yl)-4-fluoro-3-(isobutyryloxy)tetrahydrofuran-2-yl)methoxy)-2-(4-(trifluoromethoxy)benzyl)malonate |

-continued

| Cpd. # | Compound | Name |
|---|---|---|
| 26 | | 2-(((2R,3R,4S,5R)-5-(6-(benzylamino)-2-chloro-9H-purin-9-yl)-4-fluoro-3-hydroxytetrahydrofuran-2-yl)methoxy)malonic acid |
| 27 | | 2-(((2R,3R,4S,5R)-5-(6-amino-2-chloro-9H-purin-9-yl)-4-fluoro-3-hydroxytetrahydrofuran-2-yl)methoxy)-2-(3-aminobenzyl)malonic acid |
| 28 | | 2-benzyl-2-(((2R,3R,4S,5R)-5-(6-(benzylamino)-2-chloro-9H-purin-9-yl)-4-fluoro-3-hydroxytetrahydrofuran-2-yl)methoxy)malonic acid |
| 29 | | (1-(((2R,3R,4S,5R)-5-(6-amino-2-chloro-9H-purin-9-yl)-4-fluoro-3-hydroxytetrahydrofuran-2-yl)methoxy)-2-(methylamino)-2-oxoethyl)phosphonic acid |
| 30 | | dimethyl 2-(((2R,3R,4S,5R)-5-(6-amino-2-chloro-9H-purin-9-yl)-4-fluoro-3-hydroxytetrahydrofuran-2-yl)methoxy)succinate |

| Cpd. # | Compound | Name |
|---|---|---|
| 31 | | 2-(((2R,3R,4S,5R)-5-(6-amino-2-chloro-9H-purin-9-yl)-4-fluoro-3-hydroxytetrahydrofuran-2-yl)methoxy)succinic acid |
| 32 | | 2-(((2R,3R,4S,5R)-5-(6-amino-2-chloro-9H-purin-9-yl)-4-fluoro-3-hydroxytetrahydrofuran-2-yl)methoxy)-2-((6-(trifluoromethyl)pyridin-3-yl)methyl)malonic acid |
| 33 | | 2-(((2R,3R,4S,5R)-5-(6-amino-2-chloro-9H-purin-9-yl)-4-fluoro-3-hydroxytetrahydrofuran-2-yl)methoxy)-2-(cyanomethyl)malonic acid |
| 34 | | 2-(((2R,3R,4S,5R)-5-(6-amino-2-chloro-9H-purin-9-yl)-4-fluoro-3-hydroxytetrahydrofuran-2-yl)methoxy)-2-(4-cyanobenzyl)malonic acid |
| 35 | | 2-(((2R,3R,4S,5R)-5-(6-amino-2-chloro-9H-purin-9-yl)-4-fluoro-3-hydroxytetrahydrofuran-2-yl)methoxy)-2-(3-cyanobenzyl)malonic acid |

-continued

| Cpd. # | Compound | Name |
|---|---|---|
| 36 | | 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)malonic acid |
| 37 | | (S)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxo-2-(4-(trifluoromethoxy)benzyl)propanoic acid |
| 38 | | (R)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxo-2-(4-(trifluoromethoxy)benzyl)propanoic acid |
| 39 | | 2-(((2R,3R,4S,5R)-5-(6-amino-2-chloro-9H-purin-9-yl)-4-fluoro-3-hydroxytetrahydrofuran-2-yl)methoxy)-2-(4-(hydroxymethyl)benzyl)malonic acid |
| 40 | | 2-(((2R,3R,4S,5R)-5-(6-amino-2-azido-9H-purin-9-yl)-4-fluoro-3-hydroxytetrahydrofuran-2-yl)methoxy)-2-(3-cyanobenzyl)malonic acid |

| Cpd. # | Compound | Name |
| --- | --- | --- |
| 41 | | 2-(((2R,3R,4S,5R)-5-(2-azido-6-((tert-butoxycarbonyl)amino)-9H-purin-9-yl)-4-fluoro-3-hydroxytetrahydrofuran-2-yl)methoxy)-2-(3-cyanobenzyl)malonic acid |
| 42 | | 2-(((2R,3R,4S,5R)-5-(6-amino-2-chloro-9H-purin-9-yl)-4-fluoro-3-hydroxytetrahydrofuran-2-yl)methoxy)-2-(3-carboxybenzyl)malonic acid |
| 43 | | 2-(3-(2H-tetrazol-5-yl)benzyl)-2-(((2R,3R,4S,5R)-5-(6-amino-2-azido-9H-purin-9-yl)-4-fluoro-3-hydroxytetrahydrofuran-2-yl)methoxy)malonic acid |
| 44 | | 2-(((2R,3R,4S,5R)-5-(6-amino-2-chloro-9H-purin-9-yl)-4-fluoro-3-hydroxytetrahydrofuran-2-yl)methoxy)-2-(3-fluorobenzyl)malonic acid |
| 45 | | diethyl 2-(((2R,3R,4S,5R)-5-(6-amino-2-chloro-9H-purin-9-yl)-4-fluoro-3-hydroxytetrahydrofuran-2-yl)methoxy)-2-(3-fluorobenzyl)malonate |

| Cpd. # | Compound | Name |
|---|---|---|
| 46 | 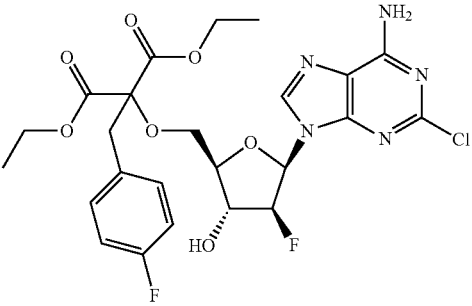 [SMILES: CCOC(=O)C(Cc1ccc(F)cc1)(OC[C@H]1O[C@@H](n2cnc3c(N)nc(Cl)nc32)[C@@H](F)[C@@H]1O)C(=O)OCC] | diethyl 2-(((2R,3R,4S,5R)-5-(6-amino-2-chloro-9H-purin-9-yl)-4-fluoro-3-hydroxytetrahydrofuran-2-yl)methoxy)-2-(4-fluorobenzyl)malonate |
| 47 | 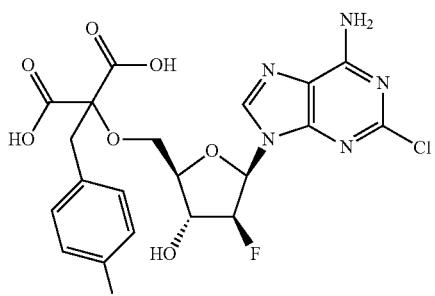 | 2-(((2R,3R,4S,5R)-5-(6-amino-2-chloro-9H-purin-9-yl)-4-fluoro-3-hydroxytetrahydrofuran-2-yl)methoxy)-2-(4-fluorobenzyl)malonic acid |
| 48 | 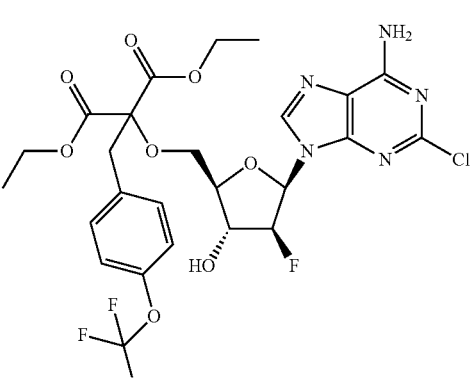 | diethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethoxy)benzyl)malonate |
| 49 | 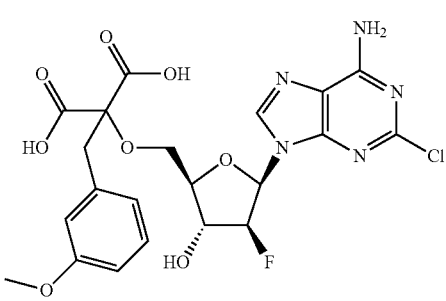 [SMILES: COc1cccc(CC(OC[C@H]2O[C@@H](n3cnc4c(N)nc(Cl)nc43)[C@@H](F)[C@@H]2O)(C(=O)O)C(=O)O)c1] | 2-(((2R,3R,4S,5R)-5-(6-amino-2-chloro-9H-purin-9-yl)-4-fluoro-3-hydroxytetrahydrofuran-2-yl)methoxy)-2-(3-methoxybenzyl)malonic acid |
| 50 | 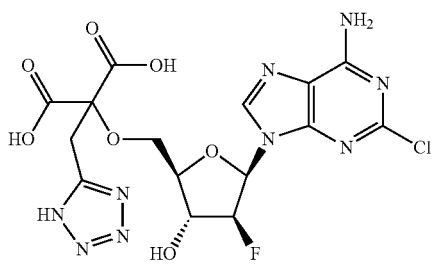 [SMILES: Nc1nc(Cl)nc2c1ncn2[C@@H]1O[C@H](COC(Cc2nnn[nH]2)(C(=O)O)C(=O)O)[C@@H](O)[C@@H]1F] | 2-((1H-tetrazol-5-yl)methyl)-2-(((2R,3R,4S,5R)-5-(6-amino-2-chloro-9H-purin-9-yl)-4-fluoro-3-hydroxytetrahydrofuran-2-yl)methoxy)malonic acid |

-continued

| Cpd. # | Compound | Name |
|---|---|---|
| 51 | | 2-(((2S,3S,4R,5R)-3-amino-5-(6-amino-2-chloro-9H-purin-9-yl)-4-hydroxytetrahydrofuran-2-yl)methoxy)-2-benzylmalonic acid |
| 52 | | 2-(((2S,3S,4R,5R)-5-(6-amino-2-chloro-9H-purin-9-yl)-3-azido-4-hydroxytetrahydrofuran-2-yl)methoxy)malonic acid |
| 53 | | 2-(3-(2H-tetrazol-5-yl)benzyl)-2-(((2R,3R,4S,5R)-5-(6-amino-2-chloro-9H-purin-9-yl)-4-fluoro-3-hydroxytetrahydrofuran-2-yl)methoxy)malonic acid |
| 54 | | 2-(4-(2H-tetrazol-5-yl)benzyl)-2-(((2R,3R,4S,5R)-5-(6-amino-2-chloro-9H-purin-9-yl)-4-fluoro-3-hydroxytetrahydrofuran-2-yl)methoxy)malonic acid |

| Cpd. # | Compound | Name |
|---|---|---|
| 55 | | 2-(((2R,3S,4R,5R)-4-amino-5-(6-amino-2-chloro-9H-purin-9-yl)-3-hydroxytetrahydrofuran-2-yl)methoxy)-2-benzylmalonic acid |
| 56 | | 2-(((2R,3R,4S,5R)-5-(6-amino-2-chloro-9H-purin-9-yl)-4-fluoro-3-hydroxytetrahydrofuran-2-yl)methoxy)-2-(3-hydroxybenzyl)malonic acid |
| 57 | | 2-(((2R,3R,4S,5R)-5-(6-amino-2-chloro-9H-purin-9-yl)-4-fluoro-3-hydroxytetrahydrofuran-2-yl)methoxy)-2-(4-carboxy-2-fluorobenzyl)malonic acid |
| 58 | | 2-(((2R,3R,4S,5R)-5-(6-amino-2-chloro-9H-purin-9-yl)-4-fluoro-3-hydroxytetrahydrofuran-2-yl)methoxy)-2-(4-carboxy-3-fluorobenzyl)malonic acid |
| 59 | | 2-(((2R,3R,4S,5R)-5-(6-amino-2-chloro-9H-purin-9-yl)-4-fluoro-3-hydroxytetrahydrofuran-2-yl)methoxy)-2-((5-(trifluoromethyl)furan-2-yl)methyl)malonic acid |

-continued

| Cpd. # | Compound | Name |
|---|---|---|
| 60 | | 2-(((2R,3R,4S,5R)-5-(6-amino-2-chloro-9H-purin-9-yl)-4-fluoro-3-hydroxytetrahydrofuran-2-yl)methoxy)-2-(3-fluoro-4-(trifluoromethyl)benzyl)malonic acid |
| 61 | | 2-(((2R,3R,4S,5R)-5-(6-amino-2-chloro-9H-purin-9-yl)-4-fluoro-3-hydroxytetrahydrofuran-2-yl)methoxy)-2-((3-phenylisoxazol-5-yl)methyl)malonic acid |
| 62 | | dimethyl 2-(((2R,3R,4S,5R)-5-(6-amino-2-chloro-9H-purin-9-yl)-4-fluoro-3-hydroxytetrahydrofuran-2-yl)methoxy)-2-(4-(trifluoromethyl)benzyl)malonate |
| 63 | | 2-(((2R,3R,4S,5R)-5-(6-amino-2-chloro-9H-purin-9-yl)-4-fluoro-3-hydroxytetrahydrofuran-2-yl)methoxy)-2-((1-benzyl-1H-pyrazol-4-yl)methyl)malonic acid |

| Cpd. # | Compound | Name |
|---|---|---|
| 64 | | 2-((1H-pyrazol-4-yl)methyl)-2-(((2R,3R,4S,5R)-5-(6-amino-2-chloro-9H-purin-9-yl)-4-fluoro-3-hydroxytetrahydrofuran-2-yl)methoxy)malonic acid |
| 65 | | 2-(((2R,3R,4S,5R)-5-(6-amino-2-chloro-9H-purin-9-yl)-4-fluoro-3-hydroxytetrahydrofuran-2-yl)methoxy)-2-(4-(benzyloxy)benzyl)malonic acid |
| 66 | | 2-(((2R,3R,4S,5R)-5-(6-amino-2-chloro-9H-purin-9-yl)-4-fluoro-3-hydroxytetrahydrofuran-2-yl)methoxy)-2-(4-hydroxybenzyl)malonic acid |
| 67 | | 2-(((2R,3R,4S,5R)-5-(6-amino-2-chloro-9H-purin-9-yl)-4-fluoro-3-hydroxytetrahydrofuran-2-yl)methoxy)-2-((2-carboxythiazol-5-yl)methyl)malonic acid |

| Cpd. # | Compound | Name |
|---|---|---|
| 68 | | 2-(((2R,3R,4S,5R)-5-(6-amino-2-chloro-9H-purin-9-yl)-4-fluoro-3-hydroxytetrahydrofuran-2-yl)methoxy)-2-((2-carboxythiazol-4-yl)methyl)malonic acid |
| 70 | | diethyl 2-(((2R,3R,4S,5R)-5-(6-amino-2-chloro-9H-purin-9-yl)-4-fluoro-3-hydroxytetrahydrofuran-2-yl)methoxy)-2-(4-(2-methoxy-2-oxoethyl)benzyl)malonate |
| 71 | | diethyl 2-(((2R,3R,4S,5R)-5-(6-amino-2-chloro-9H-purin-9-yl)-4-fluoro-3-(isobutyryloxy)tetrahydrofuran-2-yl)methoxy)-2-((5-(methoxycarbonyl)thiophen-3-yl)methyl)malonate |
| 72 | | diethyl 2-(((2R,3R,4S,5R)-5-(6-amino-2-chloro-9H-purin-9-yl)-4-fluoro-3-hydroxytetrahydrofuran-2-yl)methoxy)-2-((5-(methoxycarbonyl)-1-methyl-1H-pyrazol-3-yl)methyl)malonate |

-continued

| Cpd. # | Compound | Name |
|---|---|---|
| 73 | | 2-(((2R,3R,4S,5R)-5-(6-amino-2-chloro-9H-purin-9-yl)-4-fluoro-3-hydroxytetrahydrofuran-2-yl)methoxy)-2-((5-carboxy-1-methyl-1H-pyrazol-3-yl)methyl)malonic acid |
| 74 | | 2-benzyl-2-(((2R,3R,4S,5R)-5-(2-chloro-6-hydroxy-9H-purin-9-yl)-4-fluoro-3-hydroxytetrahydrofuran-2-yl)methoxy)malonic acid |
| 75 | | 2-(((2R,3R,4S,5R)-5-(6-amino-2-chloro-9H-purin-9-yl)-4-fluoro-3-hydroxytetrahydrofuran-2-yl)methoxy)-2-(4-cyano-3-fluorobenzyl)malonic acid |
| 76 | | 2-(((2R,3R,4S,5R)-5-(6-amino-2-chloro-9H-purin-9-yl)-4-fluoro-3-hydroxytetrahydrofuran-2-yl)methoxy)-2-((5-carboxythiophen-3-yl)methyl)malonic acid |
| 77 | | 2-(((2R,3R,4S,5R)-5-(6-amino-2-chloro-9H-purin-9-yl)-4-fluoro-3-hydroxytetrahydro-furan-2-yl)methoxy)-2-((5-carboxythiophen-2-yl)methyl)malonic acid |

-continued

| Cpd. # | Compound | Name |
|---|---|---|
| 78 | | 2-(((2R,3R,4S,5R)-5-(6-amino-2-chloro-9H-purin-9-yl)-4-fluoro-3-hydroxytetrahydrofuran-2-yl)methoxy)-2-(4-(carboxymethyl)benzyl)malonic acid |
| 79 | | 2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)malonic acid |
| 80 | | 2-(((2R,3R,4S,5R)-5-(6-amino-2-chloro-9H-purin-9-yl)-4-fluoro-3-hydroxytetrahydrofuran-2-yl)methoxy)-2-(4-chloro-2-fluorobenzyl)malonic acid |
| 81 | | (R)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-methoxy-3-oxopropanoic acid |

| Cpd. # | Compound | Name |
|---|---|---|
| 82 | | (S)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-methoxy-3-oxopropanoic acid |
| 83 | | 2-(((2R,3R,4S,5R)-5-(6-amino-2-chloro-9H-purin-9-yl)-4-fluoro-3-hydroxytetrahydrofuran-2-yl)methoxy)-2-((3-carboxyisoxazol-5-yl)methyl)malonic acid |
| 84 | | (S)-2-([1,1'-biphenyl]-4-ylmethyl)-2-(((2R,3R,4S,5R)-5-(6-amino-2-chloro-9H-purin-9-yl)-4-fluoro-3-hydroxytetrahydrofuran-2-yl)methoxy)-3-ethoxy-3-oxopropanoic acid |
| 85 | | 2-(((2R,3R,4S,5R)-5-(6-amino-2-chloro-9H-purin-9-yl)-4-fluoro-3-hydroxytetrahydrofuran-2-yl)methoxy)-2-(3-chloro-4-methoxybenzyl)malonic acid |

| Cpd. # | Compound | Name |
|---|---|---|
| 86 | | 2-(((2R,3R,4S,5R)-5-(6-amino-2-chloro-9H-purin-9-yl)-4-fluoro-3-hydroxytetrahydrofuran-2-yl)methoxy)-2-(4-sulfamoylbenzyl)malonic acid |
| 87 | | 2-(((2R,3R,4S,5R)-5-(6-amino-2-chloro-9H-purin-9-yl)-4-fluoro-3-hydroxytetrahydro-furan-2-yl)methoxy)-2-(4-((2-carboxyethyl)carbamoyl)benzyl)malonic acid |
| 88 | | 2-(((2R,3R,4S,5R)-5-(6-amino-2-chloro-9H-purin-9-yl)-4-fluoro-3-hydroxytetrahydro-furan-2-yl)methoxy)-2-((2-carboxybenzofuran-5-yl)methyl)malonic acid |
| 89 | | 2-(((2R,3R,4S,5R)-5-(6-amino-2-chloro-9H-purin-9-yl)-4-fluoro-3-hydroxytetrahydrofuran-2-yl)methoxy)-2-(4-(2,2,2-trifluoroethoxy)benzyl)malonic acid |

-continued

| Cpd. # | Compound | Name |
|---|---|---|
| 90 | 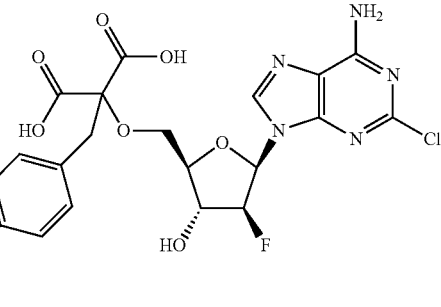 | 2-(((2R,3R,4S,5R)-5-(6-amino-2-chloro-9H-purin-9-yl)-4-fluoro-3-hydroxytetrahydrofuran-2-yl)methoxy)-2-(4-((E)-2-carboxyvinyl)benzyl)malonic acid |
| 91 | 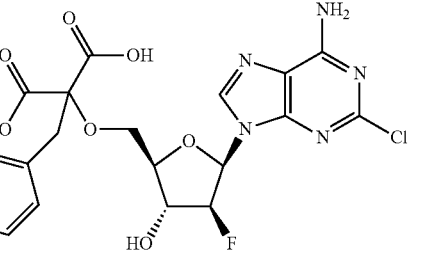 | 2-(((2R,3R,4S,5R)-5-(6-amino-2-chloro-9H-purin-9-yl)-4-fluoro-3-hydroxytetrahydrofuran-2-yl)methoxy)-2-(4-(methoxycarbonyl)benzyl)malonic acid |
| 92 | 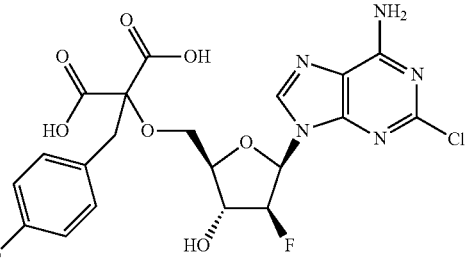 | 2-(((2R,3R,4S,5R)-5-(6-amino-2-chloro-9H-purin-9-yl)-4-fluoro-3-hydroxytetrahydrofuran-2-yl)methoxy)-2-(4-(carboxymethoxy)benzyl)malonic acid |
| 94 | 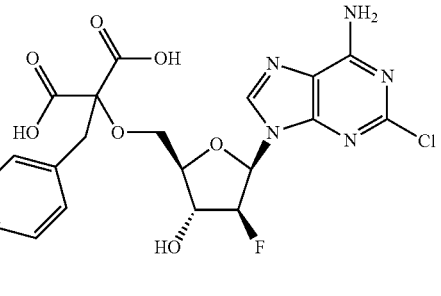 | 2-(((2R,3R,4S,5R)-5-(6-amino-2-chloro-9H-purin-9-yl)-4-fluoro-3-hydroxytetrahydrofuran-2-yl)methoxy)-2-(4-(5-methyl-1,3,4-oxadiazol-2-yl)benzyl)malonic acid |
| 95 | 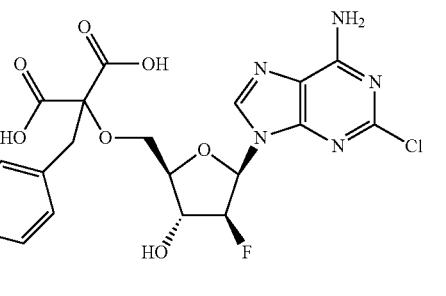 | 2-(((2R,3R,4S,5R)-5-(6-amino-2-chloro-9H-purin-9-yl)-4-fluoro-3-hydroxytetrahydrofuran-2-yl)methoxy)-2-((2'-cyano-[1,1'-biphenyl]-4-yl)methyl)malonic acid |

| Cpd. # | Compound | Name |
|---|---|---|
| 96 | | 2-(((2R,3R,4S,5R)-5-(6-amino-2-chloro-9H-purin-9-yl)-4-fluoro-3-hydroxytetrahydrofuran-2-yl)methoxy)-2-((5-chlorobenzo[b]thiophen-3-yl)methyl)malonic acid |
| 97 | | 2-(((2R,3R,4S,5R)-5-(6-amino-2-chloro-9H-purin-9-yl)-4-fluoro-3-hydroxytetrahydrofuran-2-yl)methoxy)-2-(benzo[d]thiazol-2-ylmethyl)malonic acid |
| 98 | | 2-(((2R,3R,4S,5R)-5-(6-amino-2-chloro-9H-purin-9-yl)-4-fluoro-3-hydroxytetrahydrofuran-2-yl)methoxy)-2-(4-(methylcarbamoyl)benzyl)malonic acid | or a pharmaceutically acceptable salt thereof.

55. The method of claim 1, wherein the cancer is selected from bladder cancer, breast cancer, colon cancer, esophageal cancer, leukemia, lung cancer, lymphoma, melanoma, and ovarian cancer.

56. The method of claim 55, wherein the cancer is selected from breast cancer, colon cancer, lung cancer, melanoma, ovarian cancer, and prostate cancer.

57. The method of claim 55, wherein the cancer is breast cancer.

58. The method of claim 1, further comprising conjointly administering one or more additional chemotherapeutic agents.

59. The method of claim 58, wherein the one or more additional chemotherapeutic agents are selected from 1-amino-4-phenyl amino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carb oxyphenyl amino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, *Bacillus* Calmette-Guérin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA).

60. The method of claim 58, wherein the one or more additional chemotherapeutic agents are selected from 1-amino-4-phenyl amino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carb oxyphenyl amino]-9,10-dioxo-9,10-dihydroanthracene-2-sulfonate, 1-amino-4-[2-anthracenyl amino]-9,10-dioxo-9,10-dihydroanthracene-2-sulfonate, APCP, β-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

61. The method of claim 58, wherein the additional chemotherapeutic agent is an immuno-oncology agent.

* * * * *